United States Patent
Preuss et al.

(10) Patent No.: US 8,981,183 B2
(45) Date of Patent: Mar. 17, 2015

(54) SUGARCANE CENTROMERE SEQUENCES AND MINICHROMOSOMES

(75) Inventors: Daphne Preuss, Chicago, IL (US); Gregory P. Copenhaver, Chapel Hill, NC (US); Jennifer M. Mach, Chicago, IL (US); Pierluigi Barone, Charleston, IL (US); Shawn R. Carlson, Bondville, IL (US); Song Luo, Chicago, IL (US)

(73) Assignee: Chromatin, Inc., Chicago, IL (US)

( * ) Notice: Subject to any disclaimer, the term of this patent is extended or adjusted under 35 U.S.C. 154(b) by 360 days.

(21) Appl. No.: 13/386,366

(22) PCT Filed: Jul. 23, 2010

(86) PCT No.: PCT/US2010/043052
§ 371 (c)(1),
(2), (4) Date: Jan. 20, 2012

(87) PCT Pub. No.: WO2011/011685
PCT Pub. Date: Jan. 27, 2011

(65) Prior Publication Data
US 2012/0117868 A1    May 17, 2012

Related U.S. Application Data

(60) Provisional application No. 61/228,019, filed on Jul. 23, 2009.

(51) Int. Cl.
*C12N 15/82* (2006.01)
*C12N 15/11* (2006.01)
*C12N 15/00* (2006.01)
*C12Q 1/68* (2006.01)

(52) U.S. Cl.
CPC .............. *C12Q 1/6895* (2013.01); *C12N 15/82* (2013.01); *C12N 2800/20* (2013.01)
USPC ........... 800/298; 435/468; 435/410; 435/419; 435/430; 435/320.1; 435/69.1; 536/23.1

(58) Field of Classification Search
None
See application file for complete search history.

(56) References Cited

U.S. PATENT DOCUMENTS

2008/0060093 A1*   3/2008   Zieler et al. ................... 800/278

OTHER PUBLICATIONS

Menzel et al. Diversity of a complex centromerix satellite and molecular characterization of dispersed sequence families in sugar beet (Beta vulgaris). Annals of Botany. 2008. 102: 521-530.*
Bower et al. Transgenic sugarcane plants via microprojectile bombardment. The Plant Journal. 1992. 2(3): 409-416.*
Nagaki et al. Characterization of CENH3 and centromere-associated DNA sequences in sugarcane. Chromosome Research. 2005. 13: 195-203.*
Notification of Transmittal of the International Search Report and the Written Opinion of the International Searching Authority, or the Declaration in corresponding PCT Application No. PCT/US10/43052 mailed Oct. 21, 2010 (10 pages).
Genbank EI968873.1. SB_BBc155-J19.F SB_BBc Sorghum bicolor genomic 5-, genomic survey sequence. [online] May 15, 2007 [retrieved Sep. 21, 2010]. Available on the internet: <URL: http://www.ncbi.nlm.nih.gov/nucgss/146568970>.

* cited by examiner

*Primary Examiner* — Anne Kubelik
*Assistant Examiner* — Ashley K Buran
(74) *Attorney, Agent, or Firm* — Marshall, Gerstein & Borun LLP

(57) ABSTRACT

The invention is generally related to Sugarcane mini-chromosomes and recombinant chromosomes containing Sugarcane centromere sequences. In addition, the invention provides for methods of generating Sugarcane plants transformed with these Sugarcane mini-chromosomes. Sugarcane mini-chromosomes with novel compositions and structures are used to transform Sugarcane cells which are in turn used to generate Sugarcane plants. Methods for generating Sugarcane plants include methods for delivering the Sugarcane mini-chromosomes into Sugarcane cell to transform the cell, methods for selecting the transformed cell, and methods for isolating Sugarcane plants transformed with the Sugarcane mini-chromosome or recombinant chromosome.

31 Claims, No Drawings

SUGARCANE CENTROMERE SEQUENCES AND MINICHROMOSOMES

RELATED APPLICATION INFORMATION

This application claims priority under 35 U.S.C. §371 from PCT Application No. PCT/US2010/043052, filed Jul. 23, 2010, which claims the benefit of U.S. Provisional Application No. 61/228,019, filed Jul. 23, 2009, the disclosures of which are incorporated by reference herein in their entireties.

FIELD OF THE INVENTION

The present invention generally relates to Sugarcane minichromosomes and recombinant chromosomes containing Sugarcane centromere sequences as well as Sugarcane cells and plants comprising the same.

BACKGROUND OF THE INVENTION

Two general approaches are used for introduction of new heritable genetic information ("transformation") into cells. One approach is to introduce the new genetic information as part of another DNA molecule, referred to as an "episomal vector," or "mini-chromosome", which can be maintained as an independent unit (an episome) apart from the host chromosomal DNA molecule(s). Episomal vectors contain all the necessary DNA sequence elements required for DNA replication and maintenance of the vector within the cell. Many episomal vectors are available for use in bacterial cells (for example, see Maniatis et al., "Molecular Cloning: a Laboratory Manual," Cold Spring Harbor Laboratory, Cold Spring Harbor, N.Y. 1982). However, only a few episomal vectors that function in higher eukaryotic cells have been developed. Higher eukaryotic episomal vectors were primarily based on naturally occurring viruses. In higher plant systems gemini viruses are double-stranded DNA viruses that replicate through a double-stranded intermediate upon which an episomal vector could be based, although the gemini virus is limited to an approximately 800 bp insert. Although an episomal plant vector based on the Cauliflower Mosaic Virus has been developed, its capacity to carry new genetic information also is limited (Brisson et al., Nature, 310:511, 1984.).

The other general method of genetic transformation involves integration of introduced DNA sequences into the recipient cell's chromosomes, permitting the new information to be replicated and partitioned to the cell's progeny as a part of the natural chromosomes. The introduced DNA usually can be broken and joined together in various combinations before it is integrated at random sites into the cell's chromosome (see, for example Wigler et al., Cell, 11:223, 1977). Common problems with this procedure are the rearrangement of introduced DNA sequences and unpredictable levels of expression due to the location of the transgene integration site in the host genome or so called "position effect variegation" (Shingo et al., Mol. Cell. Biol., 6:1787, 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Chepko et al., Cell, 37:1053, 1984).

One common genetic transformation method used in higher plants is based on the transfer of bacterial DNA into plant chromosomes that occurs during infection by the phytopathogenic soil bacterium *Agrobacterium* (see Nester et al., Ann. Rev. Plant Phys., 35:387-413, 1984). By substituting genes of interest for a portion of the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., Mol. Gen. Genet., 207:478, 1987). Second, the expression of the introduced DNA sequences varies between individual transformants (see Jones et al., Embo J., 4:2411-2418, 1985). This variability is presumably caused by rearranged sequences and the influence of surrounding sequences in the plant chromosome (i.e., position effects), as well as methylation of the transgene. Finally, insertion of extra elements into the genome can disrupt the genes, promoters or other genetic elements necessary for normal plant growth and function.

Another widely used technique to genetically transform plants involves the use of microprojectile bombardment to integrate DNA sequences into the genome. In this process, a nucleic acid containing the desired genetic elements to be introduced into the plant's native chromosome is deposited on or in small metallic particles, e.g., tungsten, platinum, or preferably gold, which are then delivered at a high velocity into the plant tissue or plant cells. However, similar problems arise as with *Agrobacterium*-mediated gene transfer, and as noted above expression of the inserted DNA can be unpredictable and insertion of extra elements into the genome can disrupt and adversely impact plant processes.

One attractive alternative to the commonly used methods of transformation is the use of an artificial chromosome. Artificial chromosomes are episomal nucleic acid molecules that exist autonomously from the native chromosomes of the host genome. They can be linear or circular DNA molecules that are comprised of cis-acting nucleic acid sequence elements that provide replication and partitioning activities (see Murray et al., Nature, 305:189-193, 1983). Desired elements include: (1) origin of replication, which are the sites for initiation of DNA replication, (2) centromeres (site of kinetochore assembly and responsible for proper distribution of replicated chromosomes into daughter cells at mitosis or meiosis), and (3) if the chromosome is linear, telomeres (specialized DNA structures at the ends of linear chromosomes that function to stabilize the ends and facilitate the complete replication of the extreme termini of the DNA molecule). An additional desired element is a chromatin organizing sequence. It is well documented that centromere function is crucial for stable chromosomal inheritance in almost all eukaryotic organisms (reviewed in Nicklas 1988). The centromere accomplishes this by attaching, via centromere binding proteins, to the spindle fibers during mitosis and meiosis, thus ensuring proper gene segregation during cell divisions.

Artificial chromosomes have been engineered using one of two approaches. The first approach identifies and assembles the desired chromosomal elements into an artificial construct. This approach has been described as "bottom-up" and involves the use of a heterologous system (i.e. bacteria or fungal) to perform the various cloning steps necessary to assemble the artificial chromosome. Artificial chromosomes of this type will be referred to in this application as "minichromosomes". The second approach derives the artificial chromosome from existing chromosomes through chromosome fragmentation and, optionally, subsequent addition of desired elements including transgenes. For example, an existing chromosome can be induced to undergo breakage events that result in chromosomal fragments. Minimal fragments that possess the elements for replication and segregation during cell division (e.g. centromere, origins of replication and/ or telomeres) can be identified. These derived artificial chromosomes can then be used as targets for further manipulation including the addition of one or more transgenes. This approach has been described as "top-down" and does not require the use of a heterologous system (e.g. bacterial or fungal) since it doesn't require in vitro-based cloning steps. Artificial chromosomes of this type will be referred to in this application as "recombinant chromosomes".

The essential chromosomal elements for construction of artificial chromosomes have been precisely characterized in lower eukaryotic species, and more recently in mouse and human. Autonomous replication sequences (ARSs) have been isolated from unicellular fungi, including *Saccharomyces cerevisiae* (brewer's yeast) and *Schizosaccharomyces pombe* (see Stinchcomb et al., 1979 and Hsiao et al., 1979). An ARS behaves like an origin of replication allowing DNA molecules that contain the ARS to be replicated in concert with the rest of the genome after introduction into the cell nuclei of these fungi. DNA molecules containing these sequences replicate, but in the absence of a centromere they are not partitioned into daughter cells in a controlled fashion that ensures efficient chromosome inheritance.

Artificial chromosomes have been constructed in yeast using the three cloned essential chromosomal elements (see Murray et al., Nature, 305:189-193, 1983). None of the essential components identified in unicellular organisms, however, function in higher eukaryotic systems. For example, a yeast centromere sequence will not confer stable inheritance upon vectors transformed into higher eukaryotes.

In contrast to the detailed studies done in yeast, less is known about the molecular structure of functional centromeric DNA of higher eukaryotes. Ultrastructural studies indicate that higher eukaryotic kinetochores, which are specialized complexes of proteins that form on the centromere during late prophase, are large structures (mammalian kinetochore plates are approximately 0.3 µm in diameter) which possess multiple microtubule attachment sites (reviewed in Rieder, 1982). It is therefore possible that the centromeric DNA regions of these organisms will be correspondingly large, although the minimal amount of DNA necessary for centromere function may be much smaller.

While the above studies have been useful in elucidating the structure and function of centromeres, it was not known whether information derived from lower eukaryotic or mammalian higher eukaryotic organisms would be applicable to Sugarcane. There exists a need for cloned centromeres from Sugarcane, which would represent a first step in the production of Sugarcane artificial chromosomes, or in the identification of Sugarcane recombinant chromosomes. There further exists a need for Sugarcane cells, plants, seeds and progeny containing functional, stable, and autonomous artificial or recombinant chromosomes capable of carrying a large number of different genes and genetic elements.

SUMMARY OF THE INVENTION

In one aspect, the present invention addresses Sugarcane mini-chromosomes comprising a Sugarcane centromere having one or more repeated nucleotide sequences, described in further detail herein. In some embodiments, such mini-chromosomes comprise a centromere comprising one or more selected repeated nucleotide sequences derived from Sugarcane, including those isolated from Sugarcane genomic DNA and synthetic arrays of repeat sequences. In other embodiments, the invention addresses Sugarcane recombinant chromosomes.

In another aspect, the invention provides modified or "adchromosomal" Sugarcane plants, containing functional, stable, autonomous mini-chromosomes or recombinant chromosomes.

The invention provides for isolated Sugarcane mini-chromosomes comprising a centromere, wherein the centromere comprises at least two copies of a repeated nucleotide sequence(s), and wherein the centromere confers the ability to segregate to daughter cells. The repeated nucleotide sequence(s) may be short Sugarcane satellite sequences such as those sequences set out as SEQ ID NOS: 1-201, the consensus Sugarcane satellite sequence set out as SEQ ID NO: 202, or the block of Sugarcane satellite sequence set out as SEQ ID NO:204. The repeated nucleotide sequences may be longer sequences such as the Sugarcane retrotransposon sequence CRS, set out as SEQ ID NO: 203.

The invention also provides cells comprising a polynucleotide, nucleic acid, vector, Sugarcane centromere, Sugarcane artificial mini-chromosome and/or Sugarcane recombinant chromosome of the invention. In embodiments, the cell is an isolated cell. In other representative embodiments, the cell is a Sugarcane cell.

Accordingly, as one aspect, the invention provides a polynucleotide comprising a nucleotide sequence selected from the group consisting of: (a) the nucleotide sequence of any of SEQ ID NOS: 1-204; (b) a nucleotide sequence that is at least about 80%, 85%, 90%, 95%, 97%, 98% or 99% identical to the nucleotide sequence of any of SEQ ID NOS: 1-204, optionally wherein the nucleotide sequence is functional as a sugar cane plant centromere (e.g., confers the ability to segregate to a daughter cell); and/or (c) a nucleotide sequence that hybridizes to the nucleotide sequence of any of SEQ ID NOS: 1-204 under stringent conditions comprising hybridization at 65° C. and washing three times for 15 minutes with 0.25×SSC, 0.1% SDS at 65° C., optionally wherein the nucleotide sequence is functional as a sugar cane plant centromere.

As another aspect, the invention provides a nucleic acid comprising an array comprising at least about two, at least about ten, at least about 100, from about 2 to about 1000, or from about 5 to about 250 copies of a polynucleotide of the invention. In representative embodiments, the array is from about 1 to about 200 kb in length, optionally from about 15 to about 28 kb in length. In exemplary embodiments, the nucleic acid is functional as a sugar cane plant centromere.

The invention further encompasses a Sugarcane centromere comprising a polynucleotide or nucleic acid of the invention.

Also provided by the invention is a Sugarcane artificial chromosome comprising a polynucleotide, nucleic acid or centromere of the invention. In embodiments of the invention, the Sugarcane artificial chromosome further comprises an exogenous nucleic acid (e.g., at least three exogenous nucleic acids), at least one of which may optionally be linked to a heterologous regulatory sequence functional in Sugarcane plant cells.

In further representative embodiments, the Sugarcane artificial chromosomes of the invention exhibit a mitotic segregation efficiency in Sugarcane plant cells of at least about 60%, 70%, 80%, 85%, 90%, 95% or more.

Also encompassed by the present invention is a vector comprising a polynucleotide, nucleic acid, Sugarcane centromere, or Sugarcane artificial chromosome of the invention.

As still another aspect, the invention provides a cell comprising a polynucleotide, nucleic acid, Sugarcane centromere, Sugarcane artificial chromosome, or vector of the invention. In representative embodiments, the cell is a Sugarcane plant cell.

In particular embodiments, the invention provides a Sugarcane plant cell comprising a Sugarcane artificial chromosome, wherein the Sugarcane artificial chromosome is not integrated into the genome of the Sugarcane plant cell. The Sugarcane plant cell can optionally comprise a Sugarcane artificial chromosome that comprises an exogenous nucleic acid, wherein the Sugarcane plant cell exhibits an altered phenotype associated with the expression of the exogenous nucleic acid. The altered phenotype can be any phenotypic change of interest that can be detected and, optionally, measured. In an exemplary embodiment, the altered phenotype comprises altered expression (e.g., increased or decreased expression) of a native gene. In other embodiments, the altered phenotype comprises altered expression of an exogenous gene.

As yet a further aspect, the invention provides a Sugarcane plant tissue, a Sugarcane plant, and/or a Sugarcane plant part comprising a Sugarcane plant cell of the invention.

The invention also provides a Sugarcane seed obtained from a Sugarcane plant of the invention.

The invention also contemplates a Sugarcane plant progeny comprising a Sugarcane artificial chromosome, wherein the plant progeny is the result of breeding a Sugarcane plant of the invention that comprises the sugarcane artificial chromosome.

As still another aspect, the invention provides a method of using a Sugarcane plant of the invention, wherein the Sugarcane plant comprises a Sugarcane artificial chromosome comprising an exogenous nucleic acid encoding a recombinant protein, the method comprising growing the plant to produce the recombinant protein. The method can optionally further comprise the step of harvesting and/or processing the Sugarcane plant.

In exemplary embodiments, the invention provides for a Sugarcane plant cell comprising a Sugarcane mini-chromosome comprising a Sugarcane centromere that comprises at least two repeat nucleotide sequences that have a sequence that hybridizes under conditions comprising hybridization at 65° C. and washing three times for 15 minutes with 0.25× SSC, 0.1% SDS at 65° C. to a nucleotide sequence selected from the group consisting of SEQ ID NOS: 1-204, and wherein the centromere confers the ability to segregate to daughter Sugarcane cells. Alternatively, the hybridization conditions may comprise hybridization at 65° C. and washing three times for 15 minutes with 0.25×SSC, 0.1% SDS at 65° C.

In another exemplary embodiment, the invention provides for a Sugarcane plant cell comprising a Sugarcane mini-chromosome comprising a Sugarcane centromere, wherein the centromere comprises at least two copies of a repeated nucleotide sequence(s) that has a sequence that is at least 80% identical to a nucleotide sequence selected from the group consisting of SEQ ID NOS: 1-204, and wherein the centromere confers the ability to segregate to daughter Sugarcane cells. The invention also provides for a Sugarcane plant cell comprising a Sugarcane mini-chromosome wherein the repeated nucleotide sequence comprises a sequence that is at least 85% identical, or 90% identical, or 95% identical or 98% identical to a nucleotide sequence selected from the group consisting of SEQ ID NOS: 1-204.

In another embodiment, the invention provides for a Sugarcane plant cell comprising a Sugarcane Applied Mini-chromosome comprising at least two copies of a repeated nucleotide sequence that is at least 80% identical to the nucleotide sequence of any one of SEQ ID NOS: 1-204 or hybridizes to the nucleotide sequence of any one of SEQ ID NOS: 1-204 under stringent conditions comprising hybridization at 65° C. and washing three times for 15 minutes with 0.25×SSC, 0.1% SDS at 65° C., and a Transgene Expression Cassette.

In a further embodiment, the invention provides for a Sugarcane plant cell comprising a Sugarcane mini-chromosome comprising a Sugarcane centromere, wherein the centromere comprises (a) at least two copies of a Sugarcane satellite nucleotide sequence (e.g., SEQ ID NO:204), and (b) at least two copies of a Sugarcane CRS nucleotide sequence (SEQ ID NO: 203), and wherein the centromere confers the ability to segregate to daughter Sugarcane cells. In another embodiment, the invention provides for a Sugarcane plant cell comprising a Sugarcane mini-chromosome comprising a Sugarcane centromere, wherein the centromere comprises (a) at least one array of Sugarcane satellite nucleotide sequences, and (b) at least one array of a Sugarcane CRS nucleotide sequence (SEQ ID NO: 203), and wherein the centromere confers the ability to segregate to daughter Sugarcane cells. The Sugarcane satellite nucleotide sequence may be one of the sequences set out as SEQ ID NOS: 1-202 or SEQ ID NO: 204, or a sequence that hybridizes under conditions comprising hybridization at 65° C. and washing three times for 15 minutes with 0.25×SSC, 0.1% SDS at 65° C. to a nucleotide sequence selected from the group consisting of SEQ ID NOS: 1-202 and SEQ ID NO: 204, or a sequence that is at least 80% identical to a nucleotide sequence selected from the group consisting of SEQ ID NOS: 1-202 and SEQ ID NO: 204.

In addition, the invention provides for a Sugarcane plant cell comprising a Sugarcane Applied Mini-chromosome comprising a Sugarcane centromere, wherein the Sugarcane centromere comprises (a) at least 5 copies of a repeated nucleotide sequence within 1 kb of nucleotide sequence, wherein the repeated nucleotide sequence is at least 80% identical to the nucleotide sequence of any one of SEQ ID NOS: 1-202 or SEQ ID NO: 204 or hybridizes to the nucleotide sequence of any one of SEQ ID NOS: 1-202 or SEQ ID NO: 204 under stringent conditions comprising hybridization at 65° C. and washing three times for 15 minutes with 0.25×SSC, 0.1% SDS at 65° C., and (b) at least 2 copies of a repeated nucleotide sequence that is at least 80% identical over its length to the nucleotide sequence of any one of SEQ ID NO: 203 or hybridizes to the nucleotide sequence of any one of SEQ ID NO: 203 under stringent conditions comprising hybridization at 65° C. and washing three times for 15 minutes with 0.25× SSC, 0.1% SDS at 65° C.

In another embodiment, the invention provides a Sugarcane plant cell comprising (a) a polynucleotide sequence that is transcribed as a first RNA, (b) a polynucleotide sequence that is transcribed as a second RNA, and (c) a polynucleotide sequence that is transcribed as a third RNA, wherein transcription of the polynucleotide sequences results in increased biomass of a Sugarcane plant.

In an additional embodiment, the invention provides for a Sugarcane plant cell comprising a transgene expression cassette not integrated into the plant cell genome, wherein the Transgene Expression Cassette comprises (a) a polynucleotide sequence that is transcribed as a first RNA, (b) a polynucleotide sequence that is transcribed as a second RNA, and (c) a polynucleotide sequence that is transcribed as a third RNA, wherein transcription of the polynucleotide sequences results in increased biomass of a Sugarcane plant.

The invention provides for a Sugarcane plant cell comprising a recombinant chromosome comprising at least two copies of a repeated nucleotide sequence(s), and wherein the centromere confers the ability to segregate to daughter cells. The repeated nucleotide sequence(s) may be short Sugarcane satellite sequences such as those sequences set out as SEQ ID NOS: 1-201, the consensus Sugarcane satellite sequence set out as SEQ ID NO: 202, or the block of Sugarcane satellite sequence set out as SEQ ID NO: 204. The repeated nucleotide sequences may be longer sequences such as the Sugarcane retrotransposon sequence CRS, set out as SEQ ID NO: 203.

In exemplary embodiments, the invention provides for a Sugarcane plant cell comprising a recombinant chromosome comprising a Sugarcane centromere that comprises at least two repeat nucleotide sequences that have a sequence that hybridizes under conditions comprising hybridization at 65° C. and washing three times for 15 minutes with 0.25×SSC, 0.1% SDS at 65° C. to a nucleotide sequence selected from the group consisting of SEQ ID NOS: 1-204, and wherein the centromere confers the ability to segregate to daughter Sugarcane cells. Alternatively, the hybridization conditions may comprise hybridization at 65° C. and washing three times for 15 minutes with 0.25×SSC, 0.1% SDS at 65° C.

In another exemplary embodiment, the invention provides for a Sugarcane plant cell comprising a recombinant chromosome comprising at least two copies of a repeated nucleotide sequence(s) that has a sequence that is at least 80% identical to a nucleotide sequence selected from the group consisting of SEQ ID NOS: 1-204, and a transgene expression cassette comprising at least three exogenous nucleic acids. The invention also provides for Sugarcane recombinant chromosomes wherein the repeated nucleotide sequence comprise a sequence that is at least 85% identical, or 90% identical, or 95% identical or 98% identical to a nucleotide sequence selected from the group consisting of SEQ ID NOS: 1-204.

In a further embodiment, the invention provides for a Sugarcane plant cell comprising a Sugarcane recombinant chromosome comprising a Sugarcane centromere, wherein the centromere comprises (a) at least two copies of a Sugarcane satellite nucleotide sequence, and (b) at least two copies of a Sugarcane CRS nucleotide sequence (SEQ ID NO: 203), and wherein the centromere confers the ability to segregate to daughter Sugarcane cells. In another embodiment, the invention provides for a Sugarcane recombinant chromosome comprising a Sugarcane centromere, wherein the centromere comprises (a) at least one array of Sugarcane satellite nucleotide sequences, and (b) at least one array of a Sugarcane CRS nucleotide sequence (SEQ ID NO: 203), and wherein the centromere confers the ability to segregate to daughter Sugarcane cells. The Sugarcane satellite nucleotide sequence may be one of the sequences set out as SEQ ID NOS: 1-202 or SEQ ID NO: 204, or a sequence that hybridizes under conditions comprising hybridization at 65° C. and washing three times for 15 minutes with 0.25×SSC, 0.1% SDS at 65° C. to a nucleotide sequence selected from the group consisting of SEQ ID NOS: 1-202 and SEQ ID NO: 204, or a sequence that is at least 80% identical to a nucleotide sequence selected from the group consisting of SEQ ID NOS: 1-202 and SEQ ID NO: 204.

Alternatively, the invention provides for Sugarcane plant cells comprising a recombinant chromosome that has not been maintained in a cell of a heterologous organism.

In another embodiment, the invention provides for a Sugarcane plant cell comprising (a) at least two copies of a repeated nucleotide sequence that is at least 80% identical to the nucleotide sequence of any one of SEQ ID NOS: 1-204 or hybridizes to the nucleotide sequence of any one of SEQ ID NOS: 1-204 under stringent conditions comprising hybridization at 65° C. and washing three times for 15 minutes with 0.25×SSC, 0.1% SDS at 65° C., and (b) a Transgene Expression Cassette comprising at least three exogenous nucleic acids, wherein the nucleotide sequence and the Transgene Expression Cassette are not integrated into the genome of the Sugarcane plant cell.

The invention also provides for a Sugarcane plant cell comprising a Sugarcane mini-chromosome comprising a Sugarcane centromere, wherein the centromere comprises at least two synthetic repeat sequences or a synthetic array of repeated nucleotide sequence, wherein the array comprises at least two copies of a repeated nucleotide sequence, and wherein the centromere confers the ability to segregate to daughter Sugarcane cells. These artificially synthesized repeated nucleotide sequences may be based on sequence information from natural Sugarcane centromere sequences, combinations or fragments of natural Sugarcane centromere sequences including a combination of repeats of different lengths, a combination of different sequences, a combination of both different repeat lengths and different sequences, a combination of different artificially synthesized sequences or a combination of natural Sugarcane centromere sequence(s) and artificially synthesized Sugarcane sequence(s). The polynucleotides comprising synthetic arrays of Sugarcane repeat sequences and synthetic arrays of Sugarcane repeat sequences may be generated using any technique known in the art including PCR from Sugarcane genomic DNA (or a clone thereof) or by custom oligonucleotide synthesis.

The invention provides for any of the Sugarcane mini-chromosomes or recombinant chromosomes described herein having a centromere comprising an array of repeated nucleotide sequence that ranges from about 1 kb to about 200 kb in length, 1 kb to about 100 kb in length, about 1 kb to about 10 kb in length, about 2 kb to about 12 kb in length, about 5 kb to about 25 kb in length, about 10 kb to about 50 kb in length, about 25 kb to 100 kb in length.

The invention further contemplates any of the Sugarcane mini-chromosomes or recombinant chromosomes of the invention having centromeres comprising at least 300 bp, 400 bp, 500 bp, 600 bp, 700 bp, 750 bp, 1 kb, 1.5 kb, 2 kb, 2.5 kb, 3 kb, 3.5 kb, 4 kb, 4.5 kb, 5 kb, 5.5 kb, 6 kb, 6.5 kb, 7 kb, 7.5 kb, 8 kb, 8.5 kb, 9 kb, 9.5 kb, 10 kb, 10.5 kb, 11 kb, 11.5 kb, 12 kb, 12.5 kb, 13 kb, 13.5 kb, 14 kb, 14.5 kb, 15 kb, 16 kb, 17 kb, 18 kb, 19 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, 150 kb, 160 kb, 170 kb, 180 kb, 190 kb, 200 kb, 225 kb, 250 kb, 275 kb, 300 kb, 325 kb, 350 kb or 375 kb.

In another embodiment, any of the Sugarcane mini-chromosomes or recombinant chromosomes of the invention comprise centromeres having n copies of a repeated nucleotide sequence, wherein n is less than 2000, less than 1500, less than 1000, less than 500, less than 400, less than 300, less than 250, less than 200, less than 100, less than 90, less than 80, less than 70, less than 60, less than 50, less than 40, less than 30, less than 25, less than 20, less than 15, less than 10, less than 9, less than 8, less than 7, less than 6 or less than 5. In exemplary embodiments, the centromeres of the Sugarcane mini-chromosomes of the invention comprise n copies of a repeated nucleotide sequence, wherein n is at least 2, 3, 4, 5, 6, 7, 8, 9, 10, 15, 20, 25, 30, 35, 40, 50, 60, 70, 80, 90, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900 or 1000. In additional exemplary embodiments, the centromeres of the Sugarcane mini-chromosomes or recombinant chromosomes of the invention comprise n copies of a repeated nucleotide sequence where n ranges from 2 to 10, 2 to 20, 2 to 50, 2 to 100, 2 to 250, 2 to 500, 2 to 1000, 5 to 15, 5 to 25, 5 to 50, 5 to 100, 5 to 250, 5 to 500, 5 to 1000, to 25, 15 to 50, 15 to 100, 15 to 250, 15 to 500, 15 to 1000, 25 to 50, 25 to 100, 25 to 250, 25 to 500, 25 to 1000, 50 to 100, 50 to 250, 50 to 500, 50 to 1000, 100 to 250, 100 to 500, 100 to 1000, 250 to 500, 250 to 1000, or 500 to 1000.

In an embodiment of the invention, any of the Sugarcane mini-chromosomes or recombinant chromosomes of the invention comprise a centromere having at least 5 consecutive repeated nucleotide sequences (e.g., SEQ ID NO: 204) in "head to tail orientation." In an embodiment of the invention, any of the Sugarcane mini-chromosomes or recombinant chromosomes of the invention comprise a centromere having at least 5 consecutive repeated nucleotide sequences in "tandem," in which one repeat sequence is immediately adjacent to another repeat sequence in any orientation, e.g. head to tail, tail to tail, or head to head. The invention also provides for any of the Sugarcane mini-chromosomes or recombinant chromosomes of the invention comprising a centromere having at least 5 repeated nucleotide sequences that are consecutive. The term "consecutive" refers to the same or similar repeated nucleotide sequences (e.g., at least 70% identical) that follow one after another without being interrupted by other significant sequence elements. Consecutive repeated nucleotide sequences may be in any orientation, e.g. head to tail, tail to tail, or head to head, and need not be directly adjacent to each other (e.g., may be 1-50 bp apart).

The invention further provides for any of the Sugarcane mini-chromosomes or recombinant chromosomes of the invention comprising a centromere having at least 5 of the consecutive repeated nucleotide sequences (e.g., SEQ ID NO: 204) separated by less than n number of nucleotides, wherein n ranges from 1 to 10, or 1 to 20, or 1 to 30, or 1 to 40, or 1 to 50 or wherein n is less than 10 bp or n is less than 20 bp or n is less than 30 bp or n is less that 40 bp or n is less than 50 bp.

The invention also provide for any of the Sugarcane mini-chromosomes or recombinant chromosomes of the invention comprising a centromere having at least two arrays of consecutive repeated nucleotide sequences (e.g., SEQ ID NO: 204), wherein the array comprises at least 2, 3, 4, 5, 6, 7, 8, 9, 10, 15, 20, 25, 30, 40, 50, 60, 70, 80, 90, 100, 150, 200, 250, 300, 350, 400, 450, 500, 600, 700, 800, 900, 1000 or 2000 repeated nucleotide sequences. The repeats within an array may be in tandem in any orientation, e.g. head to tail, tail to tail, or head to head, or consecutive in any orientation, e.g. head to tail, tail to tail, or head to head. The arrays may be separated by less than n number of nucleotides, wherein n ranges from 1 to 10, or 1 to 20, or 1 to 30, or 1 to 40, or 1 to 50, or 1 to 60, or 1 to 70, or 1 to 80, or 1 to 90, or 1 to 100, or wherein n is less than 10 bp or n is less than 20 bp or n is less than 30 bp or n is less that 40 bp or n is less than 50 bp. The two arrays may comprise the same repeated nucleotide sequence or two different repeated nucleotide sequences (i.e. the first array can be comprised of repeat type 1 and the second array can be comprised of repeat type 2—here "type 1" and "type 2" are arbitrary designations).

In one embodiment, the Sugarcane mini-chromosomes or recombinant chromosomes of the invention are 1000 kb or less in length, 900 kb or less in length, 800 kb or less in length or 700 kb or less in length. In exemplary embodiments, the Sugarcane mini-chromosome is 600 kb or less in length, 500 kb or less in length, 250 kb or less in length, 100 kb or less in length, 50 kb or less in length, 10 kb or less in length, 5 kb or less in length, or 1 kb or less in length. For example, the Sugarcane mini-chromosomes of the invention are 50 to 250 kb in length, 50 to 100 kb in length, 50 to 75 kb in length, 50 to 100 kb in length, 60 kb to 85 kb in length, 70 to 90 kb in length, 75 to 100 kb in length, 100 to 250 kb in length, 250 to 500 kb in length, 500 to 1000 kb in length. In an exemplary embodiment, the Sugarcane mini-chromosome is 28 kb in length, 42 kb in length, 82 kb in length, 87 kb in length, 88 kb in length, 97 kb in length, 130 kb in length, 150 kb in length, 200 kb in length or ranges from 28-200 kb in length. The mini-chromosome of the invention preferably has a segregation efficiency during mitotic division of at least 60%, at least 80%, at least 90% or at least 95% and/or a transmission efficiency during meiotic division of, e.g., at least 60%, at least 80%, at least 85%, at least 90% or at least 95%.

The Sugarcane mini-chromosome or recombinant chromosomes of the invention preferably has a segregation efficiency during mitotic division of at least 60%, at least 80%, at least 90% or at least 95% and/or a transmission efficiency during meiotic division of, e.g., at least 60%, at least 80%, at least 85%, at least 90% or at least 95%.

In another embodiment, the Sugarcane mini-chromosomes or recombinant chromosomes of the invention comprise a site for site-specific recombination.

The invention also provides for a Sugarcane mini-chromosome, wherein the mini-chromosome is derived from a donor clone or a centromere clone and has substitutions, deletions, insertions, duplications or arrangements of one or more nucleotides in the mini-chromosome compared to the nucleotide sequence of the donor clone or centromere clone. In one embodiment, the Sugarcane mini-chromosome is obtained by passage of the Sugarcane mini-chromosome through one or more hosts. In another embodiment, the mini-chromosome is obtained by passage of the mini-chromosome through two or more different hosts. The host may be selected from the group consisting of viruses, bacteria, yeasts. In another embodiment, the Sugarcane mini-chromosome is obtained from a donor clone by in vitro methods that introduce sequence variation during template-based replication of the donor clone, or its complementary sequence. In one embodiment this variation may be introduced by a DNA-dependent DNA polymerase. In a further embodiment a Sugarcane minichromosome derived by an in vitro method may be further modified by passage of the mini-chromosome through one or more hosts.

The invention also provides for a Sugarcane mini-chromosome or recombinant chromosome, wherein the mini-chromosome comprises at least one exogenous nucleic acid. In further exemplary embodiments, the Sugarecane mini-chromosome or recombinant chromosome comprises at least two or more, at least three or more, at least four or more, at least five or more, at least ten or more, at least 20 or more, at least 30 or more, at least 40 or more, at least 50 or more exogenous nucleic acids.

In one embodiment, at least one exogenous nucleic acid of any of the Sugarcane mini-chromosomes or recombinant chromosomes of the invention is operably linked to a heterologous regulatory sequence functional in plant cells, including but not limited to a plant regulatory sequence.

The invention also provides for exogenous nucleic acids linked to a non-plant regulatory sequence, such as an arthropod, viral, bacterial, vertebrate or yeast regulatory sequence. The invention also provides for exogenous nucleic acids linked to a regulatory sequence from Sugarcane.

The invention also provides for a mini-chromosome or recombinant chromosome comprising a gene or group of genes that act to improve the total recoverable sugar from Sugarcane. Such genes may act to increase the sugar concentration of the stem juice, increase the amount of juice, increase the stem strength to improve yield, or increase total biomass of the plant. Such genes may be derived from bacterial sequences such as a sucrose isomerase or from animal, plant fungal, or protist sequences. Such genes from plants may include genes involved in sugar metabolism or transport or genes of unknown function or genes not known to be associated with sugar metabolism or transport but that have been shown to quantitatively increase total recoverable sugar. Such genes may also include genes that affect plant height, stem diameter, water metabolism or total biomass. Such genes may also include those that regulate the equilibrium between starch and sugar. Several genes have been shown to improve sugar accumulation. For example, expression of a bacterial sucrose isomerase can increase Sugarcane sugar content by as much as two-fold (Birch, R. G., and Wu, L. (2007). Doubled sugar content in Sugarcane plants modified to produce a sucrose isomer. Plant Biotechnology Journal 5: 109-117.). The lignin-deficient "brown midrib" mutations improve sorghum sugar content via their effects on lignin; this phenotype is caused by mutations in cinnamyl alcohol dehydrogenase (CAD), and 14 CAD-like genes are present in the sorghum genome (Saballos, A., Ejeta, G., Sanchez, E., Kang, C., and Vermerris, W. (2008). A Genome-Wide Analysis of the Cinnamyl Alcohol Dehydrogenase Family in *Sorghum* (*Sorghum bicolor* (L.) Moench) Identifies SbCAD2 as the Brown midrib6 Gene. Genetics).

In another embodiment, the Sugarcane mini-chromosome or recombinant chromosome comprises an exogenous nucleic acid that comprises a QTL that confers a desirable trait. QTLs that affect total recoverable sugars have been mapped in Sugarcane (Murray, S. C., Sharma, A., Rooney, W. L., Klein, P., Mullet, J. E., Mitchell, S. E., Kresovitch, S. (2008) Genetic Improvement of *Sorghum* as a Biofuel Feedstock: I. QTL for Stem Sugar and Grain Nonstructural Carbohydrates. Crop Sci. 48:2165-2179).

In another embodiment, the Sugarcane mini-chromosome or recombinant chromosome comprises an exogenous nucleic acid that confers herbicide resistance, insect resistance, disease resistance, or stress resistance on the Sugarcane plant. The invention provides for Sugarcane mini-chromosomes or recombinant chromosomes comprising an exogenous nucleic acid that confers resistance to phosphinothricin or glyphosate herbicide. Nonlimiting examples include an exogenous nucleic acid that encodes a phosphinothricin acetyltransferase, glyphosate acetyltransferase, acetohydroxyadic synthase or a mutant enoylpyruvylshikimate phosphate (EPSP) synthase. Nonlimiting examples of exogenous nucleic acids that confer insect resistance include a *Bacillus thuringiensis* toxin gene or *Bacillus cereus* toxin gene. In related embodiments, the Sugarcane mini-chromosome or recombinant chromosome comprises an exogenous nucleic acid conferring herbicide resistance, an exogenous nucleic acid conferring insect resistance, and optionally at least one additional exogenous nucleic acid.

The invention further provides for Sugarcane mini-chromosomes or recombinant chromosomes comprising additional copies of genes already found in the Sugarcane genome. The invention also provides for the additional copies of Sugarcane genes carried on the Sugarcane mini-chromosome or recombinant chromosomes to be operably linked to either their native regulatory sequences or to heterologous regulatory sequences.

The invention further provides for Sugarcane mini-chromosomes or recombinant chromosomes comprising an exogenous nucleic acid that confers resistance to drought, heat, chilling, freezing, excessive moisture, ultraviolet light, ionizing radiation, toxins, pollution, mechanical stress or salt stress. The invention also provides for a Sugarcane mini-chromosome that comprises an exogenous nucleic acid that confers resistance to a virus, bacteria, fungi or nematode.

The invention provides for Sugarcane mini-chromosomes or recombinant chromosomes comprising an exogenous nucleic acid selected from the group consisting of a nitrogen fixation gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an interleukin gene, a clotting factor gene, a cytokine gene, an antibody gene, a growth factor gene, a transcription factor gene, a transcriptional repressor gene, a DNA-binding protein gene, a recombination gene, a DNA replication gene, a programmed cell death gene, a kinase gene, a phosphatase gene, a G protein gene, a cyclin gene, a cell cycle control gene, a gene involved in transcription, a gene involved in translation, a gene involved in RNA processing, a gene involved in RNAi, an organellar gene, a intracellular trafficking gene, an integral membrane protein gene, a transporter gene, a membrane channel protein gene, a cell wall gene, a gene involved in protein processing, a gene involved in protein modification, a gene involved in protein degradation, a gene involved in metabolism, a gene involved in biosynthesis, a gene involved in assimilation of nitrogen or other elements or nutrients, a gene involved in controlling carbon flux, a gene involved in respiration, a gene involved in photosynthesis, a gene involved in light sensing, a gene involved in organogenesis, a gene involved in embryogenesis, a gene involved in differentiation, a gene involved in meiotic drive, a gene involved in self incompatibility, a gene involved in development, a gene involved in nutrient, metabolite or mineral transport, a gene involved in nutrient, metabolite or mineral storage, a calcium-binding protein gene, or a lipid-binding protein gene.

The invention also provides for a Sugarcane mini-chromosome or recombinant chromosome comprising an exogenous enzyme gene selected from the group consisting of a gene that encodes an enzyme involved in metabolizing biochemical wastes for use in bioremediation, a gene that encodes an enzyme for modifying pathways that produce secondary plant metabolites, a gene that encodes an enzyme that produces a pharmaceutical, a gene that encodes an enzyme that improves changes in the nutritional content of a plant, a gene that encodes an enzyme involved in vitamin synthesis, a gene that encodes an enzyme involved in carbohydrate, polysaccharide or starch synthesis, a gene that encodes an enzyme involved in mineral accumulation or availability, a gene that encodes a phytase, a gene that encodes an enzyme involved in fatty acid, fat or oil synthesis, a gene that encodes an enzyme involved in synthesis of chemicals or plastics, a gene that encodes an enzyme involved in synthesis of a fuel, a gene that encodes an enzyme involved in synthesis of a fragrance, a gene that encodes an enzyme involved in synthesis of a flavor, a gene that encodes an enzyme involved in synthesis of a pigment or dye, a gene that encodes an enzyme involved in synthesis of a hydrocarbon, a gene that encodes an enzyme involved in synthesis of a structural or fibrous compound, a gene that encodes an enzyme involved in synthesis of a food additive, a gene that encodes an enzyme involved in synthesis of a chemical insecticide, a gene that encodes an enzyme involved in synthesis of an insect repellent, or a gene controlling carbon flux in a plant.

In another embodiment of the invention, any of the Sugarcane mini-chromosomes or recombinant chromosomes of the invention comprise a telomere.

The invention also provides embodiments wherein any of the Sugarcane mini-chromosomes or recombinant chromosomes of the invention are linear or circular.

In one embodiment, the invention provides for Sugarcane plants or plant cells comprising any of the Sugarcane mini-chromosomes or recombinant chromosomes of the invention.

The invention also provides for Sugarcane plant tissue and Sugarcane seed obtained from the Sugarcane plants of the invention.

In another embodiment, the invention provides for Sugarcane plants comprising any of the Sugarcane mini-chromosomes or recombinant chromosomes of the invention, which may be referred to herein as "adchromosomal" Sugarcane plants. In addition, the invention provides for Sugarcane plant cells, tissues and seeds obtained from these modified plants.

In one embodiment, the invention provides for a Sugarcane plant cell comprising any of the Sugarcane mini-chromosomes or recombinant chromosomes of the invention that (i) is not integrated into the Sugarcane plant cell genome and (ii) confers an altered phenotype on the Sugarcane plant cell associated with the expression of at least one structural gene within the Sugarcane mini-chromosome. The altered phenotype comprises increased expression of a native gene, decreased expression of a native gene, or expression of an exogenous gene. In a further embodiment, these Sugarcane plant cells also comprise one or more integrated exogenous structural gene(s).

Another embodiment of the invention is a part of any of the Sugarcane plants of the invention. Exemplary Sugarcane plant parts of the invention include a pod, root, sett root, shoot root, root primordial, shoot, primary shoot, secondary shoot, tassle, panicle, arrow, midrib, blade, ligule, auricle, dewlap, blade joint, sheath, node, internode, bud furrow, leaf scar, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk, ovule or embryo. Other exemplary Sugarcane plant parts are a meiocyte or gamete or ovule or pollen or endosperm of any of the plants described herein. Other exemplary plant parts are a seed, seed-piece, embryo, protoplast, cell culture, any group of plant cells organized into a structural and functional unit, ratoon, or propagule of any of the Sugarcane plants of the invention.

An embodiment of the invention is a progeny of any of the Sugarcane plants of the invention. These progeny of the invention may be the result of self-breeding, cross-breeding, apomyxis or clonal propagation. In exemplary embodiments, the invention also provides for progeny that comprise a Sugarcane mini-chromosome or recombinant chromosome that is descended from a parental Sugarcane mini-chromosome or recombinant chromosome that contained a centromere less than about 1000 kilobases in length, less than about 750 kilobases in length, less than about 600 kilobases in length, less than about 500 kilobases in length, less than about 400 kilobases in length, less than about 300 kilobases in length, less than about 250 kilobases in length, less than about 200 kilobases in length, less than about 150 kilobases in length, less than about 100 kilobases in length, less than about 90 kilobases in length, less than about 85 kilobases in length, less than about 80 kilobases in length, less than about 75 kilobases in length, less than about 70 kilobases in length, less than about 65 kilobases in length, less than about 60 kilobases in length, less than about 55 kilobases in length, less than about 50 kilobases in length, less than about 45 kilobases in length, less than about 40 kilobases in length, less than about 35 kilobases in length, less than about 30 kb in length, less than about 25 kilobases in length, less than about 20 kb in length, less than about 15 kilobases in length, less than about 12 kilobases in length, less than about 10 kb in length, less than about 7 kb in length, less than about 5 kb in length, or less than about 2 kb in length.

In another aspect, the invention provides for methods of making a Sugarcane mini-chromosome for use in any of the Sugarcane plants of the invention. In representative embodiments, these methods comprise identifying a centromere nucleotide sequence in a Sugarcane genomic DNA library using a multiplicity of diverse probes, and constructing a Sugarcane mini-chromosome comprising the centromere nucleotide sequence. These methods may further comprise determining hybridization scores for hybridization of the multiplicity of diverse probes to genomic clones within the Sugarcane genomic nucleic acid library, determining a classification for genomic clones within the Sugarcane genomic nucleic acid library according to the hybridization scores for at least two of the diverse probes, and selecting one or more genomic clones within one or more classifications for constructing the Sugarcane mini-chromosome.

The invention also contemplates methods of using any of the Sugarcane plants of the invention to produce a recombinant protein, by growing a Sugarcane plant comprising a Sugarcane mini-chromosome or recombinant chromosome that comprises an exogenous nucleic acid encoding the desired recombinant protein. Optionally the Sugarcane plant is harvested and the desired protein product is isolated from the plant. Exemplary protein products include industrial enzymes such as those useful for biofuel production.

The invention also contemplates methods of using any of the Sugarcane plants of the invention to produce a chemical product, by growing a Sugarcane plant comprising a Sugarcane mini-chromosome or recombinant chromosome that comprises an exogenous nucleic acid encoding an enzyme involved in the synthesis of the chemical product. Optionally the Sugarcane plant is harvested and the desired chemical product is isolated from the plant. Exemplary chemical products include sugars, lipids and carbohydrates useful in the production of biofuels.

Another aspect of the invention provides for methods of using any of the Sugarcane plants of the invention comprising a Sugarcane mini-chromosomes or recombinant chromosome for a food product, a pharmaceutical product or chemical product, according to which a suitable exogenous nucleic acid is expressed in Sugarcane plants or plant cells and the plant or plant cells are grown. The plant may secrete the product into its growth environment or the product may be contained within the plant, in which case the plant is harvested and desirable products are extracted.

Thus, the invention contemplates methods of using any of the Sugarcane plants of the invention comprising a Sugarcane mini-chromosome or recombinant chromosome to produce a modified food product, for example, by growing a plant that expresses an exogenous nucleic acid that alters the nutritional content of the plant, and harvesting or processing the Sugarcane plant.

The invention also provides for methods of constructing a synthetic array of repeated nucleotide sequence having Sugarcane centromere function comprising the steps of: (a) PCR amplifying a Sugarcane satellite sequence, (b) cloning the PCR amplified satellite sequence into a cloning vector, (c) sequencing the cloned satellite DNA, (d) using a restriction enzyme with an asymmetric recognition sequence to excise the cloned satellite sequence from the cloning vector, (e) ligating the satellite sequence to one another forming a synthetic tandem array, and (f) ligating the synthetic array into a Sugarcane mini-chromosome backbone vector. The invention also provides for an isolated Sugarcane mini-chromosome comprising a synthetic array of repeated nucleotide sequence constructed according to the method of the invention, and Sugarcane plant cells and plants comprising these mini-chromosomes.

In another embodiment, the invention provides for methods of contacting a Sugarcane cell with a Sugarcane mini-chromosome comprising the steps of (a) delivering the mini-chromosome to immature differentiated leaves of the apical region of the stem of a Sugarcane plant, wherein the mini-chromosome comprises a selectable marker gene, and (b) selecting the Sugarcane cells expressing the marker gene, wherein expression of the marker gene indicates transformation with the mini-chromosome. The leaves used in this method are immature but are fully differentiated, such as the inner immature leaves of the Sugarcane stem. In an exemplary embodiment, the mini-chromosome may be delivered by bombarding the immature leaves with micro-particles comprising the Sugarcane mini-chromosome.

The invention also provides for methods of regenerating a Sugarcane plant transformed with a Sugarcane mini-chromosome comprising the steps of (a) obtaining a callus comprising a Sugarcane cell that is transformed by any of the methods of the invention, and (b) growing the callus in media that may comprise 1%-3% polyvinylpyrrolidone to form a plantlet, wherein the cells of the plantlet are transformed with the Sugarcane mini-chromosome. In a further embodiment, the methods of culturing the callus comprise growing the cells in liquid media for a time period and subsequently culturing the cells in a solid culture media. In an exemplary embodiment, the Sugarcane mini-chromosome comprises a growth regulating gene such as a gene in the auxin biosynthesis or perception pathways. Such genes may include iaaM (Trp monooxygenase), iaaH (indole-3-acetamide hydrolase), and ipt (AMP iso-pentenyl transferase). When these three genes are expressed on a mini-chromosome(s), IaaM converts Trp into indole-3-acetamide, which IaaH converts into auxin. Ipt converts AMP into a cytokinin. The expression of all three genes allows a cultured cell to grow in the absence of exogenously supplied hormones.

A further embodiment of the invention is a sugar cane artificial chromosome comprising at least two repeats of a nucleic acid with at least 98% identity to SEQ ID NO: 204. A still further embodiment of the invention is plant cell comprising a sugar cane artificial chromosome comprising at least two repeats of a nucleic acid with at least 98% identity to SEQ ID NO: 204. The plant cell can be a sugar cane plant cell. A further embodiment is a sugar cane artificial chromosome comprising at least two repeats of a nucleic acid with at least 98% identity to SEQ ID NO: 204 wherein the orientation of the repeats is selected from the group consisting of head to tail, tail to tail, and head to head. In other embodiments, the percent identity of the nucleic acid to SEQ ID NO: 204 is at least 95%. In still other embodiments, the percent identity of the nucleic acid to SEQ ID NO: 204 is at least 99%.

Another embodiment of the invention is a sugar cane artificial chromosome comprising at least 15 kbp of a nucleic acid with at least 98% identity to SEQ ID NO: 204. A further embodiment of the invention is a plant cell comprising at least 15 kbp of a nucleic acid with at least 98% identity to SEQ ID NO: 204. In other embodiments, the percent identity of the nucleic acid to SEQ ID NO: 204 is at least 95%. In still other embodiments, the percent identity of the nucleic acid to SEQ ID NO: 204 is at least 99%. The plant cell can be a sugar cane plant cell.

Another embodiment of the invention is a sugar cane artificial chromosome comprising at least 28 kbp of a nucleic acid with at least 98% identity to SEQ ID NO: 204. A further embodiment of the invention is a plant cell comprising a sugar cane artificial chromosome comprising at least 28 kbp of a nucleic acid with at least 98% identity to SEQ ID NO: 204. In other embodiments, the percent identity of the nucleic acid to SEQ ID NO: 204 is at least 95%. In still other embodiments, the percent identity of the nucleic acid to SEQ ID NO: 204 is at least 99%. The plant cell can be a sugar cane plant cell.

Another embodiment of the invention is a sugar cane artificial chromosome comprising a centromere wherein the centromere comprises at least two repeats of a nucleic acid with at least 98% identity to SEQ ID NO: 204. A further embodiment of the invention is a plant cell comprising a sugar cane artificial chromosome comprising a centromere wherein the centromere comprises at least two repeats of a nucleic acid with at least 98% identity to SEQ ID NO: 204. The plant cell can be a sugar cane plant cell. A further embodiment is a sugar cane artificial chromosome comprising a centromere wherein the centromere comprises at least two repeats of a nucleic acid with at least 98% identity to SEQ ID NO: 204 wherein the orientation of the repeats is selected from the group consisting of head to tail, tail to tail and head to head. In other embodiments, the percent identity of the nucleic acid to SEQ ID NO: 204 is at least 95%. In still other embodiments, the percent identity of the nucleic acid to SEQ ID NO: 204 is at least 99%.

Another embodiment of the invention is a sugar cane artificial chromosome comprising a centromere wherein the centromere comprises at least 15 kbp of a nucleic acid with at least 98% identity to SEQ ID NO: 204. A further embodiment of the invention is a plant cell comprising a centromere wherein the centromere comprises at least 15 kbp of a nucleic acid with at least 98% identity to SEQ ID NO: 204. The plant cell can be a sugar cane plant cell. In other embodiments, the percent identity of the nucleic acid to SEQ ID NO: 204 is at least 95%. In still other embodiments, the percent identity of the nucleic acid to SEQ ID NO: 204 is at least 99%.

Another embodiment of the invention is an isolated nucleic acid comprising at least 98% identity to SEQ ID NO: 204. A further embodiment of the invention is a plant cell comprising an isolated nucleic acid comprising at least 98% identity to SEQ ID NO: 204. The plant cell can be a sugar cane plant cell. In other embodiments, the percent identity of the nucleic acid to SEQ ID NO: 204 is at least 95%. In still other embodiments, the percent identity of the nucleic acid to SEQ ID NO: 204 is at least 99%.

Another embodiment of the invention is an isolated nucleic acid comprising at least two repeats of a nucleic acid with at least 98% identity to SEQ ID NO: 204. A further embodiment of the invention is a plant cell comprising an isolated nucleic acid comprising at least two repeats of a nucleic acid with at least 98% identity to SEQ ID NO: 204. The plant cell can be a sugar cane plant cell. A further embodiment is an isolated nucleic acid comprising at least two repeats of a nucleic acid with at least 98% identity to SEQ ID NO: 204 wherein the orientation of the repeats is selected from the group consisting of head to tail, tail to tail and head to head. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising at least two repeats of a nucleic acid with at least 98% identity to SEQ ID NO: 204; transforming a sugar cane plant cell with the nucleic acid; and obtaining a sugar cane plant cell wherein the nucleic acid is autonomously replicating during sugar cane plant cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising at least 15 kbp of a nucleic acid with at least 98% identity to SEQ ID NO: 204; transforming a sugar cane plant cell with the nucleic acid; and obtaining a sugar cane plant cell wherein the nucleic acid is autonomously replicating during sugar cane plant cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising at least 28 kbp of a nucleic acid with at least 98% identity to SEQ ID NO: 204; transforming a sugar cane plant cell with the nucleic acid; and obtaining a sugar cane plant cell wherein the nucleic acid is autonomously replicating during sugar cane plant cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising a centromere comprising at least two repeats of a nucleic acid with at least 98% identity to SEQ ID NO: 204; transforming a sugar cane plant cell with the nucleic acid; and obtaining a sugar cane plant cell wherein the nucleic acid is autonomously replicating during sugar cane plant cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising a centromere comprising at least 15 kbp of a nucleic acid with at least 98% identity to SEQ ID NO: 204; transforming a sugar cane plant cell with the nucleic acid; and obtaining a sugar cane plant cell wherein the nucleic acid is autonomously replicating during sugar cane plant cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising a centromere comprising at least 28 kbp of a nucleic acid with at least 98% identity to SEQ ID NO: 204; transforming a sugar cane plant cell with the nucleic acid; and obtaining a sugar cane plant cell wherein the nucleic acid is autonomously replicating during sugar cane plant cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising at least two repeats of a nucleic acid with at least 98% identity to SEQ ID NO: 204; transforming a sugar cane plant cell with the nucleic acid; and obtaining a sugar cane plant cell wherein the nucleic acid segregates to daughter sugar cane cells during sugar cane cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising at least 15 kbp of a nucleic acid with at least 98% identity to SEQ ID NO: 204; transforming a sugar cane plant cell with the nucleic acid; and obtaining a sugar cane plant cell wherein the nucleic acid segregates to daughter sugar cane cells during sugar cane cell division. In other embodiments, the percent identity of the nucleic acid to SEQ ID NO: 204 is at least 95%. In still other embodiments, the percent identity of the nucleic acid to SEQ ID NO: 204 is at least 99%.

Another embodiment is a method of stably incorporating an autonomously replicating nucleic acid in a sugar cane plant cell comprising the steps of obtaining a nucleic acid comprising at least 28 kbp of a nucleic acid with at least 98% identity to SEQ ID NO: 204; transforming a sugar cane plant cell with the nucleic acid; and obtaining a sugar cane plant cell wherein the nucleic acid segregates to daughter sugar cane cells during sugar cane cell division. In other embodiments, the percent identity of the nucleic acid to SEQ ID NO: 204 is at least 95%. In still other embodiments, the percent identity of the nucleic acid to SEQ ID NO: 204 is at least 99%.

SEQUENCES OF THE INVENTION

The following list indicates the identity of the SEQ ID NOs in the sequence listing:
SEQ ID NOS: 1-201—Sugarcane satellite sequences
SEQ ID NO: 202—Consensus Sugarcane satellite sequence
SEQ ID NO: 203—Sugarcane CRS sequence
SEQ ID NOS: 204—Block of Sugarcane satellite repeat sequence
SEQ ID NOS: 205—221—Primer sequences
SEQ ID NOS: 222—241—Promoter sequences
SEQ ID NOS: 242—251—Primers

DETAILED DESCRIPTION OF THE INVENTION

While this invention is susceptible of embodiment in many different forms, and will be described herein in detail, specific embodiments thereof with the understanding that the present disclosure is to be considered as an exemplification of the principles of the invention and is not intended to limit the invention to the specific embodiments illustrated.

The invention provides novel, functional, stable, autonomous Sugarcane mini-chromosomes and recombinant chromosomes comprising centromeres comprising Sugarcane repeat sequences including synthetic sequences. Optionally, the Sugarcane mini-chromosome or recombinant chromosome is "isolated." The invention also provides for "adchromosomal" Sugarcane plants described in further detail herein.

One aspect of the invention is related to Sugarcane plants containing functional, stable, autonomous Sugarcane mini-chromosomes or recombinant chromosomes, optionally carrying one or more exogenous nucleic acids or carrying extra copies of a nucleic acid that already exists in the Sugarcane genome. Such plants carrying Sugarcane mini-chromosomes or recombinant chromosomes are contrasted to transgenic plants whose genome has been altered by integrating exogenous nucleic acid transgenes into the native Sugarcane chromosomes. In representative embodiments, expression of the exogenous nucleic acid, either constitutively or in response to a signal (which may be induced by challenge or a stimulus), or tissue specific expression, or time specific expression, results in an altered phenotype of the plant.

The invention provides for Sugarcane mini-chromosomes or recombinant chromosomes comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 250, 500, 1000 or more exogenous nucleic acids.

The invention contemplates that Sugarcane plants may be used to carry the autonomous Sugarcane mini-chromosomes or recombinant chromosomes as described herein. A related aspect of the invention is Sugarcane plant parts or plant tissues, including a pod, root, sett root, shoot root, root primordial, shoot, primary shoot, secondary shoot, tassle, panicle, arrow, midrib, blade, ligule, auricle, dewlap, blade joint, sheath, node, internode, bud furrow, leaf scar, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk, ovule or embryo. Other exemplary Sugarcane plant parts are a meiocyte or gamete or ovule or pollen or endosperm of any of the plants of the invention. Other exemplary plant parts are a seed, seed-piece, embryo, protoplast, cell culture, any group of plant cells organized into a structural and functional unit, ratoon or propagule of any of the Sugarcane plants of the invention.

In one embodiment, the exogenous nucleic acid is primarily expressed in a specific location or tissue of a Sugarcane plant, for example, stem, epidermis, vascular tissue, meristem, cambium, cortex, pith, leaf, sheath, flower, root or seed. Tissue-specific expression can be accomplished with, for example, localized presence of the Sugarcane mini-chromosome or recombinant chromosome, selective maintenance of the Sugarecane mini-chromosome or recombinant chromosomes, or with promoters that drive tissue-specific expression.

Another related aspect of the invention is Sugarcane meiocytes, pollen, ovules, endosperm, seed, somatic embryos, apomyctic embryos, embryos derived from fertilization, vegetative propagules and progeny of the originally adchromosomal plant and of its filial generations that retain the functional, stable, autonomous Sugarcane mini-chromosome or recombinant chromosome. Such progeny include clonally propagated Sugarcane plants, embryos and plant parts as well as filial progeny from self- and cross-breeding, and from apomyxis.

In representative embodiments, the Sugarcane mini-chromosome or recombinant chromosome is transmitted to subsequent generations of viable daughter cells during mitotic cell division with a transmission efficiency of at least 60%, 70%, 80%, 85%, 90%, 95%, 96%, 97%, 98%, or 99%.

In embodiments of the invention, during meiotic division, the Sugarcane mini-chromosome or recombinant chromosome is transmitted to viable gametes with a transmission efficiency of at least 60%, 70%, 80%, 85%, 90%, 95%, 96%, 97%, 98%, or 99% when more than one copy of the Sugarcane mini-chromosome recombinant chromosome is present in the gamete mother cells of the plant. The Sugarcane mini-chromosome or recombinant chromosome can optionally be transmitted to viable gametes during meiotic cell division with a transmission frequency of at least 1%, 10%, 20%, 30%, 40%, 45%, 46%, 47%, 48%, or 49% when one copy of the mini-chromosome or recombinant chromosome is present in the gamete mother cells of the Sugarcane plant. According to embodiments of the invention, for production of seeds via sexual reproduction or by apomyxis the Sugarcane mini-chromosome or recombinant chromosome is transferred into at least 60%, 70%, 80%, 85%, 90%, 95%, 96%, 97%, 98%, or 99% of viable embryos when cells of the plant contain more than one copy of the Sugarcane mini-chromosome or recombinant chromosome. For production of seeds via sexual reproduction or by apomyxis from Sugarcane plants with one mini-chromosome or recombinant chromosome per cell, the Sugarcane mini-chromosome or recombinant chromosome is optionally transferred into at least 1%, 10%, 20%, 30%, 40%, 45%, 46%, 47%, 48%, or 49% of viable embryos.

In representative embodiments of the invention, a Sugarcane mini-chromosome or recombinant chromosome that comprises an exogenous selectable trait or exogenous selectable marker can be employed to increase the frequency in subsequent generations of adchromosomal cells, tissues, gametes, embryos, endosperm, seeds, plants or progeny that comprise the Sugarcane minichromosome or recombinant chromosome. In particular embodiments, the frequency of transmission of Sugarcane mini-chromosomes or recombinant chromosome into viable cells, tissues, gametes, embryos, endosperm, seeds, plants or progeny can be at least 95%, 96%, 97%, 98%, 99% or 99.5% after mitosis or meiosis by applying at least one selection that favors the survival of adchromosomal cells, tissues, gametes, embryos, endosperm, seeds, plants or progeny over such cells, tissues, gametes, embryos, endosperm, seeds, plants or progeny lacking the mini-chromosome or recombinant chromosome.

Transmission efficiency may be measured as the percentage of Sugarcane progeny cells or Sugarcane plants that carry the Sugarcane mini-chromosome or recombinant chromosome as measured by one of several assays taught herein including detection of reporter gene fluorescence, PCR detection of a sequence that is carried by the mini-chromosome or recombinant chromosome, RT-PCR detection of a gene transcript for a gene carried on the Sugarcane mini-chromosome or recombinant chromosome, Western analysis of a protein produced by a gene carried on the Sugarcane mini-chromosome or recombinant chromosome, Southern analysis of the DNA (either in total or a portion thereof) carried by the Sugarcane mini-chromosome or recombinant chromosome, fluorescence in situ hybridization (FISH) or in situ localization by repressor binding, to name a few. Any assay used to detect the presence of the Sugarcane mini-chromosome (or a portion of the mini-chromosome) or recombinant chromosome may be used to measure the efficiency that a parental cell or plant transmits the mini-chromosome or recombinant chromosome to its progeny. Efficient transmission as measured by some benchmark percentage should indicate the degree to which the Sugarcane mini-chromosome or recombinant chromosome is stable through the mitotic and meiotic cycles.

Sugarcane plants of the invention may also contain chromosomally integrated exogenous nucleic acid in addition to the autonomous Sugarcane mini-chromosomes or recombinant chromosome. The modified Sugarcane plants or plant parts, including plant tissues of the invention may include Sugarcane plants that have chromosomal integration of some portion of the mini-chromosome (e.g. exogenous nucleic acid or centromere sequences) or recombinant chromosome in some or all cells of the plant. In one aspect of the invention, the autonomous Sugarcane mini-chromosome or recombinant chromosome can be isolated from integrated exogenous nucleic acid by crossing the modified Sugarcane plant containing the integrated exogenous nucleic acid with Sugarcane plants producing some gametes lacking the integrated exogenous nucleic acid and subsequently isolating offspring of the cross, or subsequent crosses, that are modified but lack the integrated exogenous nucleic acid. This independent segregation of the Sugarcane mini-chromosome or recombinant chromosome is one measure of the autonomous nature of the mini-chromosome.

Another aspect of the invention relates to methods for producing and, optionally, isolating such modified Sugarcane plants containing functional, stable, autonomous Sugarcane mini-chromosomes.

In one embodiment, the invention contemplates improved methods for isolating native Sugarcane centromere sequences. In another embodiment, the invention contemplates methods for generating variants of native or artificial Sugarcane centromere sequences by passage through other host cells such as bacterial or fungal hosts.

In a further embodiment, the invention contemplates methods for delivering the Sugarcane mini-chromosome into Sugarcane plant cells or tissues to transform the cells or tissues, optionally detecting mini-chromosome presence or assessing mini-chromosome performance, and optionally generating a Sugarcane plant from such cells or tissues.

Exemplary assays for assessing Sugarcane mini-chromosome or recombinant chromosome performance include lineage-based inheritance assays, use of chromosome loss agents to demonstrate autonomy, exonuclease digestion, global mitotic mini-chromosome inheritance assays (sectoring assays) with or without the use of agents inducing chromosomal loss, assays measuring expression levels of genes (including marker genes) carried by the Sugarcane mini-chromosome over time and space in a Sugarcane plant, physical assays for separation of autonomous Sugarcane mini-chromosomes or recombinant chromosomes from endogenous nuclear chromosomes of Sugarcane plants, molecular assays demonstrating conserved Sugarcane mini-chromosome structure or recombinant chromosomes, such as PCR, Southern blots, Sugarcane mini-chromosome rescue, cloning and characterization of Sugarcane mini-chromosome sequences present in the Sugarcane plant, cytological assays detecting Sugarcane mini-chromosome or recombinant chromosome presence in the Sugarcane cell's genome (e.g. FISH) and meiotic Sugarcane mini-chromosome or recombinant chromosome inheritance assays, which measure the levels of mini-chromosome or recombinant chromosome inheritance into a subsequent generation of Sugarcane plants via meiosis and gametes, embryos, endosperm or seeds.

Another aspect of the invention relates to methods for using Sugarcane plants containing a Sugarcane mini-chromosome or recombinant chromosome for producing food products, pharmaceutical products, biofuels and chemical products by appropriate expression of exogenous nucleic acid(s) contained within the mini-chromosome(s) or recombinant chromosome(s).

Yet another aspect of the invention provides novel autonomous Sugarcane mini-chromosomes with novel compositions and structures which are used to transform plant cells which are in turn used to generate a plant (or multiple plants). Exemplary Sugarcane mini-chromosomes of the invention are contemplated to be of a size 2000 kb or less in length. Other exemplary sizes of Sugarcane mini-chromosomes include less than or equal to, e.g., 1500 kb, 1000 kb, 900 kb, 800 kb, 700 kb, 600 kb, 500 kb, 450 kb, 400 kb, 350 kb, 300 kb, 250 kb, 200 kb, 150 kb, 100 kb, 80 kb, 60 kb, 40 kb, 35 kb in length. In an exemplary embodiment, the mini-chromosome is about 28 kb in length, 42 kb in length, 82 kb in length, 87 kb in length, 88 kb in length, 97 kb in length, 130 kb in length, 150 kb in length, 200 kb in length or ranges from 28 kb to 200 kb in length.

In a related aspect, novel Sugarcane centromere compositions as characterized by sequence content, size or other parameters are provided. Optionally, the minimal size of Sugarcane centromeric sequence is utilized in mini-chromosome construction. Exemplary sizes include a Sugarcane centromeric nucleic acid segment derived from a portion of Sugarcane genomic DNA or synthesized based on a Sugarcane satellite repeat sequence, that is less than or equal to 1000 kb, 900 kb, 800 kb, 700 kb, 600 kb, 500 kb, 400 kb, 300 kb, 200 kb, 190 kb, 150 kb, 100 kb, 95 kb, 90 kb, 85 kb, 80 kb, 75 kb, 70 kb, 65 kb, 60 kb, 55 kb, 50 kb, 45 kb, 40 kb, 35 kb, 30 kb, 28 kb, 25 kb, 20 kb, 17 kb, 15 kb, 12 kb, 10 kb, 7, kb, 6.4 kb, 5 kb, or 2 kb in length. Exemplary inserts may range in size from 80 kb to 100 kb, 7 kb to 190 kb, 7 kb to 12 kb, 5 kb to 10 kb, 3 kb to 10 kb, 3 kb to 7 kb, 5 kb to 7 kb, 10 to 30 kb, 15 to 30 kb, and 15 to 28 kb. Another related aspect is the novel structure of the Sugarcane mini-chromosome, particularly structures lacking bacterial sequences (e.g., sequences required for bacterial propagation), referred to as backbone-free Sugarcane mini-chromosomes.

In other exemplary embodiments, the invention contemplates Sugarcane mini-chromosomes or other vectors comprising centromeric nucleotide sequence that when hybridized to 1, 2, 3, 4, 5, 6, 7, 8 or more of the probes described in the examples herein, under hybridization conditions described herein, e.g. low, medium or high stringency, provides relative hybridization scores. Exemplary stringent hybridization conditions comprise hybridization at 65° C. and washing three times for 15 minutes with 0.25×SSC, 0.1% SDS at 65° C. Additional exemplary stringent hybridization conditions comprise hybridization in 0.02 M to 0.15 M NaCl at temperatures of about 50° C. to 70° C. or 0.5×SSC 0.25% SDS at 65° for 15 minutes, followed by a wash at 65° C. for a half hour or hybridization at 65° C. for 14 hours followed by 3 washings with 0.5×SSC, 1% SDS at 65° C. Probe hybridization can be scored visually to determine a binary (positive versus negative) value, or the probes can be assigned a score based on the relative strength of their hybridization on a 10 point scale. For example, relative hybridization scores of 5 may be used to select clones that hybridize well to the probe. Alternatively, a hybridization signal greater than background for one or more of these probes can be used to select clones. Modified or adchromosomal Sugarcane plants or plant parts containing such Sugarcane mini-chromosomes are contemplated.

The advantages of the present invention include: provision of an autonomous, independent genetic linkage group for accelerating Sugarcane breeding; lack of disruption of host Sugarcane genome; multiple gene "stacking" of large and potentially unlimited numbers of genes; uniform genetic composition of exogenous DNA sequences in plant cells and plants containing autonomous Sugarcane mini-chromosomes; defined genetic context for predictable gene expression; and higher frequency occurrence and recovery of Sugarcane plant cells and plants containing stably maintained exogenous DNA due to elimination of an inefficient integration step. in addition, Sugarcane mini-chromosomes that increase total recoverable sugars or enhance the utility of modified Sugarcane plants for use in biofuel production are specifically envisioned.

I. Composition of Mini-Chromosomes and Mini-Chromosome Construction

The Sugarcane mini-chromosome vector of the present invention may contain a variety of elements, including (1) sequences that function as Sugarcane centromeres, (2) one or more exogenous nucleic acids, including, for example, plant-expressed genes, or genes for non-coding RNAs, (3)

sequences that function as an origin of replication, which may be included in the region that functions as a plant centromere, (4) optionally, a bacterial plasmid backbone for propagation of the plasmid in bacteria, (5) optionally, sequences that function as plant telomeres, (6) optionally, additional "stuffer DNA" sequences that serve to physically separate the various components on the Sugarcane mini-chromosome from each other, (7) optionally "buffer" sequences such as MARs (Matrix Attachment Regions) or SARs (Scaffold Attachment Regions), (8) optionally marker sequences of any origin, including but not limited to plant and bacterial origin, (9) optionally, sequences that serve as recombination sites, and (10) optionally, "chromatin packaging sequences" such as cohesion and condensing binding sites.

The Sugarcane mini-chromosomes of the present invention may be constructed to include various components which are novel, which include, but are not limited to, the Sugarcane centromere comprising novel repeating centromeric sequences, as described in further detail below.

Novel Centromere Compositions

The centromere in the mini-chromosome of the present invention may comprise novel repeating Sugarcane centromeric sequences.

Vectors comprising one, two, three, four, five, six, seven, eight, nine, ten, 15 or 20 or more of the elements contained in any of the exemplary vectors described in the examples below are also contemplated.

The invention specifically contemplates the alternative use of fragments or variants (mutants) of any of the nucleic acids described herein that retain the desired activity, including nucleic acids that function as Sugarcane centromeres, nucleic acids that function as promoters or other regulatory control sequences, or exogenous nucleic acids. Variants may have one or more additions, substitutions or deletions of nucleotides within the original nucleotide sequence or consensus sequence. Variants include nucleic acid sequences that are at least 50%, 55%, 60, 65, 70, 75, 80, 81, 82, 83, 84, 85, 86, 87, 88, 89, 90, 91, 92, 93, 94, 95, 96, 97, 98, 99, or 100% identical to the original nucleic acid sequence. Variants also include nucleic acid sequences that hybridize under low, medium, high or very high stringency conditions to the original nucleic acid sequence. Similarly, the invention also contemplates the alternative use of fragments or variants of any of the polypeptides described herein.

The comparison of sequences and determination of percent identity between two nucleotide sequences can be accomplished using a mathematical algorithm. For example, the percent identity between two nucleotide sequences can be determined using the Needleman and Wunsch (1970) J. Mol. Biol. 48:444-453 algorithm which has been incorporated into the GAP program in the GCG software package (available at www.gcg.com), using either a Blossum 62 matrix or a PAM250 matrix. The parameters can be set so as to maximize the percent identity.

As used herein, the term "hybridizes under low stringency, medium stringency, and high stringency conditions" describes conditions for hybridization and washing. Guidance for performing hybridization reactions can be found in Current Protocols in Molecular Biology (1989) John Wiley & Sons, N.Y., 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.5× SSC, 0.1% SDS, at least at 50° C.; 2) medium stringency hybridization conditions in 6×SSC at about 45° C., followed by one or more washes in 0.2×SSC, 0.1% SDS at 55° C.; 3) high stringency hybridization conditions are hybridization at 65"C for 12-18 hours and washing three times for 15-90 minutes with 0.25×SSC, 0.1% SDS at 65"C. Additional exemplary stringent hybridization conditions comprise 6×SSC at about 45° C., followed by one or more washes in 0.2×SSC, 0.1% SDS at 65° C. Other exemplary highly selective or stringent hybridization conditions comprise 0.02 M to 0.15 M NaCl at temperatures of about 50° C. to 70"C or 0.5×SSC 0.25% SDS at 65° for 12-15 hours, followed three washes at 65° C. for 15-90 minutes each.

Sugarcane Mini-Chromosome Sequence Content and Structure

Sugarcane-expressed genes from non-plant sources may be modified to accommodate Sugarcane codon usage, to insert preferred motifs near the translation initiation ATG codon, to remove sequences recognized in plants as 5' or 3' splice sites, or to better reflect plant GC/AT content. Plant genes typically have a GC content of more than 35%, and coding sequences which are rich in A and T nucleotides can be problematic. For example, ATTTA motifs may destabilize mRNA; plant polyadenylation signals such as AATAAA at inappropriate positions within the message may cause premature truncation of transcription; and monocotyledons such as Sugarcane may recognize AT-rich sequences as splice sites.

Each exogenous nucleic acid or Sugarcane-expressed gene may include a promoter, a coding region and a terminator sequence, which may be separated from each other by restriction endonuclease sites or recombination sites or both. Genes may also include introns, which may be present in any number and at any position within the transcribed portion of the gene, including the 5'untranslated sequence, the coding region and the 3' untranslated sequence. Introns may be natural plant introns derived from any plant, or artificial introns based on the splice site consensus that has been defined for plant species. Some intron sequences have been shown to enhance expression in plants. Optionally the exogenous nucleic acid may include a plant transcriptional terminator, non-translated leader sequences derived from viruses that enhance expression, a minimal promoter, or a signal sequence controlling the targeting of gene products to plant compartments or organelles.

The coding regions of the genes can encode any protein, including but not limited to visible marker genes (for example, fluorescent protein genes, other genes conferring a visible phenotype to the plant) or other screenable or selectable marker genes (for example, conferring resistance to antibiotics, herbicides or other toxic compounds or encoding a protein that confers a growth advantage to the cell expressing the protein) or genes which confer some commercial or agronomic value to the modified or adchromosomal Sugarcane plant. Multiple genes can be placed on the same Sugarcane mini-chromosome vector. The genes may be separated from each other by restriction endonuclease sites, horning endonuclease sites, recombination sites or any combinations thereof. Alternatively, the cloning process can be executed in a manner that destroys the intervening restriction sites. Any number of genes can be present.

The Sugarcane mini-chromosome vector may also contain a bacterial plasmid backbone for propagation of the plasmid in bacteria such as E. coli, A. tumefaciens, or A. rhizogenes. The plasmid backbone may be that of a low-copy vector or in other embodiments it may be desirable to use a mid to high level copy backbone. In one embodiment of the invention, this backbone contains the replicon of the F' plasmid of E. coli. However, other plasmid replicons, such as the bacteriophage P1 replicon, or other low-copy plasmid systems such as the RK2 replication origin, may also be used. The backbone may include one or several antibiotic-resistance genes conferring resistance to a specific antibiotic to the bacterial cell in which the plasmid is present. Bacterial antibiotic-resistance genes include but are not limited to kanamycin-, ampicillin-, chloramphenicol-, streptomycin-, spectinomycin-, tetracycline- and gentamycin-resistance genes.

The Sugarcane mini-chromosome vector may also contain plant telomeres. An exemplary telomere sequence is TTTAGGG or its complement. Telomeres are specialized DNA structures at the ends of linear chromosomes that function to stabilize the ends and facilitate the complete replication of the extreme termini of the DNA molecule (Richards et al., Cell, 1988 Apr 8; 53(1):127-36; Ausubel et al., Current Protocols in Molecular Biology, Wiley & Sons, 1997).

Additionally, the Sugarcane mini-chromosome vector may contain "stuffer DNA" sequences that serve to separate the various components on the mini-chromosome (centromere, genes, telomeres) from each other. The stuffer DNA may be of any origin, prokaryotic or eukaryotic, and from any genome or species, plant, animal, microbe or organelle, or may be of synthetic origin. The stuffer DNA can range from 100 bp to 10 Mb in length and can be repetitive in sequence, with unit repeats from 10 to 1,000,000 bp. Examples of repetitive sequences that can be used as stuffer DNAs include but are not limited to: rDNA, satellite repeats, retroelements, transposons, pseudogenes, transcribed genes, microsatellites, tDNA genes, short sequence repeats and combinations thereof. Alternatively, the stuffer DNA can consist of unique, non-repetitive DNA of any origin or sequence. The stuffer sequences may also include DNA with the ability to form boundary domains, such as but not limited to scaffold attachment regions (SARs) or matrix attachment regions (MARs). The stuffer DNA may be entirely synthetic, composed of random sequence. In this case, the stuffer DNA may have any base composition, or any A/T or G/C content. For example, the G/C content of the stuffer DNA could resemble that of the plant (~30-40%), or could be much lower (0-30%) or much higher (40-100%). Alternatively, the stuffer sequences could be synthesized to contain an excess of any given nucleotide such as A, C, G or T. Different synthetic stuffers of different compositions may also be combined with each other. For example a fragment with low G/C content may be flanked or abutted by a fragment of medium or high G/C content, or vice versa.

In one embodiment of the invention, the Sugarcane mini-chromosome has a circular structure without telomeres. In another embodiment, the Sugarcane mini-chromosome has a circular structure with telomeres. In a third embodiment, the Sugarcane mini-chromosome has a linear structure with telomeres, for example, as would result if a "linear" structure were to be cut with a unique endonuclease, exposing the telomeres at the ends of a DNA molecule that contains all of the sequence contained in the original, closed construct with the exception of an antibiotic-resistance gene. In a fourth embodiment of the invention, the telomeres could be placed in such a manner that the bacterial replicon, backbone sequences, antibiotic-resistance genes and any other sequences of bacterial origin and present for the purposes of propagation of the Sugarcane mini-chromosome in bacteria, can be removed from the plant-expressed genes, the centromere, telomeres, and other sequences by cutting the structure with, for example, a unique endonuclease. This results in a Sugarcane mini-chromosome from which much of, or even all, bacterial sequences have been removed. In this embodiment, bacterial sequence present between or among the plant-expressed genes or other Sugarcane mini-chromosome sequences would be excised prior to removal of the remaining bacterial sequences by cutting the Sugarcane mini-chromosome with an endonuclease and re-ligating the structure such that the antibiotic-resistance gene has been lost. The unique endonuclease site may be the recognition sequence of any of a number of endonucleases including but not limited to restriction endonucleases, meganucleases, or homing endonuclease. Alternatively, the endonucleases and their sites can be replaced with any specific DNA cutting mechanism and its specific recognition site such as rare-cutting endonuclease or recombinase and its specific recognition site, as long as that site is present in the Sugarcane mini-chromosomes only at the indicated positions.

Various structural configurations are possible by which Sugarcane mini-chromosome elements can be oriented with respect to each other. A Sugarcane centromere can be placed on a Sugarcane mini-chromosome either between genes or outside a cluster of genes next to one telomere or next to the other telomere. Stuffer DNAs can be combined with these configurations to place the stuffer sequences inside the telomeres, around the centromere between genes or any combination thereof. Thus, a large number of alternative Sugarcane mini-chromosome structures are possible, depending on the relative placement of centromere DNA, genes, stuffer DNAs, bacterial sequences, telomeres, and other sequences. The sequence content of each of these variants is the same, but their structure may be different depending on how the sequences are placed. These variations in architecture are possible both for linear and for circular Sugarcane mini-chromosomes.

Exemplary Centromere Components

Sugarcane centromere components may be isolated or derived from a native plant genome, for example, modified through recombinant techniques or through the cell-based techniques described below. Alternatively, wholly artificial centromere components may be constructed using as a general guide the sequence of native Sugarcane centromeres such as native satellite repeat sequences. Combinations of centromere components derived from natural sources and/or combinations of naturally derived and artificial components are also contemplated.

In one embodiment, the Sugarcane centromere contains n copies of a repeated nucleotide sequence obtained by the methods disclosed herein; wherein n is at least 2. In another embodiment, the Sugarcane centromere contains n copies of interdigitated repeats. An interdigitated repeat is a DNA sequence that consists of two distinct repetitive elements that combine to create a unique permutation. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. Moreover, the copies, while largely identical, can vary from each other. Such repeat variation is commonly observed in naturally occurring centromeres. The length of the repeat may vary, and can range from about 20 bp to about 360 bp, from about 20 bp to about 250 bp, from about 50 bp to about 225 bp, from 20 bp to 137 bp, from about 75 bp to about 210 bp, from about 100 bp to about 205 bp, from about 125 bp to about 200 bp, from about 150 bp to about 195 bp, from about 160 bp to about 190 and from about 170 bp to about 185 bp including about 180 bp. Exemplary repeats include without limitation a 92 bp repeat, a 97 bp repeat or a 100 bp repeat. Larger repeats including those up to 3,465 bp or 3,500 bp or 3,600 bp or 3,700 bp are also anticipated by the current invention.

The invention contemplates that two or more of these Sugarcane repeated nucleotide sequences, or similar Sugarcane repeated nucleotide sequences, may be oriented head to tail within the centromere. The term "head to tail" refers to multiple consecutive copies of the same or similar repeated nucleotide sequence (e.g., at least 70% identical) that are in the same 5'-3' orientation. The invention also contemplates that two or more of these repeated nucleotide sequences may be consecutive within the Sugarcane centromere. The term "consecutive" refers to the same or similar repeated nucleotide sequences (e.g., at least 70% identical) that follow one after another without being interrupted by other significant sequence elements. Such consecutive repeated nucleotide sequences may be in any orientation, e.g. head to tail, tail to tail, or head to head, and may be separated by n number of nucleotides, wherein n ranges from 1 to 10, or Ito 20, or 1 to 30, or 1 to 40, or 1 to 50. Exemplary repeated nucleotide sequences derived from Sugarcane, and identified by the methods described herein, are set out as SEQ ID NOS: 1-202, SEQ ID NO: 204 and CRS (SEQ ID NO: 203).

Modification of Sugarcane Centromeres Isolated from Native Plant Genome

Modification and changes may be made in the Sugarcane centromeric DNA segments specifically described hereinand still obtain a functional molecule with desirable characteristics. Such modified Sugarcane centromeres are also encompassed by the present invention. The following is a discussion based upon changing the nucleic acids of a Sugarcane centromere to create an equivalent, or even an improved, second generation molecule.

In particular embodiments of the invention, mutated Sugarcane centromeric sequences are contemplated to be useful for increasing the utility of the Sugarcane centromere. Without being bound by any theory of the invention, it is specifically contemplated that the function of the Sugarcane centromeres of the current invention may be based in part or in whole upon the secondary structure of the DNA sequences of the Sugarcane centromere, modification of the DNA with methyl groups or other adducts, and/or the proteins which interact with the Sugarcane centromere. By changing the DNA sequence of the Sugarcane centromere, one may alter the affinity of one or more centromere-associated protein(s) for the Sugarcane centromere and/or the secondary structure or modification of the Sugarcane centromeric sequences, thereby changing the activity of the Sugarcane centromere. Alternatively, changes may be made in the Sugarcane centromeres of the invention which do not affect the activity of the Sugarcane centromere. Changes in the Sugarcane centromeric sequences which reduce the size of the DNA segment needed to confer Sugarcane centromere activity are contemplated to be particularly useful in the current invention, as would changes which increased the fidelity with which the Sugarcane centromere was transmitted during mitosis or meiosis.

Modification of Sugarcane Centromeres by Passage Through Bacteria, Sugarcane or Other Hosts or Processes In the methods of the present invention, the resulting Sugarcane mini-chromosome DNA sequence may also be a derivative of the parental clone or Sugarcane centromere clone having substitutions, deletions, insertions, duplications and/or rearrangements of one or more nucleotides in the nucleic acid sequence. Such nucleotide mutations may occur individually or consecutively in stretches of about 1, 2, 3, 4, 5, 6, 7, 8, 9 10, 15, 20, 25, 30, 35, 40, 50, 60, 70, 80, 90, 100, 125, 150, 175, 200, 250, 300, 350, 400, 450, 500, 600, 700, 800, 900, 1000, 2000, 4000, 8000, 10000, 50000, 100000, and about 200000, including all ranges in-between.

Variations of Sugarcane mini-chromosomes may arise through passage of Sugarcane mini-chromosomes through various hosts including virus, bacteria, yeast, or another prokaryotic or eukaryotic organism and may occur through passage of multiple hosts or an individual host. Variations may also occur by replicating the Sugarcane mini-chromosome in vitro.

Derivatives may be identified through sequence analysis, or variations in Sugarcane mini-chromosome molecular weight through electrophoresis such as, but not limited to, CHEF gel analysis, column or gradient separation, or any other methods used in the field to determine and/or analyze DNA molecular weight or sequence content. Alternately, derivatives may be identified by the altered activity of a derivative in conferring Sugarcane centromere function to a Sugarcane mini-chromosome.

Production or Synthesis of Synthetic Sugarcane Centromere Repeat Sequences

These artificially synthesized repeated nucleotide sequences of the invention may be derived from natural Sugarcane centromere sequences, combinations or fragments of natural Sugarcane centromere sequences including a combination of repeats of different lengths, a combination of different sequences, a combination of both different repeat lengths and different sequences, a combination of different artificially synthesized sequences or a combination of natural Sugarcane centromere sequence(s) and artificially synthesized sequence(s). The synthetic nucleotide sequences and arrays of these synthetic repeat sequences may be generated using any technique known in the art including PCR from genomic DNA, e.g. the methods described in Example 1, or by custom polynucleotide synthesis.

Polynucleotide synthesis is the non-biological, chemical synthesis of defined sequences of nucleic acids using automated synthesizers. Oligonucleotides may be chemically synthesized, purified and then these oligonucleotides are connected by specific annealing and standard ligation or polymerase reactions. Exemplary ligation methods include ligation of phosphorylated overlapping oligonucleotides (Gupta et al. Proc. Natl. Acad. Sci. USA, 60, 1338-1344, Fuhrmann et al. Plant J. 1999 August; 19(3):353-61), the FokI method (Mandecki et al. Gene, 68, 101-107) and a modified form of ligase chain reaction for gene synthesis. In addition, PCR assembly approaches may be used which generally employ oligonucleotides of 40-50 nt long that overlap each other. These oligonucleotides are designed to cover most of the sequence of both strands, and the full-length molecule is generated progressively by overlap extension PCR (Stemmer et al. Gene, 164, 49-53)., thermodynamically balanced inside-out PCR (Gao et al. Nucleic Acids Res. 2003 Nov. 15; 31 (22):e143) or combined approaches (Young et al. Nucleic Acids Res. 2004 Apr. 15; 32 (7):e59).

Exemplary Exogenous Nucleic Acids Including Plant-Expressed Genes

Of particular interest in the present invention are exogenous nucleic acids which when introduced into Sugarcane plants will alter the phenotype of the plant, a plant organ, plant tissue, or a portion of the plant. Exemplary exogenous nucleic acids encode polypeptides. Other exemplary exogenous nucleic acids alter expression of exogenous or endogenous genes, either increasing or decreasing expression, optionally in response to a specific signal or stimulus.

As used herein, the term "trait" can refer either to the altered phenotype of interest or the nucleic acid which causes the altered phenotype of interest.

One of the major purposes of transformation of Sugarcane is to add some commercially desirable, agronomically important traits to the plant. Such traits include, but are not limited to, enhanced production of total recoverable sugars; utility for production of biofuels; herbicide resistance or tolerance; insect (pest) resistance or tolerance; disease resistance or tolerance (viral, bacterial, fungal, nematode or other pathogens); stress tolerance and/or resistance, as exemplified by resistance or tolerance to drought, heat, chilling, freezing, excessive moisture, salt stress, mechanical stress, extreme acidity, alkalinity, toxins, UV light, ionizing radiation or oxidative stress; increased yields, increased biomass, whether in quantity or quality; enhanced or altered nutrient acquisition and enhanced or altered metabolic efficiency; enhanced or altered nutritional content and makeup of plant tissues used for food, feed, fiber or processing; physical appearance; male sterility; drydown; standability; prolificacy; starch quantity and quality; oil quantity and quality; protein quality and quantity; amino acid composition; modified chemical production; altered pharmaceutical or nutraceutical properties; altered bioremediation properties; increased biomass; altered growth rate; altered fitness; altered biodegradability; altered $CO_2$ fixation; presence of bioindicator activity; altered digestibility by humans or animals; altered allergenicity; altered mating characteristics; altered pollen dispersal; improved environmental impact; altered nitrogen fixation capability; the production of a pharmaceutically active protein; the production of a small molecule with medicinal properties; the production of a chemical including those with industrial utility; the production of nutraceuticals, food additives, carbohydrates, RNAs, lipids, fuels, dyes, pigments, vitamins, scents, flavors, vaccines, antibodies, hormones, and the like; and alterations in plant architecture or development, including changes in developmental timing, photosynthesis, signal transduction, cell growth, reproduction, or differentiation. Additionally one could create a library of an entire genome (or a portion thereof) from any organism or organelle including mammals, plants, microbes, fungi, or bacteria, represented on Sugarcane mini-chromosomes.

In one embodiment, the Sugarcane plant comprising a Sugarcane mini-chromosome or recombinant chromosome may exhibit increased or decreased expression or accumulation of a product of the plant, which may be a natural product of the plant or a new or altered product of the plant. Exemplary products include an enzyme, an RNA molecule, a nutritional protein, a structural protein, an amino acid, a lipid, a fatty acid, a polysaccharide, a sugar, an alcohol, an alkaloid, a carotenoid, a propanoid, a phenylpropanoid, or terpenoid, a steroid, a flavonoid, a phenolic compound, an anthocyanin, a pigment, a vitamin or a plant hormone. In another embodiment, the Sugarcane plant comprising a Sugarcane mini-chromosome or recombinant chromosome has enhanced or diminished requirements for light, water, nitrogen, or trace elements. In another embodiment the Sugarcane plant comprising a Sugarcane mini-chromosome or recombinant chromosome has an enhanced ability to capture or fix nitrogen from its environment. In yet another embodiment, the Sugarcane plant comprising a Sugarcane mini-chromosome or recombinant chromosome is enriched for an essential amino acid as a proportion of a protein fraction of the plant. The protein fraction may be, for example, total seed protein, soluble protein, insoluble protein, water-extractable protein, and lipid-associated protein. The Sugarcane mini-chromosome or recombinant chromosome may include genes that cause the overexpression, underexpression, antisense modulation, sense suppression, inducible expression, inducible repression, or inducible modulation of another gene.

A brief summary of exemplary improved properties and polypeptides of interest for either increased or decreased expression is provided below.

(i) Herbicide Resistance

An herbicide resistance (or tolerance) trait is a characteristic of a Sugarcane plant comprising a Sugarcane mini-chromosome or recombinant chromosome that is resistant to dosages of an herbicide that is typically lethal to a wild type plant. Exemplary herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Other herbicides would be useful as would combinations of herbicide genes on the same Sugarcane mini-chromosome or recombinant chromosome.

The genes encoding phosphinothricin acetyltransferase (bar), glyphosate tolerant EPSP synthase genes, glyphosate acetyltransferase, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar gene codes for an enzyme, phosphinothricin acetyltransferase (PAT), which inactivates the herbicide phosphinothricin and prevents this compound from inhibiting glutamine synthetase enzymes. The enzyme 5 enolpyruvylshikimate 3 phosphate synthase (EPSP Synthase), is normally inhibited by the herbicide N (phosphonomethyl)glycine (glyphosate). However, genes are known that encode glyphosate resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non herbicidal degradation product. The glyphosate acetyl transferase gene inactivates the herbicide glyphosate and prevents this compound from inhibiting EPSP synthase.

Polypeptides that may produce plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

(ii) Insect Resistance

Potential insect resistance (or tolerance) genes that can be introduced include *Bacillus thuringiensis* toxin genes or Bt genes (Watrud et al., In: Engineered Organisms and the Environment, 1985). Bt genes may provide resistance to lepidopteran or coleopteran pests such as European Corn Borer (ECB). Exemplary Bt toxin genes for use in such embodiments include the CryIA(b) and CryIA(c) genes. Endotoxin genes from other species of *B. thuringiensis* which affect insect growth or development also may be employed in this regard.

It is contemplated that in some embodiments Bt genes for use in the Sugarcane mini-chromosomes or recombinant chromosomes disclosed herein will be those in which the coding sequence has been modified to effect increased expression in plants, and for example, in monocot plants including Sugarcane. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., Proc. Natl. Acad. Sci. USA, 88:33241328, 1991), and the synthetic CryIA(c) gene termed 180° b. (PCT Application WO 95/06128). Some examples of other Bt toxin genes known to those of skill in the art are given in Table 1 below.

TABLE 1

Bacillus thuringiensis Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]Adapted from: http://epunix.biols.susx.ac.uk/Home/Neil_Crickmore/Bt/index.html Protease inhibitors also may provide insect resistance (Johnson et al., Proc Natl Acad Sci U S A. 1989 December; 86(24): 9871-9875.), and will thus have utility in Sugarcane transformation. The use of a pinII gene in combination with a Bt toxin gene, the combined effect of which has been discovered to produce synergistic insecticidal activity is envisioned to be particularly useful. Other genes which encode inhibitors of the insect's digestive system, or those that encode enzymes or co factors that facilitate the production of inhibitors, also may be useful. This group may be exemplified by oryzacystatin and amylase inhibitors such as those from wheat and barley.

Amylase inhibitors are found in various plant species and are used to ward off insect predation via inhibition of the digestive amylases of attacking insects. Several amylase inhibitor genes have been isolated from plants and some have been introduced as exogenous nucleic acids, conferring an insect resistant phenotype that is potentially useful ("Plants, Genes, and Crop Biotechnology" by Maarten J. Chrispeels and David E. Sadava (2003) Jones and Bartlett Press).

Genes encoding lectins may confer additional or alternative insecticide properties. Lectins are multivalent carbohydrate binding proteins which have the ability to agglutinate red blood cells from a range of species. Lectins have been identified recently as insecticidal agents with activity against weevils, ECB and rootworm (Murdock et al., Phytochemistry, 29:85-89, 1990, Czapla & Lang, J. Econ. Entomol., 83:2480-2485, 1990). Lectin genes contemplated to be useful include, for example, barley and wheat germ agglutinin (WGA) and rice lectins (Gatehouse et al., J. Sci. Food. Agric., 35:373-380, 1984).

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., Nature, 344:458-461, 1990).

Genes that encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP glucosyl transferase, also fall within the scope of the useful exogenous nucleic acids of the present invention.

Genes that code for enzymes that facilitate the production of compounds that reduce the nutritional quality of the host Sugarcane plant to insect pests also are encompassed by the present invention. It may be possible, for instance, to confer insecticidal activity on a Sugarcane plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti nutritional effects on insects and to reduce the nutritional quality of their diet. Therefore, further embodiments of the invention concern modified plants with enhanced lipoxygenase activity which may be resistant to insect feeding.

*Tripsacum dactyloides* is a species of grass that is resistant to certain insects, including root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, Proceedings North Central Branch Entomological Society of America, 27:91-95, 1972). It is further anticipated that other cereal, monocot or dicot plant species may have genes encoding proteins that are toxic to insects which would be useful for producing insect resistant Sugarcane plants.

Further genes encoding proteins characterized as having potential insecticidal activity also may be used as exogenous nucleic acids in accordance herewith. Such genes include, for example, the cowpea trypsin inhibitor (CpTI; Hilder et al., Nature, 330:160-163, 1987) which may be used as a rootworm deterrent; genes encoding avermectin (Avermectin and Abamectin., Campbell, W. C., Ed., 1989; Ikeda et al., J. Bacteriol., 169:5615-5621, 1987) which may prove particularly useful as a corn rootworm deterrent; ribosome inactivating protein genes; and even genes that regulate plant structures. Sugarcane plants comprising a Sugarcane mini-chromosome or recombinant chromosome comprising anti insect antibody genes and genes that code for enzymes that can convert a non toxic insecticide (pro insecticide) applied to the outside of the plant into an insecticide inside the plant also are contemplated.

Polypeptides that may improve Sugarcane tolerance to the effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects. It is also anticipated that combinations of different insect resistance genes on the same Sugarcane mini-chromosome or recombinant chromosome will be particularly useful.

Vegetative Insecticidal Proteins (VIP) are another class of proteins originally found to be produced in the vegetative growth phase of the bacterium, *Bacillus cereus*, but do have a spectrum of insect lethality similar to the insecticidal genes found in strains of *Bacillus thuringiensis*. Both the vip1a and vip3A genes have been isolated and have demonstrated insect toxicity. It is anticipated that such genes may be used in modified plants to confer insect resistance ("Plants, Genes, and Crop Biotechnology" by Maarten J. Chrispeels and David E. Sadava (2003) Jones and Bartlett Press).

(iii) Environment or Stress Resistance

Improvement of a Sugarcane plant's ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al., J. Plant Physiol., 135:351-354, 1989) or synthetic gene derivatives thereof. Improved chilling tolerance also may be conferred through increased expression of glycerol 3 phosphate acetyltransferase in chloroplasts (Wolter et al., The EMBO J., 4685-4692, 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., Ann Rev. Plant Physiol., 43:83-116, 1992). Such strategies may allow for tolerance to freezing in newly emerged fields as well as extending later maturity higher yielding varieties to earlier relative maturity zones.

It is contemplated that the expression of novel genes that favorably affect Sugarcane plant water content, total water potential, osmotic potential, or turgor will enhance the ability of the plant to tolerate drought. As used herein, the terms "drought resistance" and "drought tolerance" are used to refer to a Sugarcane plant's increased resistance or tolerance to stress induced by a reduction in water availability, as compared to normal circumstances, and the ability of the plant to function and survive in lower water environments. In this aspect of the invention it is proposed, for example, that the expression of genes encoding for the biosynthesis of osmotically active solutes, such as polyol compounds, may impart protection against drought. Within this class are genes encoding for mannitol L phosphate dehydrogenase (Lee and Saier, 1982) and trehalose 6 phosphate synthase (Kaasen et al., J. Bacteriology, 174:889-898, 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., Science, 259:508-510, 1993, Tarczynski et al Proc. Natl. Acad. Sci. USA, 89:1-5, 1993).

Similarly, the efficacy of other metabolites in protecting either enzyme function (e.g., alanopine or propionic acid) or membrane integrity (e.g., alanopine) has been documented (Loomis et al., J. Expt. Zoology, 252:9-15, 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., Biotropica, 24:121-133, 1992), sorbitol, dulcitol (Karsten et al., Botanica Marina, 35:11-19, 1992), glucosylglycerol (Reed et al., J. Gen. Microbiology, 130:1-4, 1984; Erdmann et al., J. Gen. Microbiology, 138:363-368, 1992), sucrose, stachyose (Koster and Leopold, Plant Physiol., 88:829-832, 1988; Blackman et al., Plant Physiol., 100:225-230, 1992), raffinose (Bernal Lugo and Leopold, Plant Physiol., 98:1207-1210, 1992), proline (Rensburg et al., 3. Plant Physiol., 141: 188-194, 1993), glycine betaine, ononitol and pinitol (Vernon and Bobnert, The EMBO 3., 11:2077-2085, 1992). Continued growth and increased reproductive fitness during times of stress may be augmented by introduction and expression of genes such as those controlling the osmotically active compounds discussed above and other such compounds. Genes which promote the synthesis of an osmotically active polyol compound include genes which encode the enzymes mannitol 1 phosphate dehydrogenase, trehalose 6 phosphate synthase and myoinositol 0 methyltransferase.

It is contemplated that the expression of specific proteins also may increase drought tolerance in Sugarcane. Three classes of Late Embryogenic Abundant (LEA) Proteins have been assigned based on structural similarities (see Dure et al., Plant Molecular Biology, 12:475-486, 1989). All three classes of LEAs have been demonstrated in maturing (e.g. desiccating) seeds. Within these 3 types of LEA proteins, the Type II (dehydrin type) have generally been implicated in drought and/or desiccation tolerance in vegetative plant parts (e.g. Mundy and Chua, The EMBO J., 7:2279-2286, 1988; Piatkowski et al., Plant Physiol., 94:1682-1688, 1990; Yamaguchi Shinozaki et al., Plant Cell Physiol., 33:217-224, 1992). Expression of a Type III LEA (HVA 1) in tobacco was found to influence plant height, maturity and drought tolerance (Fitzpatrick, Gen. Engineering News, 22:7, 1993). In rice, expression of the HVA 1 gene influenced tolerance to water deficit and salinity (Xu et al., Plant Physiol., 110:249-257, 1996). Expression of structural genes from any of the three LEA groups may therefore confer drought tolerance. Other types of proteins induced during water stress include thiol proteases, aldolases or transmembrane transporters (Guerrero et al., Plant Molecular Biology, 15:11-26, 1990), which may confer various protective and/or repair type functions during drought stress. It also is contemplated that genes that effect lipid biosynthesis and hence membrane composition might also be useful in conferring drought resistance in Sugarcane.

Many of these genes for improving drought resistance have complementary modes of action. Thus, it is envisaged that combinations of these genes might have additive and/or synergistic effects in improving drought resistance in Sugarcane. Many of these genes also improve freezing tolerance (or resistance); the physical stresses incurred during freezing and drought are similar in nature and may be mitigated in similar fashion. Benefits may be conferred via constitutive expression of these genes; alternatively, one means of expressing these novel genes may be through the use of a turgor induced promoter (such as the promoters for the turgor induced genes described in Guerrero et al., Plant Molecular Biology, 15:11-26, 1990 and Shagan et al., Plant Physiol., 101:1397-1398, 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, e.g., silks, would be of benefit. In addition it is proposed that expression of genes that minimize kernel abortion during times of stress would increase the amount of grain to be harvested and hence be of value.

Given the overall role of water in determining yield, it is contemplated that enabling Sugarcane to utilize water more efficiently, through the introduction and expression of novel genes, will improve overall performance even when soil water availability is not limiting. By introducing genes that improve the ability of Sugarcane plants to maximize water usage across a full range of stresses relating to water availability, yield stability or consistency of yield performance may be realized.

Polypeptides that may improve stress tolerance in Sugarcane under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in Sugarcane plants comprising a Sugarcane mini-chromosome or recombinant chromosome will provide changes in the ability of the plants to respond to a variety of environmental stresses, such as chemical stress, drought stress and pest stress.

Other polypeptides that may improve Sugarcane tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins or uncoupling protein.

Other polypeptides that may improve Sugarcane tolerance to heat include polypeptides involved in biosynthesis of trehalose, polypeptides involved in glycerolipid biosynthesis or membrane lipid metabolism (for altering membrane fatty acid composition), heat shock proteins or mitochondrial NDK.

Other polypeptides that may improve Sugarcane tolerance to extreme osmotic conditions include polypeptides involved in proline biosynthesis.

Other polypeptides that may improve Sugarcane tolerance to drought conditions include aquaporins, polypeptides involved in biosynthesis of trehalose or wax, LEA proteins or invertase.

(iv) Disease Resistance

It is proposed that increased resistance (or tolerance) to diseases may be realized through introduction of genes into Sugarcane. It is possible to produce resistance to diseases caused by viruses, viroids, bacteria, fungi and nematodes. It also is contemplated that control of mycotoxin producing organisms may be realized through expression of introduced genes. Resistance can be affected through suppression of endogenous factors that encourage disease-causing interactions, expression of exogenous factors that are toxic to or otherwise provide protection from pathogens, or expression of factors that enhance Sugarcane's own defense responses.

Resistance to viruses may be produced through expression of novel genes in Sugarcane. For example, it has been demonstrated that expression of a viral coat protein in a modified plant can impart resistance to infection of the plant by that virus and perhaps other closely related viruses (Cuozzo et al., Bio/Technology, 6:549-553, 1988, Hemenway et al., The EMBO J., 7:1273-1280, 1988, Abel et al., Science, 232:738-743, 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi Sugarcane may be realized through introduction of novel genes. It is contemplated that genes encoding so called "peptide antibiotics," pathogenesis related (PR) proteins, toxin resistance, or proteins affecting host pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in Sugarcane may be useful in conferring resistance to bacterial disease. These genes are induced following pathogen attack on a host plant and have been divided into at least five classes of proteins (Bol, Linthorst, and Cornelissen, 1990). Included amongst the PR proteins are beta 1, 3 glucanases, chitinases, and osmotin and other proteins that are believed to function in plant resistance to disease organisms. Other genes have been identified that have antifungal properties, e.g., UDA (stinging nettle lectin), or hevein (Broakaert et al., 1989; Barkai Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the Sugarcane host and pathogen may be useful in reducing the ability of the disease organism to invade the tissues of the host plant, e.g., an increase in the waxiness of the leaf cuticle or other morphological characteristics.

Polypeptides useful for imparting improved disease responses to Sugarcane include polypeptides encoded by cercosporin induced genes, antifungal proteins and proteins encoded by R-genes or SAR genes.

Agronomically important diseases in Sugarcane include but are not limited to: pineapple disease of Sugarcane, pokkah boeng disease of Sugarcane, Sugarcane eye spot disease, Sugarcane leaf scald disease, Sugarcane mosaic virus disease, Sugarcane ratoon stunting disease, Sugarcane red rot Disease, Sugarcane rust Disease, Sugarcane smut disease, *Metarhizium anisopliae, Ustilago scitaminea, Colletotrichum falcatum, Fusarium moniliformae, Cephalosporium sacchari, Certocystis paradoxa, Cercospora, Helminthosporium* and *Leptosphaeria, Puccinia. graminicolum, Puccinia aphaniderinatum* and *Puccinia catenulatum, Xanthomonas albilineans, Leifsonia xyli,* Sugarcane mosaic virus (SCMV) (Potyvirdae), Sugarcane bacilliform virus (SCBV) (Pararetroviridae), Sugarcane yellow leaf syndrome (YLS), and Sugarcane yellow leaf virus (ScYLV).

(v) Plant Agronomic Characteristics

Temperature also influences where Sugarcane can be grown. Within the areas where it is possible to grow Sugarcane, there are varying limitations on the maximal time it is allowed to grow to maturity and be harvested. For example, a variety to be grown in a particular area is selected for its ability to mature within the required period of time with maximum possible yield. It is considered that genes that influence maturity can be identified and introduced into Sugarcane lines to create new varieties adapted to different growing locations or the same growing location, but having improved yield at harvest. Expression of genes that are involved in regulation of plant development may be especially useful.

It is contemplated that genes may be introduced into Sugarcane that would improve standability and other plant growth characteristics. Expression of novel genes in Sugarcane which confer stronger stalks, improved root systems, or prevent or reduce ear droppage or shattering would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in Sugarcane may be advantageous. Expression of such a gene may reduce apical dominance, confer semidwarfism on a plant, or increase shade tolerance (U.S. Pat. No. 5,268,526). Such approaches would allow for increased Sugarcane populations in the field.

(vi) Nutrient Utilization

The ability to utilize available nutrients may be a limiting factor in growth of Sugarcane. It is proposed that it would be possible to alter nutrient uptake, tolerate pH extremes, mobilization through the plant, storage pools, and availability for metabolic activities by the introduction of novel genes. These modifications would allow a Sugarcane plant to more efficiently utilize available nutrients. It is contemplated that an increase in the activity of, for example, an enzyme that is normally present in the plant and involved in nutrient utilization would increase the availability of a nutrient or decrease the availability of an antinutritive factor. An example of such an enzyme would be phytase. It is further contemplated that enhanced nitrogen utilization by Sugarcane is desirable. Expression of a glutamate dehydrogenase gene in plants, e.g., *E. coli* gdhA genes, may lead to increased fixation of nitrogen in organic compounds. Furthermore, expression of gdhA in Sugarcane may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

Polypeptides useful for improving nitrogen flow, sensing, uptake, storage and/or transport include those involved in aspartate, glutamine or glutamate biosynthesis, polypeptides involved in aspartate, glutamine or glutamate transport, polypeptides associated with the TOR (Target of Rapamycin) pathway, nitrate transporters, nitrate reductases, amino transferases, ammonium transporters, chlorate transporters or polypeptides involved in tetrapyrrole biosynthesis.

Polypeptides useful for increasing the rate of photosynthesis include phytochrome, ribulose bisphosphate carboxylase-oxygenase, Rubisco activase, photosystem I and II proteins, electron carriers, ATP synthase, NADH dehydrogenase or cytochrome oxidase.

Polypeptides useful for increasing phosphorus uptake, transport or utilization include phosphatases or phosphate transporters.

(vii) Male Sterility

Male sterility is useful in the production of hybrid varieties of Sugarcane. It is proposed that male sterility may be produced through expression of novel genes. For example, it has been shown that expression of genes that encode proteins, RNAs, or peptides that interfere with development of the male inflorescence and/or gametophyte result in male sterility. Chimeric ribonuclease genes that express in the anthers of transgenic tobacco and oilseed rape have been demonstrated to lead to male sterility (Mariani et al., Nature, 347:737-741, 1990).

A number of mutations were discovered in maize that confer cytoplasmic male sterility. One mutation in particular, referred to as T cytoplasm, also correlates with sensitivity to Southern corn leaf blight. A DNA sequence, designated TURF 13 (Levings, Science, 250:942-947, 1990), was identified that correlates with T cytoplasm. It is proposed that it would be possible through the introduction of TURF 13 via transformation, to separate male sterility from disease sensitivity. As it is necessary to be able to restore male fertility for breeding purposes and for grain production, it is proposed that genes encoding restoration of male fertility also may be introduced.

(viii) Altered Nutritional Content

Genes may be introduced into Sugarcane to improve or alter the nutrient quality or content. Introduction of genes that alter the nutrient composition may greatly enhance the feed, food or forage value. Limiting essential amino acids may include lysine, methionine, tryptophan, threonine, valine, arginine, and histidine. The levels of these essential amino acids may be elevated by mechanisms which include, but are not limited to, the introduction of genes to increase the biosynthesis of the amino acids, decrease the degradation of the amino acids, increase the storage of the amino acids in proteins, or increase transport of the amino acids to particular tissues.

Polypeptides useful for providing increased protein quantity and/or quality include polypeptides involved in the metabolism of amino acids in Sugarcane, particularly polypeptides involved in biosynthesis of methionine/cysteine and lysine, amino acid transporters, amino acid efflux carriers, seed storage proteins, proteases, or polypeptides involved in phytic acid metabolism.

The protein composition of Sugarcane may be altered to improve the balance of amino acids in a variety of ways including elevating expression of native proteins, decreasing expression of those with poor composition, changing the composition of native proteins, or introducing genes encoding entirely new proteins possessing superior composition.

The introduction of genes that alter the ail content of Sugarcane may also be of value. Increases in oil content may result in increases in metabolizable-energy-content. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, alpha-ketoacyl-ACP synthase, or other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in Sugarcane.

Genes may be introduced that enhance the nutritive value of Sugarcane, or of foods derived from Sugarcane by increasing the level of naturally occurring phytosterols, or by encoding for proteins to enable the synthesis of phytosterols in Sugarcane. The phytosterols from these Sugarcane can be processed directly into foods, or extracted and used to manufacture food products.

Genes may be introduced that enhance the nutritive value or energy value of the starch component of Sugarcane, for example by altering the degree of branching of starch molecules, resulting in improved utilization of the starch in biofuel or feedstock applications. Additionally, other major constituents of Sugarcane may be altered, including genes that affect a variety of other nutritive, processing, or other quality aspects. For example, pigmentation may be increased or decreased.

Carbohydrate metabolism may be altered, for example by increased sucrose production and/or transport. Polypeptides useful for affecting carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, or polypeptides involved in glucose signaling, such as SNF1 complex proteins.

Sugarcane may also possess sub-optimal quantities of vitamins, antioxidants or other nutraceuticals, requiring supplementation to provide adequate nutritive value and ideal health value. Introduction of genes that enhance vitamin biosynthesis may be envisioned including, for example, vitamins A, E, B12, choline, or the like. Mineral content may also be sub-optimal. Thus genes that affect the accumulation or availability of compounds containing phosphorus, sulfur, calcium, manganese, zinc, or iron among others would be valuable.

Numerous other examples of improvements of Sugarcane may be used with the invention. Introduction of DNA to accomplish this might include sequences that alter lignin production such as those that result in the "brown midrib" phenotype associated with superior feed value for cattle. Other genes may encode for enzymes that alter the structure of extracellular carbohydrates, or that facilitate the degradation of the carbohydrates so that it can be efficiently fermented into ethanol or other useful carbohydrates.

It may be desirable to modify the nutritional content of Sugarcane by reducing undesirable components such as fats, starches, etc. This may be done, for example, by the use of exogenous nucleic acids that encode enzymes which increase plant use or metabolism of such components so that they are present at lower quantities. Alternatively, it may be done by use of exogenous nucleic acids that reduce expression levels or activity of native Sugarcane enzymes that synthesize such components.

Likewise the elimination of certain undesirable traits may improve the food or feed value of Sugarcane. Many undesirable traits must currently be eliminated by special post-harvest processing steps and the degree to which these can be engineered into Sugarcane prior to harvest and processing would provide significant value. Examples of such traits are the elimination of anti-nutritionals such as phytates and phenolic compounds which are commonly found in many crop species. Also, the reduction of fats, carbohydrates and certain phytohormones may be valuable for the food and feed industries as they may allow a more efficient mechanism to meet specific dietary requirements.

In addition to direct improvements in feed or food value, genes also may be introduced which improve the processing of Sugarcane and improve the value of the products resulting from the processing. Novel genes that increase the efficiency and reduce the cost of such processing, for example by decreasing the time required at a particular step, may also find use. Improving the value of products derived from processed Sugarcane may include altering the quantity or quality of sugar, starch, oil, fiber, gluten, or other components. Elevation of sugar or starch may be achieved through the identification and elimination of rate limiting steps in starch and sugar biosynthesis by expressing increased amounts of enzymes involved in biosynthesis or by decreasing levels of the other components resulting in proportional increases in sugar or starch. In addition, Sugarcane can be modified by introducing or expressing a gene or genes that produce novel products, such as secondary plant metabolites or pharmaceutical products, that could be purified during the processing step. Using Sugarcane mini-chromosomes or recombinant chromosomes to both introduce genes for new products and optionally for improving processing steps could provide a cost effective option to produce these novel products.

Oil is another product of processing, the value of which may be improved by introduction and expression of genes.

Oil properties may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids (e.g. fatty acid elongases, desaturases) and the lipids possessing them or by increasing levels of native fatty acids while possibly reducing levels of precursors or breakdown products. Alternatively, DNA sequences may be introduced which slow or block steps in fatty acid biosynthesis resulting in the increase in precursor fatty acid intermediates. Genes that might be added include desaturases, epoxidases, hydratases, dehydratases, or other enzymes that catalyze reactions involving fatty acid intermediates. Representative examples of catalytic steps that might be blocked include the desaturations from stearic to oleic acid or oleic to linolenic acid resulting in the respective accumulations of stearic and oleic acids. Another example is the blockage of elongation steps resulting in the accumulation of C8 to C12 saturated fatty acids.

Polypeptides useful for providing increased oil quantity and/or quality include polypeptides involved in fatty acid and glycerolipid biosynthesis, beta-oxidation enzymes, enzymes involved in biosynthesis of nutritional compounds, such as carotenoids and tocopherols.

Polypeptides involved in production of galactomannans or arabinogalactans are of interest for providing plants having increased and/or modified reserve polysaccharides for use in food, pharmaceutical, cosmetic, paper and paint industries.

Polypeptides involved in modification of flavonoid/isoflavonoid metabolism in plants include cinnamate-4-hydroxylase, chalcone synthase or flavones synthase. Enhanced or reduced activity of such polypeptides in Sugarcane plants comprising a Sugarcane mini-chromosome will provide changes in the quantity and/or speed of flavonoid metabolism in plants and may improve disease resistance by enhancing synthesis of protective secondary metabolites or improving signaling pathways governing disease resistance.

Polypeptides involved in lignin biosynthesis are of interest for increasing Sugarcane's resistance to lodging and for increasing the usefulness of plant materials as biofuels.

(ix) Production or Assimilation of Chemicals or Biologicals

It may further be considered that Sugarcane plants comprising a Sugarcane mini-chromosome or recombinant chromosome prepared in accordance with the invention may be used for the production or manufacturing of useful biological compounds that were either not produced at all, or not produced at the same level, in the Sugarcane plant previously. Alternatively, plants produced in accordance with the invention may be made to metabolize or absorb and concentrate certain compounds, such as hazardous wastes, thereby allowing bioremediation of these compounds.

The novel Sugarcane plants producing these compounds are made possible by the introduction and expression of one or potentially many genes with the constructs provided by the invention. The vast array of possibilities include but are not limited to any biological compound which is presently produced by any organism such as proteins, nucleic acids, primary and intermediary metabolites, carbohydrate polymers, enzymes for uses in bioremediation, enzymes for modifying pathways that produce secondary plant metabolites such as faleonoid or vitamins, enzymes that could produce pharmaceuticals, and for introducing enzymes that could produce compounds of interest to the manufacturing industry such as specialty chemicals and plastics. The compounds may be produced by the Sugarcane plant, extracted upon harvest and/or processing, and used for any presently recognized useful purpose such as pharmaceuticals, fragrances, and industrial enzymes to name a few.

(x) Other Characteristics

Cell cycle modification: Polypeptides encoding cell cycle enzymes and regulators of the cell cycle pathway are useful for manipulating growth rate in Sugarcane to provide early vigor and accelerated maturation. Improvements in quality traits, such as seed oil content, may also be obtained by expression of cell cycle enzymes and cell cycle regulators. Polypeptides of interest for modification of the cell cycle pathway include cycling and EIF5α pathway proteins, polypeptides involved in polyamine metabolism, polypeptides which act as regulators of the cell cycle pathway, including cyclin-dependent kinases (CDKs), CDK-activating kinases, cell cycle-dependent phosphatases, CDK-inhibitors, Rb and Rb-binding proteins, or transcription factors that activate genes involved in cell proliferation and division, such as the E2F family of transcription factors, proteins involved in degradation of cyclins, such as cullins, and plant homologs of tumor suppressor polypeptides.

Plant growth regulators: Polypeptides involved in production of substances that regulate the growth of various plant tissues are of interest in the present invention and may be used to provide Sugarcane plants comprising a Sugarcane mini-chromosome having altered morphologies and improved plant growth and development profiles leading to improvements in yield and stress response. Of particular interest are polypeptides involved in the biosynthesis, or degradation of plant growth hormones, such as gibberellins, brassinosteroids, cytokinins, auxins, ethylene or abscisic acid, and other proteins involved in the activity, uptake and/or transport of such polypeptides, including for example, cytokinin oxidase, cytokinin/purine permeases, F-box proteins, G-proteins or phytosulfokines.

Transcription factors in plants: Transcription factors play a key role in plant growth and development by controlling the expression of one or more genes in temporal, spatial and physiological specific patterns. Enhanced or reduced activity of such polypeptides in Sugarcane plants comprising a Sugarcane mini-chromosome will provide significant changes in gene transcription patterns and provide a variety of beneficial effects in plant growth, development and response to environmental conditions. Transcription factors of interest include, but are not limited to myb transcription factors, including helix-turn-helix proteins, homeodomain transcription factors, leucine zipper transcription factors, MADS transcription factors, transcription factors having AP2 domains, zinc finger transcription factors, CCAAT binding transcription factors, ethylene responsive transcription factors, transcription initiation factors or UV damaged DNA binding proteins.

Homologous recombination: Increasing the rate of homologous recombination in Sugarcane is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, DNA replication, nucleic acid metabolism, DNA repair pathways or homologous recombination pathways including for example, recombinases, nucleases, proteins binding to DNA double-strand breaks, single-strand DNA binding proteins, strand-exchange proteins, resolvases, ligases, helicases and polypeptide members of the RAD52 epistasis group.

Enhanced Biofuel Conversion

Biofuels may be produced from the conversion of Sugarcane biomass into liquid or gaseous fuels by converting the biomass into sugars, or by direct extraction of sugars, that can be fermented or chemically converted to form a biofuel. Biofuels can also be generated by extracting oils from the biomass, Exemplary biofuels are ethanol, propanol, butanol, methanol, methane, 2,5-dimethylfurqan, dimethyl ether, biodiesel (short chain acid alkyl esters), biogasoline, parrafins (alkanes), other hydrocarbons or co-products of hydrogen.

The invention provides for Sugarcane mini-chromosomes or recombinant chromosomes expressing at least one gene that enhances or increases sugar production or extractability, enhances or increases biomass, enhances the conversion of biomass to sugars or enhances sugar fermentation to biofuels. It may further be considered that a modified Sugarcane plant prepared in accordance with the invention may be used as biomass for the production of biofuels or the plant may facilitate conversion of biomass to sugars or facilitate fermentation of sugars to biofuels.

Enzymes that may be useful for biofuel production include those that break down glucans. In some embodiments, the enzymes are selected from the group consisting of: endo-β(1,4)-glucanase, cellobiohydrolase, β-glucosidase, α/β-glucosidase, mixed-linked glucanase, endo-β(1,3)-glucanase, exo-β(1,3)-glucanase and β-(1,6)-glucanase. In other embodiments the enzymes break down xyloglucans, xylans, mannans or lignins.

The enzyme genes may be controlled by inducible promoters that may be inactive until a desired time, such as at harvest or when the plant is added to the biofuels process (e.g. inactive at physiological conditions, then activated by heat or pH), or sequestered by subcellular localization. The enzymes may also be controlled by a tissue-specific promoter which may be active only in specific tissues (e.g. seeds or leaves).

Non-Protein-Expressing Exogenous Nucleic Acids

Sugarcane plants with decreased expression of a gene of interest can also be achieved, for example, by expression of antisense nucleic acids, dsRNA or RNAi, catalytic RNA such as ribozymes, sense expression constructs that exhibit cosuppression effects, aptamers or zinc finger proteins.

Antisense RNA reduces production of the polypeptide product of the target messenger RNA, for example by blocking translation through formation of RNA:RNA duplexes or by inducing degradation of the target mRNA. Antisense approaches are a way of preventing or reducing gene function by targeting the genetic material as disclosed in U.S. Pat. Nos. 4,801,540; 5,107,065; 5,759,829; 5,910,444; 6,184,439; and 6,198,026, all of which are incorporated herein by reference. In one approach, an antisense gene sequence is introduced that is transcribed into antisense RNA that is complementary to the target mRNA. For example, part or all of the normal gene sequences are placed under a promoter in inverted orientation so that the complementary strand is transcribed into a non-protein expressing antisense RNA. The promoter used for the antisense gene may influence the level, timing, tissue, specificity, or inducibility of the antisense inhibition.

Autonomous Sugarcane mini-chromosomes or recombinant chromosomes may comprise exogenous DNA flanked by recombination sites, for example lox-P sites, that can be recognized by a recombinase, e.g. Cre, and removed from the Sugarcane mini-chromosome or recombinant chromosome. In cases where there is a homologous recombination site or sites in the host genomic DNA, the exogenous DNA excised from the Sugarcane mini-chromosome or recombinant chromosome may be integrated into the genome at one of the specific recombination sites and the DNA flanked by the recombination sites will become integrated into the host DNA. The use of a Sugarcane mini-chromosome or recombinant chromosome as a platform for DNA excision or for launching such DNA integration into the host genome may include in vivo induction of the expression of a recombinase encoded in the genomic DNA of a transgenic host, or in a Sugarcane mini-chromosome or recombinant chromosome.

RNAi gene suppression in plants by transcription of a dsRNA is described in U.S. Pat. No. 6,506,559, U.S. patent application Publication No. 2002/0168707, WO 98/53083, WO 99/53050 and WO 99/61631, all of which are incorporated herein by reference. The double-stranded RNA or RNAi constructs can trigger the sequence-specific degradation of the target messenger RNA. Suppression of a gene by RNAi can be achieved using a recombinant DNA construct having a promoter operably linked to a DNA element comprising a sense and anti-sense element of a segment of genomic DNA of the gene, e.g., a segment of at least about 23 nucleotides, optionally about 50 to 200 nucleotides where the sense and anti-sense DNA components can be directly linked or joined by an intron or artificial DNA segment that can form a loop when the transcribed RNA hybridizes to form a hairpin structure.

Catalytic RNA molecules or ribozymes can also be used to inhibit expression of the target gene or genes or facilitate molecular reactions. Ribozymes are targeted to a given sequence by hybridization of sequences within the ribozyme to the target mRNA. Two stretches of homology are required for this targeting, and these stretches of homologous sequences flank the catalytic ribozyme structure. It is possible to design ribozymes that specifically pair with virtually any target mRNA and cleave the target mRNA at a specific location, thereby inactivating it. A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include Tobacco Ringspot Virus (Prody et al., *Science*, 231:1577-1580, 1986), Avocado Sunblotch Viroid (Palukaitis et al., *Virology*, 99:145-151, 1979; Symons, *Nucl. Acids Res.*, 9:6527-6537, 1981), and Lucerne Transient Streak Virus (Forster and Symons, *Cell*, 49:211-220, 1987), and the satellite RNAs from velvet tobacco mottle virus, *Solanum* nodiflorum mottle virus and subterranean clover mottle virus. The design and use of target RNA-specific ribozymes is described in Haseloff, et al., Nature 334:585-591 (1988). Several different ribozyme motifs have been described with RNA cleavage activity (Symons, *Annu, Rev. Biochem.*, 61:641-671, 1992). Other suitable ribozymes include sequences from RNase P with RNA cleavage activity (Yuan et al., *Proc. Natl. Acad. Sci. USA*, 89:8006-8010, 1992; Yuan and Altman, *Science*, 263:1269-1273, 1994; U.S. Pat. Nos. 5,168,053 and 5,624,824), hairpin ribozyme structures (Berzal-Herranz et al., *Genes and Devel.*, 6:129-134, 1992; Chowrira et al., *J. Biol. Chem.*, 269:25856-25864, 1994) and Hepatitis Delta virus based ribozymes (U.S. Pat. No. 5,625,047). The general design and optimization of ribozyme directed RNA cleavage activity has been discussed in detail (Haseloff and Gerlach, 1988, Nature. 1988 Aug. 18; 334(6183):585-91, Chowrira et al., J. Biol. Chem., 269:25856-25864, 1994).

Another method of reducing protein expression utilizes the phenomenon of cosuppression or gene silencing (for example, U.S. Pat. Nos. 6,063,947; 5,686,649; or 5,283,184; each of which is incorporated herein by reference). Cosuppression of an endogenous gene using a full-length cDNA sequence as well as a partial cDNA sequence are known (for example, Napoli et al., Plant Cell 2:279-289 [1990]; van der Krol et al., Plant Cell 2:291-299 [1990]; Smith et al., Mol. Gen. Genetics 224:477-481 [1990]). The phenomenon of cosuppression has also been used to inhibit plant target genes in a tissue-specific manner.

In some embodiments, nucleic acids from one species of plant are expressed in another species of plant to effect cosuppression of a homologous gene. The introduced sequence generally will be substantially identical to the endogenous sequence intended to be repressed, for example, about 65%, 80%, 85%, 90%, 95% or even 98% or greater identical. Higher identity may result in a more effective repression of expression of the endogenous sequence. A higher identity in a shorter than full length sequence compensates for a longer, less identical sequence. Furthermore, the introduced sequence need not have the same intron or exon pattern, and identity of non-coding segments will be equally effective. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence.

Yet another method of reducing protein activity is by expressing nucleic acid ligands, so-called aptamers, which specifically bind to the protein. Aptamers may be obtained by the SELEX (Systematic Evolution of Ligands by Exponential Enrichment) method. See U.S. Pat. No. 5,270,163, incorporated herein by reference. In the SELEX method, a candidate mixture of single stranded nucleic acids having regions of randomized sequence is contacted with the protein and those nucleic acids having an increased affinity to the target are selected and amplified. After several iterations a nucleic acid with optimal affinity to the polypeptide is obtained and is used for expression in modified plants.

A zinc finger protein that binds a polypeptide-encoding sequence or its regulatory region is also used to alter expression of the nucleotide sequence. Transcription of the nucleotide sequence may be reduced or increased. Zinc finger proteins are, for example, described in Beerli et al. (1998) PNAS 95:14628-14633., or in WO 95/19431, WO 98/54311, or WO 96/06166, all incorporated herein by reference.

Other examples of non-protein expressing sequences specifically envisioned for use with the invention include tRNA sequences, for example, to alter codon usage, and rRNA variants, for example, which may confer resistance to various agents such as antibiotics.

It is contemplated that unexpressed DNA sequences, including novel synthetic sequences, could be introduced into Sugarcane cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a Sugarcane plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Exemplary Plant Promoters, Regulatory Sequences and Targeting Sequences

Exemplary classes of plant promoters are described below.

Constitutive Expression promoters: Exemplary constitutive expression promoters include the ubiquitin promoter (e.g., sunflower—Binet et al. Plant Science 79: 87-94 (1991); maize—Christensen et al. Plant Molec. Biol. 12: 619-632 (1989); and *Arabidopsis*-Caillis et al., J. Biol. Chem. 265: 12486-12493 (1990) and Norris et al., Plant Mol. Biol. 21: 895-906 (1993)); the CaMV 35S promoter (U.S. Pat. Nos. 5,858,742 and 5,322,938); or the actin promoter (e.g., rice—U.S. Pat. No. 5,641,876; McElroy et al. Plant Cell 2: 163-171 (1990), McElroy et al. Mal. Gen. Genet. 231: 150-160 (1991), and Chibbar et al Plant Cell Rep. 12: 506-509 (1993)). Exemplary promoters for use in Sugarcane include the maize polyubiquitin 1 (Mubi-1) and the Sugarcane polyubiquitin 9 (SCubi9) promoters (Wang M L, Goldstein C, Su W, Moore P H, Albert H H. Production of biologically active GM-CSF in Sugarcane: a secure biofactory. Transgenic Res. 2005, 14:167-78); and the Sugarcane polyubiquitin 4 (ubi4) promoter (Wei H, Wang M L, Moore P H, Albert H H. Comparative expression analysis of two Sugarcane polyubiquitin promoters and flanking sequences in transgenic plants. J Plant Physiol. 2003, 160:1241-51).

Inducible Expression promoters: Exemplary inducible expression promoters include the chemically regulatable tobacco PR-1 promoter (e.g., tobacco—U.S. Pat. No. 5,614, 395; *Arabidopsis*—Lebel et al., Plant J. 16: 223-233 (1998); maize—U.S. Pat. No. 6,429,362). Various chemical regulators may be employed to induce expression, including the benzothiadiazole, isonicotinic acid, and salicylic acid compounds disclosed in U.S. Pat. Nos. 5,523,311 and 5,614,395. Other promoters inducible by certain alcohols or ketones, such as ethanol, include, for example, the alcA gene promoter from *Aspergillus nidulans* (Caddick et al. (1998) Nat. Biotechnol 16:177-180). A glucocorticoid-mediated induction system is described in Aoyama and Chua (1997) The Plant Journal 11: 605-612 wherein gene expression is induced by application of a glucocorticoid, for example a dexamethasone. Another class of useful promoters are water-deficit-inducible promoters, e.g. promoters which are derived from the 5' regulatory region of genes identified as a heat shock protein 17.5 gene (HSP 17.5), an HVA22 gene (HVA22), and a cinnamic acid 4-hydroxylase (CA4H) gene of *Zea mays*. Another water-deficit-inducible promoter is derived from the rab-17 promoter as disclosed by Vilardell et al., Plant Molecular Biology, 17(5):985-993, 1990. See also U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, and U.S. Pat. No. 6,175,060 which discloses phosphorus deficiency inducible promoters.

As another example, numerous wound-inducible promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)). Logemann et al., describe 5' upstream sequences of the potato wunl gene. Xu et al. show that a wound-inducible promoter from the dicotyledon potato (pint) is active in the monocotyledon rice. Rohrmeier & Lehle describe maize Wipl cDNA which is wound induced and which can be used to isolate the cognate promoter. Firek et al. and Warner et al. have described a wound-induced gene from the monocotyledon *Asparagus officinalis*, which is expressed at local wound and pathogen invasion sites.

Tissue-Specific Promoters: Exemplary promoters that express genes only in certain Sugarcane tissues are useful according to the present invention. For example root specific expression may be attained using the promoter of the maize metallothionein-like (MTL) gene described by de Framond (FEBS 290: 103-106 (1991)) and also in U.S. Pat. No. 5,466,785, incorporated herein by reference. U.S. Pat. No. 5,837,848 discloses a root specific promoter. Another exemplary promoter confers pith-preferred expression (see Int'l. Pub. No. WO 93/07278, herein incorporated by reference, which describes the maize trpA gene and promoter that is preferentially expressed in pith cells). Leaf-specific expression may be attained, for example, by using the promoter for a maize gene encoding phosphoenol carboxylase (PEPC) (see Hudspeth & Grula, Plant Molec Biol 12: 579-589 (1989)). Pollen-specific expression may be conferred by the promoter for the maize calcium-dependent protein kinase (CDPK) gene which is expressed in pollen cells (WO 93/07278). U.S. Pat. Appl. Pub. No. 20040016025 describes tissue-specific promoters. Pollen-specific expression may be conferred by the tomato LATS2 pollen-specific promoter (Bate et. al., Plant Mol. Biol. 1998 July; 37(5):859-69).

See also U.S. Pat. No. 6,437,217 which discloses a root-specific maize RS81 promoter, U.S. Pat. No. 6,426,446 which discloses a root specific maize RS324 promoter, U.S. Pat. No. 6,232,526 which discloses a constitutive maize A3 promoter, U.S. Pat. No. 6,177,611 which discloses constitutive maize promoters, U.S. Pat. No. 6,433,252 which discloses a maize L3 oleosin promoter that are aleurone and seed coat-specific promoters, U.S. Pat. No. 6,429,357 which discloses a constitutive rice actin 2 promoter and intron, U.S. patent application Pub. No. 20040216189 which discloses an inducible constitutive leaf specific maize chloroplast aldolase promoter.

Optionally a plant transcriptional terminator can be used in place of the plant-expressed gene native transcriptional terminator. Exemplary transcriptional terminators are those that are known to function in plants and include the CaMV 35S terminator, the tm1 terminator, the nopaline synthase terminator and the pea rbcS E9 terminator. These can be used in both monocotyledons and dicotyledons.

Various intron sequences have been shown to enhance expression, particularly in monocotyledonous cells. For example, the introns of the maize Adh1 gene have been found to significantly enhance expression. Intron 1 was found to be particularly effective and enhanced expression in fusion constructs with the chloramphenicol acetyltransferase gene (Callis et al., Genes Develop. 1: 1183-1200 (1987)). The intron from the maize bronze1 gene also enhances expression. Intron sequences have been routinely incorporated into plant transformation vectors, typically within the non-translated leader. U.S. Patent Application Publication 2002/0192813 discloses 5', 3' and intron elements useful in the design of effective plant expression vectors.

A number of non-translated leader sequences derived from viruses are also known to enhance expression, and these are particularly effective in dicotyledonous cells. Specifically, leader sequences from Tobacco Mosaic Virus (TMV, the "omega-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include, but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154:9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie et al., Molecular Biology of RNA, pages 237-256 (1989); or Maize Chlorotic Mottle Virus leader (MCMV) (Lommel et al., Virology 81:382-385 (1991). See also, Della-Cioppa et al., Plant Physiology 84:965-968 (1987).

A minimal promoter may also be incorporated. Such a promoter has low background activity in plants when there is no transactivator present or when enhancer or response element binding sites are absent. One exemplary minimal promoter is the Bz1 minimal promoter, which is obtained from the bronze1 gene of maize. Roth et al., Plant Cell 3: 317 (1991). A minimal promoter may also be created by use of a synthetic TATA element. The TATA element allows recognition of the promoter by RNA polymerase factors and confers a basal level of gene expression in the absence of activation (see generally, Mukumoto (1993) Plant Mol Biol 23: 995-1003; Green (2000) Trends Biochem Sci 25: 59-63).

Sequences controlling the targeting of gene products also may be included. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein or many other proteins which are known to be chloroplast localized. Other gene products are localized to other organelles such as the mitochondrion and the peroxisome (e.g. Unger et al. Plant Molec. Biol. 13: 411-418 (1989)). Examples of sequences that target to such organdies are the nuclear-encoded ATPases or specific aspartate amino transferase isoforms for mitochondria. Targeting cellular protein bodies has been described by Rogers et al. (Proc. Natl. Acad. Sci. USA 82: 6512-6516 (1985)). In addition; amino terminal and carboxy-terminal sequences are responsible for targeting to the ER, the apoplast, and extracellular secretion from aleurone cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

Another possible element which may be introduced is a matrix attachment region element (MAR), such as the chicken lysozyme A element, which can be positioned around an expressible gene of interest to effect an increase in overall expression of the gene and diminish position dependent effects upon incorporation into the plant genome (Stief et al., Nature, 341:343, 1989; Phi-Van et al., Mol. Cell. Biol., 10:2302-2307.1990).

Use of Non-Plant Promoter Regions Isolated from *Drosophila melanogaster* and *Saccharomyces cerevisiae* to express genes in plants The promoter in the Sugarcane mini-chromosome or recombinant chromosome of the present invention can be derived from plant or non-plant species. In one embodiment, the nucleotide sequence of the promoter is derived from non-plant species for the expression of genes in plant cells. In one embodiment, the non-plant promoters are constitutive or inducible promoters derived from insect, e.g., *Drosophila melanogaster* or yeast, e.g., *Saccharomyces cerevisiae*. Table 2 lists nonlimiting examples of promoters from *Drosophila melanogaster* and *Saccharomyces cerevisiae* that can be used to derive the examples of non-plant promoters in the present invention. Promoters derived from any animal, protist, or fungi are also contemplated. SEQ ID NOS: 222-241, or fragments, mutants, hybrid or tandem promoters thereof, are examples of promoter sequences derived from *Drosophila melanogaster* or *Saccharomyces cerevisiae*. These non-plant promoters can be operably linked to nucleic acid sequences encoding polypeptides or non-protein-expressing sequences including, but not limited to, antisense RNA and ribozymes, to form nucleic acid constructs, vectors, and host cells (prokaryotic or eukaryotic), comprising the promoters.

In the Sugarcane mini-chromosomes or recombinant chromosome of the present invention, the promoter may be a mutant of the promoters having a substitution, deletion, and/or insertion of one or more nucleotides in the nucleic acid sequence of SEQ ID NOS: 222-241, hybrid or tandem promoters.

The techniques used to isolate or clone a nucleic acid sequence comprising a promoter of interest are known in the art and include isolation from genomic DNA. The cloning procedures may involve excision or amplification, for example by polymerase chain reaction, and isolation of a desired nucleic acid fragment comprising the nucleic acid sequence encoding the promoter, insertion of the fragment into a vector molecule, and incorporation of the recombinant vector into the plant cell.

Definitions

The term "adchromosomal" Sugarcane plant or plant part as used herein means a Sugarcane plant or plant part that contains functional, stable and autonomous Sugarcane mini-

TABLE 2

*Drosophila melanogaster* Promoters (Information obtained from the Flybase Web Site at http://flybase.bio.indiana.edu/ which is a database of the *Drosophila* Genome)

| SEQ ID NO: | SSym | Flybase ID | Standard promoter gene name | Gene Product | Chromosome |
|---|---|---|---|---|---|
| 222 | Pgd | FBgn0004654 | Phosphogluconate dehydrogenase | 6-phosphogluconate dehydrogenase | X |
| 223 | Grim | FBgn0015946 | grim | grim-P138 | 3 |
| 224 | Uro | FBgn0003961 | Urate oxidase | Uro-P1 | 2 |
| 225 | Sna | FBgn0003448 | Snail | sna-P1 | 2 |
| 226 | Rh3 | FBgn0003249 | Rhodopsin 3 | Rh3 | 3 |
| 227 | Lsp-1 γ | FBgn0002564 | Larval serum protein 1 | Lsp lγ-P1 | 3 |

*Saccharomyces cerevisiae* Promoters
(Information obtained from the *Saccharomyces* Genome Database Web site at http://www.yeastgenome.org/SearchContents.shtml

| Seq No. | SSymbol | Systematic Name | Standard promoter gene name | Gene Product | Chromosome |
|---|---|---|---|---|---|
| 228 | Tef-2 | YBR118W | TEF2 (Translation elongation factor promoter) | Translation elongation factor EF-1 alpha | 2 |
| 229 | Leu-1 | YGL009C | LEU1 (LEUcine biosynthesis) | isopropylmalate isomerase | 7 |
| 230 | Met16 | YPR167C | METhionine requiring | 3'phosphoadenylyl-sulfate reductase | 16 |
| 231 | Leu-2 | YCL018W | LEU2 (leucine biosynthesis) | beta-IPM (isopropylmalate dehydrogenase) | 3 |
| 232 | His-4 | YCL030C | HIS4 (HIStidine requiring) | histidinol dehydrogenase | 3 |
| 233 | Met-2 | YNL277W | MET2 (methionine requiring) | L-homoserine-O-acetyltransferase | 14 |
| 234 | Ste-3 | YKL178C | STE3 (alias DAF2 Sterile) | a-factor receptor | 11 |
| 235 | Arg-1 | YOL058W | ARG1(alias ARG10 ARGinine requiring) | arginosuccinate synthetase | 15 |
| 236 | Pgk-1 | YCR012W | PGK1 (phosphoglycerate kinase ) | phosphoglycerate kinase | 3 |
| 237 | GPD-1 | YDL022W | GPD1 (alias DAR1/HOR1/OSG1/OSR5 R5: glycerol-3-phosphate dehydrogenase activity | glycerol-3-phosphate dehydrogenase | 4 |
| 238 | ADH1 | YOL086C | ADH1 (alias ADC1) | alcohol dehydrogenase | 15 |
| 239 | GPD-2 | YOL059W | GPD2 (alias GPD3: glycerol-3 -phosphate dehydrogenase activity | glycerol-3-phosphate dehydrogenase | 15 |
| 240 | Arg-4 | YHR018C | ARGinine requiring | argininosuccinate lyase | 8 |
| 241 | Yat-1 | YAR035W | YAT-1(carnitine acetyltransferase) | carnitine acetyltransferase | 1 | chromosomes. Adchromosomal Sugarcane plants or plant parts may be chimeric or not chimeric (chimeric meaning that Sugarcane mini-chromosomes are only in certain portions of the plant, and are not uniformly distributed throughout the plant). An adchromosomal Sugarcane plant cell contains at least one functional, stable and autonomous Sugarcane mini-chromosome.

The term "autonomous" as used herein means that when delivered to plant cells, at least some Sugarcane mini-chromosomes are transmitted through mitotic division to daughter cells and are episomal in the daughter plant cells, i.e. are not chromosomally integrated in the daughter plant cells. Daughter plant cells that contain autonomous mini-chromosomes can be selected for further replication using, for example, selectable or screenable markers. During the introduction into a cell of a mini-chromosome, or during subsequent stages of the cell cycle, there may be chromosomal integration of some portion or all of the DNA derived from a mini-chromosome in some cells. The mini-chromosome is still characterized as autonomous despite the occurrence of such events if a plant may be regenerated that contains episomal descendants of the mini-chromosome, optionally distributed throughout its parts, or if gametes or progeny can be derived from the plant that contain episomal descendants of the mini-chromosome distributed through its parts.

As used herein, a "centromere" is any DNA sequence that confers an ability to segregate to daughter cells through cell division. In one context, this sequence may produce a transmission efficiency to daughter cells ranging from about 1% to about 100%, including to about 5%, 10%, 20%, 30%, 40%, 50%, 60%, 70%, 80%, 90% or about 95% of daughter cells. Variations in transmission efficiency may find important applications within the scope of the invention; for example, mini-chromosomes carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable transmission to daughter cells of a nucleic acid sequence, including a recombinant construct comprising the centromere, through mitotic or meiotic divisions, including through both meiotic and meiotic divisions. A plant centromere is not necessarily derived from plants, but has the ability to promote DNA transmission to daughter plant cells.

As used herein, the term "circular permutations" refer to variants of a sequence that begin at base n within the sequence, proceed to the end of the sequence, resume with base number one of the sequence, and proceed to base n−1. For this analysis, n may be any number less than or equal to the length of the sequence. For example, circular permutations of the sequence ABCD are: ABCD, BCDA, CDAB, and DABC.

The term "co-delivery" as used herein refers to the delivery of two nucleic acid segments to a cell. In co-delivery of plant growth inducing genes and mini-chromosomes, the two nucleic acid segments are delivered simultaneously using the same delivery method. Alternatively, the nucleic acid segment containing the growth inducing gene, optionally as part of an episomal vector, such as a viral vector or a plasmid vector, may be delivered to the plant cells before or after delivery of the mini-chromosome, and the mini-chromosome may carry an exogenous nucleic acid that induces expression of the earlier-delivered growth inducing gene. In this embodiment, the two nucleic acid segments may be delivered separately at different times provided the encoded growth inducing factors are functional during the appropriate time period.

The term "coding sequence" is defined herein as a nucleic acid sequence that is transcribed into mRNA which is translated into a polypeptide when placed under the control of promoter sequences. The boundaries of the coding sequence are generally determined by the ATG start codon located at the start of the open reading frame, near the 5' end of the mRNA, and TAG, TGA or TAA stop codons at the end of the coding sequence, near the 3' end of the mRNA, and in some cases, a transcription terminator sequence located just downstream of the open reading frame at the 3' end of the mRNA. A coding sequence can include, but is not limited to, genomic DNA, cDNA, semisynthetic, synthetic, or recombinant nucleic acid sequences.

As used herein the term "consensus" refers to a nucleic acid sequence derived by comparing two or more related sequences. A consensus sequence defines both the conserved and variable sites between the sequences being compared. Any one of the sequences used to derive the consensus or any permutation defined by the consensus may be useful in the construction of mini-chromosomes.

The term "exogenous" when used in reference to a nucleic acid, for example, is intended to refer to any nucleic acid that has been introduced into a recipient cell, regardless of whether the same or similar nucleic acid is already present in such a cell. Thus, as an example, "exogenous DNA" can include an additional copy of DNA that is already present in the plant cell, DNA from another plant, DNA from a different organism, or a DNA generated externally, such as a DNA sequence containing an antisense message of a gene, or a DNA sequence encoding a synthetic or modified version of a gene. An "exogenous gene" can be a gene not normally found in the host genome in an identical context, or an extra copy of a host gene. The gene may be isolated from a different species than that of the host genome, or alternatively, isolated from the host genome but operably linked to one or more regulatory regions which differ from those found in the unaltered, native gene.

The term "functional" as used herein to describe a mini-chromosome means that when an exogenous nucleic acid is present within the mini-chromosome the exogenous nucleic acid can function in a detectable manner when the mini-chromosome is within a plant cell; exemplary functions of the exogenous nucleic acid include transcription of the exogenous nucleic acid, expression of the exogenous nucleic acid, regulatory control of expression of other exogenous nucleic acids, recognition by a restriction enzyme or other endonuclease, ribozyme or recombinase; providing a substrate for DNA methylation, DNA glycolation or other DNA chemical modification; binding to proteins such as histones, helix-loop-helix proteins, zinc binding proteins, leucine zipper proteins, MADS box proteins, topoisomerases, helicases, transposases, TATA box binding proteins, viral protein, reverse transcriptases, or cohesins; providing an integration site for homologous recombination; providing an integration site for a transposon, T-DNA or retrovirus; providing a substrate for RNAi synthesis; priming of DNA replication; aptamer binding; or kinetochore binding. If multiple exogenous nucleic acids are present within the mini-chromosome, the function of one or more of the exogenous nucleic acids can be detected under suitable conditions permitting function thereof.

An "isolated polynucleotide" or "isolated nucleic acid" (and similar terms) can refer to a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to a coding sequence. The term "isolated" can refer to a polynucleotide or nucleic acid that is substantially free of cellular material, viral material, and/or culture medium (when produced by recombinant DNA techniques), or chemical precursors or other chemicals (when chemically synthesized). "Isolated" does not necessarily mean that the preparation is technically pure (homogeneous), but it is sufficiently pure to provide the polynucleotide or nucleic acid in a form in which it can be used for the intended purpose. In certain embodiments, the isolated polynucleotide or nucleic acid is at least about 50% pure, e.g., at least about 60%, 70%, 80%, 90%, 95%, 96%, 97%, 98%, or 99% or more pure.

An "isolated" cell refers to a cell that is at least partially separated from other components with which it is normally associated in its natural state. For example, an isolated cell can be a cell in culture medium.

As used herein, a "library" is a pool of cloned DNA fragments that represents some or all DNA sequences collected, prepared or purified from a specific source. Each library may contain the DNA of a given organism inserted as discrete restriction enzyme generated fragments or as randomly sheared fragments into many thousands of plasmid vectors. For purposes of the present invention, *E. coli*, yeast, and *Salmonella* plasmids are particularly useful for propagating the genome inserts from other organisms. In principle, any gene or sequence present in the starting DNA preparation can be isolated by screening the library with a specific hybridization probe (see, for example, Young et al., In: Eukaryotic Genetic Systems ICN-UCLA Symposia on Molecular and Cellular Biology, VII, 315-331, 1977).

As used herein, the term "linker" refers to a DNA molecule, generally up to 50 or 60 nucleotides long and composed of two or more complementary oligonucleotides that have been synthesized chemically, or excised or amplified from existing plasmids or vectors. In a representative embodiment, this fragment contains one, or more than one, restriction enzyme site for a blunt cutting enzyme and/or a staggered cutting enzyme, such as BamHI. One end of the linker is designed to be ligatable to one end of a linear DNA molecule and the other end is designed to be ligatable to the other end of the linear molecule, or both ends may be designed to be ligatable to both ends of the linear DNA molecule.

As used herein, a "mini-chromosome" is a recombinant DNA construct including a centromere that is capable of transmission to daughter cells. A mini-chromosome may remain separate from the host genome (as episomes) or may integrate into host chromosomes. The stability of this construct through cell division could range between from about 1% to about 100%, including about 5%, 10%, 20%, 30%, 40%, 50%, 60%, 70%, 80%, 90% and about 95%. The mini-chromosome construct may be a circular or linear molecule. It may include elements such as one or more telomeres, origin of replication sequences, stuffer sequences, buffer sequences, chromatin packaging sequences, linkers and genes. The number of such sequences included is only limited by the physical size limitations of the construct itself. It could contain DNA derived from a natural centromere, although it may be preferable to limit the amount of DNA from the natural centromere to the minimal amount required to obtain a transmission efficiency in the range of 1-100%. The mini-chromosome could also contain a synthetic centromere composed of tandem arrays of repeats of any sequence, either derived from a natural centromere, or of synthetic DNA. The mini-chromosome could also contain DNA derived from multiple natural centromeres. The mini-chromosome may be inherited through mitosis or meiosis, or through both meiosis and mitosis. As used herein, the term mini-chromosome specifically encompasses and includes the terms "plant artificial chromosome" or "PLAC," or engineered chromosomes or microchromosomes and all teachings relevant to a PLAC or plant artificial chromosome specifically apply to constructs within the meaning of the term mini-chromosome.

The term "non-protein expressing sequence" or "non-protein coding sequence" is defined herein as a nucleic acid sequence that is not eventually translated into protein. The nucleic acid may or may not be transcribed into RNA. Exemplary sequences include ribozymes or antisense RNA.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide, nucleotide sequence, or nucleic acid refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid, nucleotide sequence, or polynucleotide of the invention.

The term "operably linked" is defined herein as a configuration in which a control sequence, e.g., a promoter sequence, directs transcription or translation of another sequence, for example a coding sequence. For example, a promoter sequence could be appropriately placed at a position relative to a coding sequence such that the control sequence directs the production of a polypeptide encoded by the coding sequence.

"Phenotype" or "phenotypic trait(s)", as used herein, refers to an observable property or set of properties resulting from the expression of a gene. The set of properties may be observed visually or after biological or biochemical testing, and may be constantly present or may only manifest upon challenge with the appropriate stimulus or activation with the appropriate signal.

The term "recombinant chromosome" refers to an engineered or artificial chromosome that has been constructed by fragmenting a natural chromosome and identifying fragmentation products that are capable of segregation through mitotic and/or meiotic cell divisions. Recombinant chromosomes are distinct from mini-chromosomes in that they are not constructed in vitro from constituent parts and have not been passaged through an heterologous cell such as a bacteria or fungus (as is commonly used in standard cloning techniques). Recombinant chromosomes may the used as targets for addition of transgene expression cassettes.

The term "Sugarcane" refers to any species or hybrid of the genus *Saccharum* including but not limited to: *S. acinaciforme, S. aegyptiacurn, S. alopecuroides* (Silver Plume Grass), *S. alopecuroideum, S. alopecuroidum* (Silver Plumegrass), *S. alopecurus, S. angustifolium, S. antillarum, S. arenicola, S. argenteum, S. arundinaceum* (Hardy Sugar Cane (Usa)), S. arundinaceum var. *trichophyllum, S. asper, S. asperum, S. atrorubens, S. aureum, S. balansae, S. baldwini, S. baldwinii* (Narrow Plumegrass), *S. barberi* (Cultivated Sugarcane), *S. barbicostatum, S. beccarii, S. bengalense* (Munj Sweetcane), *S. benghalense, S. bicorne, S. biflorum, S. boga, S. brachypogon, S. bracteatum, S. brasilianum, S.*

*brevibarbe* (Short-Beard Plume Grass), *S. brevibarbe* var. *brevibarbe* (Shortbeard Plumegrass), *S. brevibarbe* var. *contortum* (Shortbeard Plumegrass), *S. brevifolium, S. brunneum, S. caducutn, S. canaliculatum, S. capense, S. casi, S. caudatum, S. cayennense, S. cayennense* var. *genuinum, S. cayennense* var. *laxiusculum, S. chinense, S. ciliare, S. coarctatum* (Compressed Plumegrass), *S. confertum, S. conjugatum, S. contortum, S. contortum* var. *contortum, S. contractum, S. cotuliferum, S. cylindricum, S. cylindricum* var. *contractum, S. cylindricum* var. *longifolium, S. deciduum, S. densum, S. diandrum, S. dissitiflorum, S. distichophyllum, S. dubium, S. ecklonii, S. edule, S elegans, S. elephantinum, S. erianthoides, S. europaeum, S. exaltatum, S. fasciculatum, S. fastigiatum, S. fatuum, S. filifolium, S. filiforme, S. floridulum, S. formosanum, S. fragile, S. fulvum, S. fuscum, S. giganteum* (Sugarcane Plume Grass), *S. glabrum, S. glaga, S. glaucum, S. glaza, S. grandiflorum, S. griffithii, S. hildebrandtii, S. hirsutum, S. holcoides, S. holcoides* var. *warmingianum, S. hookeri, S. hybrid, S. hybridum, S. indunt, S. infirmum, S. insulare, S. irritans, S. jaculatorium, S. jamaicense, S. japonicum, S. juncifolium, S. kajkaiense, S. kanashiroi, S. klagha, S. koenigii, S. laguroides, S. longifolium, S. longisetosum, S. longisetosum* var. *hookeri, S. longisetum, S. lota, S. luzonicum, S. macilentum, S. macrantherum, S. maximum, S. mexicanum, S. modhara, S. monandrum, S. moonja, S. munja, S. munroanum, S muticum, S. narenga* (Narenga Sugarcane), *S. negrosense, S. obscurum, S. occidentale, S. officinale, S. officinalis, S. officinarum* (Cultivated Sugarcane), *S. officinarum* 'Cheribon', *S. officinarum* 'Otaheite', S. officinarum 'Pele's Smoke' (Black Magic Repellent Plant), *S. officinarum* L. 'Laukona', *S. officinarum* L. 'violaceum', *S. officinarum* var. *brevipedicellatum, S. oficinarum* var. *officinarum, S. officinarum* var. *violaceum* (Burgundy-Leaved Sugarcane), *S. pallidum, S. paniceum, S. panicosurn, S. pappiferum, S. parviflorum, S. pedicellare, S. perrieri, S. polydactylum, S. polystachyon, S. polystachyum, S. porphyrocomum, S. procerum, S. propinquum, S. punctatum, S. rara, S. rarum, S. ravennae* (Hardy Pampas Plume Grass), *S. repens, S. reptans, S. ridleyi, S. robustum* (Wild New-Guinean Cane), *S. roseum, S. rubicundum, S. rufum, S. sagittatum, S. sanguineum, S. sape, S. sara, S. scindicus, S semidecumbens, S. sibiricum, S. sikkimense, S. sinense* (Cultivated Sugarcane), *S. sisca, S. sorghum, S. speciosissimum, S. sphacelatum, S. spicatum, S. spontaneum* (Wild Sugar Cane), *S. spontaneum* var. *insulare, S. spontanum, S. stenophyllum, S. stewartii, S. strictum, S. teneriffae, S. ternatum, S. thunbergii, S. tinctorium, S. tridentatum, S. trinii, S. tristachyum, S. velutinum, S. versicolor, S. viguieri, S. villosum, S violaceum, S. wardii, S. warmingianum, S. williamsii.*

As used herein, the term "Sugarcane Basic Mini-Chromosome" is defined as a recombinant DNA construct that when present within a Sugarcane cell is capable of mitotic and/or meiotic transmission to Sugarcane daughter cells under appropriate conditions and comprises a Sugarcane Assembled Centromere and, optionally, one or more of the following:

(a) one or more telomeres;
(b) one or more sequences for regulating, maintaining, or imparting topological or chromatin structure, molecular integrity, or stability of gene expression or inheritance in Sugarcane;
(c) the required vector DNA that allows for propagation of the mini-chromosome in Sugarcane and DNA that facilitates the selective removal of unwanted portions of the mini-chromosome prior to or after Sugarcane transformation; or
(d) a Transgene Expression Cassette, wherein the Transgene Expression Cassette serves only to regulate, maintain, or impart function or stability to a mini-chromosome in Sugarcane.

A "Sugarcane Basic Mini-Chromosome" does not include a Sugarcane Transgene Expression Cassette that imparts one or more functions other than those expressly set forth in subsection (d), above.

As used herein, a "Sugarcane Assembled Centromere" means a polynucleotide sequence having the properties of a Centromere that is assembled from one or more fragments of native Centromere(s) and/or other polynucleotide sequence, which are (i) isolated from a plant cell, and/or based on plant Centromere sequence motifs, (ii) inserted into a vector (e.g. a plasmid vector) that is propagated and maintained in a cell of a heterologous organism, and (iii) delivered back into a Sugarcane plant cell as part of a Sugarcane Basic or Sugarcane Applied Mini-Chromosome. A Sugarcane Assembled Centromere may possibly be modified by an endogenous in vivo process after it is delivered into a Sugarcane plant cell such that its sequence now differs from that contained in the parental Sugarcane Basic or Sugarcane Applied Mini-Chromosome as propagated in a cell of a heterologous organism. For the avoidance of doubt a Sugarcane Assembled Centromere does not include derivatives or deletions of native Sugarcane Centromeres that are constructed within the Sugarcane plant cell, and are never maintained in their entirety in a cell of a heterologous organism.

As used herein, a "Sugarcane Applied Mini-Chromosome" means a genetic construct formed by integrating one or more Transgene Expression Cassettes into a Sugarcane Basic Mini-Chromosome, wherein said Transgene Expression Cassettes impart one or more functions other than to regulate, maintain, or impart function or stability to a mini-chromosome.

The term "plant part" as used herein includes a pod, root, sett root, shoot root, root primordial, shoot, primary shoot, secondary shoot, tassle, panicle, arrow, midrib, blade, ligule, auricle, dewlap, blade joint, sheath, node, internode, bud furrow, leaf scar, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk, ovule or embryo. Other exemplary Sugarcane plant parts are a meiocyte or gamete or ovule or pollen or endosperm of any of the plants of the invention. Other exemplary plant parts are a seed, seed-piece, embryo, protoplast, cell culture, any group of plant cells organized into a structural and functional unit, ratoon or propagule.

The term "promoter" is defined herein as a DNA sequence that allows the binding of RNA polymerase (including but not limited to RNA polymerase I, RNA polymerase II and RNA polymerase III from eukaryotes) and directs the polymerase to a downstream transcriptional start site of a nucleic acid sequence encoding a polypeptide to initiate transcription. RNA polymerase effectively catalyzes the assembly of messenger RNA complementary to the appropriate DNA strand of the coding region.

A "promoter operably linked to a heterologous gene" is a promoter that is operably linked to a gene that is different from the gene to which the promoter is normally operably linked in its native state. Similarly, an "exogenous nucleic acid operably linked to a heterologous regulatory sequence" is a nucleic acid that is operably linked to a regulatory control sequence to which it is not normally linked in its native state.

The term "hybrid promoter" is defined herein as parts of two or more promoters that are fused together to generate a sequence that is a fusion of the two or more promoters, which is operably linked to a coding sequence and mediates the transcription of the coding sequence into mRNA.

The term "tandem promoter" is defined herein as two or more promoter sequences each of which is operably linked to a coding sequence and mediates the transcription of the coding sequence into mRNA.

The term "constitutive active promoter" is defined herein as a promoter that allows permanent stable expression of the gene of interest.

The term "Inducible promoter" is defined herein as a promoter induced by the presence or absence of a biotic or an abiotic factor.

The term "polypeptide" does not refer to a specific length of the encoded product and, therefore, encompasses peptides, oligopeptides, and proteins. The term "exogenous polypeptide" is defined as a polypeptide which is not native to the plant cell, a native polypeptide in which modifications have been made to alter the native sequence, or a native polypeptide whose expression is quantitatively altered as a result of a manipulation of the plant cell by recombinant DNA techniques.

As used herein, the term "pseudogene" refers to a non-functional copy of a protein-coding gene; pseudogenes found in the genomes of eukaryotic organisms are often inactivated by mutations and are thus presumed to be non-essential to that organism; pseudogenes of reverse transcriptase and other open reading frames found in retroelements are abundant in the centromeric regions of *Arabidopsis* and other organisms and are often present in complex clusters of related sequences.

As used herein the term "regulatory sequence" refers to any DNA sequence that influences the efficiency of transcription or translation of any gene. The term includes, but is not limited to, sequences comprising promoters, enhancers and terminators.

As used herein the term "repeated nucleotide sequence" refers to any nucleic acid sequence of at least 25 bp present in a genome or a recombinant molecule, other than a telomere repeat, that occurs at least two or more times and that are optionally at least 80% identical either in head to tail or head to head orientation either with or without intervening sequence between repeat units.

As used herein, the term "retroelement" or "retrotransposon" refers to a genetic element related to retroviruses that disperse through an RNA stage; the abundant retroelements present in plant genomes contain long terminal repeats (LTR retrotransposons) and encode a polyprotein gene that is processed into several proteins including a reverse transcriptase. Specific retroelements (complete or partial sequences) can be found in and around plant centromeres and can be present as dispersed copies or complex repeat clusters. Individual copies of retroelements may be truncated or contain mutations; intact retroelements are rarely encountered.

As used herein the term "satellite DNA" refers to short DNA sequences (typically<1000 bp) present in a genome as multiple repeats, mostly arranged in a tandemly repeated fashion, as opposed to a dispersed fashion. Repetitive arrays of specific satellite repeats are abundant in the centromeres of many higher eukaryotic organisms.

As used herein, a "screenable marker" is a gene whose presence results in an identifiable phenotype. This phenotype may be observable under standard conditions, altered conditions such as elevated temperature, or in the presence of certain chemicals used to detect the phenotype. The use of a screenable marker allows for the use of lower, sub-killing antibiotic concentrations and the use of a visible marker gene to identify clusters of transformed cells, and then manipulation of these cells to homogeneity. Illustrative screenable markers of the present include genes that encode fluorescent proteins that are detectable by a visual microscope such as the fluorescent reporter genes DsRed, ZsGreen, ZsYellow, AmCyan, Green Fluorescent Protein (GFP) and modifications of these reporter genes to excite or emit at altered wavelengths. An additional screenable marker gene is lac.

Alternative methods of screening for modified plant cells may involve use of relatively low, sub-killing concentrations of a selection agent (e.g. sub-killing antibiotic concentrations), and also involve use of a screenable marker (e.g., a visible marker gene) to identify clusters of modified cells carrying the screenable marker, after which these screenable cells are manipulated to homogeneity. As used herein, a "selectable marker" is a gene whose presence results in a clear phenotype, and most often a growth advantage for cells that contain the marker. This growth advantage may be present under standard conditions, altered conditions such as elevated temperature, specialized media compositions, or in the presence of certain chemicals such as herbicides or antibiotics. Use of selectable markers is described, for example, in Broach et al. Gene, 8:121-133, 1979. Examples of selectable markers include the thymidine kinase gene, the cellular adenine phosphoribosyltransferase gene and the dihydrylfolate reductase gene, hygromycin phosphotransferase genes, the bar gene, neomycin phosphotransferase genes and phosphomannose isomerase gene, among others. Nonlimiting examples of selectable markers in the present invention include genes whose expression confer antibiotic or herbicide resistance to the host cell, or proteins allowing utilization of a carbon source not normally utilized by plant cells. Expression of one of these markers should be sufficient to enable the survival of those cells that comprise a vector within the host cell, and facilitate the manipulation of the vector into new host cells. Of particular interest in the present invention are proteins conferring cellular resistance to kanamycin, G 418, paramomycin, hygromycin, bialaphos, and glyphosate for example, or proteins allowing utilization of a carbon source, such as mannose, not normally utilized by plant cells.

The term "stable" as used herein means that the mini-chromosome can be transmitted to daughter cells over at least 8 mitotic generations. Some embodiments of mini-chromosomes may be transmitted as functional, autonomous units for less than 8 mitotic generations, e.g. 1, 2, 3, 4, 5, 6, or 7. According to representative embodiments, the mini-chromosome can be transmitted over at least 8, 9, 10, 11, 12, 13, 14, 15, 16, 17, 18, 18, 19, 20, 21, 22, 23, 24, 25, 26, 27, 28, 29 or 30 generations, for example, through the regeneration or differentiation of an entire plant, and may even be are transmitted through meiotic division to gametes. Other representative mini-chromosomes can be further maintained in the zygote derived from such a gamete or in an embryo or endosperm derived from one or more such gametes. A "functional and stable" mini-chromosome is one in which functional mini-chromosomes can be detected after transmission of the mini-chromosomes over at least 8 mitotic generations, or after inheritance through a meiotic division. During mitotic division, as occurs occasionally with native chromosomes, there may be some non-transmission of mini-chromosomes; the mini-chromosome may still be characterized as stable despite the occurrence of such events if an adchromosomal plant that contains descendants of the mini-chromosome distributed throughout its parts may be regenerated from cells, cuttings, propagules, or cell cultures containing the mini-chromosome, or if an adchromosomal plant can be identified in progeny of the plant containing the mini-chromosome.

As used herein, a "structural gene" is a sequence which codes for a polypeptide or RNA and includes 5' and 3' ends. The structural gene may be from the host into which the structural gene is transformed or from another species. A structural gene may optionally, but not necessarily, include one or more regulatory sequences which modulate the expression of the structural gene, such as a promoter, terminator or enhancer. A structural gene may optionally, but not necessarily, confer some useful phenotype upon an organism comprising the structural gene, for example, herbicide resistance. In one embodiment of the invention, a structural gene may encode an RNA sequence which is not translated into a protein, for example a tRNA or rRNA gene.

As used herein, the term "telomere" or "telomere DNA" refers to a sequence capable of capping the ends of a chromosome, thereby preventing degradation of the chromosome end, ensuring replication and preventing fusion to other chromosome sequences. Telomeres can include naturally occurring telomere sequences or synthetic sequences. Telomeres from one species may confer telomere activity in another species. An exemplary telomere DNA is a heptanucleotide telomere repeat TTTAGGG (and its complement) found in the majority of plants.

"Transformed," "transgenic," "modified," and "recombinant" refer to a host organism such as a plant into which an exogenous or heterologous nucleic acid molecule has been introduced, and includes meiocytes, seeds, zygotes, embryos, endosperm, or progeny of such plant that retain the exogenous or heterologous nucleic acid molecule but which have not themselves been subjected to the transformation process.

When the phrase "transmission efficiency" of a certain percent is used, transmission percent efficiency is calculated by measuring mini-chromosome presence through one or more mitotic or meiotic generations. It is directly measured as the ratio (expressed as a percentage) of the daughter cells or plants demonstrating presence of the mini-chromosome to parental cells or plants demonstrating presence of the mini-chromosome. Presence of the mini-chromosome in parental and daughter cells can be demonstrated with assays that detect the presence of an exogenous nucleic acid carried on the mini-chromosome. Exemplary assays can be the detection of a screenable marker (e.g. presence of a fluorescent protein or any gene whose expression results in an observable phenotype), a selectable marker, or PCR amplification of any exogenous nucleic acid carried on the mini-chromosome.

Constructing Mini-Chromosomes by Site-Specific Recombination

Sugarcane mini-chromosomes may be constructed using site-specific recombination sequences (for example those recognized by the bacteriophage P I Cre recombinase, or the bacteriophage lambda integrase, or similar recombination enzymes). According to this embodiment, a compatible recombination site, or a pair of such sites, is present on both the Sugarcane centromere containing DNA clones and the donor DNA clones. Incubation of the donor clone and the centromere clone in the presence of the recombinase enzyme causes strand exchange to occur between the recombination sites in the two plasmids; the resulting Sugarcane mini-chromosomes contain Sugarcane centromere sequences as well as mini-chromosome vector sequences. The DNA molecules formed in such recombination reactions are introduced into *E. coli*, other bacteria, yeast or Sugarcane cells by common methods in the field including, but not limited to, heat shock, chemical transformation, electroporation, particle bombardment, whiskers, or other transformation methods followed by selection for marker genes including chemical, enzymatic, color, or other marker, allowing for the selection of transformants harboring mini-chromosomes.

II. Methods of Detecting and Characterizing Mini-Chromosomes in Plant Cells or of Scoring Mini-Chromosome Performance in Plant Cells:

Identification of Candidate Centromere Fragments by Probing BAC Libraries

Sugarcane centromere clones are identified from a large Sugarcane genomic insert library such as a Bacterial Artificial Chromosome library. Probes are labeled using nick-translation in the presence of radioactively labeled dCTP, dATP, dGTP or dTTP as in, for example, the commercially available Rediprime kit (Amersham) as per the manufacturer's instructions. Other labeling methods familiar to those skilled in the art could be substituted. The libraries are screened and deconvoluted. Sugarcane genomic clones are screened by probing with small centromere-specific clones. Other embodiments of this procedure would involve hybridizing a library with other centromere sequences. Of the BAC clones identified using this procedure, a representative set are identified as having high hybridization signals to some probes, and optionally low hybridization signals to other probes. These are selected, the bacterial clones grown up in cultures and DNA prepared by methods familiar to those skilled in the art such as alkaline lysis. The DNA composition of purified clones is surveyed using for example fingerprinting by digesting with restriction enzymes such as, but not limited to, HinfI or HindIII. In a representative embodiment the restriction enzyme cuts within the tandem centromere satellite repeat (see below). A variety of clones showing different fingerprints are selected for conversion into mini-chromosomes and inheritance testing. It can also be informative to use multiple restriction enzymes for fingerprinting or other enzymes which can cleave DNA.

Fingerprinting analysis of BACs and mini-chromosomes

Sugarcane centromere function may be associated with large tandem arrays of satellite repeats. To assess the composition and architecture of the centromere BACs, the candidate BACs are digested with a restriction enzyme, such as HindIII, which cuts with known frequency within the consensus sequence of the unit repeat of the tandemly repeated centromere satellite. Digestion products are then separated by agarose gel electrophoresis. Large insert clones containing a large array of tandem repeats will produce a strong band of the unit repeat size, as well as less intense bands at 2× and 3× the unit repeat size, and further multiples of the repeat size. These methods are well-known and there are many possible variations known to those skilled in the art.

Determining Sequence Composition of Mini-Chromosomes by Shotgun Cloning/Sequencing, Sequence Analysis To determine the sequence composition of the Sugarcane mini-chromosome, the centromeric region of the Sugarcane mini-chromosome is sequenced. To generate DNA suitable for sequencing, Sugarcane mini-chromosomes are fragmented, for example by using a random shearing method (such as sonication, nebulization, etc). Other fragmentation techniques may also be used such as enzymatic digestion. These fragments are then cloned into a vector (e.g., a plasmid) and sequenced. The resulting DNA sequence is trimmed of poor-quality sequence and of sequence corresponding to the vector. The sequence is then compared to the known DNA sequences using an algorithm such as BLAST to search a sequence database such as GenBank.

To determine the consensus of the Sugarcane satellite repeat in the Sugarcane mini-chromosome, the sequences containing the satellite repeat are aligned using a DNA sequence alignment program such as ContigExpress from Vector NTI. The sequences may also be aligned to previously determined repeats for that species. The sequences are trimmed to unit repeat length using the consensus as a template. Sequences trimmed from the ends of the alignment are realigned with the consensus and further trimmed until all sequences are at or below the consensus length. The sequences are then aligned with each other. The consensus is determined by the frequency of a specific nucleotide at each position; if the most frequent base is three times more frequent than the next most frequent base, it was considered the consensus.

Methods for determining consensus sequence are well known in the art, see, e.g., U.S. Pat. App. Pub. No. 20030124561; Hall & Preuss (2002). These methods, including DNA sequencing, assembly, and analysis, are well-known and there are many possible variations known to those skilled in the art. Other alignment parameters may also be useful such as using more or less stringent definitions of consensus.

Non-Selective Mini-Chromosome Mitotic Inheritance Assays

The following list of assays and potential outcomes illustrates how various assays can be used to distinguish autonomous events from integrated events.

Assay #1: Transient Assay

Sugarcane mini-chromosomes are tested for their ability to become established as chromosomes and their ability to be inherited in mitotic cell divisions. In this assay, Sugarcane mini-chromosomes are delivered to Sugarcane plant cells, for example suspension cells in liquid culture. The cells used can be at various stages of growth. Optionally, a population in which some cells are undergoing division can be used. The Sugarcane mini-chromosome is then assessed over the course of several cell divisions, by tracking the presence of a screenable marker, e.g. a visible marker gene such as a fluorescent protein. Sugarcane mini-chromosomes that are established and inherited well may show an initial delivery into many single cells; after several cell divisions, these single cells divide to form clusters of mini-chromosome-containing cells. Other exemplary embodiments of this method include delivering Sugarcane mini-chromosomes to other mitotic cell types, including roots and shoot meristems.

Assay #2: Non-Lineage Based Inheritance Assays on Modified Transformed Cells and Plants Sugarcane mini-chromosome inheritance is assessed on modified cell lines and plants by following the presence of the mini-chromosome over the course of multiple cell divisions. An initial population of Sugarcane mini-chromosome containing cells is assayed for the presence of the Sugarcane mini-chromosome, by the presence of a marker gene, including but not limited to a fluorescent protein, a colored protein, a protein assayable by histochemical assay, and a gene affecting cell morphology. In the use of a DNA-specific dye, all nuclei are stained with a dye including but not limited to DAPI, Hoechst 33258, OliGreen, Giemsa YOYO, or TOTO, allowing a determination of the number of cells that do not contain the mini-chromosome. After the initial determination of the percent of cells carrying the Sugarcane mini-chromosome, the remaining cells are allowed to divide over the course of several cell divisions. The number of cell divisions, n, is determined by a method including but not limited to monitoring the change in total weight of cells, and monitoring the change in volume of the cells or by directly counting cells in an aliquot of the culture. After a number of cell divisions, the population of cells is again assayed for the presence of the Sugarcane mini-chromosome. The loss rate per generation is calculated by the equation:

$$\text{Loss rate per generation} = 1 - (F/I)^{1/n}$$

The population of Sugarcane mini-chromosome-containing cells may include suspension cells, callus, roots, leaves, meristems, flowers, or any other tissue of modified plants, or any other cell type containing a mini-chromosome.

These methods are well-known and there are many possible variations known to those skilled in the art; they have been used before with human cells and yeast cells.

Assay #3: Lineage Based Inheritance Assays on Modified Cells and Plants

Sugarcane mini-chromosome inheritance is assessed on cell lines and plants comprising Sugarcane mini-chromosomes by following the presence of the Sugarcane mini-chromosome over the course of multiple cell divisions. In cell types that allow for tracking of cell lineage, including but not limited to root or leaf cell files, trichomes, and leaf stomata guard cells, Sugarcane mini-chromosome loss per generation does not need to be determined statistically over a population, it can be discerned directly through successive cell divisions. In other manifestations of this method, cell lineage can be discerned from cell position, or methods including but not limited to the use of histological lineage tracing dyes, and the induction of genetic mosaics in dividing cells.

In one simple example, the two guard cells of the stomata are daughters of a single precursor cell. To assay Sugarcane mini-chromosome inheritance in this cell type, the epidermis of the leaf of a Sugarcane plant containing a Sugarcane mini-chromosome is examined for the presence of the Sugarcane mini-chromosome by the presence of a marker gene, including but not limited to a fluorescent protein, a colored protein, a protein assayable by histochemical assay, and a gene affecting cell morphology. The number of loss events in which one guard cell contains the Sugarcane mini-chromosome (L) and the number of cell divisions in which both guard cells contain the Sugarcane mini-chromosome (B) are counted. The loss rate per cell division is determined as $L/(L+B)$. Other lineage-based cell types are assayed in similar fashion. These methods are well-known and there are many possible variations known to those skilled in the art; they have been used before with yeast cells (though, instead of observing the marker in stomates, a color marker was observed in yeast colonies).

Linear Sugarcane mini-chromosome inheritance may also be assessed by examining leaf or root files or clustered cells in callus over time. Changes in the percent of cells carrying the Sugarcane mini-chromosome will indicate the mitotic inheritance.

Assay #4: Inheritance Assays on Modified Cells and Plants in the Presence of Chromosome Loss Agents Any of the above three assays can be done in the presence of chromosome loss agents (including but not limited to colchicine, colcemid, caffeine, etopocide, nocodazole, oryzalin, trifluran). It is likely that an autonomous Sugarcane mini-chromosome will prove more susceptible to loss induced by chromosome loss agents; therefore, autonomous mini-chromosomes should show a lower rate of inheritance in the presence of chromosome loss agents. These methods have been used to study chromosome loss in fruit flies and yeast; there are many possible variations known to those skilled in the art.

III. Transformation of Plant Cells and Plant Regeneration

Various methods may be used to deliver DNA into plant cells. These include biological methods, such as *Agrobacterium, E. coli*, and viruses, physical methods such as biolistic particle bombardment, nanocopoea device, the Stein beam gun, silicon carbide whiskers and microinjection, electrical methods such as electroporation, and chemical methods such as the use of poly-ethylene glycol and other compounds known to stimulate DNA uptake into cells. Examples of these techniques are described by Paszkowski et al., EMBO J. 3: 2717-2722 (1984), Potrykus et al., Mol. Gen. Genet. 199:

169-177 (1985), Reich et al., Biotechnology 4: 1001-1004 (1986), and Klein et al., Nature 327: 70-73 (1987). Transformation using silicon carbide whiskers, e.g. in maize, is described in Brisibe, J. Exp. Bot. 51(343):187-196 (2000) and Dunwell, Methods Mol. Biol. 111:375-82 (1999) and U.S. Pat. No. 5,464,765.

Agrobacterium-Mediated Delivery

Agrobacterium-mediated transformation is one method for introducing a desired genetic element into a plant. Several Agrobacterium species mediate the transfer of a specific DNA known as "T-DNA" that can be genetically engineered to carry a desired piece of DNA into many plant species. Plasmids used for delivery contain the T-DNA flanking the nucleic acid to be inserted into the plant. The major events marking the process of T-DNA mediated pathogenesis are induction of virulence genes, processing and transfer of T-DNA.

There are three common methods to transform plant cells with Agrobacterium. The first method is co-cultivation of Agrobacterium with cultured isolated protoplasts. This method requires an established culture system that allows culturing protoplasts and plant regeneration from cultured protoplasts. The second method is transformation of cells or tissues with Agrobacterium. This method requires (a) that the plant cells or tissues can be modified by Agrobacterium and (b) that the modified cells or tissues can be induced to regenerate into whole plants. The third method is transformation of seeds, immature or mature embryos, apices or meristems with Agrobacterium. This method requires exposure of the meristematic cells of these tissues to Agrobacterium and micropropagation of the shoots or plant organs arising from these meristematic cells.

Those of skill in the art are familiar with procedures for growth and suitable culture conditions for Agrobacterium as well as subsequent inoculation procedures. Liquid, solid, or semi-solid culture media can be used. The density of the Agrobacterium culture used for inoculation and the ratio of Agrobacterium cells to explant can vary from one system to the next, as can media, growth procedures, timing and lighting conditions.

Transformation of dicotyledons using Agrobacterium has long been known in the art, and transformation of monocotyledons using Agrobacterium has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

A number of wild-type and disarmed strains of Agrobacterium tumefaciens and Agrobacterium rhizogenes harboring Ti or Ri plasmids can be used for gene transfer into plants. In embodiments of the invention, the Agrobacterium hosts contain disarmed Ti and Ri plasmids that do not contain the oncogenes that cause tumorigenesis or rhizogenesis. Exemplary strains include Agrobacterium tumefaciens strain C58, a nopaline-type strain that is used to mediate the transfer of DNA into a plant cell, octopine-type strains such as LBA4404 or succinamopine-type strains, e.g., EHA101 or EHA105. The use of these strains for plant transformation has been reported and the methods are familiar to those of skill in the art.

U.S. Application No. 20040244075 published Dec. 2, 2004 describes improved methods of Agrobacterium-mediated transformation. The efficiency of transformation by Agrobacterium may be enhanced by using a number of methods known in the art. For example, the inclusion of a natural wound response molecule such as acetosyringone (AS) to the Agrobacterium culture has been shown to enhance transformation efficiency with Agrobacterium tumefaciens (Shahla et al., (1987) Plant Molec. Biol. 8:291-298). Alternatively, transformation efficiency may be enhanced by wounding the target tissue to be modified or transformed. Wounding of plant tissue may be achieved, for example, by punching, maceration, bombardment with microprojectiles, etc. (See e.g., Bidney et al., (1992) Plant Molec. Biol. 18:301-313).

In addition, another recent method described by Broothaerts, et. al. (Nature 433: 629-633, 2005) expands the bacterial genera that can be used to transfer genes into plants. This work involved the transfer of a disarmed Ti plasmid without T-DNA and another vector with T-DNA containing the marker enzyme beta-glucuronidase, into three different bacteria. Gene transfer was successful and this method significantly expands the tools available for gene delivery into plants.

Microprojectile Bombardment Delivery

Another widely used technique to genetically transform plants involves the use of microprojectile bombardment. In this process, a nucleic acid containing the desired genetic elements to be introduced into the plant is deposited on or in small dense particles, e.g., tungsten, platinum, or 0.5 to 1.0 micron gold particles, which are then delivered at a high velocity into the plant tissue or plant cells using a specialized biolistics device. Many such devices have been designed and constructed; one in particular, the PDS1000/He sold by Bio-Rad, is the instrument most commonly used for biolistics of plant cells. The advantage of this method is that no specialized sequences need to be present on the nucleic acid molecule to be delivered into plant cells; delivery of any nucleic acid sequence is theoretically possible.

For the bombardment, cells in suspension are concentrated on filters, petri dishes or solid culture medium. Alternatively, immature embryos, seedling explants, or any plant tissue or target cells may be arranged on filters, petri dishes or solid culture medium. The cells to be bombarded are positioned at an appropriate distance below the microprojectile stopping plate.

Various biolistics protocols have been described that differ in the type of particle or the manner in which DNA is coated onto the particle. Any technique for coating microprojectiles that allows for delivery of transforming DNA to the target cells may be used. For example, particles may be prepared by functionalizing the surface of a gold particle by providing free amine groups. DNA, having a strong negative charge, will then bind to the functionalized particles.

Parameters such as the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, ranges of approximately 1 ng to approximately 10 μg (10,000 ng), approximately 5 ng to 8 μg or approximately 20 ng, 50 ng, 100 ng, 200 ng, 500 ng, 1 μg, 2 μg, 5 μg, or 7 μg of transforming DNA may be used per each 1.0-2M mg of starting gold particles (in the 0.5 to 1.0 micron range).

Other physical and biological parameters may be varied, such as manipulation of the DNA/mieroprojectile precipitate, factors that affect the flight and velocity of the projectiles, manipulation of the cells before and immediately after bombardment (including osmotic state, tissue hydration and the subculture stage or cell cycle of the recipient cells), the orientation of an immature embryo or other target tissue relative to the particle trajectory, and also the nature of the transforming DNA, such as linearized DNA or intact supercoiled plasmids. One may also want to use agents to protect the DNA during delivery. One may particularly wish to adjust physical parameters such as DNA concentration, gap distance, flight distance, tissue distance, and helium pressure.

The particles delivered via biolistics can be "dry" or "wet." In the "dry" method, the mini-chromosome DNA-coated particles such as gold are applied onto a macrocarrier (such as a metal plate, or a carrier sheet made of a fragile material such as mylar) and dried. The gas discharge then accelerates the macrocarrier into a stopping screen, which halts the macrocarrier but allows the particles to pass through; the particles then continue their trajectory until they impact the tissue being bombarded. For the "wet" method, the droplet containing the mini-chromosome DNA-coated particles is applied to the bottom part of a filter holder, which is attached to a base which is itself attached to a rupture disk holder used to hold the rupture disk to the helium egress tube for bombardment. The gas discharge directly displaces the DNA/gold droplet from the filter holder and accelerates the particles and their DNA cargo into the tissue being bombarded. The wet biolistics method has been described in detail elsewhere but has not previously been applied in the context of plants (Mialhe et al., Mol Mar Biol Biotechnol. 4(4):275-83, 1995). The concentrations of the various components for coating particles and the physical parameters for delivery can be optimized using procedures known in the art.

A variety of Sugarcane cells/tissues are suitable for transformation, including immature embryos, scutellar tissue, suspension cell cultures, immature inflorescence, shoot meristem, epithelial peels, nodal explants, callus tissue, hypocotyl tissue, cotyledons, roots, leaves, meristem cells, and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspore-derived embryos, roots, hypocotyls, cotyledons and the like. Those cells which are capable of proliferating as callus also are recipient cells for genetic transformation.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins such as picloram (4-amino-3,5,6-trichloropicolinic acid), 2,4-D (2,4-dichlorophenoxyacetic acid), naphalene-acetic acid (NAA) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Murashige and Skoog, Physiol. Plant, 15:473-497, 1962), N6 (Chu et al., Scientia Sinica 18:659, 1975), Linsmaier and Skoog (Linsmaier and Skoog, Physio. Plant., 18:100, 1965), Uchimiya and Murashige (Uchimiya and Murashige, Plant Physiol. 15:473, 1962), Gamborg's B5 media (Gamborg et al., Exp. Cell Res., 50:151, 1968), D medium (Duncan et al., Planta, 165:322-332, 1985), Mc-Cown's Woody plant media (McCown and Lloyd, HortScience 6:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be varied.

Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate or other herbicides. Consequently, such media and culture conditions disclosed in the present invention can be modified or substituted with nutritionally equivalent components, or similar processes for selection and recovery of transgenic events, and still fall within the scope of the present invention.

Sugarcane Mini-Chromosome Delivery without Selection

The Sugarcane mini-chromosome is delivered to Sugarcane plant cells or tissues, e.g., plant cells in suspension to obtain stably modified callus clones for inheritance assay. Suspension cells are maintained in a growth media, for example Murashige and Skoog (MS) liquid medium containing an auxin such as 2,4-dichlorophenoxyacetic acid (2,4-D). Cells are bombarded using a particle bombardment process, such as the helium-driven PDS-1000/He system, and propagated in the same liquid medium to permit the growth of modified and non-modified cells. Portions of each bombardment are monitored for formation of fluorescent clusters, which are isolated by micromanipulation and cultured on solid medium. Clones modified with the mini-chromosome are expanded and homogenous clones are used in inheritance assays, or assays measuring mini-chromosome structure or autonomy.

Sugarcane Mini-Chromosome Transformation with Selectable Marker Gene

Isolation of Sugarcane mini-chromosome-modified cells in bombarded calluses or explants can be facilitated by the use of a selectable marker gene. The bombarded tissues are transferred to a medium containing an appropriate selective agent for a particular selectable marker gene. Such a transfer usually occurs between 0 and about 7 days after bombardment. The transfer could also take place any number of days after bombardment. The amount of selective agent and timing of incorporation of such an agent in selection medium can be optimized by using procedures known in the art. Selection inhibits the growth of non-modified cells, thus providing an advantage to the growth of modified cells, which can be further monitored by tracking the presence of a fluorescent marker gene or by the appearance of modified explants (modified cells or explants may be green under light in selection medium, while surrounding non-modified cells are weakly pigmented). In plants that develop through shoot organogenesis, the modified cells can form shoots directly, or alternatively, can be isolated and expanded for regeneration of multiple shoots transgenic for the Sugarcane mini-chromosome. In plants that develop through embryogenesis, additional culturing steps may be necessary to induce the modified cells to form an embryo and to regenerate in the appropriate media. Sugarcane is generally regenerated through embryogenesis but can also be regenerated by shoot organogenesis.

Useful selectable marker genes are well known in the art and include, for example, herbicide and antibiotic resistance genes including but not limited to neomycin phosphotransferase TI (conferring resistance to kanamycin, paramomycin and G418), hygromycin phosphotransferase (conferring resistance to hygromycin), 5-enolpyruvylshikimate-3-phosphate synthase (EPSPS, conferring resistance to glyphosate), phosphinothricin acetyltransferase (conferring resistance to phosphinothricin/bialophos), MerA (conferring resistance to mercuric ions). Selectable marker genes may be transformed using standard methods in the art.

The first step in the production of Sugarcane plants containing novel genes involves delivery of DNA into a suitable plant tissue (described in the previous section) and selection of the tissue under conditions that allow preferential growth of any cells containing the novel genes. Selection is typically achieved with a selectable marker gene present in the delivered DNA, which may be a gene conferring resistance to an antibiotic, herbicide or other killing agent, or a gene allowing utilization of a carbon source not normally metabolized by plant cells. For selection to be effective, the plant cells or tissue need to be grown on selective medium containing the appropriate concentration of antibiotic or killing agent, and the cells need to be plated at a defined and constant density. The concentration of selective agent and cell density are generally chosen to cause complete growth inhibition of wild type plant tissue that does not express the selectable marker gene; but allowing cells containing the introduced DNA to grow and expand into adchromosomal clones. This critical concentration of selective agent typically is the lowest concentration at which there is complete growth inhibition of wild type cells, at the cell density used in the experiments. However, in some cases, sub-killing concentrations of the selective agent may be equally or more effective for the isolation of plant cells containing mini-chromosome DNA, especially in cases where the identification of such cells is assisted by a visible marker gene (e.g., fluorescent protein gene) present on the Sugarcane mini-chromosome. Such sub-killing concentrations of the selective agent may be administered during part or all of the selection timing.

In some species (e.g., tobacco or tomato), a homogenous clone of modified cells can also arise spontaneously when bombarded cells are placed under the appropriate selection. An exemplary selective agent is the neomycin phosphotransferase II (nptII) marker gene, which is commonly used in plant biotechnology and confers resistance to the antibiotics kanamycin, G418 (geneticin) and paramomycin. In other species, or in certain plant tissues or when using particular selectable markers, homogeneous clones may not arise spontaneously under selection; in this case the clusters of modified cells can be manipulated to homogeneity using the visible marker genes present on the mini-chromosomes as an indication of which cells contain mini-chromosome DNA.

Regeneration of Modified Plants from Explants to Mature, Rooted Plants

For Sugarcane, regeneration of a whole plant typically occurs via an embryogenic step that is not necessary for plant species where shoot organogenesis is more efficient. The explant tissue is cultured on an appropriate media for embryogenesis, and the embryo is cultured until shoots form. The regenerated shoots are cultured in a rooting medium to obtain intact whole plants with a fully developed root system. These plants are potted in soil and grown to maturity in a greenhouse.

Generally, regeneration and tissue culture of Sugarcane plant parts and whole plants is challenging as Sugarcane produces phenolic compounds while in culture. The present invention provides for methods of culturing Sugarcane cells and tissues in media containing polyvinylpyrrolidone (PVP), as described in Example 4. The PVP acts as a sink for the phenolic compounds produced by Sugarcane and enhances callus growth during selection as well as facilitating callus and plantlet regeneration. Furthermore, generation of Sugarcane callus can be facilitated by delivering to the plant cells and/or tissues mini-chromosomes of the invention that contain auxin genes. The presence of the auxin genes will facilitate callus induction of the transformed tissue. The invention also provides for tissue culture methods which cycle between the liquid culture media and solid culture media in order to promote the frequency and the morphogenic competence of the regenerable Sugarcane callus.

For plants that develop through shoot organogenesis, regeneration of a whole plant involves culturing of regenerable explant tissues taken from sterile organogenic callus tissue, seedlings or mature plants on a shoot regeneration medium for shoot organogenesis, and rooting of the regenerated shoots in a rooting medium to obtain intact whole plants with a fully developed root system. These plants are potted in soil and grown to maturity in a greenhouse.

Explants are obtained from any tissues of a plant suitable for regeneration. Exemplary tissues include hypocotyls, internodes, roots, cotyledons, petioles, cotyledonary petioles, leaves and peduncles, prepared from sterile seedlings or mature plants.

Explants are wounded (for example with a scalpel or razor blade) and cultured on a shoot regeneration medium (SRM) containing Murashige and Skoog (MS) medium as well as a cytokinin, e.g., 6-benzylaminopurine (BA), and an auxin, e.g., α-naphthaleneacetic acid (NAA), and an anti-ethylene agent, e.g., silver nitrate ($AgNO_3$). For example, 2 mg/L of BA, 0.05 mg/L of NAA, and 2 mg/L of $AgNO_3$ can be added to MS medium for shoot organogenesis. The most efficient shoot regeneration is obtained from longitudinal sections of internode explants.

Shoots regenerated via organogenesis are rooted in a MS medium. Plants are potted and grown in a greenhouse to sexual maturity for seed harvest.

To regenerate a whole Sugarcane plant with a Sugarcane mini-chromosome, explants are pre-incubated for 1 to 7 days (or longer) on the shoot regeneration medium prior to bombardment with mini-chromosome (see below). Following bombardment, explants are incubated on the same shoot regeneration medium for a recovery period up to 7 days (or longer), followed by selection for transformed shoots or clusters on the same medium but with a selective agent appropriate for a particular selectable marker gene (described herein).

Method of Co-Delivering Growth Inducing Genes to Facilitate Isolation of Modified Plant Cell Clones Another method used in the generation of Sugarcane cell clones containing Sugarcane mini-chromosomes involves the co-delivery of DNA containing genes that are capable of activating growth of plant cells, or that promote the formation of a specific organ, embryo or plant structure that is capable of self-sustaining growth. In one embodiment, the recipient Sugarcane cell receives simultaneously the Sugarcane mini-chromosome and a separate DNA molecule encoding one or more growth promoting, organogenesis-promoting, embryogenesis-promoting or regeneration-promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes can be combined on the same molecule, or co-bombarded on separate molecules. Use of these genes can also be combined with application of plant growth regulator molecules into the medium used to culture the Sugarcane cells, or of precursors to such molecules that are converted to functional plant growth regulators by the plant cell's biosynthetic machinery, or by the genes delivered into the Sugarcane cell.

The co-bombardment strategy of Sugarcane mini-chromosomes with separate DNA molecules encoding plant growth regulators transiently supplies the plant growth regulator genes for several generations of Sugarcane cells following DNA delivery. During this time, the Sugarcane mini-chromosome may be stabilized by virtue of its Sugarcane centromere, but the DNA molecules encoding plant growth regulator genes, or organogenesis-promoting, embryogenesis-promoting or regeneration-promoting genes will tend to be lost. The transient expression of these genes, prior to their loss, may give the cells containing Sugarcane mini-chromosome DNA a sufficient growth advantage, or sufficient tendency to develop into plant organs, embryos or a regenerable cell cluster, to outgrow the non-modified cells in their vicinity, or to form a readily identifiable structure that is not formed by non-modified Sugarcane cells. Loss of the DNA molecule encoding these genes will prevent phenotypes from manifesting themselves that may be caused by these genes if present through the remainder of Sugarcane plant regeneration. In rare cases, the DNA molecules encoding plant growth regulator genes will integrate into the Sugarcane genome or into the Sugarcane mini-chromosome.

Alternatively the genes promoting plant cell growth may be genes promoting shoot formation or embryogenesis or giving rise to any identifiable organ, tissue or structure that can be regenerated into a Sugarcane plant. In this case, it may be possible to obtain embryos or shoots harboring Sugarcane mini-chromosomes directly after DNA delivery, without the need to induce shoot formation with growth activators supplied into the medium, or lowering the growth activator treatment necessary to regenerate Sugarcane plants. The advantages of this method are more rapid regeneration, higher transformation efficiency, lower background growth of non-modified tissue, and lower rates of morphologic abnormalities in the regenerated Sugarcane plants (due to shorter and less intense treatments of the tissue with chemical plant growth activators added to the growth medium).

Determination of Mini-Chromosome Structure and Autonomy in Sugarcane Adchromosomal Plants and Tissues The structure and autonomy of the Sugarcane mini-chromosome in modified Sugarcane plants and tissues can be determined by methods including but not limited to: conventional and pulsed-field Southern blot hybridization to genomic DNA from modified tissue subjected or not subjected to restriction endonuclease digestion, dot blot hybridization of genomic DNA from modified tissue hybridized with different mini-chromosome specific sequences, mini-chromosome rescue, exonuclease activity, PCR on DNA from modified tissues with probes specific to the mini-chromosome, or Fluorescence In Situ Hybridization to nuclei of modified cells. Table 3 below summarizes these methods.

TABLE 3

Examples of methods to determine mini-chromosome structure and autonomy

| Assay | Assay details | Potential outcome | Interpretation |
|---|---|---|---|
| Southern blot | Restriction digest of genomic DNA* compared to purified mini-C | Native sizes and pattern of bands | Autonomous or integrated via CEN fragment |
| | | Altered sizes or pattern of bands | Integrated or rearranged |
| CHEF gel Southern blot | Restriction digest of genomic DNA compard to purified mini-C | Native sizes and pattern of bands | Autonomous or integrated via CEN fragment |
| | | Altered sizes or pattern of bands | Integrated or rearranged |
| | Native genomic DNA (no digest) | Mini-C band migrating ahead of genomic DNA | Autonomous circles or linears present in plant |
| | | Mini-C band co-migrating with genomic DNA | Integrated |
| | | >1 mini-C bands observed | Various possibilities |
| Exonuclease assay | Exonuclease digestion genomic DNA followed by detection of circular mini-chromosome by PCR, dot blot, or restriction digest optional), electrophoresis and southern blot (useful for circular mini-chromosomes) | Signal strength close to that w/o exonuclease | Autonomous circles present |
| | | No signal or signal strength lower that w/o exonuclease | Integrated |
| Mini-chromosome rescue | Transformation of plant genomic DNA into *E. coli* followed by selection for antibiotic resistance genes on mini-C | Colonies isolated only from mini-C plants with mini-Cs, not from controls; mini-C structure matches that of the parental mini-C | Autonomous circles present, native mini-C structure |
| | | Colonies isolated only from mini-C plants with mini-Cs, not from controls; mini-C structure different from parental mini-C | Autonomous circles present, rearranged mini-C structure OR mini-Cs integrated via centromere fragment |

TABLE 3-continued

Examples of methods to determine mini-chromosome structure and autonomy

| Assay | Assay details | Potential outcome | Interpretation |
|---|---|---|---|
| | | Colonies observed both in mini-C-modified plants and in controls | Various possibilities |
| PCR | PCR amplification of various parts of the mini chromosome | All mini-c parts detected by PCR | Complete mini-C sequences present in plant |
| | | Subset of mini-c parts detected by PCR | Partial mini-C sequence present in plant |
| FISH | Detection of mini-chromosome sequences in mitotic or meiotic nuclei by fluorescence in situ hybridization | Mini-C sequences detected, free of genome | autonomous |
| | | Mini-C sequences detected, associated with genome | integrated |
| | | Mini-C sequences detected, both free and associated with genome | Both autonomous and integrated mini-C sequences present |
| | | No mini-C sequences detected | Mini-C DNA not visible by FISH |

*Genomic DNA refers to total DNA extracted from plants containing a mini-chromosome Furthermore, Sugarcane mini-chromosome structure can be examined by characterizing mini-chromosomes 'rescued' from Sugarcane adchromosomal cells. Circular Sugarcane mini-chromosomes that contain bacterial sequences for their selection and propagation in bacteria can be rescued from a Sugarcane adchromosomal plant or plant cell and re-introduced into bacteria. If no loss of these sequences has occurred during replication of the Sugarcane mini-chromosome in plant cells, the mini-chromosome is able to replicate in bacteria and confer antibiotic resistance. Total genomic DNA is isolated from the Sugarcane adchromosomal plant cells by any method for DNA isolation known to those skilled in the art, including but not limited to a standard cetyltrimethylammonium bromide (CTAB) based method (Current Protocols in Molecular Biology (1994) John Wiley & Sons, N.Y., 2.3). The purified genomic DNA is introduced into bacteria (e.g., E. coli) using methods familiar to one skilled in the art (for example heat shock or electroporation). The transformed bacteria are plated on solid medium containing antibiotics to select bacterial clones modified with Sugarcane mini-chromosome DNA. Modified bacterial clones are grown up, the plasmid DNA purified (by alkaline lysis for example), and DNA analyzed by restriction enzyme digestion and gel electrophoresis or by sequencing. Because plant-methylated DNA containing methylcytosine residues will be degraded by wild-type strains of E. coli, bacterial strains (e.g. DH10B) deficient in the genes encoding methylation restriction nucleases (e.g. the mcr and mrr gene loci in E. coli) are suitable for this type of analysis. Sugarcane mini-chromosome rescue can be performed on any plant tissue or clone of plant cells comprising a mini-chromosome.

Sugarcane Mini-Chromosome Autonomy Demonstration by in Situ Hybridization (ISH)

To assess whether the Sugarcane mini-chromosome is autonomous from the native Sugarcane chromosomes, or has integrated into the plant genome, In Situ Hybridization is carried out (Fluorescent In Situ Hybridization or FISH is particularly well suited to this purpose). In this assay, mitotic or meiotic tissue, such as root tips or meiocytes from the anther, possibly treated with metaphase arrest agents such as colchicines or nitrous oxide is obtained, and standard FISH methods are used to label both the Sugarcane centromere and sequences specific to the Sugarcane mini-chromosome. For example, a Sugarcane centromere is labeled using a probe from a sequence that labels all Sugarcane centromeres, attached to one fluorescent tag (Molecular Probes Alexafluor 568, for example), and sequences specific to the Sugarcane mini-chromosome are labeled with another fluorescent tag (Alexafluor 488, for example). All Sugarcane centromere sequences are detected with the first tag; only Sugarcane mini-chromosomes are detected with both the first and second tag. Chromosomes are stained with a DNA-specific dye including but not limited to DAPI, Hoechst 33258, OliGreen, Giemsa YOYO, and TOTO. An autonomous Sugarcane mini-chromosome is visualized as a body that shows hybridization signal with both Sugarcane centromere probes and Sugarcane mini-chromosome specific probes and is separate from the native Sugarcane chromosomes.

Determination of Gene Expression Levels

The expression level of any gene present on the Sugarcane mini-chromosome can be determined by methods including but not limited to one of the following. The mRNA level of the gene can be determined by Northern Blot hybridization, Reverse Transcriptase—Polymerase Chain Reaction, binding levels of a specific RNA-binding protein, in situ hybridization, or dot blot hybridization.

The protein level of the gene product can be determined by Western blot hybridization, Enzyme-Linked Immunosorbant Assay (ELISA), fluorescent quantitation of a fluorescent gene product, enzymatic quantitation of an enzymatic gene product, immunohistochemical quantitation, or spectroscopic quantitation of a gene product that absorbs a specific wavelength of light.

Use of Exonuclease to Isolate Circular Sugarcane Mini-Chromosome DNA from Sugarcane Genomic DNA Exonucleases may be used to obtain pure Sugarcane mini-chromosome DNA, suitable for isolation of Sugarcane mini-chromosomes from E. coli or from Sugarcane cells. The method assumes a circular structure of the Sugarcane mini-chromosome. A DNA preparation containing Sugarcane mini-chromosome DNA and Sugarcane genomic DNA from the source organism is treated with exonuclease, for example lambda exonuclease combined with E. coli exonuclease 1, or the ATP-dependent exonuclease (Qiagen Inc). Because the exonuclease is only active on DNA ends, it will specifically degrade the linear Sugarcane genomic DNA fragments, but will not affect the circular Sugarcane mini-chromosome DNA. The result is Sugarcane mini-chromosome DNA in pure form. The resultant Sugarcane mini-chromosome DNA can be detected by a number of methods for DNA detection known to those skilled in the art, including but not limited to PCR, dot blot followed by hybridization analysis, and southern blot followed by hybridization analysis. Exonuclease treatment followed by detection of resultant circular Sugarcane mini-chromosomes may be used as a method to determine Sugarcane mini-chromosome autonomy.

Structural Analysis of Sugarcane Mini-Chromosomes by BAC-End Sequencing

BAC-end sequencing procedures, known to those skilled in the art, can be applied to characterize Sugarcane mini-chromosome clones for a variety of purposes, such as structural characterization, determination of sequence content, and determination of the precise sequence at a unique site on the chromosome (for example the specific sequence signature found at the junction between a centromere fragment and the vector sequences). In particular, this method is useful to prove the relationship between a parental Sugarcane mini-chromosome and the mini-chromosomes descended from it and isolated from plant cells by mini-chromosome rescue, described above. This method also fosters identification of specific Sugarcane mini-chromosomes if more than one unique Sugarcane mini-chromosome is present in a plant cell simultaneously.

Methods for Scoring Meiotic Sugarcane Mini-Chromosome Inheritance

A variety of methods can be used to assess the efficiency of meiotic Sugarcane mini-chromosome transmission. In one embodiment of the method, gene expression of genes encoded by the Sugarcane mini-chromosome (marker genes or non-marker genes) can be scored by any method for detection of gene expression known to those skilled in the art, including but not limited to visible methods (e.g. fluorescence of fluorescent protein markers, scoring of visible phenotypes of the plant), scoring resistance of the Sugarcane plants or plant tissues to antibiotics, herbicides or other selective agents, by measuring enzyme activity of proteins encoded by the mini-chromosome, or measuring non-visible plant phenotypes, or directly measuring the RNA and protein products of gene expression using microarray, northern blots, in situ hybridization, dot blot hybridization, RT-PCR, western blots, immunoprecipitation, Enzyme-Linked Immunosorbant Assay (ELISA), immunofluorescence and radio-immunoassays (RIA). Gene expression can be scored in the post-meiotic stages of microspore, pollen, pollen tube or female gametophyte, or the post-zygotic stages such as embryo, seed, or progeny seedlings and plants. In another embodiment of the method, the Sugarcane mini-chromosome can be directly detected or visualized in post-meiotic, zygotic, embryonal or other cells by a number of methods for DNA detection known to those skilled in the art, including but not limited to fluorescence in situ hybridization, in situ PCR, PCR, southern blot, or by Sugarcane mini-chromosome rescue described above.

FISH Analysis of Sugarcane Mini-Chromosome Copy Number in Meiocytes, Roots or Other Tissues of Modified Sugarcane Plants The copy number of the Sugarcane mini-chromosome can be assessed in any cell or plant tissue by In Situ Hybridization (Fluorescent In Situ Hybridization or FISH is particularly well suited to this purpose). In an exemplary assay, standard FISH methods are used to label the Sugarcane centromere, using a probe which labels all Sugarcane chromosomes with one fluorescent tag (Molecular Probes Alexafluor 568, for example), and to label sequences specific to the Sugarcane mini-chromosome with another fluorescent tag (Alexafluor 488, for example). All Sugarcane centromere sequences are detected with the first tag; only Sugarcane mini-chromosomes are detected with both the first and second tag. Nuclei are stained with a DNA-specific dye including but not limited to DAPI, Hoechst 33258, OliGreen, Giemsa YOYO, and TOTO. Sugarcane mini-chromosome copy number is determined by counting the number of fluorescent foci per cell that label with both tags.

Induction of Callus and Roots from Modified Sugarcane Plant Tissues for Inheritance Assays Sugarcane mini-chromosome inheritance is assessed using callus and roots induced from transformed Sugarcane plants. To induce roots and callus, tissues such as leaf pieces are prepared from adchromosomal Sugarcane plants and cultured on a Murashige and Skoog (MS) or Chus's N6 (N6) medium that may contain a cytokinin, e.g., 6-benzylaminopurine (BA), and an auxin, e.g., α-naphthaleneacetic acid (NAA). Any tissue of a modified Sugarcane plant can be used for callus and root induction, and the medium recipe for tissue culture can be optimized using procedures known in the art.

Clonal Propagation of Modified Sugarcane Plants

To produce multiple clones of plants from a mini-chromosome-transformed Sugarcane plant, any tissue of the plant can be tissue-cultured for shoot organogenesis using regeneration procedures described herein for regeneration of plants from explants. Alternatively, multiple auxiliary buds can induced from a mini-chromosome-modified Sugarcane plant by excising the shoot tip, which can be rooted and subsequently be grown into a whole plant; each auxiliary bud can be rooted and produce a whole plant. Additionally, multiple shoots that result from one plant can be subdivided in culture to produce multiple individual plants.

Scoring of Antibiotic- or Herbicide Resistance in Seedlings and Plants (Progeny of Self- and Out-Crossed Transformants)

Progeny seeds harvested from Sugarcane plants comprising a mini-chromosome can be scored for antibiotic- or herbicide resistance by seed germination under sterile conditions on a growth media (for example Murashige and Skoog (MS) medium) containing an appropriate selective agent for a particular selectable marker gene. Only seeds containing the Sugarcane mini-chromosome can germinate on the medium and further grow and develop into whole plants. Alternatively, Sugarcane seeds can be germinated in soil, and the germinating seedlings can then be sprayed with a selective agent appropriate for a selectable marker gene. Sugarcane seedlings that do not contain a Sugarcane mini-chromosome do not survive; only seedlings containing a mini-chromosome can survive and develop into mature plants.

Genetic Methods for Analyzing Sugarcane Mini-Chromosome Performance:

Though Sugarcane is typically propagated vegitatively, it is possible to use sexual propagation techniques as well. In addition to direct transformation of a Sugarcane plant with a Sugarcane mini-chromosome, Sugarcane plants containing a Sugarcane mini-chromosome can be prepared by crossing a first Sugarcane plant containing the functional, stable, autonomous Sugarcane mini-chromosome with a second Sugarcane plant lacking the Sugarcane mini-chromosome.

Fertile Sugarcane plants comprising Sugarcane mini-chromosomes can be crossed to other Sugarcane plant lines to study mini-chromosome performance and inheritance. In the first embodiment of this method, pollen from an adchromosomal Sugarcane plant can be used to fertilize the stigma of a non-adchromosomal Sugarcane plant. Sugarcane mini-chromosome presence is scored in the progeny of this cross using the methods outlined in the preceding section. In the second embodiment, the reciprocal cross is performed by using pollen from a non-adchromosomal Sugarcane plant to fertilize the flowers of an adchromosomal Sugarcane plant. The rate of Sugarcane mini-chromosome inheritance in both crosses can be used to establish the frequencies of meiotic inheritance in male and female meiosis. In a third embodiment of this method, pollen for an adchromosomal plant is used to fertilize another or the same adchromosomal plant (e.g. self or sibling pollination). In the fourth embodiment of this method, the progeny of one of the crosses just described are back-crossed to a non-adchromosomal Sugarcane parental line, and the progeny of this second cross are scored for the presence of genetic markers in the plant's natural chromosomes as well as the Sugarcane mini-chromosome. Scoring of a sufficient marker set against a sufficiently large set of progeny allows the determination of linkage or co-segregation of the Sugarcane mini-chromosome to specific chromosomes or chromosomal loci in the plant's genome. Genetic crosses performed for testing genetic linkage can be done with a variety of combinations of parental lines; such variations of the methods described are known to those skilled in the art.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

EXAMPLE 1

Sugarcane Centromere Discovery from Genomic DNA

Identification of Sugarcane Satellite Repeat Sequences

Centromere satellite repeats were amplified from Sugarcane (*Saccharum officinarum* X *Saccharum spontaneum* or *Saccharum officinarum*) genomic DNA using standard PCR methods. Briefly, PCR reaction was carried under the following conditions: 1 cycle at 95° C. for 3 minutes, 10 cycles of 94° C. for 15 seconds, 55° C. for 15 seconds, and 72° C. for 30 seconds, and 25 cycles at 94° C. for 15 seconds, 52 DC for 15 seconds and 72° C. for 30 seconds, followed by 1 cycle at 72° C. for 5 minutes. The sequences of primers used for amplifying satellite repeats were: forward: 5'-gtcacccagcagttc-catcgggtgc-3' (SEQ ID NO: 205 and reverse: 5'-actgctgggt-gacgtggetcaagt-3' (SEQ ID NO: 206). After PCR, amplified satellite repeats were cloned into a standard cloning vector (pCR2; Invitrogen Corp.; Carlsbad, Calif.; USA). Colonies with insertions were cultured, DNA was extracted and sequenced. This PCR analysis identified 201 satellite sequences, set out at SEQ ID NOS: 1-201.

To determine the consensus of the identified satellite repeat sequences, these sequences were aligned using a DNA sequence alignment program (CONTIGEXPRESS® from VECTOR NTI®(Invitrogen)). The sequences were trimmed to unit repeat length using the consensus as a template. Sequences trimmed from the ends of the alignment were realigned with the consensus and further trimmed until all sequences were at or below the consensus length. The consensus was determined by the frequency of a specific nucleotide at each position; if the most frequent base is three times more frequent than the next most frequent base, it was considered the consensus.

The Sugarcane centromere specific retrotransposon sequence CRS (Centromere Retrotransposon in Sugarcane—see Nagaki & Murata, *Chromosome Research*, 2005, 13:195-203) was PCR amplified and sequenced using primers located in different region of the CRS sequence. The PCR reaction was carried out as described above using the following primer sequences:

```
                                       (SEQ ID NO: 207)
CRSF  5'-gggaagtaca gggacgaaga gc-3'

(SEQ ID NO: 208)
CRSF15'-actaacaatg cacgggaagg-3'

(SEQ ID NO: 209)
CRSF25'-gtaggccatg gcagtttgat-3'

(SEQ ID NO: 210)
CRSF35'-aacacaccac ccaatccaat-3'

(SEQ ID NO: 211)
CRSF45'-ccaaacaagc gtgttatgat tgt-3'

(SEQ ID NO: 212)
CRSF55'-aggttatgtg cgtcagtctc ttag-3'

(SEQ ID NO: 213)
CRSF65'-ggcaaacctg ttgcatactt tag-3'

(SEQ ID NO: 214)
CRSF75'-accatgtcat aaaactgatg atg-3'

(SEQ ID NO: 215)
CRSR  5'-tgcaaccaaa ccaaatcacc ag-3'

(SEQ ID NO: 216)
CRSR15'-caagcgaaca atctcacgaa-3'

(SEQ ID NO: 217)
CRSR25'-aaatcatcat cgtgcgcata-3'

(SEQ ID NO: 218)
CRSR35'-aacacaccac ccaatccaat-3'

(SEQ ID NO: 219)
CRSR45'-gaacgctcct tgatgacac-3'

(SEQ ID NO: 220)
CRSR55'-gtacccacta cgcaaatcaa cc-3'

(SEQ ID NO: 221)
CRSR65'-caacttcagt ttgaccatca gtt-3'
The sequence for CRS is set out as SEQ ID NO:
203. The primer pairs CRSF
5'-gggaagtacagggacgaagagc-3' (SEQ ID NO:
207) and CRSR 5'-tgcaaccaaaccaaatcaccag-3'
(SEQ ID NO: 215) can be used to amplify
CRS from Sugarcane genomic DNA.
```

BAC Library Construction

A Bacterial Artificial Chromosome (BAC) library was constructed from Sugarcane genomic DNA. The Sugarcane genomic DNA was isolated from cultivar R570 (PI 504632), a hybrid between *S. officinarum* and *S. spontaneum*, and digested with the restriction enzymes Mbo I. These enzymes were chosen because they are methylation insensitive and therefore can be used to enrich BAC libraries for centromere DNA sequences.

Probe Identification and Selection

Three groups of Sugarcane repetitive genomic DNA, including specific centromere-localized sequences, were initially compiled as candidate probes for hybridization with the BAC libraries. Four probes were picked to interrogate the BAC libraries. These probes represent different groups of commonly found repetitive sequences in the Sugarcane genome. The four probes were: SCEN, SCRM and High Me/Low Methylation (HiMe and LoMe). The SCEN and SCRM probes were each pooled PCR products. Probes were prepared and labeled with standard molecular methods. The HiMe and LoMe probes were pooled genomic DNA cut with a methylation-sensitive enzyme (BfuC1); large DNA fragments were isolated for the "HighMe" probe and small DNA fragments were isolated for the "LowMe" probe. Positives reported are for the HighMe probe.

Library Interrogation and Data Analysis

The BAC clones from the libraries were spotted onto filters for further analysis. The filters were hybridized with each of the probes to identify specific BAC clones that contain DNA from the group of sequences represented by the probes. Hybridization conditions were: hybridization at 65° C. for 12-15 hours and washing three times for 15-90 minutes with 0.25×SSC, 0.1% SDS at 65° C. Other exemplary stringent hybridization conditions could be used, such as hybridization at 65° C. 0.5×SSC 0.25% SDS for 15 minutes, followed by a wash at 65° C. for a half hour.

A total of 18,453 BAC clones from the library was interrogated with each of the 4 probes (SCEN, SCRM, HiMe, and LoME), and the hybridization intensities of the BAC clones with each probe were examined to quantify hybridization intensity for each clone. Scores of 1 to 10 (based on the hybridization intensities, with 10 being the strongest hybridization) were assigned and entered into a spreadsheet for classification. The spreadsheet contained a total of 3 tables, 1 for each probe used in the interrogation (values from HiMe and LoMe) probes were entered in a single table for comparison. Each table contained the hybridization scores of each BAC clone from the Mbo I library, to one of the 4 probes. Data analysis found BACs that contained different groups of repetitive sequences.

Classification and Selection of BAC Clones for Mini-Chromosome Construction

BAC clones containing centromeric/heterochromatic DNA were identified by their visual hybridization scores to different probes. The goal was to select BAC clones that contained a diverse set of various repetitive sequences. Seven classes of centromeric BAC clones were eventually chosen to cover the broadest possible range of centromeric/heterochromatic sequences for Sugarcane mini-chromosome (MC) construction. 658 unique clones that hybridize with one or more of the probes were isolated from one filter, which comprised 18,432 clones. They fell into classes as set out in Table 4 below.

TABLE 4

Classification of Centromere containing BACs

| | Probe Hybridization Range | | | |
|---|---|---|---|---|
| Class | SCEN | SCRM | HiMe | # clones identified |
| I | + | | | 472 |
| II | | + | | 360 |
| III | | | + | 398 |
| IV | + | + | | 219 |
| V | + | | + | 343 |
| VI | | + | + | 166 |
| VII | + | + | + | 156 |

* Probes with significant hybridization signals as determined by visual scoring are indicated with a "+"

EXAMPLE 2

Construction of Sugarcane MCs Containing Genomic DNA

A subset of BAC clones identified in Example 1 were grown, and DNA was extracted for MC construction using a NUCLEOBOND® purification kit from Clontech Laboratories, Inc. (Mountain View, Calif.; USA). To determine the molecular weight of centromere fragments in the BAC libraries, a frozen sample of bacteria harboring a BAC clone was grown in selective liquid media, and the BAC DNA harvested using a standard alkaline lysis method. The recovered BAC DNA was restriction digested and resolved on an agarose gel. Centromere fragment size was determined by comparing to a molecular weight standard.

Donor DNA Containing Gene Stacks for MC Construction

Several donor DNA plasmids containing gene stacks for testing of MCs in plant tissues were built, varying depending on the specific fluorescent protein marker used for detection of transgenic events. One set of MCs was built that contained the gene stack from donor plasmid CHROM5798, which genetic elements are set out in Table 5. Another set of MCs was built that contained the gene stack from donor plasmid CHROM5434, which genetic elements are the same as in donor plasmid CHROM5798 except that the nuclear localized GFP gene was replaced with an AmCyan (Clontech) fluorescent protein gene. Another set of MCs was built that contained the gene stack from donor plasmid CHROM5436, which genetic elements are the same as in donor plasmid CHROM5798, except that the nuclear localized GFP gene was replaced with a ZsGreen (Clontech) fluorescent protein gene.

TABLE 5

Donor Components of CHROM5798

| Genetic Element | Size (bp) | Location (bp) | Details |
|---|---|---|---|
| YAT1 yeast promoter | 2000 | 6271-8270 | PCR amplified YAT1 promoter from chromosome I of *Saccharomyces cerevisiae* for expression of NptII in Sugarcane |
| Arabidopsis UBQ10 Intron | 360 | 5898-6257 | PCR amplified *Arabidopsis thaliana* intron from UBQ10 gene (At4g05320) for stabilization of NptII gene transcript and increase protein expression level |
| NPTII | 795 | 5076-5870 | Neomycin phosphotransferase II plant selectable marker |
| Rps16A terminator | 489 | 4524-5012 | Amplified from *Arabidopsis thaliana* 40S ribosomal protein S16 (At2g09990) for termination of NptII gene |
| Bacterial kanamycin | 817 | 3525-4341 | Bacterial kanamycin selectable marker |
| Terminator 6 | 332 | 3049-3380 | Terminator 6 |
| AcGFP (nuc) | 831 | 2084-2914 | Nuclear localized green fluorescent protein. |
| UBQ10 Promoter | 2038 | 10-2047 | PCR amplified *Arabidopsis thaliana* promoter from UBQ10 gene (At4g05320) for stabilization of DsRedI gene transcript and increase protein expression level |
| LoxP | 34 | 8290-8319 and 10802-10831 | Recombination site for Cre mediated recombination (Arenski et al 1983, Abremski et at 1984) |

Preparation of Donor DNA for RetroFitting

Cre recombinase-mediated exchange was used to construct Sugarcane MCs by combining the Sugarcane centromere fragments cloned in pBeloBAC11 with the donor plasmid CHROM5798 (Table 5). The recipient BAC vector carrying the Sugarcane centromere fragment contained a loxP recombination site; the donor plasmid contained two such sites, flanking the sequences to be inserted into the recipient BAC.

Sugarcane MCs were constructed using a two-step method. First, the donor plasmid was linearized to allow free contact between the two loxP sites; in this step the backbone of the donor plasmid is eliminated. In the second step, the donor molecules were combined with Sugarcane centromere BACs and were treated with Cre recombinase, generating circular Sugarcane MCs with all the components of the donor and recipient DNA. Sugarcane MCs were delivered into *E. coli* and selected on medium containing kanamycin and chloramphenicol. Only vectors that successfully cre recombined and contained both selectable markers survived in the medium. To determine the molecular weight of the Sugarcane centromere fragments in the Sugarcane MCs, three bacterial colonies from each transformation event were independently grown in selective liquid media and the Sugarcane MC DNA was harvested using a standard alkaline lysis method. The recovered Sugarcane MC was restriction digested and resolved on an agarose gel. Sugarcane centromere fragment size was determined by comparison to molecular weight standards. When variation in Sugarcane centromere size was noted, the Sugarcane MC with the largest Sugarcane centromere insert was used for further experimentation. All 84 MCs subjected to further testing had the features described in Table 6.

TABLE 6

MC constructs tested in sugarcane callus

| MC CHROM# | BAC name | Strength of Satellite signal | Strength of CRS signal | Strength of FISH signal | Original CEN fragment size (KB) | Donor plasmid CHROM# |
|---|---|---|---|---|---|---|
| 5800 | 3G17 | L | L | n/a | 90 | 5798 |
| 5801 | 5B12 | H | N | good | 115 | 5798 |
| 5802 | 18E23 | H | M | good | 80 | 5798 |
| 5803 | 19H6 | M | H | good | 102 | 5798 |
| 5804 | 24L19 | L | M | good | 35 | 5798 |
| 5805 | 21L3 | M | M | good | 120 | 5798 |
| 5806 | 4H1 | M | N | good | 90 | 5798 |
| 5807 | 3O5 | M | H | good | 100 | 5798 |
| 5808 | 1K10 | L | H | good | 150 | 5798 |
| 5809 | 17H17 | H | H | good | 110 | 5798 |
| 5810 | 21A4 | H | H | good | 150 | 5798 |
| 5811 | 18F12 | H | H | good | 110 | 5798 |
| 5812 | 20H10 | H | H | n/a | 150 | 5798 |
| 5813 | 21B1 | H | H | good | 130 | 5798 |
| 5814 | 24J1 | H | H | good | 65 | 5798 |
| 5815 | 19J18 | H | H | good | 100 | 5798 |
| 5816 | 17B4 | H | L | good | 70 | 5798 |
| 5817 | 18P24 | H | L | good | 120 | 5798 |
| 5818 | 20A3 | H | L | n/a | 160 | 5798 |
| 5819 | 24F15 | H | L | n/a | 120 | 5798 |
| 5820 | 17C9 | H | M | good | 125 | 5798 |
| 5821 | 19J8 | H | N | n/a | 120 | 5798 |
| 5822 | 18C14 | H | N | good | 130 | 5798 |
| 5823 | 17P2 | H | N | good | 110 | 5798 |
| 5824 | 17M9 | H | N | good | 150 | 5798 |
| 5825 | 24J17 | H | N | n/a | 170 | 5798 |
| 5826 | 24C6 | H | N | good | 75 | 5798 |
| 5827 | 3I9 | L | H | good | 120 | 5798 |
| 5828 | 22H16 | L | H | n/a | 135 | 5798 |
| 5829 | 6C15 | L | H | good | 70 | 5798 |
| 5830 | 20C8 | L | L | good | 90 | 5798 |
| 5831 | 19K22 | L | M | n/a | 105 | 5798 |
| 5832 | 17E7 | L | M | good | 105 | 5798 |
| 5833 | 24M21 | L | M | n/a | 130 | 5798 |
| 5834 | 18J2 | M | H | good | 105 | 5798 |
| 5835 | 17N22 | M | H | n/a | 145 | 5798 |
| 5836 | 7E2 | M | H | good | 230 | 5798 |
| 5837 | 1L6 | M | H | n/a | 90 | 5798 |
| 5838 | 1P13 | M | H | good | 90 | 5798 |
| 5839 | 4H14 | M | L | good | 70 | 5798 |
| 5840 | 17E9 | M | L | n/a | 110 | 5798 |
| 5841 | 3P16 | M | L | good | 100 | 5798 |
| 5842 | 22I13 | M | L | n/a | 130 | 5798 |
| 5843 | 23F24 | M | L | n/a | 90 | 5798 |
| 5844 | 1K6 | M | L | good | 80 | 5798 |
| 5845 | 1P14 | M | L | good | 135 | 5798 |
| 5846 | 19H7 | M | M | n/a | 150 | 5798 |
| 5847 | 18F16 | M | M | n/a | 160 | 5798 |
| 5848 | 22D19 | M | M | n/a | 100 | 5798 |
| 5849 | 6C9 | M | M | n/a | 120 | 5798 |
| 5850 | 23I19 | M | N | good | 65 | 5798 |
| 5851 | 3F1 | M | N | n/a | 75 | 5798 |
| 5852 | 2A7 | M | N | n/a | 75 | 5798 |
| 5853 | 20A22 | N | N | none CEN | 100 | 5798 |
| 5854 | 19A22 | N | N | n/a | 115 | 5798 |
| 5855 | 17A22 | N | N | n/a | 120 | 5798 |
| 5856 | 21A22 | N | N | none CEN | 80 | 5798 |
| 5857 | 18A22 | N | N | n/a | 120 | 5798 |
| 5858 | 1A4 | L | H | n/a | 65 | 5798 |
| 5859 | 1M10 | N | N | n/a | 110 | 5798 |
| 5860 | 7D11 | M | M | n/a | 80 | 5798 |
| 5861 | 7J24 | M | L | n/a | 100 | 5798 |
| 5862 | 1P1 | H | L | n/a | 125 | 5798 |
| 5863 | 21B11 | H | N | good | 150 | 5798 |
| 5864 | 8O2 | M | L | good | 70 | 5798 |
| 5865 | 8I7 | M | H | good | 135 | 5798 |
| 5866 | 17H17 | H | H | good | 110 | 5434 |
| 5867 | 21A4 | H | H | good | 140 | 5434 |
| 5868 | 19J18 | H | H | good | 95 | 5434 |
| 5869 | 18P24 | H | L | good | 120 | 5434 |
| 5870 | 17C9 | H | M | good | 120 | 5434 |
| 5871 | 18E23 | H | M | good | 85 | 5434 |
| 5874 | 4H14 | M | L | good | 85 | 5434 |
| 5876 | 17P2 | H | N | good | 100 | 5434 |
| 5878 | 6C15 | L | H | good | 80 | 5434 |
| 5881 | 17C9 | H | M | good | 120 | 5436 |
| 5882 | 17P2 | H | N | good | 100 | 5436 |
| 5883 | 4H14 | M | L | good | 85 | 5436 |
| 5884 | 18E23 | H | M | good | 85 | 5436 |
| 5885 | 6C15 | L | H | good | 80 | 5436 |
| 5886 | 18P24 | H | L | good | 120 | 5436 |
| 5887 | 19J18 | H | H | good | 95 | 5436 |
| 5888 | 21A4 | H | H | good | 140 | 5436 |
| 5889 | 17H17 | H | H | good | 110 | 5436 |

H indicates high hybridization signal in the original filter hybridization,
M indicates medium signal, and
L indicates low signal.
N indicates no signal was observed.
In column labeled "Strength of FISH signal," "good" indicates strong hybridization to centromeres observed in root tip spread, n/a indicates "not determined," and "none CEN" means no hybridization was observed to the centromeric region of any chromosomes.

EXAMPLE 3

MC Delivery into Sugarcane Cells and Regeneration

The Sugarcane MCs from Example 2 were tested in several Sugarcane cells, including *Saccharum officinarum* and a hybrid between *S. officinarum* and *S. spontaneum*, and the procedure was optimized for antibiotic selection, cell pretreatments, and bombardment conditions. MCs were tested both in leaf-roll tissue directly, or callus tissue that was initiated from leaf-rolls. The presence of MCs was determined both by direct molecular assays or indirect measurement of fluorescent cells. Preliminary results identified several MCs that successfully generated fluorescent cell clusters in *Saccharum* cells.

Sugarcane Transformation, Selection and Regeneration.

Prior to delivery of the two-gene stack containing MCs from Example 2, Sugarcane callus was initiated from leaf roll tissue. Sugarcane tops were collected from greenhouse-grown plants for preparing explants. The Sugarcane tops (minimally 3-6 months old) were cut below the highest visible node. The older leaves (approx 3-4) were removed until the internode was visible and cut about 2" below this internode, and disinfected by submerging in 20% bleach for 20 min (5-10 tops in 3 L bleach solution). Subsequently, the cane tops were rinsed with sterile distilled water 3-4 times to remove excess bleach. In a tissue culture hood, more external leaves were removed from the cane tops, and the top portion was cut off leaving about 10 to 12 cm above the internode and 1 cm below the internode. Thin stem sections (approx 1 to 1.5 mm thickness) were sliced From the lower edge of the internodes. During this process, tools were frequently dipped in antioxidant mixture (PhytoTechnology Laboratories; Shawnee Mission, Kans.; USA) to avoid browning at cut sites. Those sections with orange centers were avoided, and only those sections with green centers were used for callus induction. Approximately 9 pieces of thin stem sections were placed per plate on MS3 Medium (Murashige and Skoog, 1962. *Physiologia Plantarum*, 15:472-497), supplemented with 500 mg/L casein hydrolysate, 20 g/L sucrose and 3 mg/L 2,4-D, pH to 5.8 and solidified with 2.5 g/L GELRITE® (Sigma-Aldrich; Saint Louis, Mo.; USA) or 6 g/L Phytoblend (Caisson Laboratories; North Logan, Utah; USA). The callus was sub-cultured once after a 15-day interval onto the same medium or MS1 (MS1; 4.3 g/l MS salts and vitamins supplemented with 20 g/l sucrose, 0.5 g/l casein, 1 mg/l 2,4-D, pH to 5.8) medium. Callus was generally sufficiently established for bombardment after 2-3 months. Prior to bombardment with MCs, the white, nodular and embryogenic calli were subcultured for 3-4 days on MS3 Medium, and then transferred onto Sugarcane Osmotic Medium (SCOM) prior to bombardment (4-5 hours at 28° C.). Sugarcane Osmotic Medium consists of MS3 medium supplemented with 500 mg/L casein hydrolysate, 20 g/L sucrose and 3 mg/L 2,4-D. pH to 5.8 and solidify with 2.5 g/L GELRITE® or 6 g/L Phytoblend with the addition of 36.4 g/L sorbitol, and 36.4 g/L mannitol.

Precipitation of MC DNA onto gold particles for the purpose of delivery using the biolistic method was performed as follows: 1.8 mg of sterile, washed gold (0.6 µM. diameter was preferred) was combined with desired amount of MC DNA (in 1×TE). Careful handling of DNA was critical; wide bore tips were used for all pipetting, and solutions were preferentially dispensed into the bottom of the tube to assist with the gentle mixing process. The volume was brought to 250 µl with cold (4° C.) sterile water and 250 µl of cold (4° C.) 2.5M $CaCl_2$ was added immediately, followed by addition of 50 µl of filter sterilized 0.1M Spermidine (free base, filter sterilized). The mixture was gently finger vortexed 1-2× to ensure even mixing of all solutions, and DNA was allowed to precipitate onto the gold particles on ice for 1.5 hours; with finger vortexing 1-2× after 45 min. The gold/DNA mixture was pelleted (5 min, 800 rpm, RT) and washed once with 100% ethanol, and 36 µl 100% ethanol was added to the gold/DNA pellet, and mixed gently. Typically 6 µl of gold/DNA/ethanol was used per macrocarrier (i.e., one bombardment shot). The absolute number of molecules delivered per shot was varied by precipitating a varying amount of DNA onto the gold particles.

Bombardment conditions using the BioRad PDS-1000/He biolistic transformation system Bio-Rad Laboratories; Hercules, Calif.) were as follows. A rupture disk rating of 900-1800 psi; 1100 or 1300 psi was preferred, with one shot per plate. The preferred gap distance (distance from rupture disk to macrocarrier) was 6 mm. The target shelf for tissue was L2-L4; L2 (3rd shelf from the bottom) was preferred. Vacuum pressure of 27.5-28 in Hg; 27.5 in Hg was preferred. These bombardment conditions were tested with R570 callus, other conditions (pressure, rupture disk rating, gap distance, target shelf, duration of osmotic and rest treatments, etc.) can of course be modified for other genotypes and/or tissues. Following bombardment, callus was allowed to recover at 28° C. in the dark for an additional 12-18 hours on SCOM. Tissues were transferred onto MS3 medium for recovery for 3-4 days, and the number of calli present on each plate used for bombardment was counted. At the end of the recovery period, calli were checked for transient expression of fluorescent marker genes under the microscope, and the transient transformation efficiency was calculated.

Transient expression of MC encoded green fluorescent protein (GFF) gene AcGFPnuc was demonstrated in Sugarcane (cv. L97-128) callus induced from immature leaf tissue. Approximately $2.5 \times 10^9$ DNA molecules for 9 different MC DNAs were delivered into the callus tissues 4 hours after osmotic treatment per plate, and the bombarded tissues were examined for GPF expression 4 days later. The results are summarized in Table 7. Calli expressing GFP were observed in 6 out of the 9 MCs delivered in this experiment, with a frequency ranging from 1.7% for MC CHROM5889 to 20% for MC CHROM5886. However, no GFP expressing calli were observed for 3 MC constructs. These results demonstrated that MC DNA had been successfully delivered into sugarcane callus cells and the MC encoded fluorescent protein gene AcGFPnuc was expressed and biologically functional.

TABLE 7

Transient expression of AcGFPbuc in Sugarcane MC containing transgenic callus

| MC # | BAC Cen | # of plates observed | # of calli observed | # of calli expressing GFP | % GFP expressing callus |
|---|---|---|---|---|---|
| 5881 | 17C9 | 7 | 140 | 5 | 3.6 |
| 5882 | 17P2 | 9 | 92 | 4 | 4.3 |
| 5883 | 4H14 | 12 | 136 | 0 | 0.0 |
| 5884 | 18E24 | 12 | 140 | 6 | 4.3 |
| 5885 | 6C15 | 10 | 120 | 3 | 2.5 |
| 5886 | 18P24 | 4 | 60 | 12 | 20.0 |
| 5887 | 19J18 | 5 | 82 | 0 | 0.0 |
| 5998 | 21A4 | 5 | 94 | 0 | 0.0 |
| 5889 | 17H17 | 6 | 120 | 2 | 1.7 |

For selection of transgenic events, bombarded calli were transferred onto sub-lethal selection medium (ChromMS3G30), and culture at 28° C., in the dark, for 2 weeks. ChromMS3G30 medium consists of MS3 medium supplemented with 30 mg/l G418 sulfate (Geneticin (Sigma)) after autoclaving. The calli were broken up into small pieces and transferred onto lethal selection medium (second round of selection) MS3G50, and culture at 28° C., in the dark, for 4 weeks. MS3G50 Medium consists of MS3 medium supplemented with 50 mg/l G418 sulfate after autoclaving. Tissue growth was visually assessed to identify resistant callus. Resistant earn were subcultured for another round of selection on ChromMS3G50 for an additional 4 weeks.

For plant regeneration, surviving calli (putative resistant calli) were transferred onto RSCG25 medium to initiate regeneration and were cultured at 26° C., low light (16 hour day length, 26° C.) for 3-4 weeks. RSCG25 Medium consists of MS3 medium supplemented with 500 mg/L casein hydrolysate, 20 g/L sucrose and 0.5 mg/L kinetin, pH to 5.8 and solidified with 2.5 g/L GELRITE®, and further supplemented with 25 mg/L G418 sulfate after autoclaving. Developing plantlets were transferred to RtSC medium in sundae cups (Solo Cup Company; Lake Forest, Ill.; USA) for plantlet growth and root development and cultured at 26° C., 16 hour day length. RtSC medium consists of MS medium supplemented with 25 g/L sucrose, pH to 5.8 and solidify with 2.5 g/L GELRITE®, further supplemented with 20 mg/L G418 sulfate after autoclaving. Finally, plantlets were transferred into pre-moistened soil-less mix (LC1, BFG Supply Company; Joliet, Ill.; USA) under a humidome in an 18-well flat in a growth chamber (28° C., 16 hour day length). The dome was cracked open slightly to slowly reduce humidity 3-4 days after transplanting. The dome was removed completely 2 days later and plantlets were transferred to a greenhouse (28° C., 16 hour day length). Plants were watered from trays beneath the pots when the soil began to dry.

Identification of MC Containing Transgenic Events

More than 1200 putative transgenic Sugarcane events were generated from mini-chromosome transformation. A total of 920 (~76%) of putative transgenic calli events were analyzed using diagnostic PCR for the several DNA fragments carried on the gene stack. The presence or absence of the nptII, AcGFPnuc or ZsGreen (depending on the mini-chromosome used in transformation), and the ubiquitin (UBQ10) promoter was determined and compared to amplification of the endogenous genomic internal control ADH. The events thus screened cover a collection of 51 MCs with an average size ranging between 65 and 187 kb. Transgenic events were derived from the bombardment of six different sugarcane genotypes (R570, L97-128, Q117, NCo310, Pindar and Q63). Of the 920 events, 33% were derived from the callus bombarded with the DNA concentration of $1\times10^9$ molecules (90-200 ng of DNA) per shot, 8.7% from $2.5\times10^9$ molecules (200-500 ng of DNA), 37.6% from $5\times10^9$ molecules (450 ng-1 µg of DNA) and 6.2% from $1\times10^{10}$ molecules (800 ng-1.2 µg of DNA) per shot. The putative transgenic events were obtained after selecting the bombarded calli on different levels of G418 concentration ranging from 22.5 mg to 50 mg/l (100% potency) for a period of 4-5 months with a minimum of 4 rounds of selection. For PCR screening, total genomic DNA was isolated from approximately 40-60 mg of callus tissue by the DNA preparation method of Krysan et al, (Krysan P H, Young J C, Tax F, Sussman M R (1996) Identification of transferred DNA insertions within *Arabidopsis* genes involved in signal transduction and ion transport. *Proc Natl Acad Sci USA* 93: 8145-8150). The concentration of DNA was measured, normalized uniformly and used for either single-step or multiplex PCR analysis. The optimized PCR conditions, primers and reagents that were used for detecting the 4 PCR fragments in all the calli events generated is as follows.

Single-step PCR conditions used an initial denaturation at 95° C. for 2 minutes, followed by 35 cycles each consisting of 0.3 minutes denaturation at 94° C., 0.3 minutes annealing at 52° C., and 1.2 minutes extension at 72° C., followed by a final extension for 4 minutes at 72° C., after which the samples were kept at 4° C. indefinitely. The PCR reaction was performed in a total volume of 25 µl, consisting of 19.2 µl water, 2.5 µl 10×NEB Buffer, 0.4 µl dNTP mix (40 Mm), 0.2 µl F-Primer (20 µM), 0.2 µl R-primer (20 µM), 0.50.2 µl NEB Taq Polymerase and 2 µl DNA (100-200 ng). Multiplex PCR conditions used an initial denaturation at 95° C. for 1 minutes, followed by 40 cycles each consisting of 0.1 minutes denaturation at 95° C., 0.1 minutes annealing at 55° C. (and increasing 0.1° C. with each subsequent cycle), and 1.5 minutes extension at 72° C., followed by a final extension for 5 minutes at 72° C., after which the samples were kept at 4° C. indefinitely. The PCR reaction was performed in a total volume of 25 µl, consisting of 15 µl water, 5 µl 5× Multiplex Master Mix (New England Biolabs; Ipswich, Mass.; USA), 2 µl F-Primer (20 µM), 2 µl R-primer (20 µM), and 1µl DNA (100-200 ng). The expected PCR product sizes were 470 bp (ADH), 662 bp (AcGFPnuc), 886 bp (UBQ10),1000 bp (nptII), and 924 bp (ZsGreen). The PCR reaction was carried out as described above using the following primer sequences:

```
                                        (SEQ ID NO: 242)
ADH1      CHSL-285 5'-aagtcggcag agagcaacat-3'

(SEQ ID NO: 243)
ADH1      CHSL-286 5'-cagatgcaaa cccaacacac-3'

(SEQ ID NO: 244)
AcGFPnuc  CHSL-132 5'-cgattttctg ggtttgatcgtt ag-3'

(SEQ ID NO: 245)
AcGFPnuc  CHSL-199 5'-cattgtgggc gttgtagttg-3'

(SEQ ID NO: 246)
UBQ10     CHSL-468 5'-gttgtggttg gtgctttcct-3'

(SEQ ID NO: 247)
UBQ10     CHSL-469 5'-ccactttgac gccgtttatt-3'

(SEQ ID NO: 248)
NPTII     CHSL-132 5'-cgattttctg ggtttgatcgtt ag-3'

(SEQ ID NO: 249)
NPTII     CHND7    5'-gaactcgtca agaaggcgata-3'

(SEQ ID NO: 250)
ZsGreen   CHSL-132 5'-cgattttctg ggtttgatcgtt ag-3'

(SEQ ID NO: 251)
ZsGreen   CHSL-201 5'-tcagggcaat gcagatcc-3'
```

Among the 920 events analyzed, 358 events (38.9%) showed the presence of all three PCR amplicons (nptII, AcGFPnuc or ZsGreen, and UBQ10) (summarized in Table 8). Based on this analysis the escape frequency is around 61%. The observed escape rate appears the highest in genotype R570, in which most of the transformations were performed.

TABLE 8

Sugarcane MC containing transgenic callus

| MC # | Events analyzed | Positive events for all amplicons |
|---|---|---|
| 5800 | 24 | 12 |
| 5801 | 9 | 0 |
| 5802 | 42 | 18 |
| 5803 | 5 | 1 |
| 5804 | 10 | 2 |
| 5805 | 3 | 1 |
| 5806 | 4 | 1 |
| 5809 | 11 | 3 |
| 5810 | 7 | 5 |
| 5812 | 4 | 0 |
| 5814 | 88 | 62 |
| 5816 | 29 | 14 |
| 5817 | 42 | 12 |
| 5819 | 75 | 43 |
| 5820 | 53 | 42 |
| 5821 | 4 | 1 |
| 5822 | 18 | 1 |
| 5823 | 4 | 0 |
| 5824 | 12 | 0 |
| 5825 | 7 | 0 |
| 5827 | 6 | 0 |
| 5830 | 5 | 0 |
| 5834 | 20 | 3 |
| 5835 | 4 | 1 |
| 5837 | 12 | 1 |

TABLE 8-continued

Sugarcane MC containing transgenic callus

| MC # | Events analyzed | Positive events for all amplicons |
|---|---|---|
| 5839 | 7 | 0 |
| 5840 | 3 | 0 |
| 5842 | 2 | 0 |
| 5844 | 7 | 0 |
| 5846 | 14 | 0 |
| 5850 | 14 | 11 |
| 5851 | 14 | 0 |
| 5852 | 5 | 0 |
| 5854 | 26 | 3 |
| 5856 | 11 | 3 |
| 5857 | 6 | 1 |
| 5858 | 25 | 1 |
| 5859 | 14 | 0 |
| 5860 | 26 | 4 |
| 5862 | 11 | 0 |
| 5863 | 11 | 0 |
| 5864 | 50 | 8 |
| 5873 | 2 | 2 |
| 5874 | 14 | 8 |
| 5881 | 47 | 44 |
| 5882 | 19 | 13 |
| 5883 | 12 | 4 |
| 5884 | 35 | 16 |
| 5885 | 23 | 8 |
| 5888 | 2 | 2 |
| 5889 | 22 | 7 |
| Total | 920 | 358 |

MC transgenic events were obtained in all genotypes tested, and significant genotype dependence was noted for both transformation efficiency and escape rate for G418 selection. Table 9 summarizes transformation results for several genotypes.

TABLE 9

Sugarcane MC transgenic events in multiple genotypes

| Genotype | No. of putative events produced | No. of PCR positive events | Escape frequency (%) |
|---|---|---|---|
| R570 | 554 | 94 | 83 |
| Q117 | 151 | 95 | 37 |
| L97-128 | 182 | 142 | 22 |
| NCo310 | 6 | 6 | 0 |
| Pindar | 23 | 18 | 21.7 |
| Q63 | 4 | 3 | 25 |
| Total | 920 | 358 | |

Evaluation of autonomous MCs

To evaluate whether the candidate Sugarcane MCs were maintained autonomously, fluorescence in situ hybridization (FISH) was performed on mitotic metaphase chromosome spreads from callus tissue. FISH was performed essentially as described in Kato et al. *Proc. Natl. Acad. Sci. U.S.A.* 101: 13554-13559, 2004, using probes labeled with ALEXA FLUOR® 488 ("Alexa488") and ALEXA FLUOR®568 ("Alexa568;" Invitrogen). Alexa488 labeled CHROM5798 DNA was used as a MC-specific probe. Alexa568 labeled pBeloBAC11 DNA was used as a second MC-specific probe. Alexa568 labeled PCR amplified centromere sequences from BAC 18E23 were used as a centromere-specific probe. The latter probe was also expected to stain centromere regions on the endogenous chromosomes.

For FISH evaluation, freshly growing callus tissue was collected following a recent transfer to fresh media. Depending on genotype, different morphologies were apparent. Generally, tissue was nodular and firm, and met forceps with resistance. Using forceps or scalpel, a very small cluster of nodules was excised and transferred to a 1.7 mL microfuge tube. A few microliters of dH$_2$O were added to the tube to keep the tissue moist. The tube was covered with cap containing a small puncture to allow exposure to nitrous oxide in next step. Callus tissue was placed in the pressure chamber under 160 psi for 4.5 hours. Tissue was fixed in 90% acetic acid, and spread onto poly-lysine coated glass slides by squashing thin cross sections. Following hybridization, slides were counterstained with DAPI (0.04 mg/ml) and >15 metaphase cells were evaluated per callus using a Zeiss Axio-Imager (Carl Zeiss MicroImaging, Inc.; Thornwood, N.Y.; USA) equipped with rhodamine, FITC, and DAPI filter sets (excitation BP 550/24, emission BP 605/70; excitation BP 470/40, emission: BP525/50; and excitation G 365, emission BP 445/50, respectively). Gray-scale images were captured in each panel, merged and adjusted with pseudo-color using Zeiss AxioVision (Version 4.5; Carl Zeiss MicroImaging, Inc.) software; fluorescent signals from doubly-labeled MCs were detected in both the red and green channels.

Extra-chromosomal signals were considered to indicate autonomous Sugarcane MCs if the images showed co-localization of the Alexa488 (green) and Alexa568 (red) signals within 1 nuclear diameter of the endogenous metaphase Sugarcane chromosomes, and the signals were clearly distinct from the DAPI-stained host chromosomes. Typical Autonomous MC signals in FISH hybridization show overlapping distinct Alexa488 (green) and Alexa568 (red) signals that in computer-generated merged images, the overlap shows a yellow signal. Integrated constructs result in two distinct FISH signals, each on a replicated metaphase chromatid, and usually these FISH signals do not overlap with the centromere region. Autonomous MCs were found to co-exist in the presence of integrated constructs, indicating the ability of a specific MC to produce a purely autonomous event in transgenic lines obtained in parallel with the event characterized here, or obtained from future transformation experiments under different transformation conditions. Table 10 summarizes the preliminary FISH evaluation of selected transgenic lines that were confirmed to contain MCs identified by PCR, and demonstrated that both autonomous only (category A) and autonomous and integrated events (category A+I) were obtained for a significant number of Sugarcane MCs.

TABLE 10

Preliminary FISH evaluation of Sugarcane MC transgenic events

| CHROM # | Event ID # | Autonomous copy | Integrated copy | Category |
|---|---|---|---|---|
| 5802 | RC5802-85-12-5 | + | − | A |
| 5802 | RC5802-85-14-2 | + | − | A |
| 5802 | RC5802-85-14-2 | + | − | A |
| 5802 | RC5802-85-16-1 | + | − | A |
| 5814 | BC5814-109-6-1 | + | − | A |
| 5814 | BC5814-109-9-1 | + | − | A |
| 5819 | AC5819-109-29-1 | + | − | A |
| 5819 | AC5819-109-30-2 | + | − | A |
| 5820 | BC5820-105-13-1 | + | − | A |
| 5820 | BC5820-105-13-1 | + | − | A |
| 5820 | RC5820-74-6-3 | + | − | A |
| 5824 | RC5824-77-29-1 R | + | − | A |
| 5837 | RC5837-88-13-1 | + | − | A |
| 5840 | RC5840-99-10-1 | + | − | A |
| 5860 | RC5860-75-13-1 | + | − | A |
| 5802 | RC5802-85-14-5 | + | + | A + I |
| 5809 | RC5809-79-4-1 | + | + | A + I |
| 5810 | BC5810-112-23-1 | + | + | A + I |
| 5810 | BC5810-112-23-2 | + | + | A + I |
| 5814 | AC5814-109-12-2 | + | + | A + I |
| 5814 | AC5814-109-14-1 | + | + | A + I |

TABLE 10-continued

Preliminary FISH evaluation of Sugarcane MC transgenic events

| CHROM # | Event ID # | Autonomous copy | Integrated copy | Category |
|---|---|---|---|---|
| 5814 | AC5814-109-14-8 | + | + | A + I |
| 5814 | AC5814-109-15-10 | + | + | A + I |
| 5814 | AC5814-109-15-5 | + | + | A + I |
| 5814 | RC5814-101-16-1 | + | + | A + I |
| 5816 | BC5816-109-21-5 | + | + | A + 1 |
| 5816 | BC5816-109-21-6 | + | + | A + I |
| 5817 | PC5817-104-1-1 | + | + | A + I |
| 5817 | PC5817-104-2-1 | + | + | A + I |
| 5817 | PC5817-104-5-1 | + | + | A + I |
| 5819 | AC5819-109-26-1 | + | + | A + I |
| 5819 | AC5819-109-27-1 | + | + | A + I |
| 5819 | AC5819-109-29-1 | + | + | A + I |
| 5819 | AC5819-109-29-4 | + | + | A + I |
| 5819 | BC5819-105-3-023 | + | + | A + I |
| 5820 | BC5820-105-11-1 | + | + | A + I |
| 5820 | BC5820-105-15-1 | + | + | A + I |
| 5820 | BC5820-105-15-1 | + | + | A + I |
| 5820 | BC5820-105-15-1 | + | + | A + I |
| 5834 | RC5834-80-2-1 | + | + | A + I |
| 5850 | RC5850-74-16-2 | + | + | A + I |
| 5850 | RC5850-74-16-2 | + | + | A + I |
| 5850 | RC5850-74-16-2 | + | + | A + I |
| 5850 | RC5850-74-18-8 | + | + | A + I |

Events with high quality FISH signals as determined by visual scoring are indicated with a "+", a clear absence of signal is indicated by "−".

EXAMPLE 4

Construction of Sugarcane MCs Containing Synthetic Arrays of Repeat Sequence

A synthetic array of the satellite repeat sequences was generated using PCR and directional cloning. A block of 4 Sugarcane satellite repeats were PCR amplified and sequenced. The sequence is set out as SEQ ID NO: 204. This sequence was used as the basis for building the synthetic array. Several arrays were constructed ranging in size between S kb and 25 kb. Two Sugarcane MCs containing specific synthetic arrays of 18 kb (CHROM5613) and 25 Kb (CHROM5616) were used in further testing.

The Sugarcane MCs also contained either 5 or 8 stacked exogenous genes. The 5- or 8-gene stacks were based on the 2-gene stack construct from donor plasmid CHROM5738. The genetic elements within the donor plasmid CHROM5738 are the same as in donor plasmid CHROM5798 except that the nuclear localized GFP gene was replaced with a nuclear localized DsRed2 fluorescent protein gene (DsRed2+NLS), described in Table 11.

TABLE 11

Donor Components of CHROM5738

| Genetic Element | Size (base pair) | Location (bp) | Details |
|---|---|---|---|
| YAT1 yeast Promoter | 2000 | 7110-9109 | PCR amplified YAT1 promoter from chromosome I of *Saccharomyces cerevisiae* for expression of NptII in Sugarcane |
| Arabidopsis UBQ10 Intron | 360 | 9123-9482 | PCR amplified *Arabidopsis thaliana* intron from UBQ10 gene (At4g05320) for stabilization of NptII gene transcript and increase protein expression level |
| nptII | 795 | 9510-10304 | Neomycin phosphotransferase II plant selectable marker |
| Rps16A terminator | 489 | 10368-10856 | Amplified from *Arabidopsis thaliana* 40S ribosomal protein S16 (At2g09990) for termination of NptII gene |
| Bacterial Kanamycin | 817 | 11039-11855 | Bacterial kanamycin selectable marker |
| Terminator 6 | 332 | 12000-12331 | Terminator 6 |
| DsRed2 + NLS | 780 | 12466-13245 | Nuclear localized red fluorescent protein from *Discosoma sp.* (Matz, M et. al *Nat Biotechnol* 1999 Dec; 17(12): 1227). |
| UBQ10 Promoter | 2038 | 13282-15319 | PCR amplified *Arabidopsis thaliana* promoter from UBQ10 gene (At4g05320) for stabilization of DsRedI gene transcript and increase protein expression level |
| LoxP | 34 | 7057-7090 and 15335-15368 | Recombination site for Cre mediated recombination (Arenski et. al 1983, Abremski et. al 1984) |

The 5-gene stack included the marker genes Anthocyanin, ZsGreen, and ZsYellow in addition to NptII, DsRed in CHROM5738. The 8-gene stack included those genes in the 5-gene stack plus three additional genes from the *Agrobacterium tumefaciens* tumor-inducing (Ti) pathway. These were the iaaM (Trp mono-oxygenase), iaaH (Indole-3-acetamide hydrolase), and ipt (AMP iso-pentenyl transferase) genes.

In order to investigate whether the Sugarcane MCs could accommodate a large number of genes, Sugarcane MCs containing a gene stack, a synthetic array of repeat nucleotide sequence and about 20 kb of *A. thaliana* DNA was constructed. The total size of these Sugarcane MCs ranged between 82 kb and 87 kb. In addition, Sugarcane MCs with a gene stack with 2 genes in addition to a 28 kb synthetic Sugarcane centromere repeat array and an approximately 50 kb insertion of *A. thaliana* DNA was constructed using the methods described above. The Sugarcane MC demonstrated that the Sugarcane MCs of the invention can accommodate a large payload of genes, as 50 kb of the *A. thaliana* DNA includes a wide variety of genes. The total size of these MCs were 82 and 87 kb.

Sugarcane Transformation and Regeneration with Synthetic MCs.

To enhance the efficiency with which Sugarcane cells transformed with Sugarcane MCs can be regenerated into Sugarcane plants, Sugarcane MCs containing the auxin gene pathway were delivered into fully differentiated leaf rolls rather than undifferentiated tissue, e.g., embryos. In addition, the growth conditions were altered in order to facilitate generation of transformed Sugarcane callus. Functional Testing of Sugarcane MCs Using Transient Assays Sugarcane (variety R570; *Saccharum officinarum* X *Saccharum spontaneum*) was grown in the greenhouse for 6 months without floral initiation due to the growth time as well as the day-length settings on greenhouse supplemental lighting. Stalks from several (clonal) plants were used to generate leaf rolls that were purely leaf tissue and did not include any developing meristematic tissue. Sugarcane MCs with a synthetic Sugarcane centromere were delivered to leaf rolls. One Sugarcane MC contained an 8-gene stack (denoted herein as the "8-gene MC"), and one Sugarcane MC contained a 5-gene stack (denoted herein as the "5-gene MC"). These Sugarcane MCs are described in detail in Example 3. In addition, a control plasmid (lacking a centromere) containing eight genes was also delivered, in which the 8-gene stack is identical to that delivered on the 8-gene Sugarcane MC.

The 8-gene Sugarcane MC included *A. tumefaciens* tumor inducing (Ti) pathway genes (iaaM, iaaH, and ipt). The inclusion of these genes minimized the time the transformed cells were in tissue culture. IaaM converts Trp into indole-3-acetamide, which IaaH converts into auxin. Isopentenyl transferase (Ipt) converts 3',5'-adenosine monophosphate (AMP) into a cytokinin. The presence of the hormone auxin was used in cell culture to stimulate plant cells to form callus. Media with auxin promotes callus growth from plant cells whereas plant cells cultured on media lacking auxin either germinate (for embryogenic material) or are unable to grow (non-embryogenic or meristematic tissue such as leaf tissue). Thus, the 8-gene MC induced callus formation without supplementing the media with auxin.

A biolistic delivery method using dry gold particles was carried out to deliver MCs to the Sugarcane leaf rolls. For this method, Sugarcane MC DNA (in 1×TE) was precipitated onto 2.1 mg of sterilized and washed 0.6µ gold particles. The DNA-containing gold particles were re-suspended in cold sterile water and 2.5 M $CaCl_2$. Filter-sterilized 0.1 M spermidine (free base) was added to the mixture. Subsequently, the mixture was allowed to precipitate on ice for 1.5 hours, with gentle finger vortexing (3×) after 45 minutes. The precipitated DNA was then washed with 100% ethanol, resuspended in 100% ethanol which was allowed to fully evaporate prior to bombardment.

The apical region of the Sugarcane stem was collected (20-30 cm long), after removing the outermost mature leaves, the remaining leaves were sterilized by submersion in a solution of 50 ml bleach in 1 liter of water for 10 minutes. The remaining mature leaves were aseptically removed and the young inner immature leaves were sliced into sections/discs approximately 2-3 mm thick. The leaf rolls were placed in SCOM at 28° C. for 4-5 hours before bombardment.

The 3 constructs were each initially tested by delivery into 16 leaf rolls. For delivery, the leaf rolls were bombarded with the MC DNA using the BioRad PDS-1000/He with a rupture disk rating of 900-1800 psi (1350 psi was preferred with one shot per plate). The gap distance (distance from rupture disk to macrocarrier) was 6 mm. Target shelf for tissue was L2-L4; L2 or L3 was preferred. The vacuum pressure of 25-29 in Hg; 27.5 in Hg was preferred. The bombarded leaf rolls were stored at 28° C. (dark) for an additional 16-18 hours on SCOM.

Subsequently, the bombarded leaf rolls were transferred to MSO (4.3 g/l Murashige and Skoog (MS) salts and vitamins, supplemented with 20 g/l sucrose, 0.5 g/l casein, with NO 2,4-D, pH to 5.8 and solidified with 2 g/L GELRITE®) and stored at 28° C. in the dark for 2 weeks. The leaf rolls were visually assessed for callus production 2 and 4 weeks after bombardment. Control leaf rolls not subjected to bombardment, and the leaf rolls that were bombarded with the 5-gene stack MC showed no sign of growth or callus formation. Two of the 16 bombarded leaf rolls that were bombarded with the 8-gene stack MC produced callus (12.5% of the total explants).

Callus from the tissue was phenotypically evaluated for DsRed expression using a fluorescent dissecting microscope. DsRed was observed in the tissue. The resulting calluses were transferred to Regeneration Sugarcane Medium (RSCM; 4.3 g/l MS salts and vitamins supplemented with 20 g/l sucrose, 0.5 g/l casein, 0.5 mg/l kinetin. pH to 5.8 and solidify with 2 g/L GELRITE®) in low light (16 hour day length, 26° C.) to initiate regeneration. This media did not contain auxin. After 2 additional weeks of culture, callus had grown, but had also started to differentiate into root (primarily) and shoot material. Such differentiation is not expected in the presence of auxin, suggesting either silencing or loss of the 3 genes from the *A. tumefaciens* Ti pathway. After 2 additional weeks on media, PCR evaluation of this material was done for presence of the DsRed gene. PCR results were negative, which further suggested loss of the entire MC and verified that the genes were not silenced. Because of the loss of the entire MC, these tissues were not regenerated into plants.

The advantages of including the genes of the Ti pathway on a MC are that the non-meristematic tissues were transformed and the need for callus initiation prior to DNA delivery was eliminated. In addition, the time in culture was reduced and as a result somaclonal variation, endogenous chromosome number changes and the like were also reduced. Furthermore, the inclusion of the Ti pathway genes eliminated the need for selectable marker genes. There was an observed 12.5% transformation efficiency of Sugarcane in the initial experiments.

In a separate experiment, 5-gene (NptII, DsRed, Anthocyanin, ZsGreen, and ZsYellow) MCs were delivered into Sugarcane callus generated from Sugarcane variety R570; (*Saccharum officinarum* X *Saccharum spontaneum*) These MCs were delivered to the Sugarcane callus cells using the wet biolistic method as described above. In brief, the droplet containing the MC DNA-coated particles was delivered to cells using a BioRad PDS-1000/He with a rupture disk rating of 400-1800 psi (650 psi was preferred with one shot per plate) adapted for a filter holder, which was attached to a base which was itself attached to a rupture disk holder used to hold the rupture disk to the helium egress tube for bombardment. The gas discharge directly displaced the DNA/gold droplet from the filter holder and accelerated the particles and their DNA cargo into the tissue being bombarded.

Following delivery, callus from the tissue was phenotypically evaluated for DsRed expression using a fluorescent dissecting microscope. DsRed was observed in the tissue. The resulting calluses were transferred to Selection Sugarcane Medium MS3-50; (4.3 g/l MS salts and vitamins supplemented with 20 g/l sucrose, 0.5 g/l casein, 3.0 mg/l 2,4-D, 0.5 g/l polyvinylpyrrolidone (PVP). pH to 5.8 with 2 g/l GELRITE®; further supplemented with 50 mg/l G418 after autoclaving) for initial selection for 2 weeks. All calluses were subsequently transferred to additional selection on Selection Sugarcane Medium MS3-75 (4.3 g/l MS salts and vitamins supplemented with 20 g/l sucrose, 0.5 WI casein, 3.0 mg/l 2,4-D, 0.5 g/l polyvinylpyrrolidone (PVP) pH to 5.8 with 2 g/l GELRITE®; further supplemented with 75 mg/l G418 after autoclaving) for 4 additional weeks. Tissue was then visually assessed for Sugarcane callus tissue that was able to grow on this selection. Those identified events were transferred to Regeneration Sugarcane Medium RSCM-25 (4.3 g/l MS salts and vitamins supplemented with 20 g/l sucrose, 0.5 g/l casein, 0.5 mg/l kinetin. pH to 5.8 and solidify with 2 g/L GELRITE®; further supplemented with 25 mg/l G418 sulfate after autoclaving) in low light (16 hour day length, 26° C.) to initiate regeneration. Simultaneous with initiating regeneration, this callus tissue was evaluated by PCR for presence of the genes on the MC. PCR confirmed that these genes were indeed present in the majority of the events. After 2 additional weeks of culture, the callus events had started to differentiate into plantlets (shoot material).

After an additional 4-6 weeks on regeneration, plantlets (with and without initial root initiation) were transferred to Rooting Medium RtSC-25 (2.15 g MS salts and vitamins supplemented with 20 g/l sucrose, 0.5 g/l casein, 0.5 mg/l kinetin. pH to 5.8 and solidify with 2 g/L GELRITE®; further supplemented with 25 mg/l G418 sulfate after autoclaving). Rooting occurred in 2 to 6 additional weeks of culture with 16 hour day length at 26° C. in sundae cups (Solo Cup Company). Plantlets with well established root systems were transferred into pre-moistened soil-less mix (LC1, BFG Supply Company) under a humidome in 18-well flats in a growth chamber (28° C., 16 hour day length). The dome was opened slightly 3-4 days after transplanting to slowly reduce humidity. The dome was removed completely 2 days later and the plantlets were then transferred to a greenhouse (28° C., 16 hour day length). The plants were watered from trays beneath the pots when the soil began to dry. The plants were subsequently transplanted and grown to maturity in 1.6 gallon pots with Soil:Peat:Perlite (1:1:1) supplemented with OSMOCOTE® fertilizer (The Scotts Miracle-Gro Company; Marysville, Ohio; USA).

Sugarcane callus and tissues produced phenolic compounds while in tissue culture, and these phenolic compounds appeared to reduce or inhibit callus growth and plantlet regeneration. In order to promote Sugarcane plantlet regeneration in culture, the media described above (MSO, MS3 and variants thereof and RSCM) were supplemented with polyvinylpyrrolidone (PVP) at a concentration ranging from 1% to 3% w/v according to the intensity of the exudation of the phenolic compounds. The PVP acted as a sink for phenolic compounds and enhanced subsequent callus growth and plantlet regeneration.

In order to promote the frequency and the morphogenetic competence of regenerable Sugarcane callus, the cells were cycled from a liquid culture to a solid culture. The apical region of the Sugarcane stem (20-30 cm long) was collected, and the mature leaves were removed. The stem was surface-sterilized by submerging the tissue in a solution of 50 ml bleach in 1 liter of water for 10 minutes. The remaining outermost mature leaves were aseptically removed, and the young inner immature leaves were sliced into sections/discs approximately 2-3 mm thick. The resulting leaf roll discs were placed on Sugarcane MS3 Medium at 28° C. for 2 weeks in the dark. The resulting regenerable Sugarcane callus (white nodular embryogenic pieces) was then removed and placed into liquid Sugarcane MS1 medium at 28° C. for 2 weeks on a rotating orbital shaker (100-150 rpm) in the dark. After the two week culture in the liquid MS1 medium, the regenerable Sugarcane callus (white nodular embryogenic pieces) was removed and sub-cultured back onto Sugarcane MS3 Medium (MS3) at 28° C. for 2 additional weeks in the dark. Sugarcane callus can be sub-cultured in 2-week intervals between solid MS medium containing 3 mg/l 2,4-D and liquid MS medium containing 1 mg/l 2,4-D to maintain embryogenic callus.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. Applicant intends that the sequence listing filed herewith forms a part of the description of the specification and is hereby incorporated by reference in its entirety.

Although the foregoing invention has been described in some detail by way of illustration and example for purposes of clarity of understanding, it will be obvious that certain changes and modifications may be practiced within the scope of the appended claims.

The invention is claimed as follows:

1. An artificial sugarcane chromosome comprising a functional centromere and an exogenous nucleic acid, wherein said functional centromere comprises a polynucleotide comprising a nucleotide sequence selected from the group consisting of: (a) the nucleotide sequence of SEQ ID NO: 204; and (b) a nucleotide sequence that is at least 98% identical to the nucleotide sequence of SEQ ID NO: 204.

2. The artificial chromosome of claim 1, wherein the polynucleotide comprises the nucleotide sequence of SEQ ID NO:204.

3. An artificial sugarcane chromosome comprising a functional centromere and an exogenous nucleic acid, wherein said functional centromere comprises an array comprising at least two copies of a polynucleotide, wherein the polynucleotide comprises a nucleotide sequence selected from the group consisting of: (a) the nucleotide sequence of SEQ ID NO: 204; and (b) a nucleotide sequence that is at least 98% identical to the nucleotide sequence of SEQ ID NO: 204.

4. The artificial chromosome of claim 3 wherein the array comprises at least ten copies of the polynucleotide.

5. The artificial chromosome of claim 3 wherein the array comprises at least 100 copies of the polynucleotide.

6. The artificial chromosome of claim 3 wherein the array comprises from 2 to 1000 copies of the polynucleotide.

7. The artificial chromosome of claim 3 wherein the array comprises from five to 250 copies of the polynucleotide.

8. The artificial chromosome of claim 3 wherein the array is from 1 to 200 kb in length.

9. The artificial chromosomes of claim 8, wherein the array is from 15 to 28 kb in length.

10. The sugarcane artificial chromosome of claim 1, wherein the sugarcane artificial chromosome comprises at least three exogenous nucleic acids.

11. The sugarcane artificial chromosome of claim 1, wherein at least one exogenous nucleic acid is operably linked to a heterologous regulatory sequence functional in a sugarcane plant cell.

12. The sugarcane artificial chromosome of claim 11, wherein the exogenous nucleic acid is an herbicide resistance gene, a nitrogen fixation gene, an insect resistance gene, a disease resistance gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an antibody gene, a growth factor gene, a drought resistance gene, a heat resistance gene, a chilling resistance gene, a freezing resistance gene, an excessive moisture resistance gene, a salt stress resistance gene or a biofuel gene.

13. The sugarcane artificial chromosome of claim 1, wherein the sugarcane artificial chromosome exhibits a mitotic segregation efficiency in sugarcane plant cells of at least 90%.

14. A vector comprising a functional centromere and an exogenous nucleic acid, wherein the functional centromere comprises a nucleotide sequence selected from the group consisting of: (a) the nucleotide sequence of SEQ ID NO: 204; and (b) a nucleotide sequence that is at least 98% identical to the nucleotide sequence of SEQ ID NO: 204.

15. A vector comprising a functional centromere and an exogenous nucleic acid, wherein the functional centromere comprises an array comprising at least two copies of a polynucleotide, wherein the polynucleotide comprises a nucleotide sequence selected from the group consisting of: (a) the nucleotide sequence of SEQ ID NO: 204; and (b) a nucleotide sequence that is at least 98% identical to the nucleotide sequence of SEQ ID NO: 204.

16. A cell comprising the artificial chromosome of claim 1.

17. A cell comprising the artificial chromosome of claim 3.

18. A cell comprising the vector of claim 15.

19. A cell comprising the vector of claim 14.

20. The cell of claim 16, wherein the cell is a sugarcane plant cell.

21. The sugarcane plant cell of claim 20 comprising a sugarcane artificial chromosome, wherein the sugarcane artificial chromosome is not integrated into the genome of the sugarcane plant cell.

22. The sugarcane plant cell of claim 20 comprising a sugarcane artificial chromosome that comprises an exogenous nucleic acid, wherein the sugarcane plant cell exhibits an altered phenotype associated with the expression of the exogenous nucleic acid.

23. The sugarcane plant cell of claim 22, wherein the altered phenotype comprises altered expression of a native gene.

24. The sugarcane plant cell of claim 22, wherein the altered phenotype comprises altered expression of an exogenous gene.

25. A sugarcane plant tissue comprising the sugarcane plant cell of claim 20.

26. A sugarcane plant comprising the sugarcane plant cell of claim 20.

27. A sugarcane plant part comprising the sugarcane plant cell of claim 20.

28. A sugarcane seed obtained from the sugarcane plant of claim 26, wherein said sugarcane seed comprises the artificial sugarcane chromosome.

29. A sugarcane plant progeny, wherein the plant progeny is the result of breeding the plant of claim 26 and the resulting plant progeny comprises the artificial sugarcane chromosome.

30. A method of using the sugarcane plant of claim 26, wherein the sugarcane plant comprises the artificial sugarcane chromosome comprising an exogenous nucleic acid encoding a recombinant protein, the method comprising growing the plant to produce the recombinant protein.

31. The method of claim 30, further comprising the step of harvesting or processing the sugarcane plant.

\* \* \* \* \*

SEQUENCE LISTING

```
<160> NUMBER OF SEQ ID NOS: 251

<210> SEQ ID NO 1
<211> LENGTH: 137
<212> TYPE: DNA
<213> ORGANISM: Saccharum officinarum

<400> SEQUENCE: 1
cccagcagtt ccatcgggtg catcctagat aaattttgag ccgatggtac attcgacaca        60
aaacgcgcac ctatcttgcg tcaagattgg cactatctcc aaacggactc aaacaagcat       120
ccacttgagc ctcatca                                                      137

<210> SEQ ID NO 2
<211> LENGTH: 136
<212> TYPE: DNA
<213> ORGANISM: Saccharum officinarum

<400> SEQUENCE: 2
cctaggagta tcgtcgggtg cgtccaaaac aatttctgag ccgatggtac gttcggtgga        60
aaccgtgcac ctatattgca ccaacactaa cactgtctcc aaacggaccg aaagaagatt       120
ccacatgacc cactcg                                                       136

<210> SEQ ID NO 3
<211> LENGTH: 136
<212> TYPE: DNA
<213> ORGANISM: Saccharum officinarum
```

```
<400> SEQUENCE: 3
tcttggactt ccaccgggtg cattcaagac gatatctgag cctatggtac gtttggcaca    60
aaccgtgcac ctatattgca ccgacactga cactgtctcc aaatggaccg aaaggagatt   120
ccacatgacc cactcg                                                   136

<210> SEQ ID NO 4
<211> LENGTH: 136
<212> TYPE: DNA
<213> ORGANISM: Saccharum officinarum

<400> SEQUENCE: 4
tctaggactt ccatcaggtg cgttcaagat gatttccgag cctatggtac atttggcaca    60
aaccgcacac atatcttgcg tcaagttagc actatctcca aacggactca acaagcttc   120 cacttgagcc acgtca                                                   136

<210> SEQ ID NO 5
<211> LENGTH: 137
<212> TYPE: DNA
<213> ORGANISM: Saccharum officinarum

<400> SEQUENCE: 5
cccagcagtt ccatcgggtg cctccaatac tatttccaag cctacggtat gtttgacgca    60
aaccatgcac ctatcttgcg tcaagattag cactatctcc aaacggaccc aaccgagctt   120
ccacttgagc cacgtca                                                  137

<210> SEQ ID NO 6
<211> LENGTH: 137
<212> TYPE: DNA
<213> ORGANISM: Saccharum officinarum

<400> SEQUENCE: 6
cccagcagtt ccatcgggtg catccaaatt gatttctgag cctatggtat gtatggcgca    60
gaccgtgcaa ttatcttgca ccgacactaa acctatatcc aaacggactt aaacgagatt   120
ccacatggcc ccctgca                                                  137

<210> SEQ ID NO 7
<211> LENGTH: 137
<212> TYPE: DNA
<213> ORGANISM: Saccharum officinarum

<400> SEQUENCE: 7
cctaggagtt ccattgggtg cgtccaaaat gattctcgag cctccgatac gttctgcaca    60
aaccgtgcac gtatcttaca gaaagattag caccatctcc aaacggaacg aaacgagctt   120
ccacttgagc ctcgtca                                                  137

<210> SEQ ID NO 8
<211> LENGTH: 137
<212> TYPE: DNA
<213> ORGANISM: Saccharum officinarum

<400> SEQUENCE: 8
ccaagtggta ccatcgagtg tgttcaaaat gatttttgag ccaatggtac gtctagcgca    60
aaccatgcac ccatcttgca ctggcactaa cactatctcc aaacagaaag aatcaagatg   120
ccacatgacc catgtca                                                  137
```

```
<210> SEQ ID NO 9
<211> LENGTH: 137
<212> TYPE: DNA
<213> ORGANISM: Saccharum officinarum

<400> SEQUENCE: 9
cccagcagtt ccatcgggtg cctccaatac tatttccgag cctacggcac attcgacgca      60
aatcgagcac caatcgtgca tcaagagtag cactatctcc aaacgtaccg aatcgagctt     120
ccacttgagc cacgtca                                                    137

<210> SEQ ID NO 10
<211> LENGTH: 137
<212> TYPE: DNA
<213> ORGANISM: Saccharum officinarum

<400> SEQUENCE: 10
cccagcagtt ccatcgggtg cctccaatac tatttccgag cctacggcac attcgacgta      60
aaccgagcac caatcttgca tcaagagtag cactatctcc aaacgtaccg aatcgagctt     120
ccacttgagc ctcatca                                                    137

<210> SEQ ID NO 11
<211> LENGTH: 137
<212> TYPE: DNA
<213> ORGANISM: Saccharum officinarum

<400> SEQUENCE: 11
cctaggagtc ccctagagtg cgtccaaaac gatttctatg cctatgctac atttggtgca      60
aaccaagcac caatcttgca tcaagagaag cactatcccc aaacggaccg acctaagctt     120
ccacttgagc cacgtca                                                    137

<210> SEQ ID NO 12
<211> LENGTH: 128
<212> TYPE: DNA
<213> ORGANISM: Saccharum officinarum

<400> SEQUENCE: 12
cccagcagtt ccatcgggtg cgtccaaaac tatttatgac ctatggtacg ttcaatgcaa      60
accgtggacc tatcttctgt agcactatct ccaaacggac caaacagatc tccaccaggc     120
cctcatca                                                              128

<210> SEQ ID NO 13
<211> LENGTH: 136
<212> TYPE: DNA
<213> ORGANISM: Saccharum officinarum

<400> SEQUENCE: 13
cctaggagta ccacgggtgc ttctaaaacg atttatgaac caatggtgcg tttgacgaaa      60
actgagcacc tatcttgcac cgaccctaac actgtttcaa aatagatcga aacaagattc     120
cacatgaccc acgtaa                                                     136

<210> SEQ ID NO 14
<211> LENGTH: 137
<212> TYPE: DNA
<213> ORGANISM: Saccharum officinarum

<400> SEQUENCE: 14
cctaggagtt ccttcgggtg cctccaatac tatttctaag cctactatac gtttgacgca      60
```

```
aaccttgcac caatcgtgca tcaagagtag cactatcccc aaacggaccg aaccgagctt    120
ccacttgagc cacgtca                                                   137

<210> SEQ ID NO 15
<211> LENGTH: 137
<212> TYPE: DNA
<213> ORGANISM: Saccharum officinarum

<400> SEQUENCE: 15
cccagcagtt ccatcgggtg catctaaaat gatttccgag cctacggtac gtccggcaca    60
aactgtgcac ctatcttgaa acaagattag cacaatctcc aaactaacgg aaatgagctt   120
ccacttgagc cacgtca                                                   137

<210> SEQ ID NO 16
<211> LENGTH: 136
<212> TYPE: DNA
<213> ORGANISM: Saccharum officinarum
<220> FEATURE:
<221> NAME/KEY: misc_feature
<222> LOCATION: (1)..(9)
<223> OTHER INFORMATION: n is a, c, g, or t
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 16
nnnnnnnnnc catcgggtgc gttcaagatg atttctgggc ctannnaang ntaggcacaa    60
actgcccatc tatctcgtgt caagattagc actatctcca aacggactca aacgagcttc   120
cacttgagcc ttctca                                                    136

<210> SEQ ID NO 17
<211> LENGTH: 137
<212> TYPE: DNA
<213> ORGANISM: Saccharum officinarum

<400> SEQUENCE: 17
cctaggagta ccaccgggtg cgtccaaaat gattttcgag cctgtggtac gttcggcgca    60
aaccgtgcac ctatcttgcg tcaagattag cactatctcc aaatgaacta atcaagcat    120 ccacttgagc cacgtca                                                   137

<210> SEQ ID NO 18
<211> LENGTH: 137
<212> TYPE: DNA
<213> ORGANISM: Saccharum officinarum

<400> SEQUENCE: 18
cccagcagtt ccatcgggtg cctccaatac tatttctgag cctaaggtat gtttgacgca    60
aactgtgcac caatcgtgca tcaagagtag tactatctcc aaacggaccg aaccgagctt   120
ccacttgagc ctcatca                                                   137

<210> SEQ ID NO 19
<211> LENGTH: 137
```

```
<212> TYPE: DNA
<213> ORGANISM: Saccharum officinarum

<400> SEQUENCE: 19
cctaggagtc ccatcgagtg cgtccaaaat gatttctatg cctatggtat gttcggtgca     60
aaccgtgcac ctctcttgca ctgacattaa cactgtctcc aaatggacta aaatgaaatt    120
ccacatgacc cacgcca                                                    137

<210> SEQ ID NO 20
<211> LENGTH: 136
<212> TYPE: DNA
<213> ORGANISM: Saccharum officinarum

<400> SEQUENCE: 20
cttatgtgtt ccattgggtg cgtccacaac tatttatgag cctatgctac cttcaaagca     60
aaccgtgcac ctatcttgtg ttaagattgg cactatctcc aaacggacca aacagggctc    120
cactagaccc tcgtca                                                     136

<210> SEQ ID NO 21
<211> LENGTH: 138
<212> TYPE: DNA
<213> ORGANISM: Saccharum officinarum

<400> SEQUENCE: 21
cttaggagta ccattgggtg cttttaaaat gatttatgag actatggtac gttttgacgc     60
aaattgagca cttatcttgg accgacgcta acactgtctc aaaactgatc gaaacaagat    120
tccacaagac ccacgtta                                                   138

<210> SEQ ID NO 22
<211> LENGTH: 137
<212> TYPE: DNA
<213> ORGANISM: Saccharum officinarum

<400> SEQUENCE: 22
actaggagtt ccatcgggtg cctccaatac tatttacgag cctacggtac atttgacgca     60
aaccgtgcac caatcgtgca tcaagagtag cactatctcc aaacggaccg aaccgagctt    120
ccacttgagc cacgtca                                                    137

<210> SEQ ID NO 23
<211> LENGTH: 137
<212> TYPE: DNA
<213> ORGANISM: Saccharum officinarum

<400> SEQUENCE: 23
cccagcagtt ccatcgggtg cctctaatac tatttctgag cctattgtac gtttgatgca     60
aaccgtacac caatcgtgca tcaagagtag cactatcccc aaacggaccg aaccgagctt    120
ccacttgagc cacgtca                                                    137

<210> SEQ ID NO 24
<211> LENGTH: 137
<212> TYPE: DNA
<213> ORGANISM: Saccharum officinarum

<400> SEQUENCE: 24
cccagcagtt ccatcgggtg cggtcaacac gacttccgag ccgatgatac gttcggctca     60
aaccgcgcac ctttcttgtg tcaagattac cactatctcc aaatagactc aaacaagctt    120
```
ccacttgagc ctcatca                                              137

<210> SEQ ID NO 25
<211> LENGTH: 136
<212> TYPE: DNA
<213> ORGANISM: Saccharum officinarum

<400> SEQUENCE: 25
tctaggagta tcgtcgggtg cctccaaaac aatttctgag ccgatggtac gttcggcgca    60
aaccatgcac ctatattgca ccgacactaa cactgtctcc aaacgaaccg aaatgagatt   120
ccacttgacc cactcg                                                  136

<210> SEQ ID NO 26
<211> LENGTH: 137
<212> TYPE: DNA
<213> ORGANISM: Saccharum officinarum

<400> SEQUENCE: 26
tctaggactt ccatcgggtg cgttcaagac gatttccaag cctatggtac gtttgacaca    60
aaccgcgcac ctatcttgcg tcaaaattag cactatctcc aaacggactc aaacaagctt   120
ccacttgagc cacgtca                                                 137

<210> SEQ ID NO 27
<211> LENGTH: 137
<212> TYPE: DNA
<213> ORGANISM: Saccharum officinarum

<400> SEQUENCE: 27
cccagcagtt ccatcgggtg cgtccaacat gatttccgag ccaatggtac gttcgacaca    60
aaccacgcat atttcttaca tcaagattag cactatttcc aaacagactc aaacaagctt   120
ccacttgagc cacgtca                                                 137

<210> SEQ ID NO 28
<211> LENGTH: 137
<212> TYPE: DNA
<213> ORGANISM: Saccharum officinarum

<400> SEQUENCE: 28
cccagcagtt ccatcgggtg cgtccaagat gattttcggg cctacggaaa gctaggcaca    60
aactgcacac ctatattgtg tcaagattgg cactatctcc aaacggactc aaacaagctt   120
ccacttgagc cttgtca                                                 137

<210> SEQ ID NO 29
<211> LENGTH: 137
<212> TYPE: DNA
<213> ORGANISM: Saccharum officinarum

<400> SEQUENCE: 29
cctaggagta ccaccaggtg catccaaaat gatttctgag cctatggtac gttcaacgcg    60
aactgtggac ctatcttgcg gcaagattat caccatctcc aaacagaacg aaacgagctt   120
ccacttgagc cacgtca                                                 137

<210> SEQ ID NO 30
<211> LENGTH: 137
<212> TYPE: DNA
<213> ORGANISM: Saccharum officinarum

<400> SEQUENCE: 30

-continued

```
cccagcagtt ccatcgggtg cctccaatac tatttccgag cctacggcac attcgacgca    60
aatcgagcac caatcttgca tcaagagtag cactatctcc aaacgtaccg aatcgagctt    120
ccacttgagc ctcgtca                                                    137
```

<210> SEQ ID NO 31
<211> LENGTH: 137
<212> TYPE: DNA
<213> ORGANISM: Saccharum officinarum

<400> SEQUENCE: 31

```
cctacgagtc ccctcgagtg cgtccaaaac gattcctatg cctatgctac atttggtgca    60
aaccaagcac caatcttgca tcaagagaag cactatcatc aaacggaccg agccaagctt    120
ccacttgagc ctcatca                                                    137
```

<210> SEQ ID NO 32
<211> LENGTH: 137
<212> TYPE: DNA
<213> ORGANISM: Saccharum officinarum

<400> SEQUENCE: 32

```
cctaggagtc ccatcgagtg tgtccaaaat gatttctatg cccatggtac gttcagtgca    60
aaccgtgcac ctatcttgca tcgacgctaa cactgtctca aaatagatct aaatgagatt    120
ccacatgacc tatgtca                                                    137
```

<210> SEQ ID NO 33
<211> LENGTH: 116
<212> TYPE: DNA
<213> ORGANISM: Saccharum officinarum

<400> SEQUENCE: 33

```
cccagcagtt ccatcgggtg cgtccacaac tatttatgtg cctatggtac cttcatttca    60
aaccatgcac ctatcttgtg tcaagattag cactatcatc aaacggaccc atgtca        116
```

<210> SEQ ID NO 34
<211> LENGTH: 137
<212> TYPE: DNA
<213> ORGANISM: Saccharum officinarum

<400> SEQUENCE: 34

```
cccagcagtt ccatcgggtg cctccaatac tatttccgag cctaaggtac gtttgacgca    60
aaccgtgcac caatcgtgca tcaaggatag tactatctct aaacggacca aaccgagctt    120
caacttgagc cacgtca                                                    137
```

<210> SEQ ID NO 35
<211> LENGTH: 137
<212> TYPE: DNA
<213> ORGANISM: Saccharum officinarum

<400> SEQUENCE: 35

```
cccagcagtt ccatcgggtg catcctaaat gatttccaag cctatggtac gttcaacgca    60
aaccatccac ctatcttgcg ataagattag cactatctcc aaacagacag aaacaagctt    120
ccacttgagc ctcaaca                                                    137
```

<210> SEQ ID NO 36
<211> LENGTH: 126
<212> TYPE: DNA

<213> ORGANISM: Saccharum officinarum

<400> SEQUENCE: 36

```
cctaggagaa ccgtcgagtg cgtctaaaat tatttctatg tttggcgcaa accgtgtacc    60
tatcttgcac tgacactaat atcgtctgca aacagatctt aacgagactt gacttgaccc   120
acatca                                                              126
```

<210> SEQ ID NO 37
<211> LENGTH: 137
<212> TYPE: DNA
<213> ORGANISM: Saccharum officinarum

<400> SEQUENCE: 37

```
actaggagtt ctatcgggtg tgtccaaaat gatttccgag cctatggtac attcggcgta    60
aacaatgctc ctatcttgca tcaagattag cactatctcc aaatggaccg aaacgagctt   120
ccacttgagc cacgtca                                                  137
```

<210> SEQ ID NO 38
<211> LENGTH: 137
<212> TYPE: DNA
<213> ORGANISM: Saccharum officinarum

<400> SEQUENCE: 38

```
cccagcagtt ccatcgggtg cctccaatac tatatccgag cctacggtat gttcgacaca    60
aaccatgcac caatcatgca tcaatagtgg cactatctcc aaatggaccg taccgagctt   120
ccacttgagc ctcgtca                                                  137
```

<210> SEQ ID NO 39
<211> LENGTH: 137
<212> TYPE: DNA
<213> ORGANISM: Saccharum officinarum

<400> SEQUENCE: 39

```
cctaggagtc ccatcgagtg tgtccaaaac gatttctatg cctatggtac gttcagtgca    60
aaccatgcac ctatcttgca ccgacactaa tactgtctca aaatagatca aaacgagatt   120
ccacaagacc cacgtca                                                  137
```

<210> SEQ ID NO 40
<211> LENGTH: 137
<212> TYPE: DNA
<213> ORGANISM: Saccharum officinarum

<400> SEQUENCE: 40

```
cccagcagtt ccatcgggtg cctccaatac tatttctgag cctacggaac attcgatgca    60
aaccgagcac caatcttgca tcaagagtag cactatctcc aaacgtatcg aatcgagctt   120
ccacttgagc cacgtca                                                  137
```

<210> SEQ ID NO 41
<211> LENGTH: 136
<212> TYPE: DNA
<213> ORGANISM: Saccharum officinarum

<400> SEQUENCE: 41

```
cccagcagtt ccatcgggtg cgtccaaaaa catttctgag cttacggtac ggtcggcgca    60
aaccgtgccc tatcttgagt caagataagc actatctcca aacgaaccga aacgagcttc   120
gatttgagcc ccgtcg                                                   136
```

<210> SEQ ID NO 42
<211> LENGTH: 137
<212> TYPE: DNA
<213> ORGANISM: Saccharum officinarum

<400> SEQUENCE: 42
ccatggagta ccatccggtg cgtccaaaac gatttctgag gctatggtac atttggcgca      60
aaccgtgcac ctaccttaaa ctaaaactta cactgtctcc aaacagaccg aaacgatctt     120
ccacttgagc cacgtca                                                    137

<210> SEQ ID NO 43
<211> LENGTH: 137
<212> TYPE: DNA
<213> ORGANISM: Saccharum officinarum

<400> SEQUENCE: 43
cccagcagtt ccatcgggtg cctccaaatc gatttctgag cctacggtat gtttggcgca      60
gaccgtgcaa ttatcttgca ccgacactaa acctatctcc aaacggactt aaacgagatt     120
ccacatggcc cccgaca                                                    137

<210> SEQ ID NO 44
<211> LENGTH: 137
<212> TYPE: DNA
<213> ORGANISM: Saccharum officinarum

<400> SEQUENCE: 44
cctaggagtt ccattggttg catccaaaat gattctcgag cctccggtac gttctgcgca      60
aaccgtgcac ctgtcttgca gaaagattag cgccatctcc aaacggaacg aaacgagctt     120
ccacttgagc ctcgtca                                                    137

<210> SEQ ID NO 45
<211> LENGTH: 137
<212> TYPE: DNA
<213> ORGANISM: Saccharum officinarum

<400> SEQUENCE: 45
cctatgagtt ccattaggtg tgtccaaaat gatttctaag cctatggtat gtttgttgca      60
aaccgtgcac ctatcttgca tcaagtttag caccatctcc aatcggaccg taacgtgctt     120
tcacttgagc cacgtca                                                    137

<210> SEQ ID NO 46
<211> LENGTH: 137
<212> TYPE: DNA
<213> ORGANISM: Saccharum officinarum
<220> FEATURE:
<221> NAME/KEY: misc_feature
<222> LOCATION: (6)..(6)
<223> OTHER INFORMATION: n is a, c, g, or t

<400> SEQUENCE: 46
cccagnagtt ccatcgggtg catctaaaac gatttctgag cctagggtat gttcaacgga      60
aaccgtgcac gtatcttgcg tcaagatttg cactatctca aaacatacca aaacgagcat     120
ccacttgagc cacgtca                                                    137

<210> SEQ ID NO 47
<211> LENGTH: 137
<212> TYPE: DNA

<213> ORGANISM: Saccharum officinarum

<400> SEQUENCE: 47

| cccagcggtt ccatcgggtg catgtaaaat gatttttgag cttatggtat gttcggcgca | 60 |
| aaccatgaac ctatcttgcg tcaagattgg cactatcaac aagtggaccg aaaggagctt | 120 |
| tgacttgagc cttgtca | 137 |

<210> SEQ ID NO 48
<211> LENGTH: 136
<212> TYPE: DNA
<213> ORGANISM: Saccharum officinarum

<400> SEQUENCE: 48

| cccagcagtt ccatcgggtg cgtccaaaat gatttctgag cctgtgctac gttcggcgaa | 60 |
| accttgcacc catcttgtgt catgattagc tctatgtcca acagaccaa acgagcatc | 120 |
| cacgtgtgcc tcgtca | 136 |

<210> SEQ ID NO 49
<211> LENGTH: 137
<212> TYPE: DNA
<213> ORGANISM: Saccharum officinarum

<400> SEQUENCE: 49

| cctaggagta ccatcgagtg cgtccaaaat gactttcaag cctatggtac gttcgacgca | 60 |
| aaccgtgcac ctatcttgcg tcaagattag cactatctcc aaacatacaa aaatgagcat | 120 |
| ccacttgagc cacgtca | 137 |

<210> SEQ ID NO 50
<211> LENGTH: 137
<212> TYPE: DNA
<213> ORGANISM: Saccharum officinarum

<400> SEQUENCE: 50

| cccagcagtt ccatcgggtg cgtccaacac gatttctgtg cctatggtac gtttagcgca | 60 |
| aaccgtgcac gtaacttgca ctaacactgc cactgtcacc aactggattg aaacgagatt | 120 |
| cctcatgacc aaagtca | 137 |

<210> SEQ ID NO 51
<211> LENGTH: 138
<212> TYPE: DNA
<213> ORGANISM: Saccharum officinarum

<400> SEQUENCE: 51

| cataggagat ccatcgggtg catccaaaac gattttctga gcctatgcta cgttcggcgc | 60 |
| aaaccgtgca cctatcttgc gtcaaggtta gcactatgtc taaacagacc aaaacgagca | 120 |
| tccacttgag ccttatca | 138 |

<210> SEQ ID NO 52
<211> LENGTH: 137
<212> TYPE: DNA
<213> ORGANISM: Saccharum officinarum

<400> SEQUENCE: 52

| cctaggagta ctatcgagtg cgtccaaaat gatttccgag cctatggtac gtttgacgca | 60 |
| aatcgtgcac caatctcgca tcaaggttag cactatcccc aaacagacca aaacgagctt | 120 |
| ccacttgagc cacgtca | 137 |

<210> SEQ ID NO 53
<211> LENGTH: 137
<212> TYPE: DNA
<213> ORGANISM: Saccharum officinarum

<400> SEQUENCE: 53
cccagcagtt ccatcgggtg catcaaaaac aatttctgag cctatgctac atttggcgca    60
aaccattcac ctttcttgcg tcaagattag cacaatctcc aaatggattg aaacgagctt   120
cctgttgagc ctcgtaa                                                  137

<210> SEQ ID NO 54
<211> LENGTH: 137
<212> TYPE: DNA
<213> ORGANISM: Saccharum officinarum

<400> SEQUENCE: 54
cctaagagta ccatcgggtg tgtccaaaat gatttatgag cctagggtac gtttggcgca    60
aaccgtgcac ctatcttgga ttgaaactac cattgtctcc aaatggattg aaatgagatt   120
ccacatgacc aatgtca                                                  137

<210> SEQ ID NO 55
<211> LENGTH: 137
<212> TYPE: DNA
<213> ORGANISM: Saccharum officinarum

<400> SEQUENCE: 55
catagtagat ctatcgggtg cgtccacatg gatttctgac cctatgttac gttcggcgca    60
aaccgtgcat ctatcttgcg tcaagattag cactatctcc aaatagactt aaacaagtaa   120
ccacttgagc cacgtca                                                  137

<210> SEQ ID NO 56
<211> LENGTH: 137
<212> TYPE: DNA
<213> ORGANISM: Saccharum officinarum

<400> SEQUENCE: 56
cccagcagtt ccatcgggtg cctccaaaac tattttcgag cctacggcac attcgacgta    60
aaccgagcac caatcttgca tcaagagtag cactatctcc aaacataccg aatcgagctt   120
ccacttgagc ctcgtca                                                  137

<210> SEQ ID NO 57
<211> LENGTH: 137
<212> TYPE: DNA
<213> ORGANISM: Saccharum officinarum

<400> SEQUENCE: 57
cctaggagtc ccctagagtg cgtccaaaat gatttctgtg cctatgctac atttggtgca    60
aaccaagcac caatcttgca tcaagagaag cactatcccc aaacggaccg acctgagctt   120
ccacttgagc cacgtca                                                  137

<210> SEQ ID NO 58
<211> LENGTH: 137
<212> TYPE: DNA
<213> ORGANISM: Saccharum officinarum

<400> SEQUENCE: 58

```
cccagcagtt ccatcgggtg cctccaaagc tatttatgag cctacggtac gtttgacaca    60
aaccgttcac caatcttgca ccaagagcag cactatctcg aaatagacgg aaccgagctt   120
ccacttgggc ctcgtca                                                  137

<210> SEQ ID NO 59
<211> LENGTH: 137
<212> TYPE: DNA
<213> ORGANISM: Saccharum officinarum

<400> SEQUENCE: 59
cctaggaacc taccgagtgc atccaaaata attttccatg cctatggtat gttcggtgca    60
aaccgtgcac ctatcttaca ttgatactaa cactatctcc aaatggacta aaacgagatt   120
ccacatgacc cacgtca                                                  137

<210> SEQ ID NO 60
<211> LENGTH: 136
<212> TYPE: DNA
<213> ORGANISM: Saccharum officinarum

<400> SEQUENCE: 60
cttacgagtt ccattgggtg cgtccaaaac tatttatgag cctatagtac gtttagtgca    60
aaccatgcac ctatcttgca ttaagattag cactatctcc aaacggatcg aacagagctc   120
caccagagcc acgtca                                                   136

<210> SEQ ID NO 61
<211> LENGTH: 137
<212> TYPE: DNA
<213> ORGANISM: Saccharum officinarum

<400> SEQUENCE: 61
cctagaagta ccatcgggtg cgtctgaaac gacttatgag cctatggtac gtttgatgca    60
aaccgagcac ctatcttgca ccaacggtaa cactgtctca aaaactatcg aaaagggatt   120
ctacatgacc cacgtca                                                  137

<210> SEQ ID NO 62
<211> LENGTH: 137
<212> TYPE: DNA
<213> ORGANISM: Saccharum officinarum

<400> SEQUENCE: 62
cctaggagtt ccatcggttg cctcaaatac tatttccgag cctacagtac gttcgacgca    60
aaccgtgcac caatctttca tcaagagtag cactacctcc aaacggaccg aaccgagctt   120
ccacttgagc cacgtca                                                  137

<210> SEQ ID NO 63
<211> LENGTH: 134
<212> TYPE: DNA
<213> ORGANISM: Saccharum officinarum

<400> SEQUENCE: 63
cccagcagtt ccatcgggtg cgtccaaaat aatttctaag cctatggtaa attcagcaca    60
aaccatgcac ctatcttgca ccggcactaa cactgtctcc aaatgaacca aaacgatcca   120
cttgacccac gtta                                                     134

<210> SEQ ID NO 64
<211> LENGTH: 121
```

```
<212> TYPE: DNA
<213> ORGANISM: Saccharum officinarum

<400> SEQUENCE: 64
cctaggagtt ccatcaggtg cgtccaaaat gattttcgag cctatggaat gttcggcaca      60
aaccgtgcac ctatcttgct caagatttgg accgaaacga tcttccactt gagcctcatc     120
t                                                                     121

<210> SEQ ID NO 65
<211> LENGTH: 137
<212> TYPE: DNA
<213> ORGANISM: Saccharum officinarum

<400> SEQUENCE: 65
ccttggagta ccatcgggtg catccaaatt gatttataag cctctggtac gtttggtgca      60
aaccctggac ctatcttgca ctgatagtaa cactgtctcc aaatggaccg aaatgagatt     120
ccatatgacc cacgtca                                                    137

<210> SEQ ID NO 66
<211> LENGTH: 137
<212> TYPE: DNA
<213> ORGANISM: Saccharum officinarum

<400> SEQUENCE: 66
cctaggagtt ccattgggtg cgtccacaat aattttccga gcctatggtg cgttcggtgc      60
aaactatgca cctatcttgt gttatgatta gtactatcgc caatcgtacc gaaatagctt     120
ccacttgagc cacgtca                                                    137

<210> SEQ ID NO 67
<211> LENGTH: 128
<212> TYPE: DNA
<213> ORGANISM: Saccharum officinarum

<400> SEQUENCE: 67
cccagcagtt ccatcgggtg cgtccaaaac tatttatgac ctatggtacg ttcaatgcaa      60
accgtgcacc tatcttctac agcactatct ccaaacggac caaacagatc tccaccagac     120
cctcgtca                                                              128

<210> SEQ ID NO 68
<211> LENGTH: 135
<212> TYPE: DNA
<213> ORGANISM: Saccharum officinarum

<400> SEQUENCE: 68
cctaggagta ccgtgggtgc ttctaaaatg atttatgaac ctatggtgcg tttgacgcaa      60
accgtgcacc tatattgcac cgacactaac actgtctcca aacggatcga acatgattc     120 cacttgaccc actcg                                                      135

<210> SEQ ID NO 69
<211> LENGTH: 137
<212> TYPE: DNA
<213> ORGANISM: Saccharum officinarum

<400> SEQUENCE: 69
tctaggactt ccatcgcgtg cgttcaagat gatttctgag cctatggtgc gtttggcaca      60
aaccacgcag ctatcttgca ttaaaattag cactatctcc aaatggactc aaacaagctt     120
```
tcacttgagc cacgtca                                                         137

<210> SEQ ID NO 70
<211> LENGTH: 137
<212> TYPE: DNA
<213> ORGANISM: Saccharum officinarum
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 70
cccngnagtt ccatcgggtg cctccaatac tatttctgag cctactgtcc gtttgacgca      60
aaccgtgcac caatcgtgca tcaagagtag cactatcccc aaatggaccg aaccgagctt     120
ccacttgagc cacgtca                                                    137

<210> SEQ ID NO 71
<211> LENGTH: 137
<212> TYPE: DNA
<213> ORGANISM: Saccharum officinarum

<400> SEQUENCE: 71
cccagcagtt ccatcgggtg cgttcaaaac gatatctgag cctacggtat gtttggcgca      60
aaccgtgcgc ctatcttaca ccgatactaa cactgtctct aaacagaccg aaatgagatt     120
ccacatgacc cacatca                                                    137

<210> SEQ ID NO 72
<211> LENGTH: 135
<212> TYPE: DNA
<213> ORGANISM: Saccharum officinarum

<400> SEQUENCE: 72
cctaggtgtt ccatctggtg tgtccaaaat gattttcaag cctatggtac gctcggcgca      60
agccgtgcac ctatcttgct ccaatactaa gactctccaa acaaactgaa ataagattcc     120
acatgaccca ggtca                                                      135

<210> SEQ ID NO 73
<211> LENGTH: 137
<212> TYPE: DNA
<213> ORGANISM: Saccharum officinarum

<400> SEQUENCE: 73
cctaggtgtt ctgtcgggtg tgtctaaagc gattttggag cctgtggtac gttcagggca      60
aacagtgcac ctatcttgcg ttaagaatag tagtatctct aaacggaccg aaacgagcat     120
ccacttgagc cacgtca                                                    137

<210> SEQ ID NO 74
<211> LENGTH: 137
<212> TYPE: DNA
<213> ORGANISM: Saccharum officinarum

<400> SEQUENCE: 74
cccagcagtt ccatcgggtg cgtccaaaat gatttctgag cccgtggaaa gttcggcgca      60
aactgtgcac caatcttgcg tcaagattag cactatctcc aaacagaccg aatcgaactt     120
ccacttgagc cacgtca                                                    137

<210> SEQ ID NO 75
<211> LENGTH: 137
<212> TYPE: DNA
<213> ORGANISM: Saccharum officinarum

<400> SEQUENCE: 75
cccagcagtt ccatcgggtg catccagaac gatttccgag cctatggtat attcggcaca        60
aacaatgcac ctatcttgca ccgacactaa cactgtctcc aaacggacct aaatgagaat       120
ccacacgacc cacgtca                                                      137

<210> SEQ ID NO 76
<211> LENGTH: 138
<212> TYPE: DNA
<213> ORGANISM: Saccharum officinarum

<400> SEQUENCE: 76
cctaggagct tcatcaggtg cctgtaaaaa ctattctcga gcctttggta tgttcggcgc        60
aaaccatgcc cctatcctac atcaagatta gcagtatctc caaacggacc gaaacgagtt      120
tccacttgag ccacgtca                                                     138

<210> SEQ ID NO 77
<211> LENGTH: 137
<212> TYPE: DNA
<213> ORGANISM: Saccharum officinarum

<400> SEQUENCE: 77
cccagcagtt ccatcgggtg cgtccaaaat gatttctaag cctatggtac attcggcgca        60
aaccgtgcaa ctatcttgtg tcaagattag ctctatgtcc aaacagacca aaactagcat       120
ccatgtgtgc ctcgtca                                                      137

<210> SEQ ID NO 78
<211> LENGTH: 130
<212> TYPE: DNA
<213> ORGANISM: Saccharum officinarum

<400> SEQUENCE: 78
cctaggagta ccatcaggtg cgtccaaaat gatttctaac cctatggtac atttggcaca        60
aaccttgcac ctatcaagat tagctctatc tccaaacaga ccaaaaggac tatccaattg       120
agcctcgtca                                                              130

<210> SEQ ID NO 79
<211> LENGTH: 137
<212> TYPE: DNA
<213> ORGANISM: Saccharum officinarum

<400> SEQUENCE: 79
cctaggagta gcatcagata cgtccaaaat gatttctgag cctatggtac gttcaatgca        60
aaccatgcac ctatcttgcg tcaagattag cactgtctcc aaacatacca aaatgagcat       120
ccacttaagc cacgtca                                                      137

<210> SEQ ID NO 80
<211> LENGTH: 137
<212> TYPE: DNA
<213> ORGANISM: Saccharum officinarum

<400> SEQUENCE: 80

```
cctaggagta ccatcgggtg cgtccaaaat gatttctgag cctatggtat gtttggcgca    60
aattgtgcac ctatcttgca tcaagtttag caacatctcc aatcggaccg taacgagctt   120
tcacttgagc cacgtca                                                  137

<210> SEQ ID NO 81
<211> LENGTH: 135
<212> TYPE: DNA
<213> ORGANISM: Saccharum officinarum

<400> SEQUENCE: 81
cccagcagtt ccatcgggtg cgtccaaaac aatttctatg cctatggtac gtttggtgca    60
aacagtgcac ctatcttgca ctgacagtac cactgtcttc taatgttgaa atgagattcc   120
acatgaccaa tgtca                                                    135

<210> SEQ ID NO 82
<211> LENGTH: 137
<212> TYPE: DNA
<213> ORGANISM: Saccharum officinarum

<400> SEQUENCE: 82
ccttagagat ccattggttg cgtccaaaac gattctgac cctaagttac gttcggcgca     60
aaccgtgcaa caatcttgcg tcaagattag cactatctcc aaacagacca aaacgagcat   120
ccacttgagc ctcatca                                                  137

<210> SEQ ID NO 83
<211> LENGTH: 136
<212> TYPE: DNA
<213> ORGANISM: Saccharum officinarum

<400> SEQUENCE: 83
ccaagagtac catcaggtgt gtctgaaacg attttcaagc ttgtggtacg ttcgccgcaa    60
accgtgcacc tatcttgcgt caagattagt actatctcca aatagcctaa aataaataac   120
cacttgagcc acgtca                                                   136

<210> SEQ ID NO 84
<211> LENGTH: 137
<212> TYPE: DNA
<213> ORGANISM: Saccharum officinarum

<400> SEQUENCE: 84
cccagcagtt ccatcgggtg cctccagtac tatttccaag cgtacggtac gtttgacgca    60
aaccgtgcac caatcgtgca tcaagagtag cactatctcc aaatggactg aaccaagctt   120
ccacttgagc cacgtca                                                  137

<210> SEQ ID NO 85
<211> LENGTH: 137
<212> TYPE: DNA
<213> ORGANISM: Saccharum officinarum

<400> SEQUENCE: 85
cccagcagtt ccatcgggtg cctccaatac tatttctgag cctatgattt atccgatgca    60
aaccatgcat caatcatgcg tcaagagtag cactatctcc aaatggaccg taccgagctt   120
ccacttgagc ctcgtca                                                  137

<210> SEQ ID NO 86
<211> LENGTH: 137
```

```
<212> TYPE: DNA
<213> ORGANISM: Saccharum officinarum

<400> SEQUENCE: 86
cctaggagtc ccatcgagtg tgtccaaaac gatttatatg cctatggtat gtttagtgca      60
aaccgtgcac ctatcttgca ctgacactaa cactgtctta aagtagatca aaacgagatt     120
ccacaagacc cacgtca                                                    137

<210> SEQ ID NO 87
<211> LENGTH: 137
<212> TYPE: DNA
<213> ORGANISM: Saccharum officinarum

<400> SEQUENCE: 87
cctaggagtt ccaccgggtg cctccaatac tatttccgag cctacggcac attcgacgca      60
aaccgagcac caatcttgca tcaagagtag cactatctcc aaacataccg aatcgagatt     120
ccacttgagc cacgtca                                                    137

<210> SEQ ID NO 88
<211> LENGTH: 131
<212> TYPE: DNA
<213> ORGANISM: Saccharum officinarum

<400> SEQUENCE: 88
cccagcagtt ccatcgggtg catctaaacc aatttccgag cctatggtag gttccacgca      60
acccgtgcac ctcgtcaaga ttagcactat ctccaaacgg accaaaacaa gcttccactt     120
cagcctcgtc a                                                          131

<210> SEQ ID NO 89
<211> LENGTH: 138
<212> TYPE: DNA
<213> ORGANISM: Saccharum officinarum

<400> SEQUENCE: 89
cctatgagtt ccatggggtg tgtccaaaat gattttccaa gcctatggta tgtttggcgt      60
aatccgtgca cctatcttgc atcaagttta gcaccatctc caatcggacc gtaacgagct     120
tccacttgag ccatgtca                                                   138

<210> SEQ ID NO 90
<211> LENGTH: 137
<212> TYPE: DNA
<213> ORGANISM: Saccharum officinarum

<400> SEQUENCE: 90
cccagcagtt ccatcgggtg cctccaaaac tatttccgag cctacgacac attcgacgta      60
aaccgagcac caatcttgca tcaagagtag cactatctcc aaacgtaccg aatcgagctt     120
ccacttgagc cacgtca                                                    137

<210> SEQ ID NO 91
<211> LENGTH: 137
<212> TYPE: DNA
<213> ORGANISM: Saccharum officinarum

<400> SEQUENCE: 91
cccagcagtt ccatcgggtg cgctcaaaat gatgttcgag cctacggtac atttggcgca      60
aaccatgcac ctatcttgtg tcaacattag tactatctcc aaatagaccg aaataagctt     120
```

```
tcacttgagc cacgtca                                                     137
```

<210> SEQ ID NO 92
<211> LENGTH: 137
<212> TYPE: DNA
<213> ORGANISM: Saccharum officinarum

<400> SEQUENCE: 92

```
cccagcagtt ccatcgggtg cgtccaaaat gatttctgac cgtatgttac gttcggcgca    60
aatcgtgcat ctatcttgcg tcaagattag cactatctcc aaagagacca aaacgagcat   120
ccacttgagc ctcttca                                                   137
```

<210> SEQ ID NO 93
<211> LENGTH: 137
<212> TYPE: DNA
<213> ORGANISM: Saccharum officinarum

<400> SEQUENCE: 93

```
gcaaggagta ccatcgggtg tgtctgaaat gagtttcaag cttgtggtac gttcggcgca    60
aaccgtgcaa ctatcttgca tcaagattag cactatctct aaacagacta aaacaagtaa   120
ccacttgagc cacgtca                                                   137
```

<210> SEQ ID NO 94
<211> LENGTH: 137
<212> TYPE: DNA
<213> ORGANISM: Saccharum officinarum

<400> SEQUENCE: 94

```
cccagcagtt ccatcgggtg cctccaatac tagttccgag cctacagtac gttcaacgca    60
aaccgtgcac caatcatgca tcaagagtag cactatctcc aaatggactg taccgagctt   120
ccacttgagc ctcgtca                                                   137
```

<210> SEQ ID NO 95
<211> LENGTH: 136
<212> TYPE: DNA
<213> ORGANISM: Saccharum officinarum

<400> SEQUENCE: 95

```
cctaggagtc ccatcgagtg tgtccaaaat gatttttatg cctatggtac gttcagtgca    60
aaccgtgcac ctatcttgca ccgaagctaa cactgtctca aaatagatca aaatgagatt   120
ccacatgacc cacgcc                                                    136
```

<210> SEQ ID NO 96
<211> LENGTH: 137
<212> TYPE: DNA
<213> ORGANISM: Saccharum officinarum

<400> SEQUENCE: 96

```
cctaggagtt ccattgggtg cctccaatac tatttccgag cctacggcac attcgacgca    60
aatcgagcac caatcttgca tcaagagtag cactatctcc aaacgtaacg aatcgaactt   120
ccacttgagc cacgtca                                                   137
```

<210> SEQ ID NO 97
<211> LENGTH: 128
<212> TYPE: DNA
<213> ORGANISM: Saccharum officinarum

<400> SEQUENCE: 97

```
cccagcagtt ccatcgggtg cgtccaaaac tatttatgac ctatggtacg ttcaatgcaa    60
accgtgcacc tatcttctgt agcgctatct ccaaacggac cgaacagatc tccactagac   120
cctcatca                                                            128

<210> SEQ ID NO 98
<211> LENGTH: 136
<212> TYPE: DNA
<213> ORGANISM: Saccharum officinarum

<400> SEQUENCE: 98
ccaaagagta ccgcgggtgc ttctaaaacg atttattaac ctatggtacg tttgacgcaa    60
accgagcacc tatcttgcac tgacgctaat actgtctcaa aatagatcaa acaagattc   120 cacatgaccc atgtca                                                   136

<210> SEQ ID NO 99
<211> LENGTH: 137
<212> TYPE: DNA
<213> ORGANISM: Saccharum officinarum

<400> SEQUENCE: 99
cctaggagtt ccattgggtg cctccaatac tatttccgag cctacggcac attcgacgca    60
aaccgagcac caatcttgca tcaagagtag cactatctcc aaacgcaccg aatcgagctt   120
ccacttgagc cacgtca                                                  137

<210> SEQ ID NO 100
<211> LENGTH: 137
<212> TYPE: DNA
<213> ORGANISM: Saccharum officinarum

<400> SEQUENCE: 100
cccagcagtt ccatcgggtg cgtccaagac gattttcgag tcgatggtac aatgaacaca    60
aaccaggcac ctatcttgca tcaagaatag cactatctcc aaacggactc aaacaagctt   120
ccacttgagc ctcgcca                                                  137

<210> SEQ ID NO 101
<211> LENGTH: 128
<212> TYPE: DNA
<213> ORGANISM: Saccharum officinarum

<400> SEQUENCE: 101
cctagtagta tcatcaggcg tgtccaaagt gatttcaggg ccaatggcac attctgagca    60
aaccatttgc accgacacta acactatccc caaacagacc gaaatgagct tccacttgat   120
cctcatca                                                            128

<210> SEQ ID NO 102
<211> LENGTH: 137
<212> TYPE: DNA
<213> ORGANISM: Saccharum officinarum

<400> SEQUENCE: 102
cctaggagta ccatcagatg cgcccaaaat gattgctaag cctatgacat gtttcacgca    60
aaccatgcac ctatcttgca ccgacgcaaa ctctgtctcc aaacagacca aaacaagttt   120
ccacatgacc cacatca                                                  137

<210> SEQ ID NO 103
```

```
<211> LENGTH: 134
<212> TYPE: DNA
<213> ORGANISM: Saccharum officinarum

<400> SEQUENCE: 103
cctaggagtt ccatcgggtg cgtccaaaac gattttcgag cctatggtac gctcagcgca    60
aatcgtgctt tcttgcatca atgttagccc tatctccaaa tggaccgaaa cgagcttcca   120
cttgagccac gtca                                                     134

<210> SEQ ID NO 104
<211> LENGTH: 137
<212> TYPE: DNA
<213> ORGANISM: Saccharum officinarum

<400> SEQUENCE: 104
cccagcagtt ccatcgggtg cgtccaatat gatttctgag cctatggtac gttcggcata    60
aaccatgcac caatcttgct tccagattag cactatctct aaatggacca aaatgagctt   120
ccacttaagc ctcatca                                                  137

<210> SEQ ID NO 105
<211> LENGTH: 137
<212> TYPE: DNA
<213> ORGANISM: Saccharum officinarum

<400> SEQUENCE: 105
cctaggtgta ccaccgggtg cgtccaaaac gattactgag cctatggtat gtttgaccca    60
aaccatgcac ctatcttgta ctaacactaa caccatctcc aaacggacca aaacgagctt   120
tgacacaacc caagtca                                                  137

<210> SEQ ID NO 106
<211> LENGTH: 137
<212> TYPE: DNA
<213> ORGANISM: Saccharum officinarum

<400> SEQUENCE: 106
cctaggggtt ccttcgggtg cgtccaaaat aattttttaag cctatggtac gttcagcgga   60
aactgtgcat ctgtcttgtg tcaagattag cactgtcttc aaatggacca aaacgagctt   120
gcacttgagc cacgtca                                                  137

<210> SEQ ID NO 107
<211> LENGTH: 132
<212> TYPE: DNA
<213> ORGANISM: Saccharum officinarum

<400> SEQUENCE: 107
cccagcagtt ccatcgggtg catcccaaaa ggatttctga tctacgtttc gcgcaaaccg    60
tgcaccgatc ttgcactgac tctaatactg tctccaaatg gattgaaaca agattccaca   120
cgaccaatgt ga                                                       132

<210> SEQ ID NO 108
<211> LENGTH: 137
<212> TYPE: DNA
<213> ORGANISM: Saccharum officinarum

<400> SEQUENCE: 108
ccgaggagat ccatcgggtg cgtccaaaat gatttctgag cctgtcctac gttcggagca    60
aaccttgcac ccatcttgtg tcatgattag ctctatgtcc aaacagacca aaacgagcat   120
```

```
gcacgtgtgc ctcatca                                                      137

<210> SEQ ID NO 109
<211> LENGTH: 137
<212> TYPE: DNA
<213> ORGANISM: Saccharum officinarum

<400> SEQUENCE: 109
cctaggagta ccatcgagtg cgacaaaaat gattttcgag cctatggtac gttcgacgta       60
aaccgtgcac ctatcttgtg tcaatattag cactatgtct aaatagactg aaacaaataa      120
ccacttgagc cacgtca                                                      137

<210> SEQ ID NO 110
<211> LENGTH: 137
<212> TYPE: DNA
<213> ORGANISM: Saccharum officinarum

<400> SEQUENCE: 110
cccagcagtt ccatcgggtg cgtccaaaat gatttctgag cccgtggtaa gttcggcgca       60
aacagtgcac caatcttgcg tcaagattag cactatctcc aaacagaccg aatcgaactt      120
ccacttgagc cacgtca                                                      137

<210> SEQ ID NO 111
<211> LENGTH: 136
<212> TYPE: DNA
<213> ORGANISM: Saccharum officinarum

<400> SEQUENCE: 111
cccagcagtt ccatcgggtg cgtccaaaat gatttccaag ctatgatacg tttggtgcaa       60
actgtatacc tatcttgcgt aaagattagt actatctcca aacggatcga aacgagcttc      120
tacttgagcc acgtca                                                       136

<210> SEQ ID NO 112
<211> LENGTH: 137
<212> TYPE: DNA
<213> ORGANISM: Saccharum officinarum

<400> SEQUENCE: 112
cccagcagtt ccatcgggtg cattcaaaat gattgccgag cttatggtac attcggcgca       60
aactgtgcac ctatcttgag tcaaggttag cactatctac aaaccaactg aaacgagccc      120
ccatttgagc ctcgtga                                                      137

<210> SEQ ID NO 113
<211> LENGTH: 137
<212> TYPE: DNA
<213> ORGANISM: Saccharum officinarum

<400> SEQUENCE: 113
cctaggagtt ccattcggtg tgtccaaaac aatttacgag cctatggtac gtttggcgca       60
aactatgcac ctatcttgca gtgaaactaa cactatctcc aaaaggaccg aaaggagatt      120
ctacatgacc cacatca                                                      137

<210> SEQ ID NO 114
<211> LENGTH: 137
<212> TYPE: DNA
<213> ORGANISM: Saccharum officinarum
```

-continued

<400> SEQUENCE: 114
cctagaagta ccatatggtg tgtccaaaat gatttctgag cctatgggac atttggcgca      60
aactgtgccc ccatcttgca ctgaaactaa cacagtctcc aaacacaccg aaacgagctt     120
ccacttgagc cacgtca                                                    137

<210> SEQ ID NO 115
<211> LENGTH: 137
<212> TYPE: DNA
<213> ORGANISM: Saccharum officinarum

<400> SEQUENCE: 115
cacagcagtt ccatcgggtg cgtccaaaat aacttctgag cctatggtac gttcgacgca      60
gactgtgtac ctatcttgcg tcaggattag aactatctcc aattggaccg aaccaagctt     120
ccacttgagc cacgtca                                                    137

<210> SEQ ID NO 116
<211> LENGTH: 137
<212> TYPE: DNA
<213> ORGANISM: Saccharum officinarum

<400> SEQUENCE: 116
cccagcagtt ccatcgggtg cgtccaaaac aatttctgag gctatggtac gttcgacaca      60
aaacgtgcac ctttcttgtg tcaagattag cactatcttt gaacggtccg aatcgaggtt     120
cgacttcagc cacatca                                                    137

<210> SEQ ID NO 117
<211> LENGTH: 137
<212> TYPE: DNA
<213> ORGANISM: Saccharum officinarum

<400> SEQUENCE: 117
cctagcagta ccatcgggtg cacccaaaat gatttctcag cctatggtac attcggtgca      60
aaccgtacac ctatcttgcg tcaagattag cactatctcc aaacaaactg aatcaagcat     120
ccacttgagc cacgtca                                                    137

<210> SEQ ID NO 118
<211> LENGTH: 128
<212> TYPE: DNA
<213> ORGANISM: Saccharum officinarum

<400> SEQUENCE: 118
cccagcagtt ccatcgggtg cctccaaaaa tttctatgac ctatggtacg ttcaatgcaa      60
accgtgcacc catcttctgt agcattatct ccaagtggac caaacagatc tccaccagac     120
cctcatca                                                              128

<210> SEQ ID NO 119
<211> LENGTH: 136
<212> TYPE: DNA
<213> ORGANISM: Saccharum officinarum

<400> SEQUENCE: 119
cctaggagta ccgcgggcgc ttcgaaaaca atttatgaac ctatggtaca tttgacgcaa      60
accgagcacc tatcttgcac cgacgctaac actatttcaa aatagatcga aacaagattc     120
cacatgaccc acgtaa                                                     136

<210> SEQ ID NO 120
<211> LENGTH: 137
<212> TYPE: DNA
<213> ORGANISM: Saccharum officinarum

<400> SEQUENCE: 120

```
cctaggagtt ccatcgggtg cgtccaacac gatttctgat ctgatggtac attcgataca    60
aatcgtgcac ttttcttgca tcgagattac cactatctcc aaatggactc aaacaagctt   120
ccacttgagc cacgtca                                                  137
```

<210> SEQ ID NO 121
<211> LENGTH: 137
<212> TYPE: DNA
<213> ORGANISM: Saccharum officinarum

<400> SEQUENCE: 121

```
cccagcagtt ccatcgggtg cctctaatac tatttctgag cctattgtac gtttgatgca    60
aaccgtacac caatcgtgca tcaagagtag cactatcccc aaacggaccg aaccgagctt   120
ccacttgagc cacgtca                                                  137
```

<210> SEQ ID NO 122
<211> LENGTH: 137
<212> TYPE: DNA
<213> ORGANISM: Saccharum officinarum

<400> SEQUENCE: 122

```
cccagcagtt ccatcgggtg catccaaaat gatttctgat cctacggtat gctcggcgta    60
aactgtgcac ctttcttgcg tcaaggttag cactatctcc aaacagacca gaacgagcat   120
ccacttgagc cacgtca                                                  137
```

<210> SEQ ID NO 123
<211> LENGTH: 137
<212> TYPE: DNA
<213> ORGANISM: Saccharum officinarum

<400> SEQUENCE: 123

```
cccagcagtt ccatcgggtg cctccaaagc tatttatgag cctacggtac gtttgacaca    60
aaccgttcac caatcttgca ccaagagcag cactatctcg aaatagacgg aaccgagctt   120
ccacttgggc ctcgtca                                                  137
```

<210> SEQ ID NO 124
<211> LENGTH: 137
<212> TYPE: DNA
<213> ORGANISM: Saccharum officinarum

<400> SEQUENCE: 124

```
cctaggaacc taccgagtgc atccaaaata attttccatg cctatggtat gttcggtgca    60
aaccgtgcac ctatcttaca ttgatactaa cactatctcc aaatggacta aaacgagatt   120
ccacatgacc cacgtca                                                  137
```

<210> SEQ ID NO 125
<211> LENGTH: 136
<212> TYPE: DNA
<213> ORGANISM: Saccharum officinarum

<400> SEQUENCE: 125

```
cttacgagtt ccattgggtg cgtccaaaac tatttatgag cctatagtac gtttagtgca    60
```

```
aaccatgcac ctatcttgca ttaagattag cactatctcc aaacggatcg aacagagctc    120
caccagagcc acgtca                                                    136

<210> SEQ ID NO 126
<211> LENGTH: 137
<212> TYPE: DNA
<213> ORGANISM: Saccharum officinarum

<400> SEQUENCE: 126
cctagaagta ccatcgggtg cgtctgaaac gacttatgag cctatggtac gtttgatgca     60
aaccgagcac ctatcttgca ccaacggtaa cactgtctca aaaactatcg aaaagggatt    120
ctacatgacc cacgtca                                                   137

<210> SEQ ID NO 127
<211> LENGTH: 137
<212> TYPE: DNA
<213> ORGANISM: Saccharum officinarum

<400> SEQUENCE: 127
cctaggagtt ccatcggttg cctcaaatac tatttccgag cctacagtac gttcgacgca     60
aaccgtgcac caatctttca tcaagagtag cactacctcc aaacggaccg aaccgagctt    120
ccacttgagc cacgtca                                                   137

<210> SEQ ID NO 128
<211> LENGTH: 134
<212> TYPE: DNA
<213> ORGANISM: Saccharum officinarum

<400> SEQUENCE: 128
cccagcagtt ccatcgggtg cgtccaaaat gattttgaag catgtggtac gtttggtgta     60
aaacgtgcac taatcttgca tagccactaa cactgccttc aaatagaccg atagattcca    120
catgtcccaa gtca                                                      134

<210> SEQ ID NO 129
<211> LENGTH: 136
<212> TYPE: DNA
<213> ORGANISM: Saccharum officinarum

<400> SEQUENCE: 129
cctaggagtt ccatcgggtg cgtccaaaac gattttgag cctatggtac gtttggcgca      60
aagtgtgcac ctatcctgcg tcaagattag cactatctac aaacggatca aatgagcttc    120
cacttgagcc acgtca                                                    136

<210> SEQ ID NO 130
<211> LENGTH: 137
<212> TYPE: DNA
<213> ORGANISM: Saccharum officinarum

<400> SEQUENCE: 130
cccagcagtt ccatcgggtg cttgtcaaat gatttatgag cctatggtac gtttgacgca     60
aattgagcac ctatcttgga ccgacgctaa cactgtctca aaacggatcg aaacgagatt    120
ccacaagacc cacgtca                                                   137

<210> SEQ ID NO 131
<211> LENGTH: 137
<212> TYPE: DNA
<213> ORGANISM: Saccharum officinarum
```

<400> SEQUENCE: 131

```
actaggagtt ccatcgggtg cctccaatac tatttctgag cctattgtcc gtttgatgca      60
aaccgtacac caatcgtgca tctagagtag cactatcccc aaacggaccg aaccgagctt     120
ccacttgagc cacgtca                                                   137
```

<210> SEQ ID NO 132
<211> LENGTH: 137
<212> TYPE: DNA
<213> ORGANISM: Saccharum officinarum
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t

<400> SEQUENCE: 132

```
cccagcagtt ccatcgggtg cctccaatac gatttccaag actactgcac attcgacgca      60
aaccgagcac cnatcttgca tcangagtag cactatctcc aaacgtaccg aatcgagttt     120
ccacttgagc ctcgtca                                                   137
```

<210> SEQ ID NO 133
<211> LENGTH: 141
<212> TYPE: DNA
<213> ORGANISM: Saccharum officinarum
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t

<400> SEQUENCE: 133

```
cctaggagtc ccctcganng cgtgcaaaat gatttctatg cctatgctat atttggtgca      60
aaccaaaggc ccatcttgca tcaagagaag cactatcccc aaacggaccg aaccgagctt     120
ccacttgagc cacgggnccc a                                              141
```

<210> SEQ ID NO 134
<211> LENGTH: 137
<212> TYPE: DNA
<213> ORGANISM: Saccharum officinarum

<400> SEQUENCE: 134

```
cccagcagtt ccatcgggtg cgtccaatac gatttctgag cctacggtat gtttggcgca      60
gaccgtgcaa ttatcttgct ccgacactaa acctatctcc aaacggactt aaacgagatt     120
ccacatggcc cccgaca                                                   137
```

<210> SEQ ID NO 135
<211> LENGTH: 137
<212> TYPE: DNA
<213> ORGANISM: Saccharum officinarum

<400> SEQUENCE: 135

```
ccttggagtt ccattgggtg catccaaaat gattctcgag cctccggtac gttctgcgca      60
aaccgtgcac ctatcttgca gaaagattag cgccatctcc aaacagaacg aaacgagctt     120
```

```
ccacttgagc cacgtca                                                   137

<210> SEQ ID NO 136
<211> LENGTH: 137
<212> TYPE: DNA
<213> ORGANISM: Saccharum officinarum

<400> SEQUENCE: 136
cccagcagtt ccatcgggtg cgtgcaaaat aatttctaag gctatggtac gttcggcaca    60
aaccgtgcac ctatctggtg tcaagattag cactatcttt gagtggtccg aatcgagctt   120
gcacttgagc cttgtca                                                   137

<210> SEQ ID NO 137
<211> LENGTH: 137
<212> TYPE: DNA
<213> ORGANISM: Saccharum officinarum

<400> SEQUENCE: 137
cccagcagtt ccatcgggtg cgttcgaaac aattgcatag ccggtggtag gttcggcaca    60
aaccgtgcag ctatcttgcg tcatgattag cactatctcc aaacgaactg aatcaagcat   120
gcacttgagc cacgtca                                                   137

<210> SEQ ID NO 138
<211> LENGTH: 137
<212> TYPE: DNA
<213> ORGANISM: Saccharum officinarum

<400> SEQUENCE: 138
cccagcagtt ccatcgggtg cgtccaaaat gatttccgag cctatggtac ttttaacata    60
aactgtgcac ctatcttgcg tcaagattag cactatctct gaaaggaccg aaacgagctt   120
ccacttgagc cacgtca                                                   137

<210> SEQ ID NO 139
<211> LENGTH: 128
<212> TYPE: DNA
<213> ORGANISM: Saccharum officinarum
<220> FEATURE:
<221> NAME/KEY: misc_feature
<222> LOCATION: (6)..(6)
<223> OTHER INFORMATION: n is a, c, g, or t

<400> SEQUENCE: 139
cccagnagtt ccatcgggtg cgtccaaaac tgtttacgac ctatggtacg ttcaatgcaa    60
accgtgcacc tatcttctgt agcactatct ccaaacggac caaacagatc tccaccagac   120
cctcatca                                                             128

<210> SEQ ID NO 140
<211> LENGTH: 136
<212> TYPE: DNA
<213> ORGANISM: Saccharum officinarum

<400> SEQUENCE: 140
cctaggagta ccacaggtgc ttctaaaaca atttatgaac ctatggtacg tttgacgcaa    60
actgagcacc tatcttgcac cgatgctaac actatttcaa aacagatcga aacaagattc   120
cacatgaccc acgtaa                                                    136

<210> SEQ ID NO 141
<211> LENGTH: 137
```

```
<212> TYPE: DNA
<213> ORGANISM: Saccharum officinarum

<400> SEQUENCE: 141
cctaggagtt ccatcgggtg cctccaattc tatttctgag cctacggtac gatcgacgca    60
aaccgtgcac caatcatgca tcaaaagtag cactatctcc aaatgtaccg taccgagctt   120
ccactggagc ctcgtca                                                  137

<210> SEQ ID NO 142
<211> LENGTH: 137
<212> TYPE: DNA
<213> ORGANISM: Saccharum officinarum

<400> SEQUENCE: 142
cctaggagtc ccatcgagtg tatccaaaac gatttctatg cccatggtac gttcagtgca    60
aaccgtgcac ctatcttgca ctgaagctaa cactgtctca aaatagatca aaacgagatt   120
ccacatgacc cacgtca                                                  137

<210> SEQ ID NO 143
<211> LENGTH: 137
<212> TYPE: DNA
<213> ORGANISM: Saccharum officinarum

<400> SEQUENCE: 143
cctaggagtt ccatcgggtg cctccaatac tatttccaag cctacggcac attcaacgca    60
aaccgagcaa caatcttgca ccaagagtag cactatctcc aaacgtgccg tatcgagctt   120
ctacttgagc cacgtca                                                  137

<210> SEQ ID NO 144
<211> LENGTH: 137
<212> TYPE: DNA
<213> ORGANISM: Saccharum officinarum

<400> SEQUENCE: 144
cccagcagtt ccatcgggtg cgtcaaaaat gattgctgag cctgtggtac gttcggcaca    60
aactgtgcac ctatcttgca tcaagattcc cactatctcc aaacaaactg aaccgagctt   120
ccacttgagc cacgtca                                                  137

<210> SEQ ID NO 145
<211> LENGTH: 137
<212> TYPE: DNA
<213> ORGANISM: Saccharum officinarum
<220> FEATURE:
<221> NAME/KEY: misc_feature
<222> LOCATION: (6)..(6)
<223> OTHER INFORMATION: n is a, c, g, or t

<400> SEQUENCE: 145
cccagnagtt ccatcgggtg cgtccaagac gattttcgag ccgatagtac attcgacaca    60
aaccacagac ctatcttgcg tcaagtttag cactatctcc aaacaaactc aaacaagctt   120
tcacttgagc cacgtca                                                  137

<210> SEQ ID NO 146
<211> LENGTH: 126
<212> TYPE: DNA
<213> ORGANISM: Saccharum officinarum

<400> SEQUENCE: 146
```

```
cccagcagtt ccatcgggtg cctccaatac tatttccgag cctacggtac atatgacgca    60
aactgtgcat caagggtagc actatctcca aacggaccga accgagcttc cacttgagcc   120
ttgtca                                                              126
```

```
<210> SEQ ID NO 147
<211> LENGTH: 137
<212> TYPE: DNA
<213> ORGANISM: Saccharum officinarum

<400> SEQUENCE: 147
ccaaggagtc ccatcgtgtg catccaaaac aatttctatg cctttggtat attcggtgca    60
aaccgtgcac ctgtcttgca ctgacactaa cactgtctcg aaacagacta aaacgagatt   120
ccacacgacc catgtca                                                  137
```

```
<210> SEQ ID NO 148
<211> LENGTH: 135
<212> TYPE: DNA
<213> ORGANISM: Saccharum officinarum

<400> SEQUENCE: 148
cttacgagtc catcgggtgc gtcaaaaact atttgtgagc ctatggtacg ttcagtgcaa    60
accgtgcacc tatcctgtgt cacgattagc actatctcca aatgcaccga acagagctcc   120
accagaccca cgtca                                                    135
```

```
<210> SEQ ID NO 149
<211> LENGTH: 137
<212> TYPE: DNA
<213> ORGANISM: Saccharum officinarum

<400> SEQUENCE: 149
cttaggagta ccatcgggtg cgtctaaact gatttatgac cctatggtac gcttgacgca    60
aatcgtgcac ctatcttgca ccgacgctaa cactatctca aaacagatcg aaacgagatt   120
ccacaagacc cacatca                                                  137
```

```
<210> SEQ ID NO 150
<211> LENGTH: 137
<212> TYPE: DNA
<213> ORGANISM: Saccharum officinarum

<400> SEQUENCE: 150
actaggagtt ccaataggtg cctccaatac tatttccaag cctatggtac gtttgacgca    60
aaccgtgcac caaccatgca tcaagagtag cactatctcc aaacggaacg aatcgagttt   120
ccacttgagc cacgtca                                                  137
```

```
<210> SEQ ID NO 151
<211> LENGTH: 137
<212> TYPE: DNA
<213> ORGANISM: Saccharum officinarum

<400> SEQUENCE: 151
cccagcagtt ccatcgggtg cgaccaaaat aatttctgag cctgtgttat gtttggcgca    60
aatcaagcac ctatgttgtg tcaagattag cactatctac aaacggaatg aaacgagcat   120
ccacttgagc ctcggca                                                  137
```

```
<210> SEQ ID NO 152
<211> LENGTH: 137
```

-continued

```
<212> TYPE: DNA
<213> ORGANISM: Saccharum officinarum

<400> SEQUENCE: 152
cctaggagta ccatcgggtg cgtccaaaac gatttgtgag cctatggtac gtttggcaca    60
aaccgtgcaa ttatctttag tcaagaatag cattatcttc aaacggaatg aaacgagcat   120
ccacttgagc ctcgtca                                                   137

<210> SEQ ID NO 153
<211> LENGTH: 137
<212> TYPE: DNA
<213> ORGANISM: Saccharum officinarum

<400> SEQUENCE: 153
cctatgagta ccatggggtg cttccaatac gatttctgag ctaatggtac gtttggcaca    60
aaccgtgcac ctatcaagcg tcaagattag cactatctcc aaatggaatg aaatgagcat   120
gcacttgagc cacgtca                                                   137

<210> SEQ ID NO 154
<211> LENGTH: 137
<212> TYPE: DNA
<213> ORGANISM: Saccharum officinarum
<220> FEATURE:
<221> NAME/KEY: misc_feature
<222> LOCATION: (6)..(6)
<223> OTHER INFORMATION: n is a, c, g, or t

<400> SEQUENCE: 154
cccagnagtt ccatcgggtg cgtataacaa gacttgcgag ccgatggtag gtttgacaca    60
aaccacgtac ctttcttacg tcaagattac cactatctcc aaacagactc aaacaagctt   120
ccacttgagc cacgtca                                                   137

<210> SEQ ID NO 155
<211> LENGTH: 137
<212> TYPE: DNA
<213> ORGANISM: Saccharum officinarum

<400> SEQUENCE: 155
cccagcagtt ccatcgggtg cgtcaaaaat gatttatgag cctgtggtac gttcggcgca    60
aactgtgcac ctatcttgcg tcaagattcc cactatctcc aaacgaactg aatcgagctt   120
ccacttgagc cacgtca                                                   137

<210> SEQ ID NO 156
<211> LENGTH: 136
<212> TYPE: DNA
<213> ORGANISM: Saccharum officinarum

<400> SEQUENCE: 156
cccagcagtt ccatcgggtg catccaaaat gacatccgag cctatggtcg ttcggagcaa    60
accatgcacc tatcttggat aaggattagc actatcttca aacagactga aatgagcttc   120
cacatgaacc tcgtca                                                    136

<210> SEQ ID NO 157
<211> LENGTH: 137
<212> TYPE: DNA
<213> ORGANISM: Saccharum officinarum

<400> SEQUENCE: 157
```

```
cctaggagta ccatcgggtg cgtccaaaat gattttgag cctatggtac gcttggcgca    60
aactgggcac ctatcttgaa acgacactaa cattgtttcc aaatagaaca aaacgagatt   120
ccacatgaca cacatca                                                  137
```

<210> SEQ ID NO 158
<211> LENGTH: 138
<212> TYPE: DNA
<213> ORGANISM: Saccharum officinarum

<400> SEQUENCE: 158

```
cctaggagtt ccatcggggg cgtccaaaat gaatttccga gcctatggta tgttctgcgc    60
aaaccgcgca cctatcttgc gtcaatatta gcactatctc caaacggacc aatacgagct   120
tccacttgag ccacgtca                                                 138
```

<210> SEQ ID NO 159
<211> LENGTH: 137
<212> TYPE: DNA
<213> ORGANISM: Saccharum officinarum

<400> SEQUENCE: 159

```
cccagcagtt ccatcgggtg cgtgcaaaac gatttctgag catatggtac gtttggcgca    60
aaccgtgcaa caaacttgca ctaacactac cactgtctca aaatggattg aaatgagatt   120
ccacatgacc aatgtca                                                  137
```

<210> SEQ ID NO 160
<211> LENGTH: 137
<212> TYPE: DNA
<213> ORGANISM: Saccharum officinarum

<400> SEQUENCE: 160

```
cctaggagat ccatcgggtg catccaaaat gatttttgaa cctttggtac gttcgacgca    60
aaccgtgcac ctatcttatg tcaagattag cactatatcc aaatagactg aaacgagcat   120
ccacttgagc ctcatca                                                  137
```

<210> SEQ ID NO 161
<211> LENGTH: 137
<212> TYPE: DNA
<213> ORGANISM: Saccharum officinarum

<400> SEQUENCE: 161

```
cctaggagta ccatcgtgtg cgtccaaaac tatttctgag cctatggtac gtttggtgca    60
aaccatgcac ctatcttaga ccaatactaa cactatctcc aaatggacca aaattatatt   120
ccacctaact catgtca                                                  137
```

<210> SEQ ID NO 162
<211> LENGTH: 137
<212> TYPE: DNA
<213> ORGANISM: Saccharum officinarum

<400> SEQUENCE: 162

```
cctaggtgtt ctatcgagtg tgcccaaaac tattttcatg cttatggtac attcggcgca    60
aaccgtgatc ctatcttgcg tcaggattag tgtaatcccc aaacagactg aaacaagcat   120
ccacttgagc cacgtca                                                  137
```

<210> SEQ ID NO 163
<211> LENGTH: 137

<212> TYPE: DNA
<213> ORGANISM: Saccharum officinarum

<400> SEQUENCE: 163
cccagcagtt ccatcgggtg cgcctaaaac ggtttatgag cctatggtac gtttgatgca    60
aaccgagcac ctatcctgca atgacgctaa cactgtctca aaatagattg aaacgagatt   120
ccacatgacc cacgtca                                                  137

<210> SEQ ID NO 164
<211> LENGTH: 137
<212> TYPE: DNA
<213> ORGANISM: Saccharum officinarum

<400> SEQUENCE: 164
cctaggagtt ccatcgggtg ccgccaatac tatttctgag ccaacgatac gttcgacgca    60
aaccatgcac caatcttgca tcaagtgtag cactatctcc aaatggatcg aaccgagctt   120
ccacttgagc cacgtca                                                  137

<210> SEQ ID NO 165
<211> LENGTH: 132
<212> TYPE: DNA
<213> ORGANISM: Saccharum officinarum

<400> SEQUENCE: 165
cccagcagtt ccatcgggtg catcctaaaa tgatttttaa tctatgtttg gcgcaaaccg    60
tgcacctatc ttgcactgac tctaatactg tctccaaatg cattgaaaca agattccaca   120
cgaccaatgt ca                                                       132

<210> SEQ ID NO 166
<211> LENGTH: 137
<212> TYPE: DNA
<213> ORGANISM: Saccharum officinarum

<400> SEQUENCE: 166
cccagcagtt ccatcgggtg cgtccaaaat gatttctgag ctaatggtac gttcggcgca    60
aagcgtgcag ctatcttgcg tcaagattac cacaatctcc aaatggagcg aaacgagctt   120
ccacttgagc cacgtca                                                  137

<210> SEQ ID NO 167
<211> LENGTH: 137
<212> TYPE: DNA
<213> ORGANISM: Saccharum officinarum

<400> SEQUENCE: 167
cccagcagtt ccatcgggtg cctccaatac tatttctgag cctaaggtac atttgacgca    60
aaccatgcac caatcgtgca tcaagggtag tactatctcc aaacggacca aaccgagctt   120
ccacttgagc cacgtca                                                  137

<210> SEQ ID NO 168
<211> LENGTH: 137
<212> TYPE: DNA
<213> ORGANISM: Saccharum officinarum

<400> SEQUENCE: 168
cccagcagtt ccatcgggtg cctccaaagc tatttatgag cctacggtac gtttgacaca    60
aaccgttcac caatcttgca ccaagagcag cactatctcg aaatagacgg aaccgagctt   120

```
ccacttgggc ctcgtca                                                     137

<210> SEQ ID NO 169
<211> LENGTH: 137
<212> TYPE: DNA
<213> ORGANISM: Saccharum officinarum

<400> SEQUENCE: 169
cctaggaacc taccgagtgc atccaaaata attttccatg cctatggtat gttcggtgca      60
aaccgtgcac ctatcttaca ttgatactaa cactatctcc aaatggacta aaacgagatt     120
ccacatgacc cacgtca                                                    137

<210> SEQ ID NO 170
<211> LENGTH: 136
<212> TYPE: DNA
<213> ORGANISM: Saccharum officinarum

<400> SEQUENCE: 170
cttacgagtt ccattgggtg cgtccaaaac tatttatgag cctatagtac gtttagtgca      60
aaccatgcac ctatcttgca ttaagattag cactatctcc aaacggatcg aacagagctc     120
caccagagcc acgtca                                                     136

<210> SEQ ID NO 171
<211> LENGTH: 137
<212> TYPE: DNA
<213> ORGANISM: Saccharum officinarum

<400> SEQUENCE: 171
cctagaagta ccatcgggtg cgtctgaaac gacttatgag cctatggtac gtttgatgca      60
aaccgagcac ctatcttgca ccaacggtaa cactgtctca aaaactatcg aaaagggatt     120
ctacatgacc cacgtca                                                    137

<210> SEQ ID NO 172
<211> LENGTH: 137
<212> TYPE: DNA
<213> ORGANISM: Saccharum officinarum

<400> SEQUENCE: 172
cctaggagtt ccatcggttg cctcaaatac tatttccgag cctacagtac gttcgacgca      60
aaccgtgcac caatctttca tcaagagtag cactacctcc aaacggaccg aaccgagctt     120
ccacttgagc cacgtca                                                    137

<210> SEQ ID NO 173
<211> LENGTH: 137
<212> TYPE: DNA
<213> ORGANISM: Saccharum officinarum

<400> SEQUENCE: 173
cccagcagtt ccatcgggtg catctaaaat gatttatgag cctgtggtac gtttgatgca      60
aaccgagcac ctatctttca ccgacgataa cactacctca aaatagatcg aagcgagatt     120
ccacatgacc catgtca                                                    137

<210> SEQ ID NO 174
<211> LENGTH: 137
<212> TYPE: DNA
<213> ORGANISM: Saccharum officinarum

<400> SEQUENCE: 174
```

```
cctaggagtt ccatcgggtg ccaccaatac tatttccgag cctacggtat gttcgacgca    60
aaccgtgcac caatcttgca tcaagagtag cactatctcc aaacgtaccg aattgagctt   120
ccacttgagc cacgtca                                                  137
```

<210> SEQ ID NO 175
<211> LENGTH: 137
<212> TYPE: DNA
<213> ORGANISM: Saccharum officinarum
<220> FEATURE:
<221> NAME/KEY: misc_feature
<222> LOCATION: (6)..(6)
<223> OTHER INFORMATION: n is a, c, g, or t

<400> SEQUENCE: 175

```
cccagnagtt ccatcgggtg cctccaatac tatttccaag tctacagtac gtttgatgcc    60
aaccgtgcac caatcttgca tcaagagtag tactatctcc aaacggaccg aaccgagctt   120
ccacttgagc cacgtca                                                  137
```

<210> SEQ ID NO 176
<211> LENGTH: 137
<212> TYPE: DNA
<213> ORGANISM: Saccharum officinarum

<400> SEQUENCE: 176

```
cccagcagtt ccatcgggtg catccaaaat gatttctgag cctacggtat gtttggcaca    60
aaccttgcac ctatcttatg tcaaggttag cactatctcc aaacagacca aaacgagcat   120
ctacttgagc ctcgtca                                                  137
```

<210> SEQ ID NO 177
<211> LENGTH: 137
<212> TYPE: DNA
<213> ORGANISM: Saccharum officinarum

<400> SEQUENCE: 177

```
cctaggagta ccatcgggtg cgtccaaaac aatttccgag cctatggtac gttcgacgca    60
aaccatccac caatctcgca tcaagaatag cactgtctcc aaatagacca aaacgagcat   120
ccacttgagc ctcgtca                                                  137
```

<210> SEQ ID NO 178
<211> LENGTH: 137
<212> TYPE: DNA
<213> ORGANISM: Saccharum officinarum

<400> SEQUENCE: 178

```
cctaggagta ccatcggttg cgtccaaaac gatttatgtg cctatggtac gtttggcgca    60
aacagtgcag ctattttgga ctgacagtac cgctatctcc aaatgcatta aaacaagatt   120
ccacatgacc aatgtca                                                  137
```

<210> SEQ ID NO 179
<211> LENGTH: 137
<212> TYPE: DNA
<213> ORGANISM: Saccharum officinarum

<400> SEQUENCE: 179

```
cctaggagat ccatcgggtg cgtccgaaat gatttctaag cctatggtac gttcggcgca    60
aaccgtgcac ctatcttgca tcaaggttag cactatctcc aaacttacca aaatgagcat   120
```

```
ccacttgagc cacgtca                                                    137

<210> SEQ ID NO 180
<211> LENGTH: 136
<212> TYPE: DNA
<213> ORGANISM: Saccharum officinarum

<400> SEQUENCE: 180
cccagcagtc catcgggtgc gtccaaaatg atttctgaga atatggtatg ttcggtgcaa     60
accatgcacc taccttgcgt caagattacc actatctcga aacggaccaa aatgagcttc   120
cacttgagcc acgtca                                                    136

<210> SEQ ID NO 181
<211> LENGTH: 137
<212> TYPE: DNA
<213> ORGANISM: Saccharum officinarum

<400> SEQUENCE: 181
cccagcagtt ccatcgggtg cgtccaatat aatttccgag ccaatggtag attcgacaca     60
aaccgtgcac ctttcttgca tcaagattac cactatctcc aaacagactc aaacaagctt   120
ccacttgagc cacgtca                                                   137

<210> SEQ ID NO 182
<211> LENGTH: 137
<212> TYPE: DNA
<213> ORGANISM: Saccharum officinarum

<400> SEQUENCE: 182
cccagcagtt ccatcgggtg cctccaaatac tatttccgag cctacggtat gttcgatgcg     60
aaccgtgcac caatcatgca tcaagagtag cactatatcc aaatggaccg taccgagctt   120
ccacttgagc ctcatca                                                   137

<210> SEQ ID NO 183
<211> LENGTH: 137
<212> TYPE: DNA
<213> ORGANISM: Saccharum officinarum

<400> SEQUENCE: 183
cctaggagtc ccatcgagtg tgtccaaaat gatttctatg cctatggtac gttcggtgca     60
aaccgtgcac ctatcttgca ccaacgctaa cactgtctca aaacagaacg aaacaagatt   120
tcacatgacc cacgtca                                                   137

<210> SEQ ID NO 184
<211> LENGTH: 137
<212> TYPE: DNA
<213> ORGANISM: Saccharum officinarum

<400> SEQUENCE: 184
cctaggagct ccatcgggtg cctccaatac tatttctgag cctacggtac atttgacgca     60
caccgagcga aagtcatgca tcaagcgtag gactatctcc aaacgtatcg aatcgagctt   120
ccacttgagc cacgtca                                                   137

<210> SEQ ID NO 185
<211> LENGTH: 151
<212> TYPE: DNA
<213> ORGANISM: Saccharum officinarum

<400> SEQUENCE: 185
```

```
cccagcagtt ccatcgggtg catccaaaat aattttggag cctcgatttc tgagtgtatg    60
gtacatttgg catgaaccat ccaactatct tgcaccgaca ctaacactgt ctccaaatag   120
actgaaacaa aattccacat ggcccacgtc a                                  151
```

<210> SEQ ID NO 186
<211> LENGTH: 131
<212> TYPE: DNA
<213> ORGANISM: Saccharum officinarum

<400> SEQUENCE: 186

```
cctcggagtt ccatcggatg cgtccaaacc gatttccgag cctatggtag gtttggcaca    60
acccgtgcac ctcgtcaaga ttagcactat ctccaaacag accaaaacga gcttccactt   120
gagccacgtc a                                                        131
```

<210> SEQ ID NO 187
<211> LENGTH: 137
<212> TYPE: DNA
<213> ORGANISM: Saccharum officinarum

<400> SEQUENCE: 187

```
cccagcagtt ccatcgggtg cgtccaaaat gatttctgag gctacagtat gttcgacgca    60
aaccatgcac ctatcttaca tcaagattag cactatctcc aaacagacga aaacgagcat   120
ccacttgagc cacgtca                                                  137
```

<210> SEQ ID NO 188
<211> LENGTH: 137
<212> TYPE: DNA
<213> ORGANISM: Saccharum officinarum

<400> SEQUENCE: 188

```
cccagcagtt ccatcgggtg cgtccgaacc gatttcggag cctatggtac gttcgacgca    60
gatcgtgcac ctatcttgcg tcaagattag cactatctcc aaacggatga aattgagctt   120 cccccttgagc cccgtca                                                 137
```

<210> SEQ ID NO 189
<211> LENGTH: 137
<212> TYPE: DNA
<213> ORGANISM: Saccharum officinarum

<400> SEQUENCE: 189

```
cctaggagta ccatcgggtg catccaaaat gatttcttag cctatggtat gtttggcgca    60
aaccgtgcac ctatcttgca ccgatactaa cactgtctcc aaatggactg gaacaagatt   120
tcacatgacc tacatga                                                  137
```

<210> SEQ ID NO 190
<211> LENGTH: 136
<212> TYPE: DNA
<213> ORGANISM: Saccharum officinarum

<400> SEQUENCE: 190

```
cgtaggtgtt ccatccgatg cgcccaaaat gttttctaag cctatggtca ttcagtgcaa    60
gccgtgcacc tatgttctat caagtttagc actatctcca aacagaccga aacaagattt   120
cacaggacct atgtca                                                   136
```

<210> SEQ ID NO 191

-continued

```
<211> LENGTH: 137
<212> TYPE: DNA
<213> ORGANISM: Saccharum officinarum

<400> SEQUENCE: 191
cctaggagtt ctatcgggtg agtccaaaat gttttctaag cctatggtat gttcggcgca      60
aaccatacgc ctatcttgcg tcaaaattag cactatctcc aaacggacta aaacaagctt     120
ccacttgagc cacgtca                                                    137

<210> SEQ ID NO 192
<211> LENGTH: 137
<212> TYPE: DNA
<213> ORGANISM: Saccharum officinarum

<400> SEQUENCE: 192
cccagcagtt ccatcgggtg cgtccaaaat gatttctgag gctacagtat gttcgacgca      60
aaccatgcac ctatcttaca tcaagattag cactatctcc aaacagacga aaacgagcat     120
ccacttgagc cacgtca                                                    137

<210> SEQ ID NO 193
<211> LENGTH: 128
<212> TYPE: DNA
<213> ORGANISM: Saccharum officinarum

<400> SEQUENCE: 193
cccagcagtt ccatcgggtg cgtccaaaac tatttatgac ctatggtacg ttcaatgcaa      60
accgtgcacc tatcttctac agcactatct ccaaacggac caaacagatc tccaccagac     120
cctcgtca                                                              128

<210> SEQ ID NO 194
<211> LENGTH: 135
<212> TYPE: DNA
<213> ORGANISM: Saccharum officinarum

<400> SEQUENCE: 194
cctaggagta ccgtgggtgc ttctaaaatg atttatgaac ctatggtgcg tttgacgcaa      60
accgtgcacc tatattgcac cgacactaac actgtctcca aacggatcga aacatgattc     120
cacttgaccc actcg                                                      135

<210> SEQ ID NO 195
<211> LENGTH: 137
<212> TYPE: DNA
<213> ORGANISM: Saccharum officinarum

<400> SEQUENCE: 195
tctaggactt ccatcgcgtg cgttcaagat gatttctgag cctatggtgc gtttggcaca      60
aaccacgcag ctatcttgca ttaaaattag cactatctcc aaatggactc aaacaagctt     120
tcacttgagc cacgtca                                                    137

<210> SEQ ID NO 196
<211> LENGTH: 131
<212> TYPE: DNA
<213> ORGANISM: Saccharum officinarum

<400> SEQUENCE: 196
cccagcagtt ccatcgggtg catcccaaaa tgatttctga tctacgtttg gtgcaaaccg      60
tgcatctatc ttgcactgaa tctaaagtgt ctccagatag attgaaacga gataccaaat     120
```
gaccaatgtc a                                                          131

<210> SEQ ID NO 197
<211> LENGTH: 137
<212> TYPE: DNA
<213> ORGANISM: Saccharum officinarum

<400> SEQUENCE: 197
ctgagaagat ctatcgggtg cgtccaaaat gttttctgag cctatggtac attcggcgca    60
aatcatgcac ctatcttgca tcgaggttag cattatctcc aagtggaatg aaacgagcat   120
ccacttgagc cttgtca                                                  137

<210> SEQ ID NO 198
<211> LENGTH: 137
<212> TYPE: DNA
<213> ORGANISM: Saccharum officinarum

<400> SEQUENCE: 198
cctagaagta ccatcgggtg cgtctaaaat gatttctgag cctatggtac gtttggcgta    60
aaccatgcac ctatcttgta ccgacactaa cactgtctcc aaacggacca aaataagatt   120
tgacatggcc tatgtca                                                  137

<210> SEQ ID NO 199
<211> LENGTH: 137
<212> TYPE: DNA
<213> ORGANISM: Saccharum officinarum

<400> SEQUENCE: 199
ccaaggagtt ccatcgggtg cgtccaaaat gatttctgag cctatggtgc attcggcgca    60
aaccgtgcac ctatcttgca tcaagattag cactatctcc aaacaaactg aatcgagctt   120
ccacttgagc cacgtca                                                  137

<210> SEQ ID NO 200
<211> LENGTH: 136
<212> TYPE: DNA
<213> ORGANISM: Saccharum officinarum

<400> SEQUENCE: 200
cccagcagtt ccatcggtgc gtccaaaacg atttctgtgc ctatggtatg tttggcgcaa    60
atagtgcacc catcttgcac taatagtacc gctatctcca gtggattga aatgagattc   120 cagatgacca atgtca                                                   136

<210> SEQ ID NO 201
<211> LENGTH: 137
<212> TYPE: DNA
<213> ORGANISM: Saccharum officinarum

<400> SEQUENCE: 201
cctaggagat ccatcgggtg tatccaaaat aatttctgag cctacggtat gtttggcgca    60
aaccgtgcac atatcttgcg tcatggttac cactatctct aaatagacca aaactagcat   120
ccacttgagc cacgtca                                                  137

<210> SEQ ID NO 202
<211> LENGTH: 137
<212> TYPE: DNA
<213> ORGANISM: Saccharum officinarum

<400> SEQUENCE: 202

```
ccyagsagtt ccatcgggtg cgtccaaaay gatttyygag cctatggtac gttygrcgca    60
aaccgtgcac ctatcttgca tcaagabtag cactatctcc aaacggaccg aaacgagctt   120
ccacttgagc cacgtca                                                  137
```

<210> SEQ ID NO 203
<211> LENGTH: 3465
<212> TYPE: DNA
<213> ORGANISM: Saccharum officinarum

<400> SEQUENCE: 203

```
gggaagtacc agggacgaag agctagcgca aggactaatg tttctgtagg gaaagctagt    60
tcatggcagc agcgcacgtc tacaactccg tctacatgta ctcctacgcc atcatctagt   120
gacaagactc gagctgcccc caccaattca gtmrcgaaga cagcgcaaaa gccggctgcg   180
agtacttcat ccgtggcatc gacmggtaga acaagcaaca tacaatgtca tcggtgcaag   240
ggatatggcc atatgatgcg tgactgccca aacaagcgtg ttatgattgt caaagatgat   300
ggtgagtgtt catctgctag tgattttgat gaagatacac ttgcattgct tgcgctgact   360
atgcaggtag tgaggaacac atagaagaac acatyaatgc aggtgacgcg gagcactatg   420
agagcttgat tgtacagcga gtgcttagtg tacaaatgga gaaggyagag caaaatcagc   480
gacacacttt attccaaaca agtgtgtca tcaaggagc ttcgtgccgc atgatcattg   540
atggaggtag ctgcaacaac ttggcaagta gcgacatggt acagaagctc gcctcaccac   600
caaacacacc cccatcccta ctacatccaa tggctgaaca acagtggtaa ggcaaaggta   660
acagacttgt gcgaattgat tttgccatcg gatcatacaa agatattgtt gaatgtgatg   720
ttgtgcctat gcaagcttgk aatattctgc taggtagacc atggcaattt gatagagatt   780
cgatgcatca tggtagatca aatcaatatt cgtttctata ccatgatcga aaaattgtgt   840
tgcatcctat gtctcctgaa gctattatgc aatctgatgt tactaaggct gcaaaagcaa   900
agagcgagag caataaaaat gacaaatctg ttgttgatga caaagatgag ataaaattga   960
aaggacgttg tatgcttgct acaaaatctg atattaatga gttcaatgca tccacctctg  1020
ttgcttatgc tttggtatgc aaggatgctt tgatttcatt tgaggatatg caacgttctt  1080
tgcccctgt gtgctaacat tttgcaggag tattctgatg tgttccccat tgagatacca  1140
gcggggctgc caccaatacg tgggattgag caccaaattg atcttatccc tggagcatct  1200
ttgccaaacc gtcgccata caggaccaat ccggaagaag cgaaggaaat tcagcgacaa  1260
gtgcaagaac tactagacaa aggttatgtg cgtcagtctc ttagtccttg tgctgttcca  1320
gtgattttag tgcctaagaa agatggaaca tggcgcatgt gtgttgattg tagggctatt  1380
aataatatca ccattcgata tcgaccccta ttccacgatt agatgatatg cttgatgaat  1440
tgagtggtgc tgttgtgttt tcaaaggttg atttgcgtag tgggtaccac cagattcgta  1500
tgaaattggg agatgaatgg aaaactgctt tcaaaactaa gttcggtcta tatgagtggt  1560
tagtcatgcc ttttgggtta actaatgcac ctagtacttt catgagatta atgaacgagg  1620
ttttgcgtgc tttcattggg aaatttgttg tcgtctactt tgatgatata ctgatttata  1680
gcaaatccat ggatgaacac cttgatcact acgtgctgt tttcaatgct ctacgtgatg  1740
cacgttttgtt tggtaacctt gagaagtgca ctttctgcac caatcgagta tcgtttcttg  1800
gctatgttgt cactccacag ggaattgagg ttgataaagc caaggtggaa gctatacaag  1860
gatggcctgt acccatgacg gtcacacaag tgcggagttt cctaggactt gctggtttct  1920
```

```
atcgccgttt ygtgaaggac ttcagcacca ttgctgcacc attgaatgag cttacaaaga   1980
agggagtgcc ctttcttgg ggcaaagcac aagagcacgc cttccatgtg ctgaaagata    2040
agttaacaca tgcacctcta ctccaactcc ctgattttaa taagactttc gagcttgaat   2100
gtgatgcgag tggaattgga ttgggtggtg ttttgttgca agaaggcaaa cctgttgcat   2160
actttagtga gaaattgagc gggcctattc ttaattattc tacatatgat aaggaattat   2220
atgctctagt gcggacatta gaaacatggc agcattattt gtgcccaaa gaatttgtta    2280
tacattctga tcatgaatct ttgaagcata ttcgtagtca aggaaaactg aatcgtagac   2340
atgcaaatgg gttgaattta ttgaatcttt tccttatgtt atcaaacaca agaaagggaa   2400
agataatatc attgcagatg cattgtctag agatatact ttgctgaatc aacttgatta    2460
cagattttgg gttaaaacaa ttaaagacga tatgctcatg atgctgattt taagaagtg    2520
ctgctgcatt gtaaagatgg gaaaacgtgg aacaaattca tcgtcaatga tgggtttgtg   2580
tttagagcta acaagctatg cattccagct agctccgttc gcttgttgtt gctgcaggaa   2640
gcgcatggag gtggcttgat ggggcatttt ggagcgaaga agacggagga cattcttgct   2700
ggtcatttct tttggccaaa gatgcgacga acgtgtgaga gatttgttgc tcgctgcaca   2760
acatgtcaaa aggctaatcc cggttgaatc cacacggttt gtatatgcct cttcctgttc   2820
ctagtgctcc ttgggaggat atttctatgg attttgtgtt gggattgcca cgaactagga   2880
aagggcgaga tagtgttttt gtggttgtgg atcgattctc taaaatggca catttcatac   2940
catgtcataa aactgatgat gctacaaata ttgctgattt gttctttcga gaagttgttc   3000
gcttgcatgg tgtgccaaat acaattgttt ctgatcgtga tgctaaattt cttagccatt   3060
tttggagaac tttatgggct aaattgggga ctaagctttt mttttccacc acttgtcacc   3120
cccaaactga tggtcaaact gagttgtgaa agaacttgtc tacatgtagg cttttaaag    3180
aagaatatta agattgggaa gattgtttgc ctcatttgag tttcttaaat cgtcktgcat   3240
tccacgaaga tgtgtccytt tgagtgtyta tgggttttcc acggctccat tgatttaatg   3300
cmcwttgcam stttgraaag ctasaatttt gatgctaagc aactgctaat tgatggywaa   3360
catmcmtgaa aaccacyaaa gaaaacatas agcgcatgaa tgctaartac aaatttgykg   3420
gagataargg tagaargtaa ttgcttctgg acccggggaa ttggt                   3465
```

<210> SEQ ID NO 204
<211> LENGTH: 548
<212> TYPE: DNA
<213> ORGANISM: Saccharum officinarum

<400> SEQUENCE: 204

```
cccagcagtt ccatcgggtg cgtgcaaaac gatttctgag catatggtac gtttggcgca    60
aaccgtgcaa caaacttgca ctaacactac cactgtctca aaatggattg aaatgagatt   120
ccacatgacc aatgtcacct aggagatcca tcgggtgcat ccaaaatgat ttttgaacct   180
ttggtacgtt cgacgcaaac cgtgcaccta tcttatgtca agattagcac tatatccaaa   240
tagactgaaa cgagcatcca cttgagcctc atcacctagg agtaccatcg tgtgcgtcca   300
aaactatttc tgagcctatg gtacgtttgg tgcaaaccat gcacctatct tagaccaata   360
ctaacactat ctccaaatgg accaaaatta tattccacct aactcatgtc acctaggtgt   420
tctatcgagt gtgcccaaaa ctattttcat gcttatggta cattcggcgc aaaccgtgat   480
cctatcttgc gtcaggatta gtgtaatccc caaacagact gaaacaagca tccacttgag   540
```

```
ccacgtca                                                            548

<210> SEQ ID NO 205
<211> LENGTH: 25
<212> TYPE: DNA
<213> ORGANISM: Saccharum officinarum

<400> SEQUENCE: 205
gtcacccagc agttccatcg ggtgc                                          25

<210> SEQ ID NO 206
<211> LENGTH: 24
<212> TYPE: DNA
<213> ORGANISM: Saccharum officinarum

<400> SEQUENCE: 206
actgctgggt gacgtggctc aagt                                           24

<210> SEQ ID NO 207
<211> LENGTH: 22
<212> TYPE: DNA
<213> ORGANISM: Saccharum officinarum

<400> SEQUENCE: 207
gggaagtaca gggacgaaga gc                                             22

<210> SEQ ID NO 208
<211> LENGTH: 20
<212> TYPE: DNA
<213> ORGANISM: Saccharum officinarum

<400> SEQUENCE: 208
actaacaatg cacgggaagg                                                20

<210> SEQ ID NO 209
<211> LENGTH: 20
<212> TYPE: DNA
<213> ORGANISM: Saccharum officinarum

<400> SEQUENCE: 209
gtaggccatg gcagtttgat                                                20

<210> SEQ ID NO 210
<211> LENGTH: 20
<212> TYPE: DNA
<213> ORGANISM: Saccharum officinarum

<400> SEQUENCE: 210
aacacaccac ccaatccaat                                                20

<210> SEQ ID NO 211
<211> LENGTH: 23
<212> TYPE: DNA
<213> ORGANISM: Saccharum officinarum

<400> SEQUENCE: 211
ccaaacaagc gtgttatgat tgt                                            23

<210> SEQ ID NO 212
<211> LENGTH: 24
<212> TYPE: DNA
<213> ORGANISM: Saccharum officinarum

<400> SEQUENCE: 212
```

-continued aggttatgtg cgtcagtctc ttag                                    24

<210> SEQ ID NO 213
<211> LENGTH: 23
<212> TYPE: DNA
<213> ORGANISM: Saccharum officinarum

<400> SEQUENCE: 213
ggcaaacctg ttgcatactt tag                                     23

<210> SEQ ID NO 214
<211> LENGTH: 23
<212> TYPE: DNA
<213> ORGANISM: Saccharum officinarum

<400> SEQUENCE: 214
accatgtcat aaaactgatg atg                                     23

<210> SEQ ID NO 215
<211> LENGTH: 22
<212> TYPE: DNA
<213> ORGANISM: Saccharum officinarum

<400> SEQUENCE: 215
tgcaaccaaa ccaaatcacc ag                                      22

<210> SEQ ID NO 216
<211> LENGTH: 20
<212> TYPE: DNA
<213> ORGANISM: Saccharum officinarum

<400> SEQUENCE: 216
caagcgaaca atctcacgaa                                         20

<210> SEQ ID NO 217
<211> LENGTH: 20
<212> TYPE: DNA
<213> ORGANISM: Saccharum officinarum

<400> SEQUENCE: 217
aaatcatcat cgtgcgcata                                         20

<210> SEQ ID NO 218
<211> LENGTH: 20
<212> TYPE: DNA
<213> ORGANISM: Saccharum officinarum

<400> SEQUENCE: 218
aacacaccac ccaatccaat                                         20

<210> SEQ ID NO 219
<211> LENGTH: 19
<212> TYPE: DNA
<213> ORGANISM: Saccharum officinarum

<400> SEQUENCE: 219
gaacgctcct tgatgacac                                          19

<210> SEQ ID NO 220
<211> LENGTH: 22
<212> TYPE: DNA
<213> ORGANISM: Saccharum officinarum

```
<400> SEQUENCE: 220
gtacccacta cgcaaatcaa cc                                              22

<210> SEQ ID NO 221
<211> LENGTH: 23
<212> TYPE: DNA
<213> ORGANISM: Saccharum officinarum

<400> SEQUENCE: 221
caacttcagt ttgaccatca gtt                                             23

<210> SEQ ID NO 222
<211> LENGTH: 2139
<212> TYPE: DNA
<213> ORGANISM: Drosophila melanogaster

<400> SEQUENCE: 222
gttgtccgca gcggagatgc aactgatgca acccacattt cagatcaccg acaacgtgca     60
gcgcggcaac tacgccactc tgaccgacaa ggatgtggcg catttcgagc agctcctggg    120
caagaacttc gtgctcactg aggacctgga gggatacaac atctgcttcc ttaagaggat    180
tcgaggtagg ttgtgtaacc aaattcattc acattcgtgt gcccttaat gaatttctcc    240 gatgaattgc ttcaaccagg caacagcaag ttggtgctta agcccggaag cacggcggag    300
gtggccgcca tcctgaagta ctgcaacgag cgtcgtttgg cggtggtgcc gcagggcggg    360
aacacaggtc tagtgggcgg atccgtgccg atctgcgacg agattgtcct ttctctagcg    420
cgcctgaaca aggtgttatc cgtggacgag gtcaccggca ttgctgtcgt ggaggcgggc    480
tgcatcctgg agaacttcga tcagagggcc agagaggtgg gcttgacggt gccactggac    540
ctgggcgcca aggccagttg ccacatcggg gcaatgtgt ccacaaacgc gggcggagtg    600
cgggtggtgc gttacggcaa tctgcacggc tctgttttgg gcgtggaggc ggtgctggcc    660
accggtcagg tgctggacct tatgtccaac ttcaagaagg acaacaccgg ctaccacatg    720
aagcacttgt tcataggatc cgagggcact ctgggcgtgg tcacgaagct ttcgatgctc    780
tgcccccatt cctcgcgagc ggtgaacgtg gccttcatcg gcctgaactc cttcgacgat    840
gtgctgaaga cttttgtcag tgccaagcgt aatctgggcg agattctaag ctcctgcgag    900
ctgattgacg agcgggcctt gaacaccgcc ctcgagcagt tcaagttcct gaagtgagtt    960
gcgccacctt tgtcttctct gagcgttacc aatcctgttc acaaacttat tcccatagc   1020 tccccatt cgggatttcc cttctacatg ctcatcgaga cctcgggcag caacggtgac    1080
cacgacgagg agaagatcaa ccagttcatt ggggacggta tggagcgtgg cgagatccag    1140
gatggcaccg taaccggtga tcccggcaag gtgcaggaga tctggaagat ccgcgaaatg    1200
gtgccgctgg gtctgatcga aagagcttc tgcttcaagt acgacatctc gctgcctctg    1260
cgggacttct acaacattgt ggacgtgatg cgagagaggg gcggtcccct ggccacagtt    1320
gtctgcggat acgccatct gggggactct aatctgcacc tgaacgtctc ctgcgaggag    1380
tttaacggcg agatctacaa gcgggtcgaa cccttcgtct acgagtacac ctccaagctg    1440
aagggcagca ttagtgcgga gcacggcatt ggcttcctga agaaggacta cctgcactac    1500
tccaaggacc cggtggccat ggctacatg cgcgagatga agaagctgct ggaccccaac    1560
agcatcctca atccctataa ggtgcttaac tgaaggcttc tacctaatag attctatttt    1620
ttttgtttgt gtgtaatttt cataaccttta taatacagaa atggcattag aagtgaattt    1680
tgttaacttg tgaagttaaa aaggaccatc atatttggca cgaaaccaat gggcaaaact    1740
```

```
tacttataaa atagtccgaa aaaatagtat ataccagttt ttacagtacc acattatagg    1800
tactcggagg taataataga aaaaacacta tctttgcatt tactgttaca ctacgaagca    1860
ctatatttag tagcagtact cattagagtc cactcacaaa attagcacca accggcagta    1920
attggtcaag gatcggcgat agcttcaaac tccgaagttc aaagtcaaac tgccgccctg    1980
cgaaagcttc gcgagtggag ctttctgca cttatcgata gctaacattg tggcgcgact    2040
atcgatcgac gagctgccgc ttaacagtgc catatataga ttgtaacatt agaagctcaa    2100
atcattgttg gagcacaaac cacaaagaac acacgaaac                          2139
```

<210> SEQ ID NO 223
<211> LENGTH: 2191
<212> TYPE: DNA
<213> ORGANISM: Drosophila melanogaster

<400> SEQUENCE: 223

```
aaaatatttc acctcatttt ccgcacacca tttataagca aagttacccc caacccataa      60
cttttatggt aagtaataca gaccctccaa gttcggcaaa tcgatacca gcgaccttga     120 gcttgacatt tatatatatg ccagaatata acgaccacgt gctgtcaact gtgtcaggaa     180
aagctcaccc acactttctt tggaggagct gtgctccta aacgaatttc attgtcaagg     240
tcgcacgcac aaaaatgaag aggaaaagct gaatgtgggt ggaaatgccg gccggcacga     300
ccttgaagcc agttgggtga aaataaaaa gcttttgccg gtaggagact tgtggaacat     360
cacccacaag tggcggactt ggccttggcg atggccttgt tggagctccc tcagcaaaaa     420
tgttacatag ggggaggaaa taagctcaat tggctttatg ctttccgctc cctggaagtc     480
cttttctgga atgttaaagt gttaaatgac atttattgaa catttgggac agaggaggag     540
ataatacaat atacttgtct aattaaaaaa aatcgttatt atgatttatt ccatatgtaa     600
gattttaatt catcatgatt gtaaataaat tatataaaac aaattcaata aatttacatt     660
attgataaaa tttattttt catgaaatta tacccaaaaa ttattctcaa ttttttcttat     720 aatcagtttt gcataagtat actttcttca taccctcta ccacagccac tgctttcttg     780
actttgcaac tatccgggaa cagcttatca taatggatga gctgcagcta acggaaaatg     840
ggggagctgg gatcaaacat tttccaaggt tgaaattgtc gtcagcataa tgtttgaggg     900
agctggattc gcgttagctt gaaggtcaat ccatttgggt gccctttgtt atggtcaagt     960
ttaaggctgc aataggggga atcttcaagg accattacgc aaggttttcg catcaaagat    1020
ttgccgtgca agcttttga gttgaaggat gcttaacttg aaagcgggtt agtggttcca    1080 agagattta ggtgaaggag actccgctgt tttgaaatat attaagtatg taagaagta    1140 tactataaat aacccaaagt gatacaatgt aagaaaagat ctcgttggtc cctggtataa    1200
atttgtttgc cattaatgaa tattgaaaat aataattata ctaataatag gtacaataag    1260
caagattaaa ttgcatttaa tcaccaaaaa tcagtttcta tgcgaaccaa aatgtcataa    1320
caaacaattg ttgattcatc cgtagtgaaa tccaagttcg aaattcgaaa tgagcatacg    1380
acgaccaaac ttccccctcaa aattgctaga ctcagctaga gcaagtacgc ccaagttaac    1440
ccctgaaatt cgaaatgaat tcgatgccgc gcttcgaaca acgaaatccc aaagagctta    1500
cgttttattt gacgtagcac tcttacgtga aatgattttc cccaattccg ctctcatttc    1560
ccgagtctct caccgcttct cagccacttt cccaccccct ttctagttcc gaagtaaagg    1620
taacaaaggc agccgtgtct ttggggtggt aaactggcgg tggtggtggc acattgtcag    1680
```

```
tggtgtgggt tcctgtggtt ggtggttcaa ttggttggtt gttggcataa acaaagcaca    1740
cacacaatac acacaaactc ccgggggtg gtggaaattg ggagggtgac attcactgcg    1800
agagaggaac tcgcttccta taggaaagta caaagagagc tattttataa atgtgactgc    1860
agcaaggata tttacagtca gtccactctg aaacctcgac gagagaacat tgaataacaa    1920
gcggaagcga aaagcgcagt tgaaagttcg tcaaaaagcg acaagtttcc tcgttcgttt    1980
tcccgccaaa tgagtcagaa aaattttcca agtgctcgat acgaaacata agacttaca    2040 agacttaaag tgcaagcagt gaatggaata tattattcct cagcgatatt gaaatcaaac    2100
attaaaaata tatgctacac taaagttata tattttttta aagattcata cgttttgtaa    2160
aatcacattt tgtattaaat taaataccgc c                                 2191

<210> SEQ ID NO 224
<211> LENGTH: 2035
<212> TYPE: DNA
<213> ORGANISM: Drosophila melanogaster

<400> SEQUENCE: 224
tgggtgcgtc gcaggtttca ctggaaaaca atttgcactt tgtttgtgg agtcgacaac     60 aaaagcattc acttgtctaa gactctctca ttcataactc gcactttagt tcactgaacc    120
gcacgcaaaa ctttggggcg acaacatgt tttcgaggtg ccaaaagctt cataaaacta    180
ccaatccatt agattaaatt ccaggcggta catcttttgg ggatgattca tgtggcaggg    240
gttctctact cgtttacaat catatcatca tcttcaagat catatagttt atcatatcag    300
tagagtacta caatataatg cataaactaa gccaaataac tttatgacgc gtgcttatgc    360
gaaagtaaac tttattatca aatttactta accgtgaaat caaaaccttt atataaacac    420
gaatattatt atctttgcta aataaaactc tcgcttaaca acaatgaca cttcaattcc    480 aacatagagt ttatcttaag ccaataacca aaacggaac ttacataact tgccaacaaa    540
catatgaata tagctatttc ggatcgtggg agaccattat gcatacaagg cacgctccta    600 aaaccgtgt taaacaaata tatgtcaaat gtatatctta aaaaagcgcg cacatatctt    660
ttgaaatatc ttcacccaga gtatgtatga gattaaactg gattagcact aagccacagc    720
ttctgtagat agaaatttta tgcagagagt agattatttg gctgctgagc aatttgacca    780
ccacaagata gcagagaaca tctgacattt ctatatccaa taataaaa ctgacttaac    840 actaagctga agtggtatgt ttaaatcctc cagctaataa atcgagacta aacgccctat    900
cttatagtga tatataatag tatctatatg tgtattgtca tttactgttt atgagtattt    960
gaaaaaacca ttctatattt tataggttag ttaataaata ttttgatata catatgtaga   1020
ttggctcaca cgtacttatg acccactaca taataaaatt gttttgtttt ttaatagaat   1080
aatggtttat aaaaagtta gactcacacg gaaatgataa actctttgca aatacagctt   1140
tcattttatt acaaattgca ctctttcaga tctgcagttg ctatgccaac cttttattcc   1200
ctttactaaa agggtatact aggcttactg aacagtatgt aactggtaaa gtaaagcgtt   1260
tccgattcta taattatat atctaaactt tgatcagtc gaatccatct gaacacattc    1320
tgtcacatta gattattcca gaaactcaac ttaaacatgt gtattttta agaccattat   1380 caaggatatt aaaaatggtc tcctaaaatt taataaacaa agtgtcaca tcaaatttaa    1440 gacgtaaatt aatattttt ttctatggtg aaataattgt tattttccaa tgttgtgaaa   1500
taataaatgt atcttttcaa cgcacacatt ttcaaggttt taataataat agtgactcgt   1560
gcgtgaataa gagagaaatt aagatttaa aaaagaataa aattcagaga tgtgatctgt   1620
```

```
aaaaattatt taccaatttt catttacccc cgaaagtgat gctaatggtt aaaacggcat    1680
ttgcgactta tctcctacgt aatattgcaa aataaggat ttggttagat gagtgtgaag     1740
taaacaagat gcaaagtttt ggagataaa aacatagcct tgagtcttgg tcatgtttac    1800
ttggcaccag gccgcgatta tcagcgctac tagtcgtaat ttgagttaga cctttaatac    1860
tctaagtgag agtgatgata tacgatttcc cagccacttg ctttctacga aatgcgctaa    1920
aaaaaatccc taactacaca aagatttgtg ttgttatcca ggtgttctga tataaaaggc    1980
ggcaaggaaa ttgatggcat catcagtatc aaagtgagag tgattgcagt cacac         2035
```

<210> SEQ ID NO 225
<211> LENGTH: 2136
<212> TYPE: DNA
<213> ORGANISM: Drosophila melanogaster

<400> SEQUENCE: 225

```
atgggacggt cctattctca gcaaaaattg acaagaacaa caacaatgtc tatggaaaat      60
cgaacttcat cccagcacct gcagaaatcc cgagcgagtc ggggaaaaag tatttaaccc    120
ccgaaagggt tttccccaaa ataatgaagt aatgaatgaa gcggaaaaca ctggccgcca    180
atctacctaa tactaatgag cgggccaacc cgaccaggaa ttttttgcaag tcaggtactt    240 caacggatat atgggttcga caagtgcgga ttttcccgcg acatcaatga ggacttggcc    300
gggttatccg cggtgctcat cggcaattc cgcggccgag gacttcatcg tagtgatcat    360
taggtagata tgtgcatgga tgtgacatgg cgatcattgc gcggaataac acacgtaata    420
accgagatat ccgggatgac ccaccaggta ggatgtgagg acatatagaa aaccccccagc    480 cagttttcc actcgtcgtg gcttgttttg cttgagtttc gctgactgcg taattggata    540
agatgggaaa ttactttaaa tccttcgctg atccacatcc ggacattcgt cgaaggaaaa    600
tccattgcag ggaaatacga aatgaaatg cggctgggtt attggctcga catttcccat    660
cttccctcac gccattggtt gcaggatcgc ggggaattgg aattccgcgc tggaattttt    720
tgtcacctct tgggtttatc aaaacttttg ggttgtctat ggattttttc caattttacc    780
accgcgcctg gttttttttt tttgacgacg cggaaaatcg gacttggcta tgcgggcttg    840
tctgtttttc cgggtacaaa gtctgcatgt cagcctccat gcgggagtgg gagttgggaa    900
agtttcccat cgatagttgg agggggtggct tgaaagtctg gaggtgctag ctgggaaagt    960
tgtgtgtgcg cgatgaggca aggagtcaaa gatcagggga gttggaaagc gagaattgtg   1020
ggaatcgtcc aggactcagc tggatgctga ggggcagtat gatttttttt acgttatcaa   1080
tcgaattgat tttaagacag cagaacttca catactaata agatgaccat gggattagtt   1140
aaaatgtgta actcgtattc gaatcgtcat tctttcacgg accaatcgtg ggaacaggag   1200
atctcttcga tccaagctca caggagactt gacactcttc gtctattcct tgtcaagttt   1260
ttaatgacat ctcctatgcc ctgagctatg ttttcctagc tctcatcgat cgctgccaat   1320
gagccactgg agatgatcca taagtcagcg tagagtgcac cccagagttg acacttggtg   1380
tctcggaatt cggctcatta tcagtgctat ttttggaaca cctctctgcg aaggtgtcat   1440
ttttgtcagt gcgtatcgct caggttcaac tccccaccaa aaaccgaatt tagagcatcg   1500
gcagatgtac ttgaagcact caatctaagt gaggaaacca ccccatgaac gaagagtact   1560
aggagtccta tttgactcgt gcttaaaaat agaaaattac ttagggtgat ccataggtag   1620
ggaggcgata ttgtaacttg catttcggac ccggacctgc acgagttatt acgggtgggt   1680
```

```
tgtgagcgta tcgggaaatt ggagagccac cagatctgtc ataacttata cgggggatcc    1740
ttattcctgg gagggtgcgc ctgcgtctgc tcttccgaga gagaggtggg aaatggagga    1800
agagagagag agagagagtg agagagcagg tagagggaag tgagggaaat acgcaataag    1860
ggtatgggaa aagtgctgtt gttgttgcta ggtagcgacg cacacgtgcg agtgttttc     1920 tgttttgaag aagaaccacc accaaatggc gacagcggcg tcggcagagg cgcagagttc    1980
cgggtataaa agagcgtgct cgactgttga cctgtcacag ccacctcagc tctcgttgag    2040
aacgcaacca ccgctctata ctcgatcccg aactatataa ctcgcctctc gatcgccgat    2100
ctcccgattt acccatctcg atcagtaccg gaaacc                              2136
```

<210> SEQ ID NO 226
<211> LENGTH: 2015
<212> TYPE: DNA
<213> ORGANISM: Drosophila melanogaster

<400> SEQUENCE: 226

```
atttggctcc ccatcgccat cggttgctcc aatgacacta gggaattgtg ggccgccgac      60
agctgtcctt aattacatgg aaatccacac tagattcgtg cccctcgccc cgtactcgca     120
gccgaagtcc ccacagagtc attccccttg ccaccaccaa aaaaaaaacg aaagcaactg     180
aaggaaaagt tcgattcgaa ggctgaggga tacccttaaa ggcccatttc ccggcttcgt     240
aaatcacatt tagttagcca tttagactac agcaagtctt ttaagataca ctgcaaaata     300
aataccatta cattaataga agtgtcatgt catcggtctg tattttgtt accacagaat      360 agacttacat atatgataaa aaaatgttca acaataagtt acatcggtag ccaattctat     420
agatttaatt ccttacgaat atagtttcgt tggaatactc aatttgtaat tgtaattaat     480
tataattatt ataattttaa gaatttatat aagtaactaa aagacacggc agacacagaa     540
tgaaaacact ctatgttagg gaatgcaaaa aaacgtggcg gaagccaaaa ggcgcaagca     600
aaaatcgaaa ccaagtgaat ataacatatt atttcaacag gcaactcatt cagcatataa     660
tattaccacc catggagctt tatgtagttg atgtacgtag tctatgatgt ggagcccacg     720
ttggcggaac tgggaatggg gattgggtt tgagagctgt ggtaaattgg ggggttgaag      780
tatcaagggt ttgggttctg tagacctgcg gaatcgaggt gaataagcga agaacacatt     840
cacacacact aaaaggcaaa caagggaaa tcaatctttg tacatacttt tagcatatgc      900
acacgtatga tctccaccca cttttccctc ccaatgaaac aaacacacac acacatgcaa     960
ggccgtacgt ttgtatatgt gtgcggttgt cggcttttgcc gggaattggg gaatatttgc    1020
atgcctttgt gtactttttc catatgattt atgacctaaa ttgttgctgc tcgcgcacat    1080
ataattacac acacatcgct gtggccatgt gtgtgtgtgt cgtcttggga cgcgcgccaa    1140
agtatgctac acttttttgtt ttatgagtta ataagtaggc gtggcccag cccaattgct    1200 acactctgat tatggcaccg gatacccaga tagacgccca tccaccccac tgtaagatgg    1260
gggaatttcc aaacctatat gtatgtgcag atcagatagg atagcacaga acttttttaaa  1320 gtacactttt ggggcacgca atttagaaaa tgtacctcgg tgtcggagaa attatttttaa  1380 aagtcgactg aaccacctcg ttccatatgg agaagtctac gagttcaagt ttaatggagc    1440
agctgactgc actgaatttt gtagtttaat acacaaatcc gcaaattgca tctcacttca    1500
aatagcctgg tacatagtat ctactaacat aactcatatt aaaataaagc aaccaaccag    1560
agggccgaaa ttctattaat aaaactaata tttaactatt atatatacat tttatttact    1620
tggtacgctt atgataacct tcgaaagaga accaacacaa tacgctttgt catttgaaaa    1680
```

| | | |
|---|---|---|
| ataaatatgc tgtaactact ttacaaggtg aaactcttgt cagaagataa gaggctaggt | 1740 | |
| aagttgatta ttcaatcagt ttacttactg caacccaaaa tggtcactgc actaaccttc | 1800 | |
| agatgagctg cactcaccc tcaatcgaga atcaatgcaa acgcagtgcc agcgaaaatg | 1860 | |
| tcagcaaggg attaggccaa tcccaaacgg gtaatcccgc tgcgacaatg ctaatccaat | 1920 | |
| tccgatgggc cgtataaaag ccccaagctg ggctggctgt gatttcgtct tggcccgcag | 1980 | |
| accggagcat ggagtccggt aacgtgtcgt cgagc | 2015 | |

<210> SEQ ID NO 227
<211> LENGTH: 2082
<212> TYPE: DNA
<213> ORGANISM: Drosophila melanogaster

<400> SEQUENCE: 227

| | | |
|---|---|---|
| atcgatgacg gcatcggctt gacctctcgg agtacgtttg attttataga acaagttttc | 60 | |
| tcctttctta tactataagg aaaaattata aaaattgctg aaaatgaaac atggctagaa | 120 | |
| ttcgtttttt aacatttttt caatctgaga aaaaatttcc gattagtctt aaaataacta | 180 | |
| aaccaattcg tatacccgtt aatcgtagaa gaaaaatgaa attcatataa taagtagatg | 240 | |
| gatttgctga cccggtgagg tatatatgta ttcctgaaca tgatcagtaa acgagtcgat | 300 | |
| ctggccttat ccgtatgaac gtcgagatct cgggaaatac aaaagctaga aggttgagat | 360 | |
| taagtatgca gattctagaa gaagacgcag cgcaagtttg cgactacgct gaatctactg | 420 | |
| ctaaaaactg ccacgcccac acttcttaag aatttgatt attttcacaa gctgaggaac | 480 | |
| ggtagggtcg aggaactcga ctacaacgtt ctgccttgtt tatttcttaa caaaaactta | 540 | |
| gtagccgttt gggttggaaa ccacctgacc ttaggtctgg tagcagttat ttaatttatt | 600 | |
| ttttttattt tatacaactt gctcgctgtt tgttccccct agccctgaaa cacaagctgt | 660 | |
| caaacggtgg aggtgataag tctaatgaat gcgataagct ttatttcaat tcgcaatttt | 720 | |
| cgtgtggcat tttggcaaaa aaaaaaactc gtcggacata catgttgcca caaacataaa | 780 | |
| gtgaatacat aatgttgggt gaacgactca tacacgattg tggcaaatca aattcttta | 840 | |
| acacgggacg gggaaaggcg agtgaagata ttttagcata tatttagcac atctgttaaa | 900 | |
| tccatttttt tactctccgt tttcggccag atatggttag aaaagaaaaa aattagtaca | 960 | |
| tacccccata tataataaga aaaaagaga gagtcagcag aagtacgggg agcttaagtg | 1020 | |
| tagcaatcag aacatcacaa atagtaaata aattaataat aataataatc atatccaaaa | 1080 | |
| atattttat tcctaaccta tcgcattgtt acatcgaggg tgaaattcaa aatagacaaa | 1140 | |
| aagttgggga ataaaatgtg aaaaaagtgg taaaatgttt aatagtgtgg gcgttactgt | 1200 | |
| tttgtcggtg tgaggtgcgt ggccaccaaa gtgttttgg tataacgata gaaattggta | 1260 | |
| agacaaacaa tattgcgaag aaaacccgaa gcatttttaa aaagtgcgaa cgtggcagtt | 1320 | |
| ttaagggttt gtgggcgtgg caataatttt tggcaattcg ataaaaatgt acaggaccaa | 1380 | |
| atatatgaag aaatataaaa tattttttcaa aatgacagcc agcaaccata catatatata | 1440 | |
| aataaatgtc ggagacccctt ccttctacct gtaacatact tttccacgaa tctagtattg | 1500 | |
| gttgatatat aattatgctg tgtataagac caaaatcagt gtacatttcc attggattca | 1560 | |
| ccaaccggat ggttccggat ggtaatgcaa atattcatc taagaaacga aaacacctag | 1620 | |
| aattaaaccct gaactgatat gacttatgca catatcagtg aggtgggcag ttcaaagcaa | 1680 | |
| tcacgatgct ccaagttatt atcgcagtgc agtgaaaaat tcacagtcac cgtcgccaat | 1740 | |

-continued

| | |
|---|---|
| tgccaataaa gatcggccat tatacaacag aaccgcgttg aagacgatcg acgaggtcgt | 1800 |
| gggtcttatc ttatcaccac ctgaattgag gcatgcctcc agaatgacga gggcatccga | 1860 |
| agataatgtg gcccgctatt ttcggccggg actggaccta tgcgacgacc tatgctgatg | 1920 |
| acgggagtct gccgctgata tggtgcaatg caaggctcca gtcggggggta taaaagaccc | 1980 |
| agtttcggtg cagtcaagac aacagacttt aggtgttggt cgttgagcga accaaagccg | 2040 |
| gagcagttga ggaaccaaag aatagcagcg agaggaccaa gg | 2082 |

<210> SEQ ID NO 228
<211> LENGTH: 1999
<212> TYPE: DNA
<213> ORGANISM: Saccharomyces cerevisiae

<400> SEQUENCE: 228

| | |
|---|---|
| tgtagggacc caaatccaat tgtagtagtt accttgatta tggttggctt gtccttcgat | 60 |
| agttttgcct tttccaaagc gctagaaatg gattccatat cgtcgtctcc tttatcgact | 120 |
| tccatgactt cccaaccata tgcctcgtat cgcttcaaaa catcttcgtc gaacgagtac | 180 |
| gaggttttac cgtcaatgga aatgctatta ctgtcataaa acgtaatcaa gttacccaat | 240 |
| tgcagatgtc ccgctaagga agaggtctcc gaagaaacac cctcttgtaa gcaaccatcc | 300 |
| cctacaatag caaacgtata tgagtcggaa atgggaaagc catcctcgtt ataagtggcg | 360 |
| gcaaagttgg cctgcgctat tgccatacca acagcatttg agatacctg gcctagcgga | 420 |
| ccggaagtga tttccactcc cgctgagtgg aattctggat gacccggtgt ccttgagttt | 480 |
| acttgtctaa attgtctcaa gtcctcgata gagtaatcgt atcctaatag atggagcatt | 540 |
| gagtacagaa gagcgcatga gtgaccgttc gacagaacaa acctgtctct attgatccaa | 600 |
| tgttcattgt tagggttaca gcgcagttgc ttgaaaatta catgggcaac tggtgccaat | 660 |
| cctagtggtg cacctgggtg gccagattgt gcgctttcca cctggtcaac ggaaagtaat | 720 |
| cttaaagtga aaaccgcaag tttatcaatg tcggagaact gtgccatttt tttgttcttt | 780 |
| ttttgattag taaggtataa tcgtctacgt agaggttaca aatcgaagac tacagtaaga | 840 |
| ggggacaagc caattgaata tacgactgaa ataaatggaa taattctgca ttattacact | 900 |
| cgtttatata tccaaacagg tgatctggta ttctcttgac aacgaatgaa gctccctata | 960 |
| ttcgacactc cttattcagg actcctccca acaaggagaa gtaggtgttc cttgagctac | 1020 |
| cctttaaagc tggggagatg agcttgccct tcctgtcatc gccattatga cgagaaaagt | 1080 |
| aaaacatgta gaataaggtc cacccaaaca tgtccgagca atgacgttat atatcgtgtt | 1140 |
| ccctgttcaa agcatggcat atgtgccatt aaaggcgaat ttttgtccct agcaaaggag | 1200 |
| agacagcgag ccaccattaa gaagtgactt gaaagcaagc gaaatagct acacatatat | 1260 |
| atcaatatat tgacctataa acccaaaatg tgaaagaaat ttgataggtc aagatcaatg | 1320 |
| taaacaatta ctttgttatg tagagttttt ttagctacct atattccacc ataacatcaa | 1380 |
| tcatgcggtt gctggtgtat ttaccaataa tgtttaatgt atatatatat atatatatat | 1440 |
| ggggccgtat acttacatat agtagatgtc aagcgtaggc gcttcccctg ccggctgtga | 1500 |
| gggcgccata accaaggtat ctatagaccg ccaatcagca aactacctcc gtacattcat | 1560 |
| gttgcacccca cacatttata cacccagacc gcgacaaatt acccataagg ttgtttgtga | 1620 |
| cggcgtcgta caagagaacg tgggaacttt ttaggctcac caaaaaagaa agaaaaaata | 1680 |
| cgagttgcta acagaagcct caagaaaaaa aaaattcttc ttcgactatg ctggaggcag | 1740 |
| agatgatcga gccggtagtt aactatatat agctaaattg gttccatcac cttctttttct | 1800 |

```
ggtgtcgctc cttctagtgc tatttctggc ttttcctatt ttttttttc cattttcttt    1860 tctctctttc taatatataa attctcttgc attttctatt tttctctcta tctattctac    1920
ttgtttattc ccttcaaggt ttttttttaa ggagtacttg tttttagaat atacggtcaa    1980
cgaactataa ttaactaaa                                                 1999

<210> SEQ ID NO 229
<211> LENGTH: 2001
<212> TYPE: DNA
<213> ORGANISM: Saccharomyces cerevisiae

<400> SEQUENCE: 229
tctgctatta ttgatgcttt gaagacctcc agacaaattt ttcacagaat gtactcttac      60
gttgtttacc gtattgcttt gtctctacat ttggaaatct tcttgggtct atggattgct    120
attttggata actctttgga cattgatttg attgttttca tcgctatttt cgctgatgtt    180
gctactttgg ctattgctta cgataatgct ccttactctc caaagcccgt taaatggaac    240
ctaccaagat tatggggtat gtctattatt ttgggcatag ttttagctat aggttcttgg    300
attaccttga ctactatgtt cttaccaaag ggtggtatta tccaaaactt cggtgctatg    360
aacggtatta tgttcttgca aatttccttg actgaaaact ggttgatttt cattaccaga    420
gctgctggtc cattctggtc ttctatccca tcctggcaat ggctggtgc cgtcttcgct      480 gtcgacatca tcgctaccat gtttaccttg ttcggttggt ggtctgaaaa ctggactgat    540
attgttactg tcgtccgtgt ctggatctgg tctatcggta tcttctgtgt tttgggtggt    600
ttctactacg aaatgtccac ttctgaagcc tttgacagat tgatgaacgg taagccaatg    660
aaggaaaaga gtctaccag aagtgtcgaa gacttcatgg ctgctatgca aagagtctct    720
actcaacacg aaaaggaaac ctaatcctgt tgaagtagca tttaatcata atttttgtca    780
cattttaatc aacttgattt ttctggttta attttctaa ttttaatttt aattttttta     840
tcaatgggaa ctgatacact aaaagaatt aggagccaac aagaataagc cgcttatttc    900
ctactagagt ttgcttaaaa tttcatctcg aattgtcatt ctaatatttt atccacacac    960
acaccttaaa attttagat taaatggcat caactcttag cttcacacac acacacacac    1020
cgaagctggt tgttttattt gatttgatat aattggtttc tctggatggt acttttctt    1080 tcttggttat ttcctatttt aaaatatgaa acgcacacaa gtcataatta ttctaataga    1140
gcacaattca caacacgcac atttcaactt taatattttt ttagaaacac tttatttagt    1200
ctaattctta atttttaata tataatgc acacacacta atttattcat taattttta      1260 ttgagtagga tttgaaaata tttggtatct ttgcaagatg tttgtataga gggacaaaga    1320 atcgtctttta ttatggtcaa ggctttacgt cataatagtt cctgcccagc tcttctataa    1380
tactttaaag atctcttctc gtttgctcca tttggaagtc tcgcttacgt ttatgcgccc    1440
atacagacac tcaagataca cacttacatg aacgtataca aatttactaa cactacttga    1500
aaatatgaac cacagtacat catattaaga cgtagtattc gatgattgaa ggccgcctcc    1560
gcgaaatacc tttactgatt ttgccggtta atcgcatcga aatttcttca tcacaagaaa    1620
gcaaacaaat cgccaggcca ttctacaagt ttcctttct tatgaagatg taaaagctac    1680
taaggcgtca ttactctaga tgactcagtt tagtctgacc ttctatagta tactaccctg    1740
gcgctatgat gatgagcggt tctttattg cggaaacgaa aattccggga ccggcgaaat    1800
ttgcccggtt ttgtccgtaa ccggcttcat gagtcggctt caatagtagt tgaatactta    1860
```

```
tttaaacagc agaacttaac tcactcatca cgctgtttcc gctgaatttt ctcaaaatat    1920
ctaagcagtc aacaaatata agaatattg aaattgacag tttttgtcgc tatcgatttt     1980
tattatttgc tgttttaaat c                                              2001

<210> SEQ ID NO 230
<211> LENGTH: 2000
<212> TYPE: DNA
<213> ORGANISM: Saccharomyces cerevisiae

<400> SEQUENCE: 230
ccaaatcatt cttattcggt ttccagacgg taacaatacc ctcgcccatc ccacacaaaa      60
gggtatctgc tacttcggga tcgacgaaac aaccacaaag aacttcgtcc tcctgatcat     120
cgctgatcaa aattttacca tcctcgtttc cagctacgtt cggtttggca tctttgtcgc    180
gaacgtcaaa ataagctaac gttgtctggc ccaagaaat gaatttatat gcagatcttt      240
tatcaaagtg gaaaatatcg ttgatagagt cgccaaaatg tatcgaacga atggaatttg    300
ataatgccaa gttttccgag tttattacgt gtatattacc ggattcatcg cctattaaaa    360
tgaatgggtg agtttgagag gcgcataatt tcgtaaattt atcatttttt ttctcttcag    420
aattaaacag tgagcttaag tttacctttt tgacgactttt gccggtcata gtattggcct   480
tttttaaaac attatccgat ccaacagaaa aaatattgtc acctttagaa tcaaagcaca    540
tggcacggac actacctta tgtcttttag tcttccaaag tgttttacg cccagtctt       600 catctttttcc tgtttgcttt tgttgctgtt gttcttcaat atcaacaaat ttcaaatctc    660
cagtttctag gtctatatct aatctaatcc aagggcatac acctttcttt gcatccttgc    720
ctgtagttgc agtgtcaatt ctacgtctac gatctaggtg cgattgcaac ttagcggggt    780
cataacgatg gcacacaata tgtcctgtac caaagccagt tattataatg ggcagttcag    840
gatgtaaaag agactggaaa atgggagctt ttaatgatag taattctaga atgggcaggt    900
ttgttgaatc gacaacatct gttttttttt tgctctttgc catagctgat gcgtggattg    960
tttctaattt cccagctgct tcctcttcca attgtggcga tgatgccatg atttctatgt   1020
taaaattttt ctaaccatga aatttttttt ttctagcgag aaaaaaaatc agaaaaatta   1080
ctattagtga gtattggaga cattgtcaat gggagatgtt ctctttataa tatcttcaac   1140
aggttctttc aactctggaa attcatccac aatcttgtca gcaagtgaat ctcttaattg   1200
cttcaatcca tgcatcttgc ctctttgata ttggttggat cttcttatgg cttccacgaa   1260
ctctcttgtg taaatatctg gatttctacc gtcctcaatg tattgaacaa cttccaaggg   1320
aatgtccacc ttagacaagc tggattgagg atcgttgctt ctcacgttca gcttgtacaa   1380
gcgatccaca tttctttgca agttggtgat cattcccttg gtggcttctg gagtaccagg   1440
aaaatcatat atcgagacac ctaattcaac gaaggactca ataatcgaag ccacttggtc   1500
ttgagtagtg gccagttctt gctgcaattg ttcattgtta gtgctgtttc cattcatctt   1560
atcggtttat ttttctatat atttgcctct ttctcaaaca ggagttagta gttaaaagta   1620
cgaagttctt gttctttaat gcgcgctgac aaaagaattg gataaagag aatggtgggg    1680 ggacaagaag gaaatttgtc ctagtttaac atgaatggca tcttgttacc gggtggacat   1740
cacctattga ttctaaatat cttttacggtt tatcatactg ttctttattc cgtcgttatt   1800 cttttttattt ttatcatcat ttcacgtggc tagtaaaaga aaagccacaa catgactcag   1860
caaatctcga caaagtaaaa gctcatagag atagtattat attgatataa aaaaagtata   1920
ctgtactgtt tgtaacctttt tcaatgcttt aagatcaaaa ctaaggccag caaaggtatc   1980
```

```
aacccatagc aactcataaa                                                 2000

<210> SEQ ID NO 231
<211> LENGTH: 2001
<212> TYPE: DNA
<213> ORGANISM: Saccharomyces cerevisiae

<400> SEQUENCE: 231
gaaaccatta aatcatattt aataaattgt tgcgacatgc aagaagttcg cggatggtca      60
tgcgtattta agaatagtca agtaacaatt tgcttattcg ttgatgatat gatattattc     120
agcaaagact taaatgcaaa taagaaaatc ataacaacac tcaagaaaca atacgataca     180
aagataataa atctgggtga aagtgataac gaaattcagt acgacatact tggattagag     240
atcaaatatc aaagaagcaa gtacatgaaa ttaggtatgg aaaaatcctt gacagaaaaa     300
ttacccaaac taaacgtacc tttgaaccca aaggaaaga  aacttagagc tccaggtcaa     360
ccaggtcatt atatagacca ggatgaacta gaaatagatg aagatgaata caaagagaaa     420
gtacatgaaa tgcaaaagtt gattggtcta gcttcatatg ttggatataa atttagattt     480
gacttactat actacatcaa cacattgctc aaccatatac tattcccctc taggcaagtt     540
ttagacatga catatgagtt aatacaattc atgtgggaca ctagagataa acaattaata     600
tggcacaaaa acaaacctac caagccagat aataaactag tcgcaataag cgatgcttca     660
tatggtaacc aaccatatta caagtcacaa attggtaaca ttttcctact caacggaaaa     720
gtgattggag aaagtcgac  aaaggcttcg ttaacatgca cttcaactac agaagcagaa     780
atacacgcgg tcagtgaagc tattccgcta ttgaataacc tcagtcacct tgtgcaagaa     840
cttaacaaga aaccaattat taaaggctta cttactgata gtagatcaac gatcagtata     900
attaagtcta caaatgaaga gaaatttaga aacagatttt ttggcacaaa ggcaatgaga     960
cttagagatg aagtatcagg taataattta tacgtatact acatcgagac caagaagaac    1020
attgctgatg tgatgacaaa acctcttccg ataaaaacat ttaaactatt aactaacaaa    1080
tggattcatt agatctatta cattatgggt ggtatgttgg aataaaaatc aactatcatc    1140
tactaactag tatttacgtt actagtatat tatcatatac ggtgttagaa gatgacgcaa    1200
atgatgagaa atagtcatct aaattagtgg aagctgaaac gcaaggattg ataatgtaat    1260
aggatcaatg aatattaaca tataaaatga tgataataat atttatagaa ttgtgtagaa    1320
ttgcagattc ccttttatgg attcctaaat cctcgaggag aacttctagt atatctacat    1380
acctaatatt attgccttat taaaaatgga atcccaacaa ttacatcaaa atccacattc    1440
tcttcaaaat caattgtcct gtacttcctt gttcatgtgt gttcaaaaac gttatattta    1500
taggataatt atactctatt tctcaacaag taattggttg tttggccgag cggtctaagg    1560
cgcctgattc aagaaatatc ttgaccgcag ttaactgtgg aatactcag  gtatcgtaag    1620
atgcaagagt tcgaatctct tagcaaccat tatttttttc ctcaacataa cgagaacaca    1680
caggggcgct atcgcacaga atcaaattcg atgactggaa atttttgtt aatttcagag     1740
gtcgcctgac gcatatacct ttttcaactg aaaaattggg agaaaaagga aaggtgagag    1800
ccgcggaacc ggcttttcat atagaataga gaagcgttca tgactaaatg cttgcatcac    1860
aatacttgaa gttgacaata ttatttaagg acctattgtt ttttccaata ggtggttagc    1920
aatcgtctta ctttctaact tttcttacct tttacatttc agcaatatat atatatatat    1980
ttcaaggata taccattcta a                                              2001
```

<210> SEQ ID NO 232
<211> LENGTH: 2001
<212> TYPE: DNA
<213> ORGANISM: Saccharomyces cerevisiae

<400> SEQUENCE: 232

| | | | | | |
|---|---|---|---|---|---|
| cactaccacc | actacggttg | tccatgacgt | atcctgcgat | tttttgaatt | aatgattcaa | 60 |
| tagttgacat | ttgctcgtca | ttggggttcg | actgagctgc | ggatgtcaac | ttcgcaacag | 120 |
| cttctgcatg | gtttccttga | gaaaaatgag | actcagcctc | tgagattaac | ttatccgtat | 180 |
| ccatttcaga | tctttgctat | acgtttgtat | cgctatatgt | acgttctttt | aatgaacttt | 240 |
| ctcctttctt | tatcgtgtag | cttgcttggg | tatcttttaa | tgagttgcgg | acagtgagat | 300 |
| ttttcagaag | ggcaattggc | caagacacca | aaaacgtttg | gacgagacag | gcatcaaagg | 360 |
| acaaggtaaa | aggcgttgag | ctgtggctgg | ctgtgtatgc | gtttgaaata | ccatggatag | 420 |
| atatcaaaga | aagataggat | gtttcataca | aatcccaaat | ttggggcgcg | gacaactgaa | 480 |
| atacgtgggt | ccagtggaca | cgaaagctgg | aatgtttgct | ggtgtagact | tacttgccaa | 540 |
| cattggtaag | aacgatggat | cattcatggg | gaagaagtat | tttcaaacag | agtatcctca | 600 |
| aagtggacta | tttatccagt | tgcaaaaagt | cgcatcattg | atcgagaagg | catcgatatc | 660 |
| gcaaacctcg | agaagaacga | cgatggaacc | gctatcaata | cccaaaaaca | gatctattgt | 720 |
| gaggctcact | aaccagttct | ctcccatgga | tgatcctaaa | tcccccacac | ccatgagaag | 780 |
| tttccggatc | accagtcggc | acagcggtaa | tcaacagtcg | atggaccagg | aggcatcgga | 840 |
| tcaccatcaa | cagcaagaat | ttggttacga | taacagagaa | gacagaatgg | aggtcgactc | 900 |
| tatcctgtca | tcagacagaa | aggctaatca | caacaccacc | agcgattgga | aaccggacaa | 960 |
| tggccacatg | aatgacctca | atagcagcga | agttacaatt | gaattacgag | aagcccaatt | 1020 |
| gaccatcgaa | aagctacaaa | ggaaacaact | acactacaaa | aggctactcg | atgaccaaag | 1080 |
| aatggtcctc | gaagaagtgc | aaccgacttt | tgataggtat | gaagccacaa | tacaagaaag | 1140 |
| agagaaagag | atagaccatc | tcaagcaaca | attggagctc | gaacgcagac | agcaagccaa | 1200 |
| acaaaagcag | tttttttgacg | ctgagaatga | acagctactt | gctgtcgtaa | gccaactaca | 1260 |
| cgaagagatc | aaagaaaacg | aagagagaaa | tctttctcat | aatcaaccca | ctggtgccaa | 1320 |
| cgaagatgtc | gaactcctga | aaaaacagct | ggaacaatta | cgcaacatag | aagaccaatt | 1380 |
| tgagttacac | aagacaaagt | gggctaaaga | acgcgaacaa | ttgaaaatgc | ataacgattc | 1440 |
| gctcagtaaa | gaataccaaa | atttgagcaa | ggaactattt | ttgacaaaac | cacaagattc | 1500 |
| ctcatcggaa | gaggtggcat | ccttaacgaa | aaaacttgaa | gaggctaatg | aaaaaatcaa | 1560 |
| acagttggaa | caggctcaag | cacaaacagc | cgtggaatcg | ttgccaattt | tcgaccccc | 1620 |
| tgcaccagtc | gataccacgg | caggaagaca | acagtggtgt | gagcattgcg | atacgatggg | 1680 |
| tcataataca | gcagaatgcc | cccatcacaa | tcctgacaac | cagcagttct | tctaggcagt | 1740 |
| cgaactgact | ctaatagtga | ctccggtaaa | ttagttaatt | aattgctaaa | cccatgcaca | 1800 |
| gtgactcacg | ttttttttatc | agtcattcga | tatagaaggt | aagaaaagga | tatgactatg | 1860 |
| aacagtagta | tactgtgtat | ataatagata | tggaacgtta | tattcacctc | cgatgtgtgt | 1920 |
| tgtacataca | taaaaatatc | atagcacaac | tgcgctgtgt | aatagtaata | caatagttta | 1980 |
| caaaattttt | tttctgaata | c | | | | 2001 |

<210> SEQ ID NO 233
<211> LENGTH: 2001

```
<212> TYPE: DNA
<213> ORGANISM: Saccharomyces cerevisiae

<400> SEQUENCE: 233
acaatgagga agaacatgcc gttttacaag aattaaatag tttaacccaa agaattaatg      60
aactaggcat ggaaagtata aattcaaact ccgattcgga cagaataaac gggtcatatt     120
cacaagtgga ttttggtaac aataacgacg aggacgatat gaacctgttc gacccagatt     180
ttatggcaca agaccaattg cgtgctgaag aaagagacta caacaaggat gatagaacac     240
ccttagctaa ggtccctgcg gcctttcaat caactggatt gggcataacc cccgatgacg     300
atatcgagag acaatacata acggaacaca gatcacgaca tgaagtgcca aagcggtctc     360
ccgagaaacc ctccaacccg ctggaaatag gtaacccata cgcgaaacct ggcacaaggt     420
tgaataccac tcacacccac agcaaaactg atcgtagcat taccccctcag aggggccagc     480
cagtcccatc aggccagcag atttcctcct acgtgcagcc agcaaacatt aatagtccta     540
acaaaatgta tggtgcaaac aactcggcaa tgggttcgcc caggaatcca agacgagag     600
cgccaccagg tccatacaat cagggatgga ataaccgccc ctcgccttca aatatttacc     660
aacgtcctca tccctcagat acacaaccac aagcatatca tctccccgga aacccatact     720
caacggggaa caggccaaac atgcaagcgc aatatcaccc gcagcaggtg cccatgccta     780
tcctgcagca gcccaatcgc ccgtaccaac cttatgcgat gaatacgcac atgggctctc     840
ctggcggata tgctggggca gcaccaccat ttcagccagc taacgtcaac tacaatacta     900
ggcctcagca gccatggcct acacctaact caccatccgc acactaccgt ccgcccccta     960
acctgaacca gcctcaaaac ggtagtgctg gttactatcg tccgccggca ccacaattgc    1020
aaaactccca gcccgtccaa caaagaagg acggattctc acagttcatg ccatctgcaa    1080
ctacgaagaa cccatatgcc cagtaactcg accgactggt tgtaatttta caaaagaga    1140
gacaattaag aaaagaaaca agcgccaggc ttccgtatcc cagttttttca tctcactttc    1200
tgggcacgat tgtaataata cttcatgata ataactaaac tatataagta gtgtctcatc    1260
cgtaaatata catttagaca gattcttgta ttttctccgg gcaattttta acttttttc     1320
tgttagggca catgacactt gcctattatg gacagccagt aaagatgtgc catatattgc    1380
cccctttacg ctctctgcca gtattagtgg gaaaaaaaaa actgaaaaaa aaaaaatcgc    1440
agactactaa taatcacgtg atatttcttt tcactctctt cataaagttg ctaaaaacac    1500
acaatcgaat gagcctctga gcagtataaa ttgtacttca aagcactagt catgaaaaac    1560
gcttacatta gttcagtttg tcaaggttat gctattactt gtacttattt cttgctattg    1620
ttagtggctc cccacattga cgtatttttca cgtgatgcgc ctcactgcgg aaggcgccac    1680
acattgcctg caaaaaattg tggatgcact catttgatag taaactaagt catgttaatc    1740
gtttggattt ggcacacacc cacaaatata cacattacat atatatatat attcaaaata    1800
cagctgcgtc caatagatga gcttccgctt cgttgtacaa cctacctgct atcttgttca    1860
cggatatttc ttgcttttaa taaacaaaag taactctaga acagtcaagt cttcgataat    1920
tttttagtc acagggtccg tctaaagttt ctctttattt ggaataatag aaaagaaaga    1980
aaaaaacgta gtataaaagg a                                              2001

<210> SEQ ID NO 234
<211> LENGTH: 2000
<212> TYPE: DNA
<213> ORGANISM: Saccharomyces cerevisiae
```

<400> SEQUENCE: 234

```
aaggatggca aatacccaat cggaggaact cgaacacttc agtatctgtg tcttctagtg      60
agtctttagc ggaagttatt cagccatctt ccttcaaaag tgggagtagt tcattgcatt     120
atctatcgtc ttctatctca agccaacctg gttcgtacgg ttcttggttc aacaaaaggc     180
caacaatttc tcagttcttt caaccaagcc cttctttaaa acacaacgag tcgtgggaga     240
ggctgcaaac aactgctgga aatatgcaaa ggacttcaag ttcgtcttct ttgcagcaag     300
caacctccag gttatcacta accactccgc aacaatcacc gtctatcagc gaatatgatg     360
agtatccttg gatgggcaca cctggctctc ctaatgttgg agatgtgtct cacgcacccc     420
cattggttaa gaatatatca tataaatttc cactaaagaa cgttgagttg aaaagagatt     480
gccaaaggat ctctcaggat gatcttttgg atgaggcttt tgaaagaata tgtcagccct     540
ctttggctga ccttaattcc acttacgaaa ttttccagg taactcttct tatgcggata     600
ttttgactac tgattctgat attgatgatg cttgatgaa taaacctctg aactattgc      660
cgaaatatac aatgtattta acccatttta acaatttttt ccagttgcaa gcatgtcctg     720
ctggtcaaga atcagagagc agaataacaa attctatgaa gattgacctg ttaaaggcgg     780
attacacaag aagtctatta gtatcgttac gttcaaggga cattagggat gtcgcattga     840
aaagagagtt tactggcaat aacaacaata acagcaacca gaatatctat gatgagaatt     900
tgtcggaaaa aggaagtac gtgttgaaac agaagaccag aaaaatcttt tcctgtggca     960
agattggcaa gctaagtact agtttggaaa actgcgttaa ttttgttgaa aatagtataa    1020
agagtgcaat gatgttatat gatgataatg gaatagatag tgagcttcgc gattcagaag    1080
ctttacggat ttttcatct cttgttcatt attgtaatgc aggttaatgt tttctccttc    1140
tttacatgtt taatatattc caagttacct aagaggtgta cgatattttt ttcttttata    1200
tatatgattt tctctattca tttttagtt tttttgata cataagcgaa tcgcacattg     1260
cgcaacttca atttgttgat tcgccaaagt attcttacca taaacaacc attcgttgct    1320
ttacccttc gtaatcattt accgtgataa ccataatcag aaacttatta tttcagccta    1380
gtagaccggc caagcaggcc ttgtaatgtt tctcttgatt gcttgaatct tttaagcagc    1440
caaatctttc caaaaaaatg caattatcag aacaaaacta tttaaggtga cttctccgta    1500
tttacaccac cagaagcgtt ctggctcccc ttttctctaa acgttaaaca ttttacaatt    1560
gaaatgttac caatcctata ttattgtacc acattgccag atttatgaac tctgggtatg    1620
ggtgctaatt ttcgttagaa gcgctggtac aattttctct gtcattgtga cactaattag    1680
gaaacttctc gactatcaat gtgtaaatga aggaataatg gcggaaactt tgaaactttg    1740
tcaataattg catcattgga tgcgtttcat ttggccgtta tcacggagag gcagagttct    1800
ctccacaatt tgggcagaag tcttttgaaa agacatatat atatatatat atgtatatga    1860
gtggatgctt aaggtaagaa taatttctga attcccaagt attcattttg tgcagtattc    1920
acatattcta ttttattgct ttttaacttt agaggcaatt aaatttgtgt aggaaaggca    1980
aaatactatc aaaatttttcc                                               2000
```

<210> SEQ ID NO 235
<211> LENGTH: 2001
<212> TYPE: DNA
<213> ORGANISM: Saccharomyces cerevisiae

<400> SEQUENCE: 235

```
ttgccttcaa gatctacttt cctaagaaga tcattattac aaacacaact gcactcaaag      60
```

```
atgactgctc atactaatat caaacagcac aaacactgtc atgaggacca tcctatcaga      120
agatcggact ctgccgtgtc aattgtacat ttgaaacgtg cgcccttcaa ggttacagtg      180
attggttctg gtaactgggg gaccaccatc gccaaagtca ttgcggaaaa cacagaattg      240
cattcccata tcttcgagcc agaggtgaga atgtgggttt tgatgaaaa gatcggcgac       300 gaaaatctga cggatatcat aaatacaaga caccagaacg ttaaatatct acccaatatt     360
gacctgcccc ataatctagt ggccgatcct gatcttttac actccatcaa gggtgctgac      420
atccttgttt tcaacatccc tcatcaattt ttaccaaaca tagtcaaaca attgcaaggc      480
cacgtggccc tcatgtaag ggccatctcg tgtctaaaag ggttcgagtt gggctccaag       540
ggtgtgcaat tgctatcctc ctatgttact gatgagttag aatccaatg tggcgcacta       600 tctggtgcaa acttggcacc ggaagtggcc aaggagcatt ggtccgaaac caccgtggct      660
taccaactac caaaggatta tcaaggtgat ggcaaggatg tagatcataa gattttgaaa     720
ttgctgttcc acagacctta cttccacgtc aatgtcatcg atgatgttgc tggtatatcc      780
attgccggtg ccttgaagaa cgtcgtggca cttgcatgtg gtttcgtaga aggtatggga     840
tggggtaaca atgcctccgc agccattcaa aggctgggtt taggtgaaat tatcaagttc     900
ggtagaatgt ttttcccaga atccaaagtc gagacctact atcaagaatc cgctggtgtt     960
gcagatctga tcaccacctg ctcaggcggt agaaacgtca aggttgccac atacatggcc     1020
aagaccggta agtcagcctt ggaagcagaa aaggaattgc ttaacggtca atccgcccaa     1080
gggataatca catgcagaga agttcacgag tggctacaaa catgtgagtt gacccaagaa     1140
ttcccattat tcgaggcagt ctaccagata gtctacaaca acgtccgcat ggaagaccta     1200
ccggagatga ttgaagagct agacatcgat gacgaataga cactctcccc ccccctcccc     1260
ctctgatctt tcctgttgcc tcttttttccc caaccaatt tatcattata cacaagttct     1320
acaactacta ctagtaacat tactacagtt attataattt tctattctct ttttctttaa     1380
gaatctatca ttaacgttaa tttctatata tacataacta ccattataca cgctattatc     1440
gtttacatat cacatcaccg ttaatgaaag atacgacacc ctgtacacta acacaattaa     1500
ataatcgcca taacctttc tgttatctat agcccttaaa gctgtttctt cgagcttttt     1560
cactgcagta attctccaca tgggcccagc cactgagata agagcgctat gttagtcact     1620
actgacggct ctccagtcat ttatgtgatt ttttagtgac tcatgtcgca tttggcccgt    1680
ttttttccgc tgtcgcaacc tatttccatt aacggtgccg tatggaagag tcatttaaag    1740
gcaggagaga gagattactc atcttcattg gatcagattg atgactgcgt acggcagata     1800
gtgtaatctg agcagttgcg agacccagac tggcactgtc tcaatagtat attaatgggc    1860
atacattcgt actcccttgt tcttgcccac agttctctct ctctttactt cttgtatctt     1920
gtctccccat tgtgcagcga taaggaacat tgttctaata tacacggata caaaagaaat     1980
acacataatt gcataaaata c                                              2001
```

<210> SEQ ID NO 236
<211> LENGTH: 1999
<212> TYPE: DNA
<213> ORGANISM: Saccharomyces cerevisiae

<400> SEQUENCE: 236

```
ttttgtaaga aattattcac cgcatcttca tctggcaaac gaatgggaga ctttgaggaa       60
cccaatccat ttctgaataa cggagattta gaaatgtaaa aggtagcaaa tgtaaaaagt     120
```

| | |
|---|---|
| gccaggacca tcacagcagt caatgccaac accaatttcc cttgccatga cactgttgga | 180 |
| tcttttgaag gagatttgta acctggaatc tcactataat gaacacattc accggattca | 240 |
| cacttcaaag taatataagg gtcaccaaac acggtcaata tcaaatcatt catagaaggc | 300 |
| tcactgaatt tacattgcct tgtttctaaa tcacagctga aatctcctgg ccctttatt | 360 |
| gtctctgtca ggaaatccga gatatctata dacccttag caccacacaa cacagtgtcg | 420 |
| ggaacgcatt tgcattgaac gtcattacac ttataatggg aggtattctg ttccaagtcg | 480 |
| tattcaaagg cacaatcact taagccacaa tagaagcttt ctaactgatc tatccaaaac | 540 |
| tgaaaattac attcttgatt aggtttatca caggcaaatg taatttgtgg tatttttgccg | 600 |
| ttcaaaatct gtagaatttt ctcattggtc acattacaac ctgaaaatac tttatctaca | 660 |
| atcataccat tcttataaca tgtcccctta atactaggat caggcatgaa cgcatcacag | 720 |
| acaaaatctt cttgacaaac gtcacaattg atccctcccc atccgttatc acaatgacag | 780 |
| gtgtcatttt tgtgctcttat gggacgatcc ttattaccgc tttcatccgg tgatagaccg | 840 |
| ccacagaggg gcagagagca atcatcacct gcaaacccctt ctatacactc acatctacca | 900 |
| gtgtacgaat tgcattcaga aaactgtttg cattcaaaaa taggtagcat acaattaaaa | 960 |
| catggcgggc atgtatcatt gcccttatct tgtgcagtta dacgcgaatt tttcgaagaa | 1020 |
| gtaccttcaa agaatggggt cttatcttgt tttgcaagta ccactgagca ggataataat | 1080 |
| agaaatgata atatactata gtagagataa cgtcgatgac ttcccatact gtaattgctt | 1140 |
| ttagttgtgt attttttagtg tgcaagtttc tgtaaatcga ttaattttt ttctttcct | 1200 |
| cttttatta accttaattt ttattttaga ttcctgactt caactcaaga cgcacagata | 1260 |
| ttataacatc tgcataatag gcatttgcaa gaattactcg tgagtaagga aagagtgagg | 1320 |
| aactatcgca tacctgcatt taaagatgcc gatttgggcg cgaatccttt attttggctt | 1380 |
| cacctcata ctattatcag ggccagaaaa aggaagtgtt tccctccttc ttgaattgat | 1440 |
| gttaccctca taaagcacgt ggcctcttat cgagaaagaa attaccgtcg ctcgtgattt | 1500 |
| gtttgcaaaa agaacaaaac tgaaaaaacc cagacacgct cgacttcctg tcttcctatt | 1560 |
| gattgcagct tccaatttcg tcacacaaca aggtcctagc gacggctcac aggttttgta | 1620 |
| acaagcaatc gaaggttctg gaatggcggg aaagggttta gtaccacatg ctatgatgcc | 1680 |
| cactgtgatc tccagagcaa agttcgttcg atcgtactgt tactctctct ctttcaaaca | 1740 |
| gaattgtccg aatcgtgtga caacaacagc ctgttctcac acactctttt cttctaacca | 1800 |
| aggggggtggt ttagtttagt agaacctcgt gaaacttaca tttacatata tataaacttg | 1860 |
| cataaattgg tcaatgcaag aaatacatat ttggtctttt ctaattcgta gtttttcaag | 1920 |
| ttcttagatg ctttcttttt ctcttttta cagatcatca aggaagtaat tatctacttt | 1980 |
| ttacaacaaa tataaaaca | 1999 |

<210> SEQ ID NO 237
<211> LENGTH: 1999
<212> TYPE: DNA
<213> ORGANISM: Saccharomyces cerevisiae

<400> SEQUENCE: 237

| | |
|---|---|
| aaacaaatgg caaaataac gggcttcacc attgttcctg tatggtgtat tagaacatag | 60 |
| ctgaaaatac ttctgcctca aaaagtgtt aaaaaaaaga ggcattatat agaggtaaag | 120 |
| cctacaggcg caagataaca catcaccgct ctccccctc tcatgaaaag tcatcgctaa | 180 |
| agaggaacac tgaaggttcc cgtaggttgt ctttggcaca aggtagtaca tggtaaaaac | 240 |

```
tcaggatgga ataattcaaa ttcaccaatt tcaacgtccc ttgtttaaaa agaaaagaat     300
ttttctcttt aaggtagcac taatgcatta tcgatgatgt aaccattcac acaggttatt     360
tagcttttga tccttgaacc attaattaac ccagaaatag aaattaccca agtggggctc     420
tccaacacaa tgagaggaaa ggtgactttt taagggggcc agaccctgtt aaaaacccttt    480 gatggctatg taataatagt aaattaagtg caaacatgta agaaagattc tcggtaacga     540
ccatacaaat attgggcgtg tggcgtagtc ggtagcgcgc tcccttagca tgggagaggt     600
ctccggttcg attccggact cgtccaaatt atttttttact ttccgcggtg ccgagatgca    660
gacgtggcca actgtgtctg ccgtcgcaaa atgatttgaa ttttgcgtcg cgcacgtttc     720
tcacgtacat aataagtatt ttcatacagt tctagcaaga cgaggtggtc aaaatagaag     780
cgtcctatgt tttacagtac aagacagtcc atactgaaat gacaacgtac ttgacttttc     840
agtattttct ttttctcaca gtctggttat ttttgaaagc gcacgaaata tatgtaggca     900 agcatttttct gagtctgctg acctctaaaa ttaatgctat tgtgcacctt agtaacccaa    960
ggcaggacag ttaccttgcg tggtgttact atggccggaa gcccgaaaga gttatcgtta    1020
ctccgattat tttgtacagc tgatgggacc ttgccgtctt cattttttt ttttttcacc     1080 tatagagccg ggcagagctg cccggcttaa ctaagggccg aaaaaaaac ggaaaaaaga     1140 aagccaagcg tgtagacgta gtataacagt atatctgaca cgcacgtgat gaccacgtaa    1200
tcgcatcgcc cctcacctct cacctctcac cgctgactca gcttcactaa aaaggaaaat    1260
atatactctt tcccaggcaa ggtgacagcg gtccccgtct cctccacaaa ggcctctcct    1320
ggggtttgag caagtctaag tttacgtagc ataaaaattc tcggattgcg tcaaataata    1380 aaaaagtaa ccccacttct acttctacat cggaaaaaca ttccattcac atatcgtctt     1440
tggcctatct tgttttgtcc tcggtagatc aggtcagtac aaacgcaaca cgaaagaaca    1500
aaaaaagaag aaaacagaag gccaagacag ggtcaatgag actgttgtcc tcctactgtc    1560
cctatgtctc tggccgatca cgcgccattg tccctcagaa acaaatcaaa cacccacacc    1620
ccgggcaccc aaagtcccca cccacaccac caatacgtaa acgggcgcc cctgcaggc    1680 cctcctgcgc gcggcctccc gccttgcttc tctcccttc cttttctttt tccagttttc    1740 cctatttgt ccctttttcc gcacaacaag tatcagaatg ggttcatcaa atctatccaa    1800
cctaattcgc acgtagactg gcttggtatt ggcagtttcg tagttatata tatactacca    1860
tgagtgaaac tgttacgtta ccttaaattc tttctccctt taattttctt ttatcttact    1920
ctcctacata agacatcaag aaacaattgt atattgtaca cccccccct ccacaaacac     1980 aaatattgat aatataaag                                                1999

<210> SEQ ID NO 238
<211> LENGTH: 2009
<212> TYPE: DNA
<213> ORGANISM: Saccharomyces cerevisiae

<400> SEQUENCE: 238
ggatgagaaa cgagtgcggt ttcgagagta gatattcaac ccacccgaag tagccttcag      60
gaactggttc cgttctctct tcctccggaa tagtctgaat gtccttaaga gaccgtggct     120
cgtatactct tctattcttg ggccgcaata gcaaaaagag ccagacaaac acgacggcgg     180
taagaccgta gataatcagg gttgaaatga acgccgaagt cgaagaactg tcagccatag     240
tacgtatgtg ctataaatat ctaacctttc gctgctttga atatgatgtg ctcaaatata     300
```

```
acttaatata atagtataac aaaaaggagt actatttgct aaatatcgta gacgtagtag    360
acatagtaaa tacaataaag gatagataac caagaaccca catcaagcga atacatacat    420
atatatatac tcgatgtata catgtttcta agcacttgcg cacatacgta tttaaagtat    480
ttcagggaga ttaacgtatt aaaacaagaa gagggttgac tacatcacga tgaggggat     540 cgaagaaatg atggtaaatg aaataggaaa tcaaggagca tgaaggcaaa agacaaatat    600
aagggtcgaa cgaaaaataa agtgaaaagt gttgatatga tgtatttggc tttgcggcgc    660
cgaaaaaacg agtttacgca attgcacaat catgctgact ctgtggcgga cccgcgctct    720
tgccggcccg gcgataacgc tgggcgtgag gctgtgcccg gcggagtttt ttgcgcctgc    780
attttccaag gtttaccctg cgctaagggg cgagattgga gaagcaataa gaatgccggt    840
tggggttgcg atgatgacga ccacgacaac tggtgtcatt atttaagttg ccgaaagaac    900
ctgagtgcat ttgcaacatg agtatactag aagaatgagc caagacttgc gagacgcgag    960
tttgccggtg gtgcgaacaa tagagcgacc atgaccttga aggtgagacg cgcataaccg   1020
ctagagtact ttgaagagga aacagcaata gggttgctac cagtataaat agacaggtac   1080
atacaacact ggaaatggtt gtctgtttga gtacgctttc aattcatttg ggtgtgcact   1140
ttattatgtt acaatatgga agggaacttt acacttctcc tatgcacata tattaattaa   1200
agtccaatgc tagtagagaa gggggtaac  accctccgc gctcttttcc gattttttc     1260 taaccgtgg aatatttcgg atatccttt gttgtttccg ggtgtacaat atggacttcc     1320
tcttttctgg caaccaaacc catacatcgg gattcctata ataccttcgt tggtctccct   1380
aacatgtagg tggcggaggg gagatataca atagaacaga taccagacaa gacataatgg   1440
gctaaacaag actacaccaa ttacactgcc tcattgatgg tggtacataa cgaactaata   1500
ctgtagccct agacttgata gccatcatca tatcgaagtt tcactaccct ttttccattt   1560
gccatctatt gaagtaataa taggcgcatg caacttcttt tcttttttt tcttttctct   1620 ctccccgtt gttgtctcac catatccgca atgacaaaaa aatgatgaa gacactaaag    1680 gaaaaatta acgacaaaga cagcaccaac agatgtcgtt gttccagagc tgatgagggg   1740
tatctcgaag cacacgaaac ttttttcctt cttcattcac gcacactact ctctaatgag   1800
caacggtata cggccttcct tccagttact tgaatttgaa ataaaaaaaa gtttgctgtc   1860
ttgctatcaa gtataaatag acctgcaatt attaatcttt tgtttcctcg tcattgttct   1920
cgttcccttt cttccttgtt tcttttttctg cacaatattt caagctatac caagcataca   1980
atcaactatc tcatatacaa tgtctatcc                                     2009
```

<210> SEQ ID NO 239
<211> LENGTH: 1943
<212> TYPE: DNA
<213> ORGANISM: Saccharomyces cerevisiae

<400> SEQUENCE: 239

```
ggcagtcatc aggatcgtag gagataagca ccctgacaag taacatgccg atgaagttgt     60
ttggttcatt gggcaaaaaa atcgggattc tagaaaaccc tgagttgaag attttttcga   120
cagttttatc gtctaggatg gtatcggcac tcattgtgaa cacgttttca atcggagtca   180
tgatttcctc aaccctcttt gcctttagat ccaaaacagc agagatgatt gtaacttcgt   240
ctttagtcaa ccgttccacc cccatggtcc tatgcaaggt gaccaaagtc tttaagccgg   300
attttttgta catcgtacca tgatcttcac ccagcatata gtccaggaga gtcgcgatcg   360
gatatgcgac tgggtacatc agatacatca gtacaagaac aaaggggcag aagaatgccc   420
```

```
caacttgcag cccgtattta acacagacac tctgcggaat aatttcaccg aagatcacaa      480
ttagaatagt tgacgacact acagcctgcc aaccacccc aagacacctg tccaaaacaa      540
taggcaatgt ttcgttggtt ataacattag aaagcagcag tgtgactaga acccaatgct     600 tcccctaga tattaggtca agcacccgct tggccagttt cttttcagaa ttcgagcctg      660
aagtgctgat taccttcagg tagacttcat cttgacccat caaccccagc gtcaatcctg    720
caaatacacc acccagcagc actaggatga tagagataat atagtacgtg gtaacgcttg    780
cctcatcacc tacgctatgg ccggaatcgg caacatccct agaattgagt acgtgtgatc    840
cggataacaa cggcagtgaa tatatcttcg gtatcgtaaa gatgtgatat aagatgatgt    900 atcccaatg aggagcgcct gatcgtgacc tagaccttag tggcaaaaac gacatatcta     960
ttatagtggg gagagtttcg tgcaaataac agacgcagca gcaagtaact gtgacgatat    1020
caactctttt tttattatgt aataagcaaa caagcacgaa tggggaaagc ctatgtgcaa    1080
tcaccaaggt cgtcccttttt tcccatttg ctaatttaga atttaaagaa accaaaagaa     1140
tgaagaaaga aaacaaatac tagccctaac cctgacttcg tttctatgat aatacccctgc   1200 tttaatgaac ggtatgccct agggtatatc tcactctgta cgttacaaac tccggttatt    1260
ttatcggaac atccgagcac ccgcgccttc ctcaacccag gcaccgcccc caggtaaccg    1320
tgcgcgatga gctaatcctg agccatcacc caccccaccc gttgatgaca gcaattcggg    1380
agggcgaaaa ataaaaactg gagcaaggaa ttaccatcac cgtcaccatc accatcatat    1440
cgccttagcc tctagccata gccatcatgc aagcgtgtat cttctaagat tcagtcatca    1500
tcattaccga gtttgttttc cttcacatga tgaagaaggt ttgagtatgc tcgaaacaat    1560
aagacgacga tggctctgcc attgttatat tacgcttttg cggcgaggtg ccgatgggtt    1620
gctgagggga agagtgttta gcttacggac ctattgccat tgttattccg attaatctat    1680
tgttcagcag ctcttctcta ccctgtcatt ctagtatttt ttttttttt ttttggtttt     1740 acttttttt cttcttgcct ttttttcttg ttactttttt tctagttttt tttccttcca     1800
ctaagctttt tccttgattt atccttgggt tcttctttct actcctttag atttttttt     1860 tatatattaa ttttaagtt tatgtatttt ggtagattca attctctttc cctttccttt     1920
tccttcgctc cccttcctta tca                                            1943
```

<210> SEQ ID NO 240
<211> LENGTH: 2001
<212> TYPE: DNA
<213> ORGANISM: Saccharomyces cerevisiae

<400> SEQUENCE: 240

```
tgacaacgag taccaggaaa tcagtgcttc tgctttgaag aaggctcgta agggctgtga      60
tggtttgaag aaaaaggcag tcaagcaaaa ggaacaggag ttgaagaaac aacaaaaga      120 ggcagaaaat gctgccaagc aattgtctgc tttgaatatc accattaagg aggacgaatc     180
gctaccagct gccattaaga ctagaatttta tgactcttat tccaaggtcg acaaagagt     240 taaggttttcc ggttggatcc atagattacg ttctaacaag aaggttatt tcgtcgtcct    300 cagagacgga tctggtttca ttcaatgtgt cttgtccggt gatttggcat ggctcaaca     360 aactttggac ctgactttgg aatccaccgt tactctgtac ggtaccatag tcaaattgcc    420
tgagggtaaa accgctccag gtggtgttga attgaatgtc gactattacg aagttgtagg    480
tttggccccc ggtggtgaag actcctttac aaacaaaatc gcagagggct cagacccttc    540
```

```
tttactgttg gaccaacgtc atttggcctt gagaggagat gccttgtctg cagtcatgaa      600
agtccgtgct gctctactga aaagcgttag acgtgtttat gatgaagaac atttgacaga      660
agttacccca ccatgtatgg tgcaaactca gtcgaaggt ggttccactt tgttcaagat       720
gaactattac ggcgaggaag cttacttgac ccaaagttcc caattatatt tagaaacctg      780
tttggcctcc ctaggtgatg tttataccat ccaagaatct ttcagagctg aaaagtccca      840
cacaagaaga catttgtccg aatataccca tatcgaagct gaattggcct tcttgacttt      900
cgacgatcta ttacaacata ttgaaacttt gatcgtcaaa tccgtgcaat acgttttgga      960
agacccaatt gctggcccac tcgtaaaaca attgaatcca aactttaagg ctccaaaggc     1020
tccattcatg agattacagt acaaggatgc cattacctgg ttgaacgaac acgacatcaa     1080
gaacgaagag ggcgaagact taaaatttgg tgacgatatt gcagaagctg ctgaaagaaa     1140
gatgaccgat accatcggcg tcccaatctt tttgacgaga ttcccagtag aaatcaagtc     1200
tttctacatg aagcgttgtt ctgacgaccc ccgcgtcact gaatccgtcg acgttttgat     1260
gccaaacgtt ggtgaaatca ctggtggttc tatgagaatc gacgacatgg acgaactaat     1320
ggcagggttt aagcgtgagg gtattgatac cgacgcctac tactggttca ttgaccaaag     1380
aaaatacggt acttgcccac atggtggtta cggtatcggt accgaacgta ttttagcctg     1440
gttgtgtgac agattcactg tcagagactg ttccttgtat ccacgtttca gcggtagatg     1500
taagccatga tctttagtta ctgaagagta cgtgagcgct cacatatata caaatattta     1560
taccgattaa tatttacgtt cctccctctc tctaattatt cattgattta ttcaagaatt     1620
agcgttataa caataaatgg ttggcgcagg caattaattt ttctttactc ttccaaaccc     1680
tctgttaacg acaatcaaat aacctgatct gccaaggctc catcatatct ggcctagaac     1740
agtttttttt tttcgattat ttgttcgttc ttgtggtggt tactcattgg cagaatcccg     1800
aaaatcatga ttagtagatg aatgactcac ttttggata agctggcgca aattgaaaca     1860
tgtgaaaaaa aaaaaaaagg attataaaag gtcagcgaag cacagaactc tgagataaga     1920
ctacctttct ttagctaggg gagaatattc gcaattgaag agctcaaaag caggtaacta     1980
tataacaaga ctaaggcaaa c                                               2001
```

<210> SEQ ID NO 241
<211> LENGTH: 1999
<212> TYPE: DNA
<213> ORGANISM: Saccharomyces cerevisiae

<400> SEQUENCE: 241

```
tcctaaggac atattccgtt cgtacttgag ttattggatc tatgaaatcg ctcgctatac       60
accagtcatg attttgtccc tggtaatagg ggttttggtt ttattaatta tattttttaa      120
tgacaacgaa gcttgtgttt tcaattctgc aatatttgct tttacttctc ttgtaggttt      180
gttaataata ttaagtgatg gtaatccaaa gctagtcagt cgtcgaaatt ttaggaccga      240
gcttttagtg gatgtcatca cacgtaaacc ggcggtagaa gggaaagaat ggaggatcat      300
cacatacaac atgaaccaat atttgtttaa tcatgggcaa tggcatactc cgtattactt      360
ttacagcgat gaggattgct accgttattt tctacgcctt gttgagggag taaccccaa       420 gaagcaaaca gccacgtcaa ttggcaattc tccggtcacc gctaagcctg aagatgccat      480
cgagtcagct tctcctagtt ccagactgaa ttatcaaaac ttttttgctca aggcagcgga     540 gatcgaacga caagctcagg aaaattactg gcgaaggcgg catcccaata tcgatgcgct     600
tcttaaaaag acggaatagc ttagagacac taccatacgt aaagcgaaca taaactagag     660
```

```
tatgatatat aatcagcact aactggccgg aaaacggccg aaggaagcct cgaaaagtcg    720
attcgtgttg gacccatttg ctgaacaaag tggttcattg cctacctatt atggtagtag    780
tcgtgataat cgtgtggttg gttttgtcaa cggtgcattt gcattttcat gacaataaac    840
cttgcgtttt cgttctcggg atattacttt ccctccactt ctttcgcctc aatagctcct    900
ataagcattc tcagggcgta tgtcggtgat cgagatttcc aagcaagctt ttagtggaaa    960
tcatcgcgcg caagccagcg gtaaagggaa agaacggag gacgattaca tacaagatga    1020
acgaataaat aaattaataa taaataataa taaaaagtac agtagcatta aatattatta    1080
agtttaatga ttaaaaattg gttaattgtc aagaaaatct aaggtattaa taaataaata    1140
atactatgac aacttgcagc gaaagcatca gccccaatga aaattaatca gaattgaatc    1200
tgagcgtatt tatttgataa cggtttacgt aactgttgga ataaaaatca actatcatct    1260
actaactagt gtttacgtta ctagtatatt atcatatacg gtgttagaag atgacgcaaa    1320
tgatgagaaa tagtcatcgt tttcaacgga agctgaaata caaggattga taatgtaata    1380
ggatcaatga atatcaacat ataaaacgat gataataata tttatagaat tgtgtagaat    1440
tgcagattcc cttttatgga ttcctaaatc ctcgagaaga acttctagta tatctacgta    1500
cctaatatta ttgccttatt aaaaatggaa tcccaacaat tatctcaaaa ttcccccaat    1560
tctcatcagt aacaccccac cccgtattac ttttaccgtg atgaagattg gcatcgttac    1620
tttctaaacg taggacgtgc ggaatgacaa aaccatcagc agtgtcacga tctctccagt    1680
cacaatggca atcatgagtg catagtccaa agtaaagggg caaggaaaag catgattgaa    1740
aggactcccc atctggactc tatatgtcat cagcggctaa aaaaaagcat atagcacaac    1800
atcagcatca gcatcagcac tagagtcatc ggcccggcgg tccgcggtca tccccgcgga    1860 cttccgtcc gcccggcggg ctgtatcagc gtcaactgga acgcgcatat atatacaaga    1920
cacacataac atagaagcac acccacgaca ataaccacac gacaataacc acacccgccc    1980
acccctcctt tccgtatac                                                1999
```

<210> SEQ ID NO 242
<211> LENGTH: 20
<212> TYPE: DNA
<213> ORGANISM: Artificial
<220> FEATURE:
<223> OTHER INFORMATION: PCR primer

<400> SEQUENCE: 242
aagtcggcag agagcaacat                                                 20

<210> SEQ ID NO 243
<211> LENGTH: 20
<212> TYPE: DNA
<213> ORGANISM: Artificial
<220> FEATURE:
<223> OTHER INFORMATION: PCR primer

<400> SEQUENCE: 243
cagatgcaaa cccaacacac                                                 20

<210> SEQ ID NO 244
<211> LENGTH: 24
<212> TYPE: DNA
<213> ORGANISM: Artificial
<220> FEATURE:
<223> OTHER INFORMATION: PCR primer

```
<400> SEQUENCE: 244
cgattttctg ggtttgatcg ttag                                              24

<210> SEQ ID NO 245
<211> LENGTH: 20
<212> TYPE: DNA
<213> ORGANISM: Artificial
<220> FEATURE:
<223> OTHER INFORMATION: PCR primer

<400> SEQUENCE: 245
cattgtgggc gttgtagttg                                                   20

<210> SEQ ID NO 246
<211> LENGTH: 20
<212> TYPE: DNA
<213> ORGANISM: Artificial
<220> FEATURE:
<223> OTHER INFORMATION: PCR primer

<400> SEQUENCE: 246
gttgtggttg gtgctttcct                                                   20

<210> SEQ ID NO 247
<211> LENGTH: 20
<212> TYPE: DNA
<213> ORGANISM: Artificial
<220> FEATURE:
<223> OTHER INFORMATION: PCR primer

<400> SEQUENCE: 247
ccactttgac gccgtttatt                                                   20

<210> SEQ ID NO 248
<211> LENGTH: 24
<212> TYPE: DNA
<213> ORGANISM: Artificial
<220> FEATURE:
<223> OTHER INFORMATION: PCR primer

<400> SEQUENCE: 248
cgattttctg ggtttgatcg ttag                                              24

<210> SEQ ID NO 249
<211> LENGTH: 21
<212> TYPE: DNA
<213> ORGANISM: Artificial
<220> FEATURE:
<223> OTHER INFORMATION: PCR primer

<400> SEQUENCE: 249
gaactcgtca agaaggcgat a                                                 21

<210> SEQ ID NO 250
<211> LENGTH: 24
<212> TYPE: DNA
<213> ORGANISM: Artificial
<220> FEATURE:
<223> OTHER INFORMATION: PCR primer

<400> SEQUENCE: 250
cgattttctg ggtttgatcg ttag                                              24
```

```
<210> SEQ ID NO 251
<211> LENGTH: 18
<212> TYPE: DNA
<213> ORGANISM: Artificial
<220> FEATURE:
<223> OTHER INFORMATION: PCR primer

<400> SEQUENCE: 251
tcagggcaat gcagatcc                                                 18
```